(12) United States Patent
Kolasa et al.

(10) Patent No.: US 7,875,640 B2
(45) Date of Patent: Jan. 25, 2011

(54) COMPOUNDS AS CANNABINOID RECEPTOR LIGANDS

(75) Inventors: Teodozyj Kolasa, Lake Villa, IL (US); Jennifer M. Frost, Grayslake, IL (US); Meena V. Patel, Green Oaks, IL (US); Steven P. Latshaw, Round Lake Beach, IL (US); Arturo Perez-Medrano, Grayslake, IL (US); Xueqing Wang, Evanston, IL (US); Sridhar Peddi, Grayslake, IL (US); William A. Carroll, Evanston, IL (US); Michael J. Dart, Highland Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 490 days.

(21) Appl. No.: 12/051,538

(22) Filed: Mar. 19, 2008

(65) Prior Publication Data

US 2008/0242654 A1 Oct. 2, 2008

Related U.S. Application Data

(60) Provisional application No. 60/908,455, filed on Mar. 28, 2007.

(51) Int. Cl.
*A61K 31/426* (2006.01)
*C07D 277/08* (2006.01)
(52) U.S. Cl. ............... 514/370; 548/146; 548/190; 548/198; 514/365
(58) Field of Classification Search ............... 548/146, 548/190, 198; 514/365, 370
See application file for complete search history.

(56) References Cited

FOREIGN PATENT DOCUMENTS

| EP | 1820504 A1 | 8/2007 |
|---|---|---|
| WO | WO-2006051704 A1 | 5/2006 |

OTHER PUBLICATIONS

"IUPAC Commission on Nomenclature of Organic Chemistry Rules for the Nomenclature of Organic Chemistry, Section E: Stereochemistry (Recommendations 1974)," Pure Appl Chem, 1976, 13-30, vol. 45.
Arevalo-Martin, A., et al., "Therapeutic Action of Cannabinoids in a Murine Model of Multiple Sclerosis," Journal of Neuroscience, 2003, 2511-2516, vol. 23, No. 7.
Benito, C. et al., "Cannabinoid CB2 Receptors and Fatty Acid Amide Hydrolase Are Selectively Overexpressed in Neuritic Plaque-Associated Glia in Alzheimer's Disease Brains," Journal of Neuroscience, 2003, 11136-11141, vol. 23—Issue 35.
Berge, S.M. et al., "Journal of Pharmaceutical Sciences, Pharmaceutical Salts," J Pharmaceutical Sciences, 1977, 1-19, vol. 66.
Bouchard, J-F et al., "Contribution of endocannabinoids in the endothelial protection afforded by ischemic preconditioning in the isolated rat heart", Life Sciences, 2003, 1859-1870, vol. 72.
Boyle, W.J. et al., "Osteoclast differentiation and activation," (Binary/Image), 2003, 337-342, vol. 423.
Brennan, T.J. et al., "Characterization of a rat model of incisional pain," (Binary/Image), 1996, 493-501, vol. 64.
Buckley, N.E. et al., "Immunomodulation by cannabinoids is absent in mice deficient for the cannabinoid CB receptor," European Journal of Pharmacology, 2000, 141-149, vol. 396.
Carlisle, S.J. et al., "Differential expression of the CB2 cannabinoid receptor by rodent macrophages and macrophage-like cells in relation to cell activation," International Immunopharmacology, 2002, 69, vol. 2.
Carrier, E.J. et al., "Endocannabinoids in Neuroimmunology and Stress," Current Drug Targets CNS and Neurological Disorders, 2005, 657-665, vol. 4.
Casanova, M.L. et al., "Inhibition of skin tumor growth and angiogenesis in vivo by activation of cannabinoid receptors," Journal of Clinical Investigation, 2003, 43-50, vol. 111.
Chaplan, S.R. et al., "Quantitative assessment of tactile allodynia in the rat paw," Journal of Neuroscience Methods, 1994, 55-63, vol. 53.
Cichewicz, D.L. et al., "Synergistic interactions between cannabinoid and opioid analgesics," Life Sciences, 2004, 1317-1324, vol. 74.
Clayton, N. et al., "CB1 and CB2 cannabinoid receptors are implicated in inflammatory pain," (Binary/Image), 2002, 253-260, vol. 96.
Dixon, W.J. "Efficient analysis of experimental observations," Annual Review of Pharmacology and Toxicology, 1980, 441-462, vol. 20.
Filippo, C.D. et al., "Cannabinoid CB2 receptor activation reduces mouse myocardial ischemia-reperfusion injury: involvement of cytokine/chemokines and PMN," Journal of Leukocyte Biology, 2004, 453-459, vol. 75.
Galiégue, et al., "Expression of central and peripheral cannabinoid receptors in human immune tissues and leukocyte subpopulations," European Journal of Biochemistry, 1995, 54-61, vol. 232.
Greene, T.W. et al., "Protective Groups in Organic Synthesis", 1999, 3 rd Ed, 494-653.
Grotenhermen, F. et al., "IACM 2nd Conference on Cannabinoids in Medicine," Expert Opinion in Pharmacotherapy, 2003, 2367-2371, vol. 4—Issue 12.
Hanus, L. et al., "HU-308: A specific agonist for CB 2, a peripheral cannabinoid receptor," Proceedings of the National Academy of Science, 1999, 14228-14233, vol. 96.

(Continued)

*Primary Examiner* — Golam M Shameem
(74) *Attorney, Agent, or Firm* — Andrew M. Parial

(57) ABSTRACT

The present application relates to thiazolylidene containing compounds of formula (I)

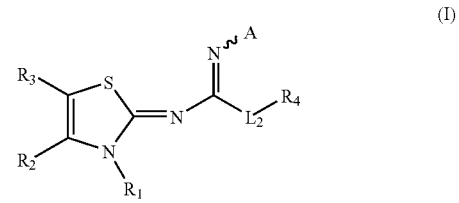

wherein $R_1$, $R_2$, $R_3$, $R_4$, $L_2$ and A are as defined in the specification. Compositions comprising such compounds, and methods for treating conditions and disorders using such compounds and compositions are also disclosed.

28 Claims, No Drawings

OTHER PUBLICATIONS

Hohmann, A.G. et al., "Selective Activation of Cannabinoid CB2 Receptors Suppresses Hyperalgesia Evoked by Intradermal Capsaicin," Journal of Pharmacology and Experimental Therapeutics, 2004, 446-453, vol. 308.

Ibrahim, M.M. et al., "Activation of CB2 cannabinoid receptors by AM1241 inhibits experimental neuropathic pain: Pain inhibition by receptors not present in the CNS," Proceedings of the National Academy of Science, 2003, 10529-10533, vol. 100—Issue 18.

Ibrahim, M.M. et al., "CB2 cannabinoid receptor activation produces antinociception by stimulating peripheral release of endogenous opioids," Proceedings of the National Academy of Science, 2005, 3093-3098, vol. 102—Issue 8.

Ihenetu, K. et al., "Inhibition of interleukin-8 release in the human colonic epithelial cell line HT-29 by cannabinoids," European Journal of Pharmacology, 2003, 207-215, vol. 458.

International Search Report for application No. PCT/US08/057460, Mailed on Aug. 20, 2008, 3 pages.

Joshi S.K. et al., "Comparison of Antinociceptive Actoins of Standard Analgesics in Attenuating Capsaicin and Nerve-Injury-Induced Mechanical Hypersensitivty," Neurosci, 587-596, vol. 143, 2006.

Julien, B, et al., "Antifibrogenic Role of the Cannabinoid Receptor CB2 in the Liver," Gastroenterology, 2005, 742-755, vol. 128.

Karsak, M, et al., "Cannabinoid receptor type 2 gene is associated with human osteoporosis," Human Molecular Genetics, 2005, 3389-3396, vol. 14—Issue 22.

Kim, S.H. and Chung, J.M. "An experimental model for peripheral neuropathy produced by segmental spinal nerve ligation in the rat," (Binary/Image), 1992, 355-363, vol. 50—Issue 3.

Lepicier, P. et al., "Endocannabinoids protect the rat isolated heart against ischaemia," British Journal of Pharmacology, 2003, 805-815, vol. 139.

Li W., Wayne G.S., Lallaman J.E., Chang S.J., Wittenberger S.J., "An improved synthesis of pyran-3,5-dione: application to the synthesis of ABT-598, a potassium channel opener, via Hantzsch reaction," J Org Chem, 2006, 1725-1727, 71/4.

Lotersztajn, S. et al., "Hepatic Fibrosis: Molecular Mechanisms and Drug Targets," Annual Review of Pharmacology and Toxicology, 2005, 605-628, vol. 45.

Malan, T.P. et al., "CB2 cannabinoid receptor-mediated peripheral antinociception," (Binary/Image), 2001, 239-245, vol. 93.

Maresz, K, et al., "Modulation of the cannabinoid CB2 receptor in microglial cells in response to inflammatory stimuli," Journal of Neurochemistry, 2005, 437-445, vol. 95.

Mathison, R, et al., "Effects of cannabinoid receptor-2 activation on accelerated gastrointestinal transit in lipopolysaccharide-treated rats," British Journal of Pharmacology, 2004, 1247-1254, vol. 142.

McKallip, R.J. et al., "Targeting CB2 cannabinoid receptors as a novel therapy to treat malignant lymphoblastic disease," (Binary/Image), 2002, 637-634, vol. 100.

Nackley, A.G. et al., "Selective activation of cannabinoid CB2 receptors suppresses spinal fos protein expression and pain behavior in a rat model of inflammation," Neuroscience, 2003, 747-757, vol. 119.

Ni, X. et al., "Win 55212-2, a cannabinoid receptor agonist, attenuates leukocyte/endothelial interactions in an experimental autoimmune encephalomyelitis model," Multiple Sclerosis, 2004, 158-164, vol. 10.

Patel, J.J. et al., "Inhibition of guinea-pig and human sensory nerve activity and the cough reflex in guinea-pigs by cannabinoid (CB2) receptor activation," British Journal of Pharmacology, 2003, 261-268, vol. 140.

Pertwee, R.G. "Cannabinoids and multiple sclerosis," Pharmacology and Therapeutics, 2002, 165-174, vol. 95.

Prescott, et al., "Lipid Vesicles as Carriers for Introducing Biologically Active Materials into Cells," Methods in Cell Biology, 1976, 33-71, vol. 14, Academic Press.

Quartilho, A. et al., "Inhibition of Inflammatory Hyperalgesia by Activation of Peripheral CB2 Cannabinoid Receptors," Anesthesiology, 2003, 955-960, vol. 99.

Ralston, S.H. "Regulation of bone mass, bone loss and osteoclast activity by cannabinoid receptors," Nature Medicine, 2005, 774-779, vol. 11.

Ramirez, B.G. et al., "Prevention of Alzheimer's Disease Pathology by Cannabinoids: Neuroprotection Mediated by Blockade of Microglial Activation," Journal of Neuroscience, 2005, 1904-1913, vol. 25—Issue 8.

Sanchez C. et al., "Inhibition of Glioma Growth in Vivo by Selective Activation of the CB2 Cannabinoid Receptor1," Cancer Research, 2001, 5784-5789, vol. 61.

Steffens S. et al., "Low dose oral cannabinoid therapy reduces progression of atherosclerosis in mice," (Binary/Image), 2005, 782-786, vol. 434.

Valenzano K.J. et al., "Pharmacological and pharmacokinetic characterization of the cannabinoid receptor 2 agonist, GW405833, utilizing rodent models of acute and chronic pain, anxiety, ataxia and catalepsy," Neuropharmacology, 2005, 658-672, vol. 48.

Warhurst A.C. et al., "Interferon ? induces differential upregulation of α and β chemokine secretion in colonic epithelial cell lines," (Binary/Image), 1998, 208-213, vol. 42.

Wright K. et al., "Differential Expression of Cannabinoid Receptors in the Human Colon: Cannabinoids Promote Epithelial Wound Healing," Gastroenterology, 2005, 437-453, vol. 129.

Yoshihara S. et al., "Cannabinoid Receptor Agonists Inhibit Sensory Nerve Activation in Guinea Pig Airways", American Journal of Respiratory and Critical Care Medicine, 2004, 941-946, vol. 170.

Yoshihara S. et al., "Endogenous Cannabinoid Receptor Agonists Inhibit Neurogenic Inflammations in Guinea Pig Airways" Allergy and Immunology, 2005, 80-87, vol. 138.

Yoshihara S. et al., "The Cannabinoid Receptor Agonist WIN 55212-2 Inhibits Neurogenic Inflammations in Airway Tissues," Journal of Pharmacological Sciences, 2005, 77-82, vol. 98—Issue 1.

COMPOUNDS AS CANNABINOID RECEPTOR LIGANDS

This application claims priority to U.S. Ser. No. 60/908,455, filed Mar. 28, 2007 and is incorporated herein by reference.

TECHNICAL FIELD

The present application relates to thiazolylidene containing compounds, compositions comprising such compounds, and methods of treating conditions and disorders using such compounds and compositions.

BACKGROUND (−)-$\Delta^9$-Tetrahydrocannabinol ($\Delta^9$-THC), the major psychoactive constituent of marijuana, exerts a broad range of therapeutic effects through its interactions with two cannabinoid (CB) receptor subtypes, $CB_1$ and $CB_2$. $CB_1$ receptors are highly expressed in the central nervous system and to a lesser degree in the periphery in a variety of tissues of the cardiovascular and gastrointestinal systems. By contrast, $CB_2$ receptors are most abundantly expressed in multiple lymphoid organs and cells of the immune system, including spleen, thymus, tonsils, bone marrow, pancreas and mast cells.

The psychotropic side effects caused by $\Delta^9$-THC and other nonselective CB agonists are mediated by $CB_1$ receptors. These $CB_1$ receptor-mediated effects, such as euphoria, sedation, hypothermia, catalepsy, and anxiety, have limited the development and clinical utility of nonselective CB agonists. Recent studies have demonstrated that $CB_2$ modulators are analgesic in preclinical models of nociceptive and neuropathic pain without causing the adverse side effects associated with $CB_1$ receptor activation. Therefore, compounds that selectively target $CB_2$ receptors are an attractive approach for the development of novel analgesics.

Pain is the most common symptom of disease and the most frequent complaint with which patients present to physicians. Pain is commonly segmented by duration (acute vs. chronic), intensity (mild, moderate, and severe), and type (nociceptive vs. neuropathic).

Nociceptive pain is the most well known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or unknown origin.

Managing the spectrum of pain etiologies remains a major public health problem and both patients and clinicians are seeking improved strategies to effectively manage pain. No currently available therapies or drugs effectively treat all types of nociceptive and neuropathic pain states. The compounds of the present invention are novel $CB_2$ receptor modulators that have utility in treating pain, including nociceptive and neuropathic pain.

The location of $CB_2$ receptors on the surface of immune cells suggests a role for these receptors in immunomodulation and inflammation. Recent studies have demonstrated that $CB_2$ receptor ligands have immunomodulatory and anti-inflammatory properties. Therefore, compounds that interact with $CB_2$ receptors offer a unique pharmacotherapy for the treatment of immune and inflammatory disorders.

SUMMARY

The present invention generally provides compounds that are $CB_2$ receptor ligands and pharmaceutical compositions and methods for the treatment of disorders using these compounds and pharmaceutical compositions.

In one embodiment, the present invention provides compounds of formula (I), or pharmaceutically acceptable salts, prodrugs, salts of prodrugs, or combinations thereof,

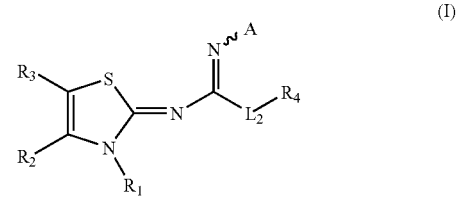

(I)

wherein

A is $OR_b$, CN, $NR_cR_d$, $NR_cC(O)R_d$, $NR_cC(S)R_d$, $C(O)OR_{w1}$, or $C(O)R_{w2}$;

$R_1$ is $C_2$-$C_{10}$ alkyl, aryl, arylalkyl, cycloalkyl, cycloalkylalkyl, heteroaryl, heteroarylalkyl, heterocycle, heterocycloalkyl, $R_{g1}R_{h1}N$—C(O)—, $R_{g1}R_{h1}N$—C(O)-alkyl, alkenyl, alkoxycarbonylalkyl, alkylcarbonylalkyl, alkylsulfinylalkyl, alkylsulfonylalkyl, alkynyl, carboxyalkyl, cyanoalkyl, $R_{n1}O$—N=$CR_z$—, $R_{n1}O$—N=$CR_z$-alkyl-, $R_{o1}R_{p1}N$—N=$CR_z$—, $R_{o1}R_{p1}N$—N=$CR_z$-alkyl-, alkoxyalkyl, alkylthioalkyl, aryloxyalkyl, arylalkoxyalkyl, alkoxyalkoxyalkyl, haloalkyl, haloalkoxyalkyl, heteroaryloxyalkyl, heterocycleoxyalkyl, hydroxyalkyl, $R_{e1}R_{f1}N$-alkyl, $R_{j1}R_{k1}N$—C(O)—$NR_{m1}$-alkyl, $R_zC(O)$—O—$C_2$-$C_6$ alkyl-, $R_{z1}SO_2NR_{z2}$-alkyl-, $R_{z1}C(O)NR_{z2}$-alkyl-, $R_{j1}R_{k1}N$—$SO_2$—$NR_{m1}$-alkyl-, or $R_{g1}R_{h1}NSO_2$-alkyl-;

$R_2$ and $R_3$ are each independently hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halo, haloalkyl, heteroaryl, heterocycle, hydroxyalkyl, $R_{e2}R_{f2}N$—, $R_{e2}R_{f2}Nalkyl$-, $R_{g2}R_{h2}N$—C(O)—, $R_{j2}R_{k2}N$—C(O)—$NR_{m2}$—, $R_{n2}O$—N=$CR_z$-alkyl-, $R_{n2}O$—N=$CR_z$—, or $R_{o2}R_{p2}N$—N=$CR_z$-alkyl-; or $R_2$ and $R_3$, taken together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R_2$ and $R_3$, taken together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl;

$R_4$ is alkyl, alkenyl, alkynyl, aryl, cycloalkyl, cycloalkenyl, heteroaryl, heterocycle, arylalkyl, cycloalkylalkyl, cycloalkenylalkyl, heteroarylalkyl, or heterocyclealkyl;

$L_2$ is a bond or —$NR_{m1}$—; $R_b$ is alkyl, alkenyl, alkoxyalkyl, or arylalkyl;

$R_c$ and $R_d$ are each independently alkyl, arylalkyl, or heteroarylalkyl, or $R_c$ and $R_d$ taken together with the nitrogen atom to which they are attached form a 5-7 membered heterocyclic ring;

$R_{c'}$, at each occurrence, is independently hydrogen or alkyl $R_{d'}$, at each occurrence, is independently alkyl, alkoxy, amino, alkylamino, dialkylamino, arylamino, heteroarylamino, cycloalkylamino, heterocycleamino, or heterocycle.

$R_{e1}$ and $R_{f1}$ are each independently hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;

$R_{g1}$ and $R_{h1}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclealkyl, hydroxyalkyl, nitroalkyl, cycloalkyl, or haloalkoxyalkyl; or $R_{g1}$ and $R_{h1}$ together with the nitrogen atom to which they are attached form a 5-7 membered heterocyclic ring;

$R_{j1}$ and $R_{k1}$, at each occurrence, are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclealkyl; cycloalkyl, or haloalkoxyalkyl; or $R_{j1}$ and $R_{k1}$ together with the nitrogen atom to which they are attached form a 5-7 membered heterocyclic ring;

$R_{m1}$, at each occurrence, is independently hydrogen, alkyl, cycloalkyl, haloalkyl, alkoxyalkyl, or haloalkoxyalkyl;

$R_{n1}$, at each occurrence, is independently hydrogen, alkyl, alkenyl, alkoxyalkyl, alkynyl, arylalkyl, cyanoalkyl, cycloalkylalkyl, heteroarylalkyl, heterocyclalkyl, haloalkyl, hydroxyalkyl, or nitroalkyl;

$R_{o1}$ and $R_{p1}$, at each occurrence, are each independently hydrogen, alkyl, alkenyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{o1}$ and $R_{p1}$ together with the nitrogen atom to which they are attached form a 5-7 membered heterocyclic ring;

$R_{e2}$ and $R_{f2}$, at each occurrence, are each independently hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;

$R_{g2}$ and $R_{h2}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{g2}$ and $R_{h2}$ together with the nitrogen atom to which they are attached form a 5-7 membered heterocyclic ring;

$R_{j2}$ and $R_{k2}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, or heterocyclalkyl;

$R_{m2}$ is hydrogen or alkyl;

$R_{n2}$, at each occurrence, is independently hydrogen, alkyl, alkenyl, alkoxyalkyl, alkynyl, arylalkyl, cyanoalkyl, cycloalkylalkyl, heteroarylalkyl, heterocyclalkyl, haloalkyl, hydroxyalkyl, or nitroalkyl;

$R_{o2}$ and $R_{p2}$, at each occurrence, are each independently hydrogen, alkyl, alkenyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{o2}$ and $R_{p2}$ together with the nitrogen atom to which they are attached form a 5-7 membered heterocyclic ring;

$R_z$ is hydrogen or alkyl;

$R_{z1}$, at each occurrence, is independently alkyl, cycloalkyl, cycloalkylalkyl, alkoxyalkyl, haloalkyl, or cyanoalkyl;

$R_{z2}$, at each occurrence, is independently hydrogen, alkyl, cycloalkyl, haloalkyl, alkoxyalkyl, or haloalkoxyalkyl; and $R_{w1}$ and $R_{w2}$ are each independently alkyl, haloalkyl, aryl, cycloalkyl, or alkoxyalkyl.

In another embodiment, the present invention provides a method for treating pain (for example, neuropathic pain or nociceptive pain) in a mammal in need of such treatment. The method comprises administering to the mammal a therapeutically effective amount of a compound of formula (I) or a pharmaceutically acceptable salt thereof.

In yet another embodiment, the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Another embodiment of the present invention relates to a method for providing neuroprotection in a mammal in need of such treatment. This method comprises administering to the mammal a therapeutically effective amount of a compound of formula (I) or a pharmaceutically acceptable salt thereof.

In another embodiment, the present invention provides a pharmaceutical composition comprising a therapeutically effective amount of a compound of the invention or a pharmaceutically acceptable salt thereof in combination with one or more pharmaceutically acceptable carriers. The composition is preferably useful for the treatment of the disease conditions described above.

Further, the present invention provides the use of compounds of the present invention or a pharmaceutically acceptable salt thereof, in the manufacture of a medicament for the treatment of the disease conditions described above.

These and other objects of the invention are described in the following paragraphs. These objects should not be deemed to narrow the scope of the invention.

DETAILED DESCRIPTION

Compounds of formula (I) are disclosed in this invention,

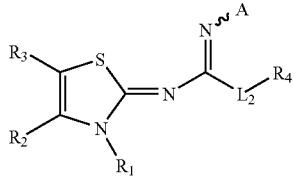

(I)

wherein $R_1$, $R_2$, $R_3$, $R_4$, $L_2$ and A are as defined above in the Summary of the Invention and below in the Detailed Description. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition of Terms

As used throughout this specification and the appended claims, the following terms have the following meanings:

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl(allyl), 2-methyl-2-propenyl, 3-butenyl, 4-pentenyl, 5-hexenyl, 2-heptenyl, 3-methylbut-2-enyl, 2-methyl-1-heptenyl, and 3-decenyl.

The term "alkenylene" denotes a divalent group derived from a straight or branched chain hydrocarbon of 2, 3, or 4 carbon atoms and contains at least one carbon-carbon double. Representative examples of alkenylene include, but are not limited to, —CH=CH— and —CH$_2$CH=CH—.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl" as used herein, means an alkoxyalkoxy group, as defined herein, appended to the parent molecular moiety through an alkylene group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl" as used herein, means an alkoxy group, as defined herein, appended to the parent molecular moiety through an alkylene group, as defined herein. Representative examples of alkoxyalkyl include, but are not limited to, tert-butoxymethyl, 3-methoxypropyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl" as used herein, means an alkoxycarbonyl group, as defined herein, appended to the parent molecular moiety through an alkylene group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkyl" as used herein, means a saturated, straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl (3-methylbutyl), neopentyl, n-hexyl, 1,2-dimethylpropyl, 3-methylhexyl, 2,2-dimethylpentyl, 2,3-dimethylpentyl, n-heptyl, n-octyl, n-nonyl, and n-decyl.

The term "$C_2$-$C_{10}$ alkyl" as used herein, means a saturated, straight or branched chain hydrocarbon containing from 2 to 10 carbon atoms. Representative examples of $C_2$-$C_{10}$ alkyl include, but are not limited to, ethyl, n-propyl, iso-propyl, n-butyl, sec-butyl, iso-butyl, tert-butyl, n-pentyl, isopentyl, neopentyl, n-hexyl, 3-methylbutyl, 3-methylhexyl, 2,2-dimethylpentyl, 2,3-dimethylpentyl, n-heptyl, n-octyl, n-nonyl, and n-decyl.

The term "alkylamino" as used herein, means a straight or branched chain hydrocarbon containing from 1 to 10 carbon atoms connected to the parent molecular moiety through an NH group. Representative examples of alkylamino include, but are not limited to, methylamino, ethylamino, isopropylamino and tert-butylamino.

The term "alkylcarbonyl" as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl" as used herein, means an alkylcarbonyl group, as defined herein, appended to the parent molecular moiety through an alkylene group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy" as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylene" means a divalent group derived from a saturated, straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$C(CH$_3$)$_2$—, and —CH$_2$CH(CH$_3$)CH$_2$—.

The term "$C_2$-$C_6$ alkylene" as defined herein means a divalent group derived from a saturated, straight or branched chain hydrocarbon of from 2 to 6 carbon atoms. Representative examples of $C_2$-$C_6$ alkylene include, but are not limited to, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$C(CH$_3$)$_2$—, and —CH$_2$CH(CH$_3$)CH$_2$—.

The term "alkylsulfinyl" as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl" as used herein, means an alkylsulfinyl group, as defined herein, appended to the parent molecular moiety through an alkylene group, as defined herein. Representative examples of alkylsulfinylalkyl include, but are not limited to, methylsulfinylmethyl and ethylsulfinylmethyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl" as used herein, means an alkylsulfonyl group, as defined herein, appended to the parent molecular moiety through an alkylene group, as defined herein. Representative examples of alkylsulfonylalkyl include, but are not limited to, methylsulfonylmethyl and ethylsulfonylmethyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl" as used herein, means an alkylthio group, as defined herein, appended to the parent molecular moiety through an alkylene group, as defined herein. Representative examples of alkylthioalkyl include, but are not limited, methylthiomethyl and 2-(ethylthio)ethyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, but-3-ynyl, and 1-butynyl.

The term "aryl," as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the bicyclic aryl include, but are not limited to, dihydroindenyl, indenyl, naphthyl (including naphth-1-yl), dihydronaphthalenyl, and tetrahydronaphthalenyl. The phenyl and the bicyclic aryls are attached to the parent molecular moiety through any carbon atom contained within the phenyl and the bicyclic aryls respectively.

The aryl groups of this application are optionally substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, cycloalkyloxy, formyl, formylalkyl, halogen, haloalkyl, haloalkoxy, haloalkoxyalkoxy, hydroxy, hydroxyalkyl, mercapto, nitro, —CR$_z$(=N—OR$_{z1}$), —NZ$_1$Z$_2$ and C(O)NZ$_3$Z$_4$ where NZ$_1$Z$_2$ and C(O)NZ$_3$Z$_4$ are as defined herein The term "arylalkenyl" as used herein, means an aryl group, as defined herein appended to the parent molecular moiety through an alkenylene group, as defined herein. Representative examples include, but are not limited to, styryl and 3-phenylprop-1-enyl.

The term "arylalkoxyalkyl" as used herein, means an aryl group, as defined herein, appended to the parent molecular moiety through an alkoxyalkyl group, as defined herein. Representative examples include, but are not limited to benzyloxymethyl.

The term "arylalkyl" as used herein, means an aryl group, as defined herein, appended to the parent molecular moiety through an alkylene group, as defined herein. Representative examples of arylalkyl include, but are not limited to, benzyl, 2-phenylethyl, 3-phenylpropyl, and 2-naphth-2-ylethyl.

The term "arylamino" as used herein, means an aryl group, as defined herein, appended to the parent molecular moiety through an NH group. Representative examples include, but are not limited to, phenylamino and m-tolylamino.

The term "aryloxyalkyl" as used herein, means an aryloxy group, as defined herein, appended to the parent molecular moiety through an alkylene group, as defined herein. Representative examples include, but are not limited to phenoxymethyl and m-tolyloxymethyl.

The term "aryloxy" as used herein, means an aryl group, as defined herein, appended to the parent molecular moiety through an oxygen atom. Representative examples include, but are not limited to phenoxy and m-tolyloxy.

The term "azido" as used herein, means a —N$_3$ group.

The term "azidoalkyl" as used herein, means an azido group, as defined herein, appended to the parent molecular moiety through an alkylene group, as defined herein.

The term "R$_z$C(O)—O—C$_2$-C$_6$ alkyl-" as used herein, means a R$_z$C(O)—O— group appended to the parent molecular moiety through a C$_2$-C$_6$ alkylene group, as defined herein.

The term "carbonyl" as used herein, means a —C(O)— group.

The term "carboxy" as used herein, means a —CO$_2$H group.

The term "carboxyalkyl" as used herein, means a carboxy group, as defined herein, appended to the parent molecular moiety through an alkylene group, as defined herein. Representative examples of carboxyalkyl include, but are not limited to, carboxymethyl, 2-carboxyethyl, and 3-carboxypropyl.

The term "cyano" as used herein, means a —CN group.

The term "cyanoalkyl" as used herein, means a cyano group, as defined herein, appended to the parent molecular moiety through an alkylene group, as defined herein. Representative examples of cyanoalkyl include, but are not limited to, cyanomethyl, 2-cyanoethyl, cyanomethyl, 3-cyanopropyl, 4-cyanobutyl, 4-cyano-4-methylpentyl, and 3-cyanopropyl.

The term "cycloalkenyl" as used herein, means a monocyclic or bicyclic ring system containing zero heteroatoms in the ring. The monocyclic cycloalkenyl has three, four, five, six, seven or eight carbon atoms and zero heteroatoms. The three or four-membered ring systems have one double bond, the five- or six-membered ring systems have one or two double bonds, and the seven- or eight-membered ring systems have one, two or three double bonds. Representative examples of monocyclic ring systems include, but are not limited to, 2-cyclohexen-1-yl, 3-cyclohexen-1-yl, 2,4-cyclohexadien-1-yl and 3-cyclopenten-1-yl. Bicyclic ring systems are exemplified by a monocyclic cycloalkenyl ring fused to a monocyclic cycloalkyl ring, or a monocyclic cycloalkenyl ring fused to a monocyclic cycloalkenyl ring. Representative examples of bicyclic ring systems include, but are not limited to 3a,4,5,6,7,7a-hexahydro-1H-indenyl, 4,5,6,7-tetrahydro-3aH-indene, and octahydronaphthalenyl. The monocyclic or the bicyclic cycloalkenyl ring can be appended to the parent molecular moiety through any substitutable carbon atom within the monocyclic or the bicyclic cycloalkenyl.

The cycloalkenyl groups of this application are optionally substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylsulfinyl, alkylsulfinylalkyl, alkylsulfonyl, alkylsulfonylalkyl, alkylthio, alkylthioalkyl, alkynyl, carboxy, carboxyalkyl, cyano, cyanoalkyl, formyl, formylalkyl, halogen, haloalkyl, hydroxy, hydroxyalkyl, oxo, mercapto, nitro, —$NZ_1Z_2$ and $C(O)NZ_3Z_4$ where $NZ_1Z_2$ and $C(O)NZ_3Z_4$ are as defined herein.

The term "cycloalkenylalkyl" as used herein, means a cycloalkenyl group, as defined herein, appended to the parent molecular moiety through an alkylene group, as defined herein.

The term "cycloalkyl" as used herein, means a monocyclic, or a bicyclic ring system, or a spirocyclic cycloalkyl. The monocyclic cycloalkyl is a carbocyclic ring system containing 3, 4, 5, 6, 7, or 8 carbon atoms, zero heteroatoms and zero double bonds. Examples of monocyclic ring systems include cyclopropyl, cyclobutyl, cyclopentyl, cyclohexyl, cycloheptyl, and cyclooctyl. Bicyclic ring systems are exemplified by a monocyclic cycloalkyl ring fused to a monocyclic cycloalkyl ring. Representative examples of bicyclic ring systems include, but are not limited to, bicyclo[4.1.0]heptane, bicyclo[6.1.0]nonane, octahydroindene, and decahydronaphthalene. Spirocyclic cycloalkyl is exemplified by a monocyclic cycloalkyl ring wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The monocyclic, bicyclic and spirocyclic cycloalkyl groups of the present invention can be appended to the parent molecular moiety through any substitutable carbon atom of the groups. The monocyclic and bicyclic cycloalkyl groups of the present invention may contain one or two alkylene bridges of 1, 2, 3, or 4 carbon atoms, each of which linking two non adjacent carbon atoms of the group. Examples of such a bridged system include, but are not limited to, adamantane (tricyclo[3.3.1.1$^{3,7}$]decane) and bicyclo[2.2.1]heptane (including bicyclo[2.2.1]hept-2-yl).

The cycloalkyl groups of the present application are optionally substituted with 1, 2, 3, or 4 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —$NZ_1Z_2$ and $C(O)NZ_3Z_4$ where $NZ_1Z_2$ and $C(O)NZ_3Z_4$ are as defined herein.

The term "cycloalkylamino" as used herein, means a cycloalkyl group appended to the parent molecular moiety through an NH group.

The term "cycloalkylalkyl," as used herein, means a cycloalkyl group appended to the parent molecular moiety through an alkylene group, as defined herein.

The term "cycloalkyloxy," as used herein, means a cycloalkyl group appended to the parent molecular moiety through an oxygen atom. Non-limiting examples of cycloalkyloxy include cyclopropyloxy and cyclobutyloxy.

The term "cycloalkylsulfonyl" as used herein means a cycloalkyl, as defined herein, appended to the parent molecular moiety through an $SO_2$ group.

The term "dialkylamino" as used herein means two alkyl groups appended to the parent molecular moiety through a nitrogen atom. Representative examples include, but are not limited to, dimethylamino and methylethylamino.

The term "formyl" as used herein, means a —C(O)H group.

The term "formylalkyl" as used herein, means a formyl group, as defined herein, appended to the parent molecular moiety through an alkylene group, as defined herein. Representative examples of formylalkyl include, but are not limited to, formylmethyl and 2-formylethyl.

The term "halo" or "halogen" as used herein, means —Cl, —Br, —I or —F.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "haloalkoxyalkoxy," as used herein, means a haloalkoxy group, as defined herein, appended to the parent molecular moiety through an alkoxy group, as defined herein.

The term "haloalkoxyalkyl," as used herein, means a haloalkoxy group, as defined herein, appended to the parent molecular moiety through an alkylene group, as defined herein.

The term "haloalkyl" as used herein, means at least one halogen, as defined herein, appended to the parent molecular moiety through an alkylene group, as defined herein. Representative examples of haloalkyl include, but are not limited to, chloromethyl, 2-fluoroethyl, trifluoromethyl, pentafluoroethyl, 4,4,4-trifluorobutyl, 3,3,3-trifluoropropyl, 4-fluorobutyl, and 2-chloro-3-fluoropentyl.

The term "heteroaryl," as used herein, means a monocyclic heteroaryl or a bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl (including pyridin-3-yl), pyridazinyl, pyrimidinyl, pyrazinyl, pyrazolyl, pyrrolyl, tetrazolyl, thiadiazolyl, thiazolyl (including 1,3-thiazol-4-yl), thienyl, triazolyl, and triazinyl. The bicyclic heteroaryl is exemplified by a monocyclic heteroaryl fused to phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, cinnolinyl, furopyridinyl, indolyl, indazolyl, isoindolyl, isoquinolinyl, naphthyridinyl, oxazolopyridine, quinolinyl (including quinolin-8-yl), thienopyridinyl and thienopyridinyl. The monocyclic and the bicyclic heteroaryl groups are connected to the parent molecular moiety through any substitutable carbon atom or any substitutable nitrogen atom contained within the groups.

The heteroaryl groups of the present application are optionally substituted with 1, 2, 3, or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, alkylsulfonyl, cycloalkylsulfonyl, —$NZ_1Z_2$ and $C(O)NZ_3Z_4$ where $NZ_1Z_2$ and $C(O)NZ_3Z_4$ are as defined herein.

The term "heteroarylalkyl," as used herein, means a heteroaryl group appended to the parent molecular moiety through an alkylene group, as defined herein. The term "monocyclic heteroarylalkyl" as used herein means a monocyclic heteroaryl, as defined herein, appended to the parent molecular moiety through an alkylene group, as defined herein. Non limiting example of heteroarylalkyl includes 1,3-thiazol-4-ylmethyl.

The term "heteroarylamino," as used herein, means a heteroaryl group appended to the parent molecular moiety through an NH group.

The term "heteroaryloxy" as used herein, means a heteroaryl group, as defined herein, appended to the parent molecular moiety through an oxygen atom.

The term "heteroaryloxyalkyl" as used herein, means a heteroaryloxy group, as defined herein, appended to the parent molecular moiety through an alkylene group, as defined herein.

The term "heterocycle" or "heterocyclic" as used herein, refers to a monocyclic, bicyclic, tricyclic or a spirocyclic ring system that contains at least one heteroatom. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl (including azetidin-3-yl), azepanyl, aziridinyl, diazepanyl, 1,3-dioxanyl, 1,4-dioxanyl, 1,3-dioxolanyl, 4,5-dihydroisoxazol-5-yl, 3,4-dihydropyran-6-yl, 1,3-dithiolanyl, 1,3-dithianyl, imidazolinyl, imidazolidinyl, isothiazolinyl, isothiazolidinyl, isoxazolinyl, isoxazolidinyl, morpholinyl (including morpholin-4-yl), oxadiazolinyl, oxadiazolidinyl, oxazolinyl, oxazolidinyl, piperazinyl, piperidinyl (including piperidin-2-yl), pyranyl, pyrazolinyl, pyrazolidinyl, pyrrolinyl, pyrrolidinyl, tetrahydrofuranyl (including tetrahydrofuran-2-yl), tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle of the present invention is exemplified by a monocyclic heterocycle fused to a phenyl group, or a monocyclic heterocycle fused to a monocyclic cycloalkyl group, or a monocyclic heterocycle fused to a monocyclic cycloalkenyl group, or a monocyclic heterocycle fused to a monocyclic heterocycle group. Representative examples of bicyclic heterocycle include, but are not limited to, 1,3-benzodioxol-4-yl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a monocyclic or bicyclic heterocycle ring wherein two substituents on the same carbon atom, together with said carbon atom, form a 4-, 5-, or 6-membered monocyclic cycloalkyl.

One example of a spiroheterocycle is 5-oxaspiro[3,4]octane. The heterocycle groups are connected to the parent molecular moiety through any substitutable carbon atom or any substitutable nitrogen atom contained within the group. The monocyclic or bicyclic heterocycle groups of the present invention may contain an alkenylene bridge of 2, 3, or 4 carbon atoms, or one or two alkylene bridges of 1, 2, 3, or 4 carbon atoms, wherein each bridge links two non-adjacent carbon atoms within the groups. Examples of such bridged heterocycles include, but are not limited to, oxaadamantane (2-oxatricyclo[3.3.1.1$^{3,7}$]decane), octahydro-2,5-epoxypentalene, hexahydro-2H-2,5-methanocyclopenta[b]furan, hexahydro-1H-1,4-methanocyclopenta[c]furan, oxabicyclo[2.2.1]heptane and 2,4-dioxabicyclo[4.2.1]nonane.

The heterocycles of this application are optionally substituted with 1, 2, or 3 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, oxo, —$NZ_1Z_2$, $C(O)NZ_3Z_4$, alkylsulfonyl, and cycloalkylsulfonyl; where $NZ_1Z_2$ and $C(O)NZ_3Z_4$ are as defined herein.

The term "heterocycleamino," as used herein, means a heterocycle group appended to the parent molecular moiety through an NH group.

The term "heterocyclealkyl," as used herein, means a heterocycle group appended to the parent molecular moiety through an alkylene group, as defined herein. The term "monocyclic heterocyclealkyl" as used herein, means a monocyclic heterocycle, as defined herein, appended to the parent molecular moiety through an alkylene group, as defined herein. Non-limiting examples of heterocyclealkyl include azetindin-3-ylmethyl, 2-morpholin-4-ylethyl, and piperidin-2-ylmethyl.

The term "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, 2,3-dihydroxypentyl, 2-hydroxy-2-methylpropyl, 1-hydroxy-1-methylethyl, and 2-ethyl-4-hydroxyheptyl.

The term "hydroxy-protecting group" or "O-protecting group" means a substituent that protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "mercapto" as used herein, means a —SH group.

The term "nitrogen protecting group" as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl (trityl).

The term "nitro" as used herein, means a —NO$_2$ group.

The term "nitroalkyl" as used herein, means a nitro group appended to the parent molecular moiety through an alkylene group as defined herein.

The term "NZ$_1$Z$_2$" as used herein, means two groups, Z$_1$ and Z$_2$, which are appended to the parent molecular moiety through a nitrogen atom. Z$_1$ and Z$_2$ are each independently hydrogen, alkoxyalkyl, alkyl, alkylcarbonyl, haloalkoxyalkyl, haloalkyl, formyl, aryl, arylalkyl, heterocycle, heteroaryl or cycloalkyl wherein the aryl, arylalkyl, heterocycle, heteroaryl and cycloalkyl are each optionally substituted with 1, 2, 3, 4 or 5 substituents chosen from the group consisting of alkyl, halo, haloalkyl, —NH$_2$, alkoxy, cyano, hydroxy and oxo. In certain instances within the present application, Z$_1$ and Z$_2$ taken together with the nitrogen atom to which they are attached form a heterocyclic ring. Representative examples of NZ$_1$Z$_2$ include, but are not limited to, amino, methylamino, acetylamino, CH$_3$C(O)N(CH$_3$)—, phenylamino, benzylamino, azetidinyl, pyrrolidinyl, and piperidinyl.

The term "NZ$_3$Z$_4$" as used herein, means two groups, Z$_3$ and Z$_4$, which are appended to the parent molecular moiety through a nitrogen atom. Z$_3$ and Z$_4$ are each independently hydrogen, alkoxyalkyl, haloalkyl, haloalkoxyalkyl, alkyl, aryl, arylalkyl, heterocycle, heteroaryl or cycloalkyl wherein the aryl, arylalkyl, heterocycle, heteroaryl and cycloalkyl are each optionally substituted with 1, 2, 3, 4 or 5 substituents chosen from the group consisting of alkyl, halo, haloalkyl, —NH$_2$, alkoxy, cyano, hydroxy and oxo; or Z$_3$ and Z$_4$ together with the nitrogen atom to which they are attached optionally form a 4-7 membered monocyclic heterocycle wherein said monocyclic heterocycle contains 0 or 1 additional heteroatom, 0 or 1 double bond, and is optionally substituted with 1, 2, or 3 independent substituents selected from the group consisting of alkyl, alkoxy, haloalkyl, halo, hydroxy, and oxo. Representative examples of NZ$_3$Z$_4$ include, but are not limited to, amino, methylamino, phenylamino and benzylamino.

The term "C(O)NZ$_3$Z$_4$" as used herein, means a NZ$_3$Z$_4$ group, as defined herein, appended to the parent molecular moiety through a carbonyl group, as defined herein. Representative examples of C(O)NZ$_3$Z$_4$ include, but are not limited to, aminocarbonyl, (methylamino)carbonyl, (dimethylamino)carbonyl, and (ethylmethylamino)carbonyl.

The term "oxo" as used herein, means a =O moiety.

The term "sulfinyl" as used herein, means a —S(O)— group.

The term "sulfonyl" as used herein, means a —SO$_2$— group.

The term "alkyl" as it appears in each of the following variables: R$_{g1}$R$_{h1}$N—C(O)-alkyl, R$_{n1}$O—N=CR$_z$-alkyl-, R$_{o1}$R$_{p1}$N—N=CR$_z$-alkyl-, R$_{e1}$R$_{f1}$N-alkyl, R$_{j1}$R$_{k1}$N—C(O)—NR$_{m1}$-alkyl, R$_{z1}$SO$_2$NR$_{z2}$-alkyl-, R$_{z1}$C(O)NR$_{z2}$-alkyl-, R$_{j1}$R$_{k1}$N—SO$_2$—NR$_{m1}$-alkyl-, R$_{g1}$R$_{h1}$NSO$_2$-alkyl-, R$_{e2}$R$_{f2}$Nalkyl-, R$_{n2}$O—N=CR$_z$-alkyl-, and R$_{o2}$R$_{p2}$N—N=CR$_z$-alkyl-, means a divalent group derived from a saturated, straight or branched chain hydrocarbon of from 1 to 10 carbon atoms. Non-limiting examples include —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, —CH$_2$C(CH$_3$)$_2$—, and —CH$_2$CH(CH$_3$)CH$_2$—.

b. Compounds

Compounds of the invention have the formula (I) as described above.

Particular values of variable groups in compounds of formula (I) are as follows. Such values may be used where appropriate with any of the other values, definitions, claims or embodiments defined hereinbefore or hereinafter.

As described generally above for compounds of formula (I), R$_2$ is hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halo, haloalkyl, heteroaryl, heterocycle, hydroxyalkyl, R$_{e2}$R$_{f2}$N—, R$_{e2}$R$_{f2}$Nalkyl-, R$_{g2}$R$_{h2}$N—C(O)—, R$_{j2}$R$_{k2}$N—C(O)—NR$_{m2}$—, R$_{n2}$O—N=CR$_z$-alkyl-, R$_{n2}$O—N=CR$_z$—, or R$_{o2}$R$_{p2}$N—N=CR$_z$-alkyl-. In certain embodiments, R$_2$ is hydrogen or alkyl. In certain embodiments, R$_2$ is hydrogen, methyl, ethyl, propyl, isopropyl or tert-butyl. In certain embodiments, R$_2$ is hydrogen, methyl, or tert-butyl.

As described generally above for compounds of formula (I), R$_3$ is hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halo, haloalkyl, heteroaryl, heterocycle, hydroxyalkyl, R$_{e2}$R$_{f2}$N—, R$_{e2}$R$_{f2}$Nalkyl-, R$_{g2}$R$_{h2}$N—C(O)—, R$_{j2}$R$_{k2}$N—C(O)—NR$_{m2}$—, R$_{n2}$O—N=CR$_z$-alkyl-, R$_{n2}$O—N=CR$_z$—, or R$_{o2}$R$_{p2}$N—N=CR$_z$-alkyl-. In certain embodiments, R$_3$ is hydrogen, alkyl (e.g. methyl, tert-butyl), alkylcarbonyl (e.g. acetyl), halo (e.g. chloro, bromo), cycloalkyl (e.g. cyclohexyl), or hydroxyalkyl (e.g. 1-hydroxy-1-methylethyl). In certain embodiments, R$_3$ is hydrogen or alkyl. In certain embodiments, R$_3$ is hydrogen, methyl, ethyl, propyl, isopropyl, or tert-butyl. In certain embodiments, R$_3$ is alkylcarbonyl. In certain embodiment, R$_3$ is acetyl. In certain embodiments, R$_3$ is cycloalkyl. In certain embodiments, R$_3$ is cyclopropyl, cyclobutyl, cyclopentyl, or cyclohexyl, each of which is optionally substituted. Examples of the optional substituents on the cycloalkyl (including cyclopropyl, cyclobutyl, cyclopentyl, or cyclohexyl) group of R$_3$ are alkyl (e.g., methyl, ethyl), alkoxy (e.g., methoxy, ethoxy), haloalkyl (e.g., trifluoromethyl), alkylcarbonyl oxy (e.g. acetyloxy), hydroxy, fluoro, chloro, bromo, iodo, oxo, cyano, and NH$_2$. In certain embodiments, R$_3$ is halo wherein the halo is fluoro, chloro, bromo or iodo. In certain embodiments, R$_3$ is hydroxyalkyl (e.g. 1-hydroxy-1-methylethyl).

In certain embodiments, R$_2$ is hydrogen or alkyl (e.g. methyl, or tert-butyl), and R$_3$ is hydrogen, alkyl (e.g. methyl, tert-butyl), alkylcarbonyl (e.g. acetyl), halo (e.g. chloro, bromo), cycloalkyl (e.g. cyclohexyl), or hydroxyalkyl (e.g. 1-hydroxy-1-methylethyl).

As described generally above for compounds of formula (I), R$_2$ and R$_3$, together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R_2$ and $R_3$, together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl.

In certain embodiments, $R_2$ and $R_3$, together with the carbon atoms to which they are attached, form a 5- or 6-membered monocyclic ring, containing one oxygen atom, zero nitrogen atom, and zero or one additional double bond, and two non-adjacent atoms of said monocyclic ring can be optionally linked by an alkenylene bridge of 2 carbon atoms. The monocyclic ring is optionally substituted.

Non-limiting examples of compounds of formula (I) having $R_2$ and $R_3$ with values as described in the preceding paragraph include those of formula (II)-(VII), wherein u2 is 0, 1, 2, 3 or 4; $R_{21}$, at each occurrence, is independently selected from the group consisting of alkyl, halo, hydroxy, alkoxy, and haloalkyl; two $R_{21}$ on the same carbon atom, together with the carbon atom to which they are attached can be optionally C=O; and two $R_{21}$ on the same carbon atom, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl, and $R_1$, A, $L_2$, and $R_4$ have values as described generally in the Summary section and in embodiments described herein.

In certain embodiments of compounds of formula (II)-(VII), $R_{21}$ is alkyl.

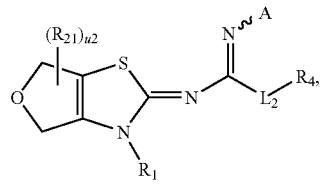

(II)

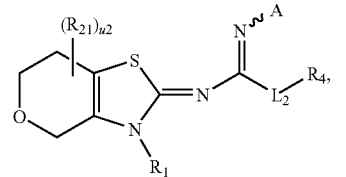

(III)

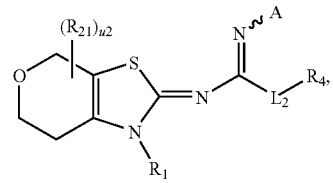

(IV)

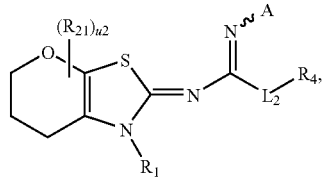

(V)

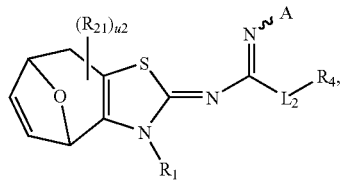

(VI)

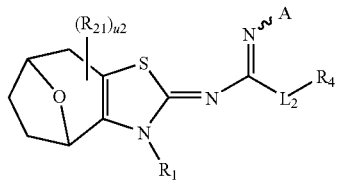

(VII)

In certain embodiments of compounds of formula (I), $R_2$ and $R_3$, together with the carbon atoms to which they are attached, form a 4-, 5-, 6-, or 7-membered monocyclic ring, containing zero oxygen atom, zero nitrogen atom, and zero or one additional double bond, and two adjacent atoms of said monocyclic ring can be optionally linked by an alkenylene bridge of 2, 3, or 4 carbon atoms. The monocyclic ring is optionally substituted as described generally in the Summary section.

Examples of compounds of formula (I) wherein $R_2$ and $R_3$, together with the carbon atoms to which they are attached, form a carbocyclic ring as described in the preceding paragraph include, but are not limited to, those of formula (VIII)

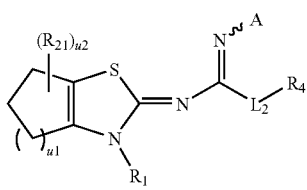

(VIII)

wherein u1 is 0, 1, 2 or 3; u2 is 0, 1, 2, 3 or 4; $R_{21}$, at each occurrence, is independently selected from the group consisting of alkyl, halo, hydroxy, alkoxy, and haloalkyl; two $R_{21}$ on the same carbon atom, together with the carbon atom to which they are attached, can be optionally C=O; and two $R_{21}$ on the same carbon atom, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl, and $R_1$, A, $L_2$, and $R_4$ have values as described generally in the Summary section and in embodiments described herein.

In certain embodiments of compounds of formula (I), $R_2$ and $R_3$, together with the carbon atoms to which they are attached, form a 6-membered monocyclic ring containing two additional double bonds, and zero or one nitrogen atom; said monocyclic ring is optionally substituted as described generally in the Summary section.

Examples of compounds of formula (I) wherein $R_2$ and $R_3$, together with the carbon atoms to which they are attached, form a monocyclic ring as described in the preceding paragraph include, but are not limited to, those of formula (IX), (X) and (XI), wherein $R_{22}$ is alkyl, halo, cyano, hydroxy, alkoxy, or haloalkyl, u3 is 0, 1, 2, 3, or 4, and $R_1$, A, $L_2$, and $R_4$ have values as described generally in the Summary section and in embodiments herein.

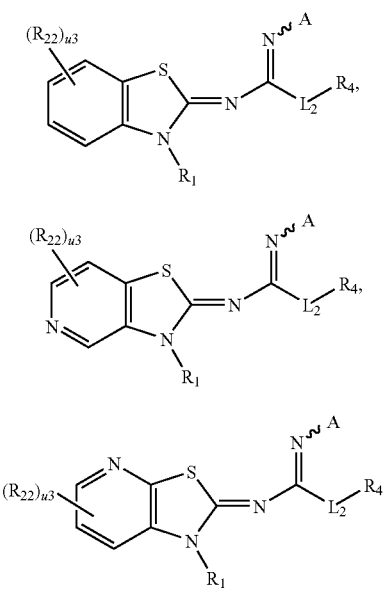

As described generally above for compounds of formula (I)-(XI), $R_1$ is $C_2$-$C_{10}$ alkyl, aryl, arylalkyl, cycloalkyl, cycloalkylalkyl, heteroaryl, heteroarylalkyl, heterocycle, heterocyclealkyl, $R_{g1}R_{h1}N$—C(O)—, $R_{g1}R_{h1}N$—C(O)-alkyl, alkenyl, alkoxycarbonylalkyl, alkylcarbonylalkyl, alkylsulfinylalkyl, alkylsulfonylalkyl, alkynyl, carboxyalkyl, cyanoalkyl, $R_{n1}O$—N=$CR_z$—, $R_{n1}O$—N=$CR_z$-alkyl-, $R_{o1}R_{p1}N$—N=$CR_z$—, $R_{o1}R_{p1}N$—N=$CR_z$-alkyl-, alkoxyalkyl, alkylthioalkyl, aryloxyalkyl, arylalkoxyalkyl, alkoxyalkoxyalkyl, haloalkyl, haloalkoxyalkyl, heteroaryloxyalkyl, heterocycleoxyalkyl, hydroxyalkyl, $R_{e1}R_{f1}N$-alkyl, $R_{j1}R_{k1}N$—C(O)—$NR_{m1}$— alkyl, $R_zC(O)$—O—$C_2$-$C_6$ alkyl-, $R_{z1}SO_2NR_{z2}$-alkyl-, $R_zC(O)NR_{z2}$-alkyl-; $R_{j1}R_{k1}N$—$SO_2$—$NR_{m1}$— alkyl-, or $R_{g1}R_{h1}NSO_2$-alkyl-.

In certain embodiments, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

In certain embodiments $R_1$ is $C_2$-$C_{10}$ alkyl.

In yet other embodiments the $C_2$-$C_{10}$ alkyl of $R_1$ is n-propyl, n-butyl, iso-butyl, n-pentyl, isopentyl (3-methylbutyl), or neopentyl.

In other embodiments, $R_1$ is cycloalkylalkyl.

In certain embodiments, the cycloalkyl portion of the cycloalkylalkyl of $R_1$ is cyclopropyl, cyclobutyl, cyclopentyl or cyclohexyl, each of which is optionally substituted. In certain embodiments, the alkyl portion of the cycloalkylalkyl is methyl or ethyl. In yet other embodiments, the alkyl portion of the cycloalkylalkyl is methyl. In certain embodiments, $R_1$ is cyclopropylmethyl, cyclobutylmethyl, cyclopentylmethyl, or cyclohexylmethyl, wherein each of the cyclopropyl, cyclobutyl, cyclopentyl, and cyclohexyl is optionally substituted. Examples of the optional substituents of the cycloalkyl (including cyclopropyl, cyclobutyl, cyclopentyl, cyclohexyl) portion of the aforementioned cycloalkylalkyl group include, but are not limited to, alkyl (e.g., methyl, ethyl), alkoxy (e.g., methoxy, ethoxy), haloalkyl (e.g., trifluoromethyl), alkylcarbonyloxy (e.g. acetyloxy), hydroxy, fluoro, chloro, bromo, iodo, oxo, cyano, and $NH_2$.

In certain embodiments, $R_1$ is heteroarylalkyl.

In certain embodiments, the heteroaryl portion of the heteroarylalkyl of $R_1$ is a monocyclic heteroaryl, including but not limited to, thiazolyl (including 1,3-thiazol-4-yl), pyridyl, furanyl, thienyl, isothiazolyl, oxazolyl, oxadiazolyl or isoxazolyl, each of which is optionally substituted. In certain embodiments, the alkyl portion of the heteroarylalkyl is methyl or ethyl. In yet other embodiments, the alkyl portion of the heteroarylalkyl is methyl. In other embodiments, heteroaryl of the heteroarylalkyl group is optionally substituted with 1, 2 or 3 substituents independently selected from the group consisting of alkyl (e.g., methyl, ethyl), alkoxy (e.g., methoxy, ethoxy), alkoxyalkyl, haloalkyl (e.g., trifluoromethyl), alkylcarbonyloxy (e.g. acetyloxy), hydroxy, fluoro, chloro, bromo, iodo, cyano, and $NH_2$. In certain embodiments, the heteroarylalkyl of $R_1$ is 1,3-thiazol-4-ylmethyl or 2-methyl-1,3-thiazol-4-ylmethyl.

In certain embodiments, $R_1$ is heterocyclealkyl.

In certain embodiments, the heterocycle portion of the heterocyclealkyl of $R_1$ is a monocyclic heterocycle, including but not limited to, tetrahydrofuranyl (e.g. tetrahydrofuran-2-yl), tetrahydropyranyl (e.g. tetrahydro-2H-pyran-4-yl), azetidinyl (e.g. azetidin-3-yl), pyrrolidinyl, piperidinyl (e.g. piperidin-2-yl), or morpholinyl (e.g. morpholin-4-yl), each of which is optionally substituted. In certain embodiments, the alkyl portion of the heterocyclealkyl is methyl or ethyl. In certain embodiments, the heterocycle portion of the heterocyclealkyl is optionally substituted with 1, 2, 3 or 4 substituents independently selected from the group consisting of alkyl (e.g., methyl, ethyl), alkoxy (e.g., methoxy, ethoxy), fluoro, chloro, bromo, iodo, haloalkoxy, haloalkyl (e.g., trifluoromethyl), hydroxy, oxo, $NH_2$, alkylsulfonyl (e.g., methylsulfonyl, ethylsulfonyl) and cycloalkylsulfonyl (e.g., cyclopropylsulfonyl, cyclobutylsulfonyl). In certain embodiments, the heterocyclealkyl of $R_1$ is tetrahydrofuran-2-ylmethyl, (R)-tetrahydrofuran-2-ylmethyl, (S)-tetrahydrofuran-2-ylmethyl, tetrahydro-2H-pyran-4-ylmethyl, 1-(methylsulfonyl)azetidin-3-ylmethyl, 1-(cyclopropylsulfonyl)azetidin-3-ylmethyl, piperidin-2-ylmethyl, (R)-piperidin-2-ylmethyl, (S)-piperidin-2-ylmethyl or morpholin-4-ylethyl.

In certain embodiments, $R_1$ is alkenyl or alkynyl.

In other embodiments, the alkenyl of $R_1$ is 3-methylbut-2-enyl.

The alkynyl of $R_1$ is, for example, but-3-ynyl.

In certain embodiments, $R_1$ is cyanoalkyl.

Non-limiting examples of the cyanoalkyl of $R_1$ include cyanomethyl, 2-cyanoethyl, 3-cyanopropyl, 4-cyanobutyl, and 4-cyano-4-methylpentyl.

In certain embodiments, $R_1$ is haloalkyl.

Non-limiting examples of haloalkyl of $R_1$ include 3,3,3-trifluoropropyl, 4,4,4-trifluorobutyl and 4-fluorobutyl.

In certain embodiments, $R_1$ is alkoxyalkyl.

Non-limiting examples of the alkoxyalkyl of $R_1$ include 2-methoxyethyl, 3-methoxypropyl, and 2-ethoxyethyl.

In certain embodiments, $R_1$ is hydroxyalkyl.

Example of the hydroxyalkyl of $R_1$ includes, but is not limited to, 2-hydroxy-2-methylpropyl.

In certain embodiments, $R_1$ is $R_zC(O)-O-C_2-C_6$ alkyl-.

In certain embodiments, $R_z$ is alkyl (e.g. methyl, ethyl or propyl).

In certain embodiments, the $R_zC(O)-O-C_2-C_6$ alkyl- group of $R_1$ is $CH_3C(O)-O-C(CH_3)_2-CH_2-$.

In certain embodiments, $R_1$ is $R_{z1}SO_2NR_{z2}$-alkyl-.

In other embodiments, $R_{z1}$ is alkyl (e.g. methyl), cycloalkyl, or haloalkyl, and $R_{z2}$ is hydrogen, alkyl (e.g. methyl), cycloalkyl or haloalkyl.

In certain embodiments, the $R_{z1}SO_2NR_{z2}$-alkyl- of $R_1$ is $CH_3SO_2N(CH_3)-(CH_2)_2-$.

As described generally above for compounds of formula (I)-(XI), A is $OR_b$, CN, $NR_cR_d$, $NR_cC(O)R_{d'}$, $NR_cC(S)R_{d'}$, $C(O)OR_{w1}$, or $C(O)R_{w2}$.

In certain embodiments, A is $OR_b$, CN, $NR_cC(O)R_{d'}$, or $C(O)OR_{w1}$.

In certain embodiments, A is $OR_b$ wherein $R_b$ is alkyl, alkenyl, alkoxyalkyl, or arylalkyl.

In certain embodiments, $R_b$ group is alkyl. In certain embodiments, $R_b$ is methyl, ethyl or tert-butyl.

In certain embodiments, $R_b$ is alkenyl. In certain embodiments, $R_b$ is allyl.

In certain embodiments, A is CN.

In certain embodiments, A is $NR_cC(O)R_{d'}$ wherein $R_{c'}$ is hydrogen or alkyl, and $R_{d'}$ is alkyl, alkoxy, $NH_2$, alkylamino, dialkylamino, arylamino, heteroarylamino, cycloalkylamino, heterocycleamino, or heterocycle.

In certain embodiments, $R_{c'}$ is hydrogen and $R_{d'}$ is ethoxy, tert-butoxy, $-NH_2$, or $-NHC_6H_5$.

In certain embodiments, A is $C(O)OR_{w1}$ wherein $R_{w1}$ is alkyl, haloalkyl, aryl, cycloalkyl, or alkoxyalkyl.

In certain embodiments, $R_{w1}$ is phenyl.

As described generally above for compounds of formula (I)-(XI), $L_2$ is a bond or $NR_{m1}$. In certain embodiments $L_2$ is a bond. In certain embodiments $L_2$ is $NR_{m1}$ wherein $R_{m1}$ is hydrogen, alkyl, cycloalkyl, haloalkyl, alkoxyalkyl, or haloalkoxyalkyl.

In certain embodiments, $R_{m1}$ is hydrogen.

As described generally above for compounds of formula (I)-(XI), $R_4$ is alkyl, alkenyl, alkynyl, aryl, cycloalkyl, cycloalkenyl, heteroaryl, heterocycle, arylalkyl, cycloalkylalkyl, cycloalkenylalkyl, heteroarylalkyl, or heterocyclealkyl.

In certain embodiments, $R_4$ is alkyl (e.g. ethyl, isopropyl, tert-butyl, tert-amyl, neopentyl, 1,2-dimethylpropyl), aryl (e.g. phenyl, naphthyl), cycloalkyl (e.g. cyclopropyl, cyclobutyl, cyclopentyl, cyclohexyl, cycloheptyl, adamantyl, noradamantyl, bicyclo[2.2.1]heptyl), heterocycle (e.g. oxa-adamantane), or heteroaryl (e.g. pyridyl, quinolinyl, benzofuranyl, thienyl, thiazolyl), wherein each of the rings is optionally substituted.

In certain embodiments, $R_4$ is aryl.

In certain embodiments, the aryl of $R_4$ is phenyl or naphthyl, each of which is optionally substituted.

Examples of the optional substituent of the aryl group of $R_4$ include, but are not limited to, alkyl, alkoxy (e.g. ethoxy, methoxy), alkoxyalkoxy (e.g. 2-methoxyethoxy), cycloalkyloxy (e.g. cyclopropyloxy, cyclobutoxy), cyano, formyl, halogen (e.g. chloro, fluoro), alkylcarbonyloxy (e.g. acetyloxy), haloalkyl (e.g. trifluoromethyl), haloalkoxy (e.g. difluoromethoxy, 2,2,2-trifluoroethoxy), hydroxy, $NH_2$, or $-CR_z(=N-OR_{n1})$ wherein $R_z$ is hydrogen or alkyl, and $R_{n1}$ is hydrogen or alkyl.

In certain embodiments, $R_4$ is alkyl.

In certain embodiments, the alkyl group of $R_4$ is ethyl, isopropyl, tert-butyl, tert-amyl, neopentyl, or 1,2-dimethylpropyl.

In certain embodiments, $R_4$ is heterocycle.

Example of the heterocycle of $R_4$ includes, but is not limited to, optionally substituted 2-oxatricyclo[3.3.1.1$^{3,7}$]decane (oxa-adamantane).

Said heterocycle of $R_4$ is optionally substituted with 1, 2, 3 or 4 substituents selected from the group consisting of alkyl, alkoxy, halo, haloalkyl, haloalkoxy, cyano, carboxy, hydroxy, $NZ_1Z_2$ and $-C(O)NZ_3Z_4$.

In certain embodiments, $R_4$ is heteroaryl.

In certain embodiments, the heteroaryl of $R_4$ is pyridyl (including pyridin-3-yl), quinolinyl (including quinolin-8-yl), benzofuranyl, thienyl, or thiazolyl, each of which is optionally substituted.

Examples of the optional substituents of said heteroaryl of $R_4$ include, but are not limited to, alkyl, alkoxy, halo, haloalkyl, haloalkoxy, cyano, carboxy, hydroxy, $NZ_1Z_2$ and $-C(O)NZ_3Z_4$.

In certain embodiments, the heteroaryl of $R_4$ is 2-ethoxy-pyridin-3-yl.

In certain embodiments, $R_4$ is cycloalkyl.

In certain embodiments, the cycloalkyl of $R_4$ is cyclopropyl, cyclobutyl, cyclopentyl, cyclohexyl, cycloheptyl, adamantyl, noradamantyl, or bicyclo[2.2.1]heptyl (including bicyclo[2.2.1]hept-2-yl), each of which is optionally substituted.

Said cycloalkyl is optionally substituted with 1, 2, 3 or 4 substituents selected from the group consisting of alkyl, alkoxy, halo, haloalkyl, haloalkoxy, cyano, carboxy, hydroxy, oxo, $NZ_1Z_2$ and $-C(O)NZ_3Z_4$.

In certain embodiments, the cycloalkyl of $R_4$ is 2,2,3,3-tetramethylcyclopropyl, adamant-1-yl, adamant-2-yl, or bicyclo[2.2.1]hept-2-yl.

It is appreciated that the present invention contemplates compounds of formula (I)-(XI) with combinations of the above embodiments, including particular, more particular and preferred embodiments.

Accordingly, one aspect of the invention is directed to groups of compounds of formula (I)-(XI) wherein A is $OR_b$, CN, $NR_cC(O)R_{d'}$, or $C(O)OR_{w1}$ and $L_2$ is a bond. $R_b$, $R_{c'}$, $R_{d'}$, and $R_{w1}$ are as described generally and in embodiments herein above.

Another aspect of the invention is directed to groups of compounds of formula (I)-(XI) wherein A is $OR_b$ and $L_2$ is a bond.

Another aspect of the invention is directed to groups of compounds of formula (I)-(XI) wherein A is $OR_b$, $R_b$ is alkyl (e.g. methyl, ethyl, tert-butyl), and $L_2$ is a bond.

Another aspect of the invention is directed to groups of compounds of formula (I)-(XI) wherein A is $OR_b$, $R_b$ is alkenyl (e.g. allyl), and $L_2$ is a bond.

Another aspect of the invention is directed to groups of compounds of formula (I)-(XI) wherein A is $NR_cC(O)R_{d'}$ and $L_2$ is a bond. Certain groups of compounds of formula (I)-(XI) include, but are not limited to, those wherein A is $NR_cC(O)R_{d'}$, $R_{c'}$ is hydrogen, $R_{d'}$ is ethoxy, tert-butoxy, $NH_2$, or $NHC_6H_5$, and $L_2$ is a bond.

Another aspect of the invention is directed to groups of compounds of formula (I)-(XI) wherein A is $C(O)OR_{w1}$ and $L_2$ is a bond. Certain groups of compounds of formula (I)-(XI) include, but are not limited to, those wherein A is $C(O)OR_{w1}$, $R_1$ is phenyl, and $L_2$ is a bond.

Another aspect of the invention is directed to groups of compounds of formula (I)-(XI) wherein A is CN and $L_2$ is a bond.

Another aspect of the invention is directed to groups of compounds of formula (I)-(XI) wherein A is $OR_b$, CN, $NR_cC(O)R_{d'}$, or $C(O)OR_{w1}$ and $L_2$ is $NR_{m1}$. $R_b$, $R_{c'}$, $R_{d'}$, $R_{w1}$, and $R_{m1}$ are as described generally and in embodiments herein above. Certain groups of compounds of formula (I)-(XI) include, but are not limited to, those wherein A is $OR_b$, CN, $NR_cC(O)R_{d'}$, or $C(O)OR_{w1}$, $L_2$ is $NR_{m1}$, and $R_{m1}$ is hydrogen.

Another aspect of the invention is directed to groups of compounds of formula (I)-(XI) wherein A is $OR_b$ and $L_2$ is $NR_{m1}$. Certain groups of compounds of formula (I)-(XI) include, but are not limited to, those wherein A is $OR_b$, $L_2$ is $NR_{m1}$, and $R_{m1}$ is hydrogen.

Another aspect of the invention is directed to groups of compounds of formula (I)-(XI) wherein A is $OR_b$, $R_b$ is alkyl (e.g. methyl, ethyl, tert-butyl), and $L_2$ is $NR_{m1}$. Certain groups of compounds of formula (I)-(XI) include, but are not limited to, those wherein A is $OR_b$, $R_b$ is alkyl (e.g. methyl, ethyl, tert-butyl), $L_2$ is $NR_{m1}$, and $R_{m1}$ is hydrogen.

Another aspect of the invention is directed to groups of compounds of formula (I)-(XI) wherein A is $OR_b$, $R_b$ is alkenyl (e.g. allyl), and $L_2$ is $NR_{m1}$. Certain groups of compounds of formula (I)-(XI) include, but are not limited to, those wherein A is $OR_b$, $R_b$ is alkenyl (e.g. allyl), $L_2$ is $NR_{m1}$, and $R_{m1}$ is hydrogen.

Another aspect of the invention is directed to groups of compounds of formula (I)-(XI) wherein A is $NR_cC(O)R_{d'}$, and $L_2$ is $NR_{m1}$. Certain groups of compounds of formula (I)-(XI) include, but are not limited to, those wherein A is $NR_cC(O)R_{d'}$, $R_c$ is hydrogen, $R_{d'}$ is ethoxy, tert-butoxy, —$NH_2$, or —$NHC_6H_5$, and $L_2$ is $NR_{m1}$. $R_{m1}$, for example, is hydrogen.

Another aspect of the invention is directed to groups of compounds of formula (I)-(XI) wherein A is $C(O)OR_{w1}$ and $L_2$ is $NR_{m1}$. Certain groups of compounds of formula (I)-(XI) include, but are not limited to, those wherein A is $C(O)OR_{w1}$, $R_1$ is phenyl, and $L_2$ is $NR_{m1}$. $R_{m1}$, for example, is hydrogen.

Another aspect of the invention is directed to groups of compounds of formula (I)-(XI) wherein A is CN and $L_2$ is $NR_{m1}$. $R_{m1}$, for example, is hydrogen.

Within each group of compounds of formula (I)-(XI) as described in the preceding paragraphs, $R_1$, $R_2$, $R_3$, and $R_4$ are each described generally above and in embodiments described above and herein.

Thus, of each groups of compounds of formula (I)-(XI) as described in the preceding paragraphs, examples of a subgroup include, but are not limited to, those wherein $R_4$ is alkyl (e.g. ethyl, isopropyl, tert-butyl, tert-amyl, neopentyl, 1,2-dimethylpropyl), aryl (e.g. phenyl, naphthyl), cycloalkyl (e.g. cyclopropyl, cyclobutyl, cyclopentyl, cyclohexyl, cycloheptyl, adamantyl, noradamantyl, bicyclo[2.2.1]heptyl), heterocycle (e.g. oxa-adamantane), or heteroaryl (e.g. pyridyl, quinolinyl, benzofuranyl, thienyl, thiazolyl), wherein each of the rings is optionally substituted.

In certain embodiments, $R_4$ is aryl or heteroaryl, each of which is optionally substituted as described generally in the Summary and in embodiments herein.

Examples of another subgroups of compounds of formula (I)-(XI) include, but are not limited to, those wherein $R_4$ is aryl. In certain embodiments, the aryl group of $R_4$ is phenyl or naphthyl, each of which is optionally substituted. In certain embodiments, the optional substituent of the aryl group is alkyl, alkoxy (e.g. ethoxy, methoxy), alkoxyalkoxy (e.g. 2-methoxyethoxy), cycloalkyloxy (e.g. cyclopropyloxy, cyclobutoxy), cyano, formyl, halogen (e.g. chloro, fluoro), alkylcarbonyloxy (e.g. acetyloxy), haloalkyl (e.g. trifluoromethyl), haloalkoxy (e.g. difluoromethoxy, 2,2,2-trifluoroethoxy), hydroxy, $NH_2$, or —$CR_z(=N-OR_{n1})$ wherein $R_z$ is hydrogen or alkyl, and $R_{n1}$ is hydrogen or alkyl.

Examples of another subgroups of compounds of formula (I)-(XI) include, but are not limited to, those wherein $R_4$ is alkyl. In certain embodiments, the alkyl group of $R_4$ is ethyl, isopropyl, tert-butyl, tert-amyl, neopentyl, or 1,2-dimethylpropyl.

Examples of another subgroups of compounds of formula (I)-(XI) include, but are not limited to, those wherein $R_4$ is a heterocycle. A non-limiting example of the heterocycle includes 2-oxatricyclo[3.3.1.1$^{3,7}$]decane (oxa-adamantane). Said heterocycle is optionally substituted with 1, 2, 3 or 4 substituents selected from the group consisting of alkyl, alkoxy, halo, haloalkyl, haloalkoxy, cyano, carboxy, hydroxy, $NZ_1Z_2$, and —$C(O)NZ_3Z_4$.

Examples of another subgroups of compounds of formula (I)-(XI) include, but are not limited to, those wherein $R_4$ is heteroaryl. In certain embodiments, the heteroaryl group of $R_4$ is pyridyl (including pyridin-3-yl), quinolinyl (including quinolin-8-yl), benzofuranyl, thienyl, or thiazolyl, each of which is optionally substituted. Examples of the optional substituents include, but are not limited to, alkyl, alkoxy, halo, haloalkyl, haloalkoxy, cyano, carboxy, hydroxy, $NZ_1Z_2$ and —$C(O)NZ_3Z_4$. In certain embodiments, $R_4$ is a heteroaryl wherein the heteroaryl is 2-ethoxypyridin-3-yl.

Examples of another subgroups of compounds of formula (I)-(XI) include, but are not limited to, those wherein $R_4$ is cycloalkyl. In certain embodiments, the cycloalkyl group of $R_4$ is cyclopropyl, cyclobutyl, cyclopentyl, cyclohexyl, cycloheptyl, adamantyl, noradamantyl, or bicyclo[2.2.1]heptyl (including bicyclo[2.2.1]hept-2-yl), each of which is optionally substituted. Said cycloalkyl is optionally substituted with 1, 2, 3 or 4 substituents selected from the group consisting of alkyl, alkoxy, halo, haloalkyl, haloalkoxy, cyano, carboxy, hydroxy, oxo, $NZ_1Z_2$ and —$C(O)NZ_3Z_4$. In certain embodiments, $R_4$ is cycloalkyl wherein the cycloalkyl is 2,2,3,3,-tetramethylcyclopropyl, adamant-1-yl, adamant-2-yl, or bicyclo[2.2.1]hept-2-yl.

Yet another aspect of the invention include compounds of formula (I)-(XI) wherein $L_2$ is a bond and $R_4$ is unsubstituted or substituted phenyl.

Examples of groups of compounds of formula (I)-(IV) wherein $L_2$ is a bond and $R_4$ is a substituted phenyl, are those having formula (XII)-(XV)

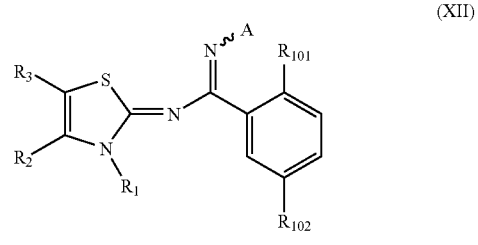

(XII)

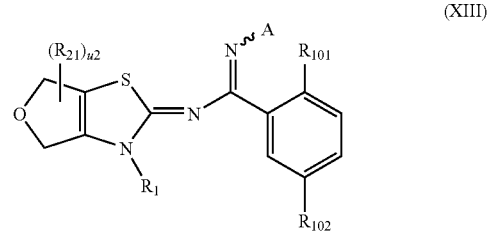

(XIII)

-continued

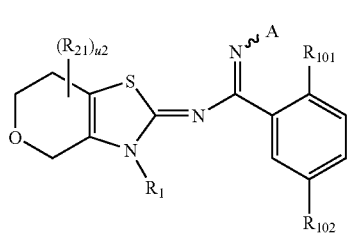

(XIV)

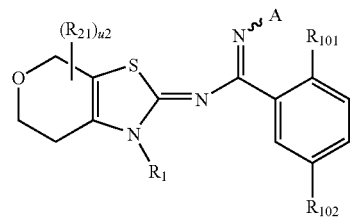

(XV)

wherein A, $R_1$, $R_2$, $R_3$, $R_{21}$, $R_{101}$, $R_{102}$, u1, and u2, are as described generally above and in embodiments described above and herein.

For example, $R_{101}$ and $R_{102}$ are each independently hydrogen, alkenyl, alkynyl, carboxy, carboxyalkyl, cyanoalkyl, alkyl, alkoxy (e.g. ethoxy, methoxy), alkoxyalkoxy (e.g. 2-methoxyethoxy), alkoxyalkoxyalkyl, alkoxyalkyl, alkoxycarbonyl, alkoxycarbonylalkyl, cycloalkyloxy (e.g. cyclopropyloxy, cyclobutoxy), cyano, formyl, halogen (e.g. chloro, fluoro), alkylcarbonyl, alkylcarbonylalkyl, alkylcarbonyloxy (e.g. acetyloxy), haloalkyl (e.g. trifluoromethyl), haloalkoxy (e.g. difluoromethoxy, 2,2,2-trifluoroethoxy), haloalkoxyalkoxy, hydroxy, hydroxyalkyl, —C(O)N$Z_3Z_4$, NH$_2$, or —C$R_z$(=N—O$R_{n1}$) wherein $R_z$ is hydrogen or alkyl, and $R_{n1}$ is hydrogen or alkyl.

For example, $R_{101}$ and $R_{102}$ are each independently alkyl, alkoxy (e.g. ethoxy, methoxy), alkoxyalkoxy (e.g. 2-methoxyethoxy), cycloalkyloxy (e.g. cyclopropyloxy, cyclobutoxy), cyano, formyl, halogen (e.g. chloro, fluoro), alkylcarbonyloxy (e.g. acetyloxy), haloalkyl (e.g. trifluoromethyl), haloalkoxy (e.g. difluoromethoxy, 2,2,2-trifluoroethoxy), hydroxy, NH$_2$, or —C$R_z$(=N—O$R_{n1}$) wherein $R_z$ is hydrogen or alkyl, and $R_{n1}$ is hydrogen or alkyl.

Thus, examples of groups of compounds of formula (XII)-(XV) include, but are not limited to, those wherein A is O$R_b$, CN, N$R_c$C(O)$R_{d'}$, or C(O)O$R_{w1}$.

Other examples of groups of compounds of formula (XII)-(XV) include, but are not limited to, those wherein A is CN.

Yet other examples of groups of compounds of formula (XII)-(XV) include, but are not limited to, those wherein A is O$R_b$.

Yet other examples of groups of compounds of formula (XII)-(XV) include, but are not limited to, those wherein A is N$R_c$C(O)$R_{d'}$.

Yet other examples of groups of compounds of formula (XII)-(XV) include, but are not limited to, those wherein A is C(O)O$R_1$.

Within each of the groups of compounds of formula (XII)-(XV) as described in the preceding paragraphs, $R_b$, $R_c$, $R_{d'}$, $R_{w1}$, $R_1$, $R_2$, $R_3$, $R_{21}$, $R_{101}$, $R_{102}$, u1, and u2, are as described generally above and in embodiments described above and herein.

For each groups and subgroups of compounds of formula (I)-(XV) as described herein above, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl-, or $R_{z1}SO_2NR_{z2}$-alkyl-.

For each groups and subgroups of compounds of formula (I)-(XV) as described herein above, $R_1$ is $C_2$-$C_{10}$ alkyl.

For each groups and subgroups of compounds of formula (I)-(XV) as described herein above, $R_1$ is cycloalkylalkyl.

For each groups and subgroups of compounds of formula (I)-(XV) as described herein above, $R_1$ is heteroarylalkyl.

For each groups and subgroups of compounds of formula (I)-(XV) as described herein above, $R_1$ is heterocyclealkyl.

For each groups and subgroups of compounds of formula (I)-(XV) as described herein above, $R_1$ is alkenyl.

For each groups and subgroups of compounds of formula (I)-(XV) as described herein above, $R_1$ is alkynyl.

For each groups and subgroups of compounds of formula (I)-(XV) as described herein above, $R_1$ is alkoxyalkyl.

For each groups and subgroups of compounds of formula (I)-(XV) as described herein above, $R_1$ is cyanoalkyl.

For each groups and subgroups of compounds of formula (I)-(XV) as described herein above, $R_1$ is haloalkyl.

For each groups and subgroups of compounds of formula (I)-(XV) as described herein above, $R_1$ is hydroxyalkyl.

For each groups and subgroups of compounds of formula (I)-(XV) as described herein above, $R_1$ is $R_zC(O)$—O—$C_2$-$C_6$ alkyl-.

For each groups and subgroups of compounds of formula (I)-(XV) as described herein above, $R_1$ is $R_{z1}SO_2NR_{z2}$-alkyl-.

For each of the groups and subgroups of compounds of formula (I) and (XII) described above, $R_2$ and $R_3$ have values as described generally and in embodiments described herein above.

For example, for each of the groups and subgroups of compounds of formula (I) and (XII) described above, $R_2$, for example, is hydrogen or alkyl, and $R_3$, for example, is hydrogen, alkyl (e.g. methyl, tert-butyl), alkylcarbonyl (e.g. acetyl), halo (e.g. chloro, bromo), cycloalkyl (e.g. cyclohexyl), or hydroxyalkyl (e.g. 1-hydroxy-1-methylethyl).

For example, for each of the groups and subgroups of compounds of formula (I) and (XII) described above, $R_2$ and $R_3$, together with the carbon atoms to which they are attached, form a monocyclic ring as described generally in the Summary and in embodiments herein above.

Examples of compounds of formula (I) include those wherein A is O$R_b$, CN, N$R_c$C(O)$R_{d'}$, or C(O)O$R_{w1}$, $L_2$ is a bond, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, and $R_2$ and $R_3$, together with the carbon atoms to which they are attached, form a monocyclic ring as described generally in the Summary.

Examples of compounds of formula (I) include those wherein A is CN, $L_2$ is a bond, $R_4$ is aryl or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, and $R_2$ and $R_3$, together with the carbon atoms to which they are attached, form a monocyclic ring as described generally in the Summary.

Examples of compounds of formula (I) include those wherein A is CN, $L_2$ is a bond, $R_4$ is aryl or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, and $R_2$ and $R_3$, together with the carbon atoms to which they are attached, form a monocyclic ring as described generally in the Summary.

Examples of compounds of formula (I) include those wherein A is CN, $L_2$ is a bond, $R_4$ is aryl or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, or $R_{z1}SO_2NR_{z2}$-alkyl-, and $R_2$ and $R_3$, together with the carbon atoms to which they are attached, form a monocyclic ring as described generally in the Summary.

Examples of compounds of formula (I)-(XI) include, but are not limited to, those wherein A is $OR_b$, CN, $NR_cC(O)R_{d'}$, or $C(O)OR_{w1}$, $L_2$ is a bond, $R_4$ is alkyl, aryl, cycloalkyl, heterocycle, or heteroaryl, and $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

Examples of compounds of formula (I) include, but are not limited to, those wherein A is $OR_b$, CN, $NR_cC(O)R_{d'}$, or $C(O)OR_{w1}$, $L_2$ is a bond, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, $R_2$ is hydrogen or alkyl, and $R_3$ is hydrogen, alkyl, alkylcarbonyl, halo, cycloalkyl, or hydroxyalkyl.

Compounds of formula (XII) include, but are not limited to, those wherein A is CN, $R_2$ is hydrogen or alkyl, $R_3$ is hydrogen, alkyl (e.g. methyl, tert-butyl), alkylcarbonyl (e.g. acetyl), halo (e.g. chloro, bromo), cycloalkyl (e.g. cyclohexyl), or hydroxyalkyl (e.g. 1-hydroxy-1-methylethyl), and $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

Exemplary compounds of the invention include, but are not limited to:

N-[(2Z)-3-butyl-4,5-dimethyl-1,3-thiazol-2(3H)-ylidene]-5-chloro-N',2-dimethoxybenzenecarboximidamide;

N-[(2Z)-3-butyl-4,5-dimethyl-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N',2-dimethoxybenzenecarboximidamide;

N-[(2Z)-3-butyl-4,5-dimethyl-1,3-thiazol-2(3H)-ylidene]-5-chloro-N'-ethoxy-2-methoxybenzenecarboximidamide;

N'-(allyloxy)-N-[(2Z)-3-butyl-4,5-dimethyl-1,3-thiazol-2(3H)-ylidene]-5-chloro-2-methoxybenzenecarboximidamide;

tert-butyl (2Z)-2-[{[(2Z)-3-butyl-4,5-dimethyl-1,3-thiazol-2(3H)-ylidene]amino}(5-chloro-2-methoxyphenyl)methylene]hydrazinecarboxylate;

N'-(tert-butoxy)-N-[(2Z)-3-butyl-4,5-dimethyl-1,3-thiazol-2(3H)-ylidene]-5-chloro-2-methoxybenzenecarboximidamide;

tert-butyl 2-[{[(2Z)-3-butyl-5-tert-butyl-1,3-thiazol-2(3H)-ylidene]amino}(5-chloro-2-methoxyphenyl)methylene]hydrazinecarboxylate;

N-[(2Z)-5-tert-butyl-3-isobutyl-1,3-thiazol-2(3H)-ylidene]-5-chloro-N'-cyano-2-methoxybenzenecarboximidamide;

N-[(2Z)-5-tert-butyl-3-[(2R)-tetrahydrofuran-2-ylmethyl]-1,3-thiazol-2(3H)-ylidene]-5-chloro-N'-cyano-2-methoxybenzenecarboximidamide;

N-[(2Z)-5-tert-butyl-3-propyl-1,3-thiazol-2(3H)-ylidene]-5-chloro-N'-cyano-2-methoxybenzenecarboximidamide;

N-[(2Z)-5-tert-butyl-3-(3-methylbutyl)-1,3-thiazol-2(3H)-ylidene]-5-chloro-N'-cyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclohexyl acetate;

N-[(2Z)-5-tert-butyl-3-[(1-hydroxycyclohexyl)methyl]-1,3-thiazol-2(3H)-ylidene]-5-chloro-N'-cyano-2-methoxybenzenecarboximidamide;

2-[(2Z)-5-tert-butyl-2-{[(5-chloro-2-methoxyphenyl)(cyanoimino)methyl]imino}-1,3-thiazol-3(2H)-yl]-1,1-dimethylethyl acetate;

N-[(2Z)-5-tert-butyl-3-(2-hydroxy-2-methylpropyl)-1,3-thiazol-2(3H)-ylidene]-5-chloro-N'-cyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclopentyl acetate;

N-[(2Z)-5-tert-butyl-3-[(1-hydroxycyclopentyl)methyl]-1,3-thiazol-2(3H)-ylidene]-5-chloro-N'-cyano-2-methoxybenzenecarboximidamide;

N-[(2Z)-5-tert-butyl-3-propyl-1,3-thiazol-2(3H)-ylidene]-N',5-dicyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclobutyl acetate;

1-{[(2Z)-5-tert-butyl-2-{[(cyanoimino)(5-cyano-2-methoxyphenyl)methyl]imino}-1,3-thiazol-3(2H)-yl]methyl}cyclobutyl acetate;

N-[(2Z)-5-tert-butyl-3-[(1-hydroxycyclobutyl)methyl]-1,3-thiazol-2(3H)-ylidene]-5-chloro-N'-cyano-2-methoxybenzenecarboximidamide;

N-[(2Z)-5-tert-butyl-3-[(1-hydroxycyclobutyl)methyl]-1,3-thiazol-2(3H)-ylidene]-N',5-dicyano-2-methoxybenzenecarboximidamide;

N-[(2Z)-5-tert-butyl-3-isobutyl-1,3-thiazol-2(3H)-ylidene]-N'-cyano-2-methoxy-5-(trifluoromethyl)benzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclopropyl acetate;

N-[(2Z)-5-tert-butyl-3-[(1-hydroxycyclopropyl)methyl]-1,3-thiazol-2(3H)-ylidene]-5-chloro-N'-cyano-2-methoxybenzenecarboximidamide;

1-{[(2Z)-5-tert-butyl-2-({(cyanoimino)[2-methoxy-5-(trifluoromethyl)phenyl]methyl}imino)-1,3-thiazol-3(2H)-yl]methyl}cyclobutyl acetate;

N-[(2Z)-5-tert-butyl-3-[(1-hydroxycyclobutyl)methyl]-1,3-thiazol-2(3H)-ylidene]-N'-cyano-2-methoxy-5-(trifluoromethyl)benzenecarboximidamide;

N-[(2Z)-5-tert-butyl-3-[(2R)-tetrahydrofuran-2-ylmethyl]-1,3-thiazol-2(3H)-ylidene]-N'-cyano-2-ethoxy-5-(trifluoromethyl)benzenecarboximidamide;

N-[(2Z)-5-tert-butyl-3-{[1-(cyclopropylsulfonyl)azetidin-3-yl]methyl}-1,3-thiazol-2(3H)-ylidene]-N'-cyano-2-methoxy-5-(trifluoromethyl)benzenecarboximidamide;

N-[(2Z)-5-tert-butyl-3-{[1-(methylsulfonyl)azetidin-3-yl]methyl}-1,3-thiazol-2(3H)-ylidene]-N'-cyano-2-methoxy-5-(trifluoromethyl)benzenecarboximidamide;

N'-(aminocarbonyl)-N-[(2Z)-3-butyl-4,5-dimethyl-1,3-thiazol-2(3H)-ylidene]-5-chloro-2-methoxybenzenecarbohydrazonamide;

N-[(2Z)-5-acetyl-3-(cyclobutylmethyl)-4-methyl-1,3-thiazol-2(3H)-ylidene]-5-chloro-N'-cyano-2-methoxybenzenecarboximidamide;

N'-(anilinocarbonyl)-N-[(2Z)-3-butyl-4,5-dimethyl-1,3-thiazol-2(3H)-ylidene]-5-chloro-2-methoxybenzenecarbohydrazonamide;

2-{{[(2Z)-3-butyl-5-tert-butyl-1,3-thiazol-2(3H)-ylidene] amino}[(phenoxycarbonyl)imino]methyl}-4-chlorophenyl acetate;

N-[(2Z)-5-tert-butyl-3-[(2R)-tetrahydrofuran-2-ylmethyl]-1,3-thiazol-2(3H)-ylidene]-3,5-dichloro-N'-cyanobenzenecarboximidamide;

N-[(2Z)-5-tert-butyl-3-[(2R)-tetrahydrofuran-2-ylmethyl]-1,3-thiazol-2(3H)-ylidene]-N'-cyano-2-formylbenzenecarboximidamide;

N-[(2Z)-5-tert-butyl-3-[(2R)-tetrahydrofuran-2-ylmethyl]-1,3-thiazol-2(3H)-ylidene]-N'-cyano-2,5-difluorobenzenecarboximidamide;

N-[(2Z)-5-tert-butyl-3-[(2R)-tetrahydrofuran-2-ylmethyl]-1,3-thiazol-2(3H)-ylidene]-N'-cyano-2-[(hydroxyimino)methyl]benzenecarboximidamide;

N-[(2Z)-3-butyl-4,5-dimethyl-1,3-thiazol-2(3H)-ylidene]-2,5-difluoro-N'-methoxybenzenecarboximidamide;

N-[(2Z)-3-butyl-5-tert-butyl-4-methyl-1,3-thiazol-2(3H)-ylidene]-5-chloro-N',2-dimethoxybenzenecarboximidamide;

ethyl 2-[{[(2Z)-3-butyl-5-tert-butyl-1,3-thiazol-2(3H)-ylidene]amino}(5-chloro-2-methoxyphenyl)methylene]hydrazinecarboxylate;

N-[(2Z)-5-tert-butyl-3-isobutyl-1,3-thiazol-2(3H)-ylidene]-5-chloro-N'-cyano-2-(2-methoxyethoxy)benzenecarboximidamide;

N-[(2Z)-5-tert-butyl-3-isobutyl-1,3-thiazol-2(3H)-ylidene]-5-chloro-N'-cyano-2-(2,2,2-trifluoroethoxy)benzenecarboximidamide;

N-[(2Z)-5-tert-butyl-3-isobutyl-1,3-thiazol-2(3H)-ylidene]-2,3-dichloro-N'-cyanobenzenecarboximidamide;

N-[(2Z)-5-tert-butyl-3-isobutyl-1,3-thiazol-2(3H)-ylidene]-N',5-dicyano-2-methoxybenzenecarboximidamide;

N-[(2Z)-5-tert-butyl-3-isobutyl-1,3-thiazol-2(3H)-ylidene]-N'-cyano-2-ethoxypyridine-3-carboximidamide;

N-[(2Z)-5-tert-butyl-3-(3-methylbut-2-enyl)-1,3-thiazol-2(3H)-ylidene]-5-chloro-N'-cyano-2-methoxybenzenecarboximidamide;

N-[(2Z)-5-tert-butyl-3-(3,3,3-trifluoropropyl)-1,3-thiazol-2(3H)-ylidene]-5-chloro-N'-cyano-2-methoxybenzenecarboximidamide;

N-[(2Z)-5-tert-butyl-3-(3,3,3-trifluoropropyl)-1,3-thiazol-2(3H)-ylidene]-N',5-dicyano-2-(2-methoxyethoxy)benzenecarboximidamide;

N-[(2Z)-5-tert-butyl-3-isobutyl-1,3-thiazol-2(3H)-ylidene]-N',5-dicyano-2-(2-methoxyethoxy)benzenecarboximidamide;

N-[(2Z)-5-tert-butyl-3-isobutyl-1,3-thiazol-2(3H)-ylidene]-5-chloro-N'-cyano-2-ethoxybenzenecarboximidamide;

N-[(2Z)-5-tert-butyl-3-isobutyl-1,3-thiazol-2(3H)-ylidene]-5-chloro-N'-cyano-2-(cyclopropyloxy)benzenecarboximidamide;

N-[(2Z)-5-tert-butyl-3-isobutyl-1,3-thiazol-2(3H)-ylidene]-N',5-dicyano-2-ethoxybenzenecarboximidamide;

N-[(2Z)-5-tert-butyl-3-{[1-(methylsulfonyl)azetidin-3-yl]methyl}-1,3-thiazol-2(3H)-ylidene]-5-chloro-N'-cyano-2-methoxybenzenecarboximidamide;

N-[(2Z)-5-tert-butyl-3-isobutyl-1,3-thiazol-2(3H)-ylidene]-N',5-dicyano-2-(cyclobutyloxy)benzenecarboximidamide;

N-[(2Z)-5-tert-butyl-3-(3,3,3-trifluoropropyl)-1,3-thiazol-2(3H)-ylidene]-N',5-dicyano-2-(cyclobutyloxy)benzenecarboximidamide;

N-[(2Z)-5-tert-butyl-3-isobutyl-1,3-thiazol-2(3H)-ylidene]-N'-cyano-2-fluoro-3-(trifluoromethyl)benzenecarboximidamide;

N-[(2Z)-5-tert-butyl-3-isobutyl-1,3-thiazol-2(3H)-ylidene]-N',5-dicyano-2-(2,2,2-trifluoroethoxy)benzenecarboximidamide;

N-[(2Z)-5-tert-butyl-3-(3,3,3-trifluoropropyl)-1,3-thiazol-2(3H)-ylidene]-N',5-dicyano-2-(2,2,2-trifluoroethoxy)benzenecarboximidamide;

N-[(2Z)-5-tert-butyl-3-isobutyl-1,3-thiazol-2(3H)-ylidene]-N'-cyano-2-fluoro-5-(trifluoromethyl)benzenecarboximidamide;

N-[(2Z)-5-tert-butyl-3-{2-[methyl(methylsulfonyl)amino]ethyl}-1,3-thiazol-2(3H)-ylidene]-5-chloro-N'-cyano-2-methoxybenzenecarboximidamide;

N-[(2Z)-5-tert-butyl-3-isobutyl-1,3-thiazol-2(3H)-ylidene]-N'-cyano-2-ethoxy-5-(trifluoromethyl)benzenecarboximidamide;

N-[(2Z)-5-tert-butyl-3-isobutyl-1,3-thiazol-2(3H)-ylidene]-N'-cyano-2-(2,2,2-trifluoroethoxy)-5-(trifluoromethyl)benzenecarboximidamide;

N-[(2Z)-5-tert-butyl-3-(tetrahydro-2H-pyran-4-ylmethyl)-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N'-cyano-2-(2,2,2-trifluoroethoxy)benzenecarboximidamide;

N-[(2Z)-5-tert-butyl-3-(cyclobutylmethyl)-1,3-thiazol-2(3H)-ylidene]-5-chloro-N'-cyano-2-methoxybenzenecarboximidamide;

N-[(2Z)-5-tert-butyl-3-(4,4,4-trifluorobutyl)-1,3-thiazol-2(3H)-ylidene]-5-chloro-N'-cyano-2-methoxybenzenecarboximidamide;

N-[(2Z)-5-tert-butyl-3-but-3-ynyl-1,3-thiazol-2(3H)-ylidene]-5-chloro-N'-cyano-2-methoxybenzenecarboximidamide;

5-chloro-N'-cyano-2-methoxy-N-[(2Z)-5-methyl-3-(1,3-thiazol-4-ylmethyl)-1,3-thiazol-2(3H)-ylidene]benzenecarboximidamide;

5-chloro-N'-cyano-2-methoxy-N-[(2Z)-5-methyl-3-[(2R)-tetrahydrofuran-2-ylmethyl]-1,3-thiazol-2(3H)-ylidene]benzenecarboximidamide;

N'-cyano-N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboximidamide;

N'-cyano-N-[(2Z)-3-(2-methoxyethyl)-4,5-dimethyl-1,3-thiazol-2(3H)-ylidene]-2,2,3,3-tetramethylcyclopropanecarboximidamide;

5-chloro-N-[(2Z)-5-chloro-3-(1,3-thiazol-4-ylmethyl)-1,3-thiazol-2(3H)-ylidene]-N'-cyano-2-methoxybenzenecarboximidamide;

N-[(2Z)-5-bromo-3-(1,3-thiazol-4-ylmethyl)-1,3-thiazol-2(3H)-ylidene]-5-chloro-N'-cyano-2-methoxybenzenecarboximidamide;

N-[(2Z)-5-tert-butyl-3-(1,3-thiazol-4-ylmethyl)-1,3-thiazol-2(3H)-ylidene]-5-chloro-N'-cyano-2-methoxybenzenecarboximidamide;

N-[(2Z)-5-tert-butyl-3-[(2R)-tetrahydrofuran-2-ylmethyl]-1,3-thiazol-2(3H)-ylidene]-5-chloro-N'-cyano-2-[(Z)-(methoxyimino)methyl]benzenecarboximidamide;

5-chloro-N'-cyano-N-[(2Z)-3-(cyclobutylmethyl)-1,3-thiazol-2(3H)-ylidene]-2-methoxybenzenecarboximidamide;

N-[(2Z)-5-tert-butyl-3-[(2-methyl-1,3-thiazol-4-yl)methyl]-1,3-thiazol-2(3H)-ylidene]-5-chloro-N'-cyano-2-methoxybenzenecarboximidamide;

5-chloro-N'-cyano-N-[(2Z)-1-isobutyl-4,4-dimethyl-1,4,6,7-tetrahydro-2H-pyrano[4,3-d][1,3]thiazol-2-ylidene]-2-methoxybenzenecarboximidamide;

N-[(2Z)-3-butyl-7,7-dimethyl-6,7-dihydro-4H-pyrano[3,4-d][1,3]thiazol-2(3H)-ylidene]-5-chloro-N'-cyano-2-methoxybenzenecarboximidamide;

5-chloro-N'-cyano-N-[(2Z)-3-isobutyl-4,4,6,6-tetramethyl-4,6-dihydrofuro[3,4-d][1,3]thiazol-2(3H)-ylidene]-2-methoxybenzenecarboximidamide;

5-chloro-N'-cyano-N-[(2Z)-3-(cyclobutylmethyl)-4,4,6,6-tetramethyl-4,6-dihydrofuro[3,4-d][1,3]thiazol-2(3H)-ylidene]-2-methoxybenzenecarboximidamide;

5-chloro-N'-cyano-N-[(2Z)-5-cyclohexyl-3-(2-methoxyethyl)-1,3-thiazol-2(3H)-ylidene]-2-methoxybenzenecarboximidamide;

5-chloro-N'-cyano-N-[(2Z)-1-isobutyl-1,4,6,7-tetrahydro-2H-pyrano[4,3-d][1,3]thiazol-2-ylidene]-2-methoxybenzenecarboximidamide;

N-[(2Z)-3-butyl-4-tert-butyl-1,3-thiazol-2(3H)-ylidene]-5-chloro-N'-cyano-2-methoxybenzenecarboximidamide;

N-[(2Z)-3-butyl-6,7-dihydro-4H-pyrano[3,4-d][1,3]thiazol-2(3H)-ylidene]-5-chloro-N'-cyano-2-methoxybenzenecarboximidamide;

N-[(2Z)-5-tert-butyl-3-(2-morpholin-4-ylethyl)-1,3-thiazol-2(3H)-ylidene]-5-chloro-N'-cyano-2-methoxybenzenecarboximidamide;

N-[(2Z)-5-tert-butyl-3-neopentyl-1,3-thiazol-2(3H)-ylidene]-N'-(5-chloro-2-methoxyphenyl)-N''-cyanoguanidine;

N-[(2Z)-5-tert-butyl-3-[(2R)-tetrahydrofuran-2-ylmethyl]-1,3-thiazol-2(3H)-ylidene]-N''-cyano-N'-(1,2-dimethylpropyl)guanidine;

N-[(2Z)-5-tert-butyl-3-neopentyl-1,3-thiazol-2(3H)-ylidene]-5-chloro-N'-cyano-2-methoxybenzenecarboximidamide;

N-2-adamantyl-N'-[(2Z)-5-tert-butyl-3-[(2R)-tetrahydrofuran-2-ylmethyl]-1,3-thiazol-2(3H)-ylidene]-N''-cyanoguanidine;

N-1-adamantyl-N'-[(2Z)-5-tert-butyl-3-[(2R)-tetrahydrofuran-2-ylmethyl]-1,3-thiazol-2(3H)-ylidene]-N''-cyanoguanidine;

N-[(1S,2S,4R)-bicyclo[2.2.1]hept-2-yl]-N'-[(2Z)-5-tert-butyl-3-[(2R)-tetrahydrofuran-2-ylmethyl]-1,3-thiazol-2(3H)-ylidene]-N''-cyanoguanidine;

N-[(2Z)-5-tert-butyl-3-[(2R)-tetrahydrofuran-2-ylmethyl]-1,3-thiazol-2(3H)-ylidene]-N''-cyano-N'-[(1R)-1,2-dimethylpropyl]guanidine;

N-[(2Z)-5-tert-butyl-3-[(2R)-tetrahydrofuran-2-ylmethyl]-1,3-thiazol-2(3H)-ylidene]-N''-cyano-N'-[(1S)-1,2-dimethylpropyl]guanidine;

N-[(2Z)-5-bromo-3-(cyclobutylmethyl)-1,3-thiazol-2(3H)-ylidene]-5-chloro-N'-cyano-2-methoxybenzenecarboximidamide;

5-chloro-N-[(2Z)-5-chloro-3-(cyclobutylmethyl)-1,3-thiazol-2(3H)-ylidene]-N'-cyano-2-methoxybenzenecarboximidamide;

N-[(2Z)-5-bromo-3-isobutyl-1,3-thiazol-2(3H)-ylidene]-5-chloro-N'-cyano-2-methoxybenzenecarboximidamide;

N-[(2Z)-5-tert-butyl-3-(2-cyanoethyl)-1,3-thiazol-2(3H)-ylidene]-5-chloro-N'-cyano-2-methoxybenzenecarboximidamide;

5-chloro-N'-cyano-N-[(2Z)-3-(cyclobutylmethyl)-4-methyl-1,3-thiazol-2(3H)-ylidene]-2-methoxybenzenecarboximidamide;

5-chloro-N'-cyano-N-[(2Z)-3-(cyclobutylmethyl)-5-(1-hydroxy-1-methylethyl)-4-methyl-1,3-thiazol-2(3H)-ylidene]-2-methoxybenzenecarboximidamide; and N-[(2Z)-5-tert-butyl-3-[(2R)-piperidin-2-ylmethyl]-1,3-thiazol-2(3H)-ylidene]-5-chloro-N'-cyano-2-methoxybenzenecarboximidamide.

Compounds of the present invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30.

The present invention contemplates various stereoisomers (including enantiomers and diastereomers) and mixtures thereof. Individual stereoisomers of compounds of the present invention may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

Geometric isomers may exist in the present compounds. The invention contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen bond are designated as being of Z or E configuration and substituents around a cycloalkyl or a heterocycle are designated as being of cis or trans configuration.

Within the present invention it is to be understood that compounds disclosed herein may exhibit the phenomenon of tautomerism.

Thus, the formulae drawings within this specification can represent only one of the possible tautomeric or stereoisomeric forms. It is to be understood that the invention encompasses any tautomeric or stereoisomeric form, and mixtures thereof, and is not to be limited merely to any one tautomeric or stereoisomeric form utilized within the naming of the compounds or formulae drawings.

c. Biological Data (i) In Vitro Methods—$CB_2$ and $CB_1$ Radioligand Binding Assays:

The $CB_1$ and $CB_2$ radioligand binding assays described herein are utilized to determine the selectivity of compounds of the present invention for binding to $CB_2$ relative to $CB_1$ receptors.

HEK293 cells stably expressing human $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 5 μg/well for human $CB_2$) into wells of a deep well plate containing ([$^3$H] CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 90 min incubation at 30° C., binding reaction was terminated by the addition of 300 μl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

HEK293 cells stably expressing rat $CB_2$ receptors were grown until a confluent monolayer was formed. Briefly, the cells were harvested and homogenized in TE buffer (50 mM Tris-HCl, 1 mM $MgCl_2$, and 1 mM EDTA) using a polytron for 2×10 second bursts in the presence of protease inhibitors, followed by centrifugation at 45,000×g for 20 minutes. The final membrane pellet was re-homogenized in storage buffer (50 mM Tris-HCl, 1 mM $MgCl_2$, and 1 mM EDTA and 10% sucrose) and frozen at −78° C. until used. Saturation binding reactions were initiated by the addition of membrane preparation (protein concentration of 20 µg/well for rat $CB_2$) into wells of a deep well plate containing [$^3$H]CP-55,940 (120 Ci/mmol, a nonselective CB agonist commercially available from Tocris) in assay buffer (50 mM Tris, 2.5 mM EDTA, 5 mM $MgCl_2$, and 0.5 mg/mL fatty acid free BSA, pH 7.4). After 45 min incubation at 30° C., binding reaction was terminated by the addition of 300 µl/well of cold assay buffer followed by rapid vacuum filtration through a UniFilter-96 GF/C filter plates (pre-soaked in 1 mg/mL BSA for 2 hours). The bound activity was counted in a TopCount using Microscint-20. Saturation experiments were conducted with twelve concentrations of [$^3$H]CP-55,940 ranging from 0.01 to 8 nM. Competition experiments were conducted with 0.5 nM [$^3$H]CP-55,940 and five concentrations of displacing ligands selected from the range of 0.01 nM to 10 µM. The addition of 10 µM unlabeled CP-55,940 (Tocris, Ellisville, Mo.) was used to assess nonspecific binding.

Compounds of the invention tested were found to bind to $CB_2$ receptors with $K_i$ of less than about 1,000 nM, preferably less than 400 nM, more preferably less than 200 nM, and most preferably lower than 100 nM.

HEK293 human $CB_1$ membranes were purchased from Perkin Elmer. Binding was initiated by the addition of membranes (8-12 µg per well) into wells (Scienceware 96-well DeepWell plate, VWR, West Chester, Pa.) containing [$^3$H]CP-55,940 (120 Ci/mmol, Perkin Elmer, Boston, Mass.) and a sufficient volume of assay buffer (50 mM Tris, 2.5 mM EDTA, 5 mM $MgCl_2$, and 0.5 mg/mL fatty acid free BSA, pH 7.4) to bring the total volume to 250 µL. After incubation (30° C. for 90 minutes), binding was terminated by the addition of 300 µL per well of cold assay buffer and rapid vacuum filtration (FilterMate Cell Harvester, Perkin Elmer, Boston, Mass.) through a UniFilter-96 GF/C filter plate (Perkin Elmer, Boston, Mass.) (pre-soaked in 0.3% PEI at least 3 hours), followed by five washes with cold assay buffer. The bound activity was counted in the TopCount using Microscint-20 (both from Perkin Elmer, Boston, Mass.). Competition experiments were conducted with 1 nM [$^3$H]CP-55,940 and five concentrations (1 nM to 10 µM) of displacing ligands. The addition of 10 µM unlabeled CP-55,940 (Tocris, Ellisville, Mo.) was used to assess nonspecific binding. The compounds of the present invention tested were found to bind to $CB_1$ receptors with $K_i$ of about 10 fold to about 1000 fold higher than that for $CB_2$ receptors. These results demonstrate that the compounds of the present invention tested preferably bind to $CB_2$ vs. $CB_1$ receptors, and therefore are selective ligands for the CB2 receptor.

ii) In Vivo Data Animals

Adult male Sprague-Dawley rats (250-300 g body weight, Charles River Laboratories, Portage, Mich.) were used. Animal handling and experimental protocols were approved by the Institutional Animal Care and Use Committee (IACUC) at Abbott Laboratories. For all surgical procedures, animals were maintained under halothane anesthesia (4% to induce, 2% to maintain), and the incision sites were sterilized using a 10% povidone-iodine solution prior to and after surgeries.

Incision Model of Postoperative Pain

A skin incision model of postoperative pain was produced using the procedures described in Brennan et al., 1996, Pain, 64, 493. All rats were anesthetized with isofluorane delivered via a nose cone. Right hind paw incision was performed following sterilization procedures. The plantar aspect of the left hind paw was placed through a hole in a sterile plastic drape. A 1-cm longitudinal incision was made through the skin and fascia of the plantar aspect of the hind paw, starting 0.5 cm from the proximal edge of the heel and extending towards the toes, the plantar muscle was elevated and incised longitudinally leaving the muscle origin and insertion points intact. The skin was then closed with two mattress sutures (5-0 nylon). After surgery, animals were then allowed to recover for 2 hours, at which time tactile allodynia was assessed as described below. To evaluate the anti-nociceptive effects, animals were i.p. administered vehicle or test compound 90 minutes following skin incision and tactile allodynia was assessed 30 minutes after compound administration.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic cage (20×12.5×20 cm) on top of a suspended wire mesh grid, and acclimated to the test chambers for 20 minutes. The von Frey filaments were applied perpendicularly from underneath the cage through openings in the wire mesh floor directly to an area within 1-3 mm (immediately adjacent) of the incision, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441.

Certain compounds of the present invention tested showed a statistically significant change in paw withdrawal latency versus a saline vehicle at less than about 300 micromoles/kg in the incision model of postoperative pain. In a more preferred embodiment, compounds of the present invention tested showed efficacy at less than about 50 micromoles/kg in the incision model of postoperative pain.

Spinal Nerve Ligation Model of Neuropathic Pain:

A model of spinal nerve ligation-induced (SNL model) neuropathic pain was produced using the procedure originally described in Kim, S. H. and J. M. Chung, 1992, An experimental model for peripheral neuropathy produced by segmental spinal nerve ligation in the rat, Pain, 50, 355. The left $L_5$ and $L_6$ spinal nerves of the rat were isolated adjacent to the vertebral column and tightly ligated with a 5-0 silk suture distal to the DRG, and care was taken to avoid injury of the $L_4$ spinal nerve. Sham rats underwent the same procedure, but without nerve ligation. All animals were allowed to recover for at least one week and not more than three weeks prior to assessment of tactile allodynia.

Tactile allodynia was measured using calibrated von Frey filaments (Stoelting, Wood Dale, Ill.) as described in Chaplan, S. R., F. W. Bach, J. W. Porgrel, J. M. Chung and T. L. Yaksh, 1994, Quantitative assessment of tactile allodynia in the rat paw, J. Neurosci. Methods, 53, 55. Rats were placed into inverted individual plastic containers (20×12.5×20 cm) on top of a suspended wire mesh grid, and were acclimated to the test chambers for 20 minutes. The von Frey filaments were presented perpendicularly to the plantar surface of the selected hind paw, and were then held in this position for approximately 8 sec with enough force to cause a slight bend in the filament. Positive responses included an abrupt withdrawal of the hind paw from the stimulus, or flinching behavior immediately following removal of the stimulus. A 50% withdrawal threshold was determined using an up-down procedure as described in Dixon, W. J., 1980, Efficient analysis of experimental observations, Ann. Rev. Pharmacol. Toxicol., 20, 441). Only rats with a baseline threshold score of less that 4.25 g were used in this study, and animals demonstrating motor deficit were excluded. Tactile allodynia thresholds were also assessed in several control groups, including naive, sham-operated, and saline infused animals as well as in the contralateral paws of nerve-injured rats.

Capsaicin-Induced Secondary Mechanical Hypersensitivity:

Rats were allowed to acclimate to the study room for 1 hour. They were then briefly restrained, and capsaicin was administered at 10 μg in 10 μL of vehicle (10% ethanol and 2-hydroxypropyl cyclodextrin) by intraplantar injection into the center of the right hind paw. Secondary mechanical hyperalgesia was measured at the heel away from the site of injection at 180 min following capsaicin (Joshi et al 2006, Neuroscience 143, 587-596). Compounds are injected (i.p.) 30 min before testing (150 min post-capsaicin).

Tactile allodynia was measured as described above.

Certain compound of the present invention showed a statistically significant change in paw withdrawal latency versus a saline vehicle at less than about 300 micromoles/kg. In a more preferred embodiment, compounds of the present invention showed efficacy of less than about 50 micromoles/kg.

d. Methods of Using the Compounds

One embodiment of the present invention provides a method for treating pain (for example, neuropathic pain or nociceptive pain) in a mammal (including human) in need of such treatment. The method comprises administering to the mammal a therapeutically effective amount of any of the compounds as described herein, or a pharmaceutically acceptable salt thereof. In certain embodiments, the method comprises administering to the mammal a therapeutically effective amount of any of the compounds as described herein, or a pharmaceutically acceptable salt thereof, in combination with one or more nonsteroidal anti-inflammatory drug (NSAID).

Another embodiment of the present invention provides a method for treating a disorder selected from the group consisting of inflammatory disorders, immune disorders, neurological disorders, cancers of the immune system, respiratory disorders, and cardiovascular disorders in a mammal in need of such treatment. The method comprises administering to the mammal a therapeutically effective amount of a compound of formula (I) or a pharmaceutically acceptable salt thereof.

Yet another embodiment of the present invention relates to a method for providing neuroprotection in a mammal in need of such treatment. This method comprises administering to the mammal a therapeutically effective amount of any compounds described herein or a pharmaceutically acceptable salt thereof.

In addition to the data contained herein, several lines of evidence support the assertion that $CB_2$ receptors play a role in analgesia. HU-308 is one of the first highly selective $CB_2$ agonists identified that elicits an antinociceptive response in the rat formalin model of persistent pain (Hanus, L., et al., Proc. Nat. Acad. Sci., 1999, 96, 14228-14233). The $CB_2$-selective cannabinoid ligand AM-1241 exhibits robust analgesic efficacy in animal models of acute thermal pain (Malan, T. P., et al., Pain, 2001, 93, 239-245; Ibrahim, M. M., et al., Proc. Nat. Acad. Sci., 2005, 102(8), 3093-3098), persistent pain (Hohmann, A. G., et al., J. Pharmacol. Exp. Ther., 2004, 308, 446-453), inflammatory pain (Nackley, A. G., et al., Neuroscience, 2003, 119, 747-757; Quartilho, A. et al., Anesthesiology, 2003, 99, 955-60), and neuropathic pain (Ibrahim, M. M., et al., Proc. Nat. Acad. Sci., 2003, 100, 10529-10533). The $CB_2$-selective partial agonist GW405833, also known as L768242, is efficacious in rodent models of neuropathic, incisional, and both chronic and acute inflammatory pain (Valenzano, K. J., et al., Neuropharmacology, 2005, 48, 658-672 and Clayton, N., et al., Pain, 2002, 96, 253-260).

The potential exists for $CB_2$ modulators to have opioid sparing effects. A synergy between the analgesic effects of morphine and the nonselective CB agonist $\Delta^9$-THC has been documented (Cichewicz, D. L., Life Sci. 2004, 74, 1317-1324). Therefore, $CB_2$ ligands have additive or synergistic analgesic effects when used in combination with lower doses of morphine or other opioids, providing a strategy for reducing adverse opioid events, such as tolerance, constipation, and respiratory depression, without sacrificing analgesic efficacy.

$CB_2$ receptors are present in tissues and cell types associated with immune functions and $CB_2$ receptor mRNA is expressed by human B cells, natural killer cells, monocytes, neutrophils, and T cells (Galiegue et al., Eur. J. Biochem., 1995, 232, 54-61). Studies with $CB_2$ knockout mice have suggested a role for $CB_2$ receptors in modulating the immune system (Buckley, N. E., et al., Eur. J. Pharmacol. 2000, 396, 141-149). Although immune cell development and differentiation are similar in knockout and wild type animals, the immunosuppressive effects of $\Delta^9$-THC are absent in the $CB_2$ receptor knockout mice, providing evidence for the involvement of $CB_2$ receptors in immunomodulation. As such, selective $CB_2$ modulators may be useful for the treatment of autoimmune diseases including but not limited to multiple sclerosis, rheumatoid arthritis, systemic lupus, myasthenia gravis, type I diabetes, irritable bowel syndrome, psoriasis, psoriatic arthritis, and hepatitis; and immune related disorders including but not limited to tissue rejection in organ transplants, gluten-sensitive enteropathy (Celiac disease), asthma, chronic obstructive pulmonary disease, emphysema, bronchitis, acute respiratory distress syndrome, allergies, allergic rhinitis, dermatitis, and Sjogren's syndrome.

Microglial cells are considered to be the immune cells of the central nervous system (CNS) where they regulate the initiation and progression of immune responses. $CB_2$ receptor expression on microglia is dependent upon inflammatory state with higher levels of $CB_2$ found in primed, proliferating, and migrating microglia relative to resting or fully activated microglial (Carlisle, S. J., et al. Int. Immunopharmacol., 2002, 2, 69). Neuroinflammation induces many changes in microglia cell morphology and there is an upregulation of $CB_2$ receptors and other components of the endocannabinoid system. —Neuroinflammation occurs in several neurodegenerative diseases, and induction of microglial $CB_2$ receptors has been observed (Carrier, E. J., et al., Current Drug Targets —CNS & Neurological Disorders, 2005, 4, 657-665). Thus, $CB_2$ ligands may be clinically useful for the treatment of neuroinflammation.

Multiple sclerosis is common immune-mediated disease of the CNS in which the ability of neurons to conduct impulses becomes impaired through demyelination and axonal damage. The demyelination occurs as a consequence of chronic inflammation and ultimately leads to a broad range of clinical symptoms that fluctuate unpredictably and generally worsen with age. These include painful muscle spasms, tremor, ataxia, motor weakness, sphincter dysfunction, and difficulty speaking (Pertwee, R. G., Pharmacol. Ther. 2002, 95, 165-174). The $CB_2$ receptor is up-regulated on activated microglial cells during experimental autoimmune encephalomyelitis (EAE) (Maresz, K., et al., J. Neurochem. 2005, 95, 437-445). $CB_2$ receptor activation prevents the recruitment of inflammatory cells such as leukocytes into the CNS (Ni, X., et al., Multiple Sclerosis, 2004, 10, 158-164) and plays a protective role in experimental, progressive demyelination (Arevalo-Martin, A.; et al., J. Neurosci., 2003, 23(7), 2511-2516), which are critical features in the development of multiple sclerosis. Thus, $CB_2$ receptor modulators may provide a unique treatment for demyelinating pathologies.

Alzheimer's disease is a chronic neurodegenerative disorder accounting for the most common form of elderly dementia. Recent studies have revealed that $CB_2$ receptor expression is upregulated in neuritic plaque-associated microglia from brains of Alzheimer's disease patients (Benito, C., et al., J. Neurosci., 2003, 23(35), 11136-11141). In vitro, treatment with the $CB_2$ agonist JWH-133 abrogated β-amyloid-induced microglial activation and neurotoxicity, effects that can be blocked by the $CB_2$ antagonist SR144528 (Ramirez, B. G., et al., J. Neurosci. 2005, 25(8), 1904-1913). $CB_2$ modulators may possess both anti-inflammatory and neuroprotective actions and thus have clinical utility in treating neuroinflammation and in providing neuroprotection associated with the development of Alzheimer's disease.

Increased levels of epithelial $CB_2$ receptor expression are observed in human inflammatory bowel disease tissue (Wright, K., et al., Gastroenterology, 2005, 129, 437-453). Activation of $CB_2$ receptors re-established normal gastrointestinal transit after endotoxic inflammation was induced in rats (Mathison, R., et al., Br. J. Pharmacol. 2004, 142, 1247-1254). $CB_2$ receptor activation in a human colonic epithelial cell line inhibited TNF-α-induced interleukin-8 (IL-8) release (Ihenetu, K. et al., Eur. J. Pharmacol. 2003, 458, 207-215). Chemokines released from the epithelium, such as the neutrophil chemoattractant IL-8, are upregulated in inflammatory bowel disease (Warhurst, A. C., et al., Gut, 1998, 42, 208-213). Thus, administration of $CB_2$ receptor modulators may represent a novel approach for the treatment of inflammation and disorders of the gastrointestinal tract including but not limited to inflammatory bowel disease, irritable bowel syndrome, secretory diarrhea, ulcerative colitis, Crohn's disease and gastroesophageal reflux disease (GERD).

Hepatic fibrosis occurs as a response to chronic liver injury and ultimately leads to cirrhosis, which is a major worldwide health issue due to the severe accompanying complications of portal hypertension, liver failure, and hepatocellular carcinoma (Lotersztajn, S., et al., Annu. Rev. Pharmacol. Toxicol., 2005, 45, 605-628). Although $CB_2$ receptors were not detectable in normal human liver, $CB_2$ receptors were expressed liver biopsy specimens from patients with cirrhosis. Activation of $CB_2$ receptors in cultured hepatic myofibroblasts produced potent antifibrogenic effects (Julien, B., et al., Gastroenterology, 2005, 128, 742-755). In addition, $CB_2$ knockout mice developed enhanced liver fibrosis after chronic administration of carbon tetrachloride relative to wild-type mice. Administration of $CB_2$ receptor modulators may represent a unique approach for the treatment of liver fibrosis.

Cough is a dominant and persistent symptom of many inflammatory lung diseases, including asthma, chronic obstructive pulmonary disease, viral infections, and pulmonary fibrosis (Patel, H. J., et al., Brit. J. Pharmacol., 2003, 140, 261-268). Recent studies have provided evidence for the existence of neuronal $CB_2$ receptors in the airways, and have demonstrated a role for $CB_2$ receptor activation in cough suppression (Patel, H. J., et al., Brit. J. Pharmacol., 2003, 140, 261-268 and Yoshihara, S., et al., Am. J. Respir. Crit. Care Med., 2004, 170, 941-946). Both exogenous and endogenous cannabinoid ligands inhibit the activation of C-fibers via $CB_2$ receptors and reduce neurogenic inflammatory reactions in airway tissues (Yoshihara, S., et al., J. Pharmacol. Sci. 2005, 98(1), 77-82; Yoshihara, S., et al., Allergy and Immunology, 2005, 138, 80-87). Thus, $CB_2$-selective modulators may have utility as antitussive agents for the treatment of pulmonary inflammation, chronic cough, and a variety of airway inflammatory diseases including but not limited to asthma, chronic obstructive pulmonary disease, and pulmonary fibrosis.

There is a substantial genetic contribution to bone mass density and the $CB_2$ receptor gene is associated with human osteoporosis (Karsak, M., et al., Human Molecular Genetics, 2005, 14(22), 3389-3396). Osteoclasts and osteoblasts are largely responsible for maintaining bone structure and function through a process called remodeling, which involves resorption and synthesis of bone (Boyle, W. J., et al., Nature, 2003, 423, 337-342). $CB_2$ receptor expression has been detected on osteoclasts and osteoblastic precursor cells, and administration of a $CB_2$ agonist in mice caused a dose-dependent increase in bone formation (Grotenhermen, F. and Muller-Vahl, K., Expert Opin. Pharmacother., 2003, 4(12), 2367-2371). Cannabinoid inverse agonists, including the $CB_2$-selective inverse agonist SR144528, have been shown to inhibit osteoclast activity and reverse ovariectomy-induced bone loss in mice, which is a model for post-menopausal osteoporosis (Ralston, S. H., et al., Nature Medicine, 2005, 11, 774-779). Thus, $CB_2$ modulators may be useful for the treatment and prevention of osteoporosis, osteoarthritis, and bone disorders.

Artherosclerosis is a chronic inflammatory disease and is a leading cause of heart disease and stroke. $CB_2$ receptors have been detected in both human and mouse atherosclerotic plaques. Administration of low doses of THC in apolipoprotein E knockout mice slowed the progression of atherosclerotic lesions, and these effects were inhibited by the $CB_2$-selective antagonist SR144528 (Steffens, S., et al., Nature, 2005, 434, 782-786). Thus, compounds with activity at the $CB_2$ receptor may be clinically useful for the treatment of atheroscelorsis.

$CB_2$ receptors are expressed on malignant cells of the immune system and targeting $CB_2$ receptors to induce apoptosis may constitute a novel approach to treating malignancies of the immune system. Selective $CB_2$ agonists induce regression of malignant gliomas (Sanchez, C., et al., Cancer Res., 2001, 61, 5784-5789), skin carcinomas (Casanova, M. L., et al., J. Clin. Invest., 2003, 111, 43-50), and lymphomas (McKallip, R. J., et al., Blood, 2002, 15(2), 637-634). Thus, $CB_2$ modulators may have utility as anticancer agents against tumors of immune origin.

Activation of $CB_2$ receptors has been demonstrated to protect the heart against the deleterious effects of ischemia and reperfusion (Lepicier, P., et al., Brit. J. Pharm. 2003, 139, 805-815; Bouchard, J.-F., et al., Life Sci. 2003, 72, 1859-1870; Filippo, C. D., et al., J. Leukoc. Biol. 2004, 75, 453-459). Thus, $CB_2$ modulators may have utility for the treatment or prophylaxis of cardiovascular disease and the development of myocardial infarction.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

Compounds of the invention can also be administered as a pharmaceutical composition comprising the compounds of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or other animal range from about 0.1 mg/kg body weight to about 100 mg/kg body weight. More preferable doses can be in the range of from about 0.3 mg/kg body weight to about 30 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise compounds of the present invention or a pharmaceutically acceptable salt or solvate thereof. The pharmaceutical compositions comprise compounds of the present invention that may be formulated together with one or more non-toxic pharmaceutically acceptable carriers.

Another aspect of the present invention is a pharmaceutical composition comprising a compound of the invention, or a pharmaceutically acceptable salt thereof, and one or more pharmaceutically acceptable carriers, alone or in combination with one or more nonsteroidal anti-inflammatory drug (NSAID).

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form.

Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in soft and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Compositions for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present invention can be used in the form of pharmaceutically acceptable salts derived from inorganic or organic acids. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66: 1 et seq). The salts can be prepared in situ during the final isolation and purification of the compounds of the invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-naphthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use.

The present invention contemplates compounds of the invention formed by synthetic means or formed by in vivo biotransformation of a prodrug.

The compounds of the invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds by metabolic processes includes those occurring in the human or animal body (in vivo) or processes occurring in vitro.

The compounds of the invention may be prepared by a variety of processes well known for the preparation of compounds of this class. For example, the compounds of the invention wherein the groups A, $L_2$, n, $R_1$, $R_2$, $R_3$, $R_4$, $R_{m1}$, $R_{z1}$, $R_{z2}$, $R_{j1}$, $R_{k1}$, $Z_3$, and $Z_4$, have the meanings as set forth in the summary and the definition sections unless otherwise noted, can be synthesized as shown in Schemes 1-18.

As used in the descriptions of the schemes and the examples, certain abbreviations are intended to have the following meanings: Ac for acetyl, dba for dibenzylideneacetone, DBU for 1,8-diazabicyclo[5.4.0]undec-7-ene, DMAP for 4-(dimethylamino)pyridine, DME for dimethoxyethane; DMF for N,N-dimethylformamide, DMSO for dimethyl sulfoxide, Et for ethyl, EDCI for 1-(3-dimethylaminopropyl)-3-ethylcarbodiimide hydrochloride, Et for ethyl; $Et_2O$ for diethyl ether; EtOAc for ethyl acetate, EtOH for ethanol; HOBt for 1-hydroxybenzotriazole hydrate, $Et_3N$ for triethyl amine; LDA for lithium diisopropylamide; MeCN for acetonitrile; MeOH for methanol; OMs or mesylate (or mesyl) for methanesulfonate, and OTs or tosylate (or tosyl) for p-toluenesulfonate; $PdCl_2(dppf)CH_2Cl_2$ for [1,1'-bis(diphenylphosphino)ferrocene]dichloropalladium(II) complex with methylene chloride; TFA for trifluoroacetic acid; and THF for tetrahydrofuran.

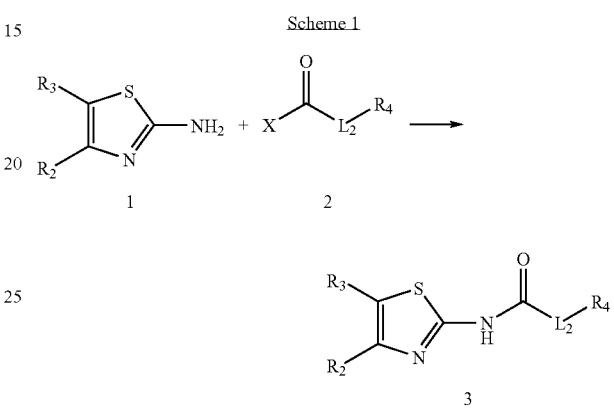

Scheme 1

Compounds of formula 1, which may be obtained from commercially sources or may be made according to the Schemes and procedures described within or according to procedures known in the literature, when treated with compounds of formula 2, wherein X is chloro or —OH, provide compounds of formula 3. Typical conditions for the reaction when compounds of formula 2 containing an X group that is chloro, and compounds of formula 1 include, but are not limited to, stirring about equimolar amount of each compound in a solvent such as chloroform, dichloromethane, or THF. The reaction is generally conducted in the presence of a base such as, but not limited to, diisopropylethylamine, at about 0-30° C. for about 8-24 hours. Typical conditions for the reaction of compounds of formula 2 wherein X group that is —OH, and compounds of formula 1, include stirring an equimolar mixture of the compounds in the presence of an acid coupling reagent, a coupling auxiliary and a base in a solvent such as but not limited to, THF, N,N-dimethylacetamide, N,N-dimethylformamide, pyridine, or chloroform. Typical acid coupling reagents include but are not limited to bis(2-oxo-3-oxazolidinyl)phosphinic chloride (BOPCl), 1,3-dicyclohexylcarbodiimide (DCC), polymer supported 1,3-dicyclohexylcarbodiimide (PS-DCC), O-(7-azabenzotriazol-1-yl)-N,N,N',N'-tetramethyluronium hexafluorophosphate (HATU), O-benzotriazol-1-yl-N,N,N',N'-tetramethyluronium tetrafluoroborate (TBTU). Typical coupling auxiliaries include but are not limited to 1-hydroxy-7-azabenzotriazole (HOAT) or 1-hydroxybenzotriazole hydrate (HOBT). Examples of the bases suitable for these reactions include, but are not limited to, N-methyl morpholine, diisopropylethylamine. Typical reactions can be carried out between about 0-65° C. or may be carried out in a microwave reactor to facilitate the coupling.

Scheme 2

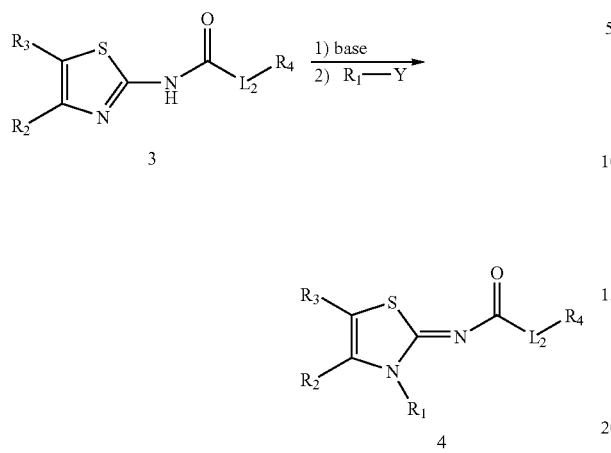

As shown in Scheme 2, compounds of formula 3 may be converted into compounds of formula 4, by treating with sodium hydride in DMF at about 0° C., followed by the addition of reagents of formula $R_1$—Y wherein Y is chloro, bromo, iodo, mesyl, triflate or tosyl. Alternatively, compounds of formula 3 can be treated with a base such as potassium hydroxide or potassium tert-butoxide in a mixture of THF and DMF, followed by treatment with $R_1$—Y to provide compounds of formula 4.

Scheme 3

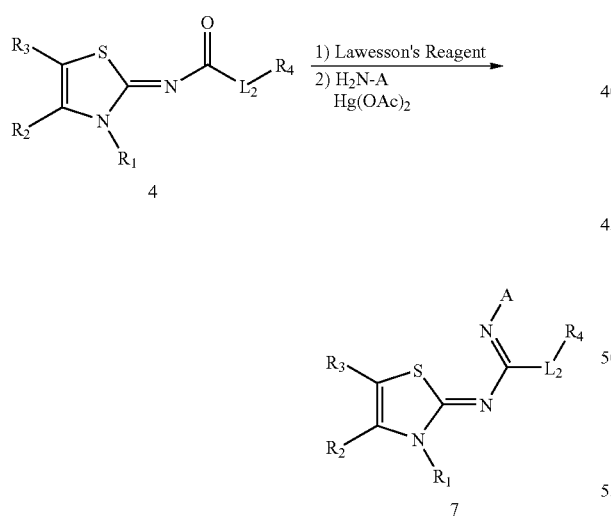

As outlined in Scheme 3, compounds of formula 4 when treated with Lawesson's reagent [19172-47-5] in toluene, and the mixture heated at temperatures ranging from about 60° C. to about 85° C., followed by treatment with mercury (II) acetate (or other similar mercury reagents), compounds of formula A-NH$_2$, and a base such as but not limited to triethylamine or diisopropylethylamine, and in a solvent such dioxane or acetonitrile, provide compounds of formula 7.

Scheme 4

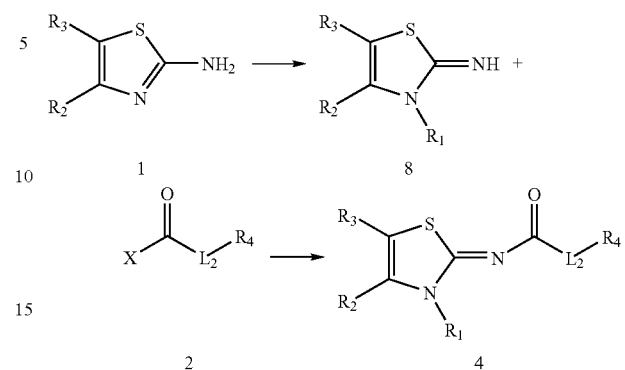

Alternatively, compounds of formula 4 may also be prepared according to the methods outlined in Scheme 4. Compounds of formula 1 when treated with sodium hydride in DMF at 0° C., followed by the addition of reagents such as $R_1$—Y, wherein Y is chloro, bromo, iodo, tosyl, mesyl or triflate to provide compounds of formula 8. Alternatively, compounds of formula 1 may be heated neat or in the presence of a minimal amount of solvent to facilitate mixing with compounds of formula $R_1$—Y to obtain compounds of formula 8. Compounds of formula 8 may be isolated as a salt or a free base. The treatment of compounds of formula 8 with compounds of formula 2, wherein X is chloro or —OH, under conditions according to that outlined in Scheme 1, generate compounds of formula 4.

Scheme 5

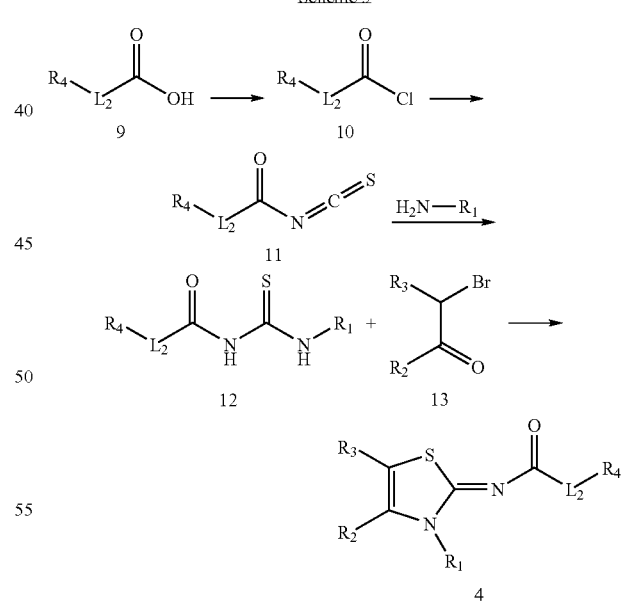

Compounds of formula (4) may also be prepared from the synthetic pathway outlined in Scheme 5. Compounds of formula 9 when treated with oxalyl chloride in dichloromethane containing a catalytic amount of DMF provide the acid chlorides of formula 10. The acid chlorides of formula 10 when treated with potassium thiocyanate in acetone provide compounds of formula 11. Compounds of formula 11 when treated with an amine of formula $R_1$—$NH_2$ in solvents such as, but not limited to, THF provide compounds of formula 12. Compounds of formula 12 when treated with substituted alpha-bromo-ketones of formula 13 in ethanol or mixtures of ethanol and toluene under heated conditions provide compounds of formula 4.

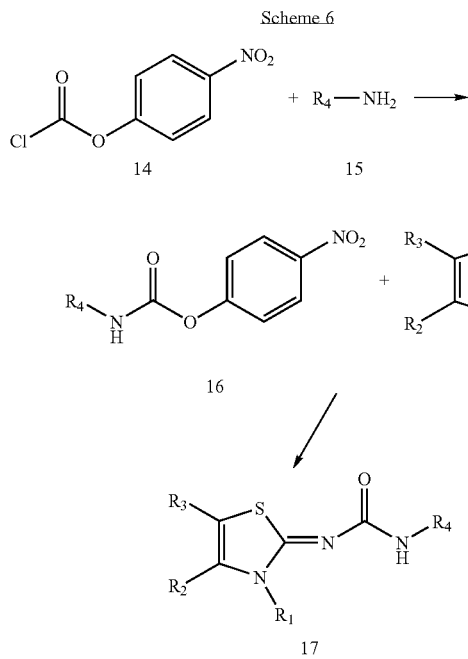

Compounds of formula 4 wherein $L_2$ is —NH—, may be prepared as outlined in Scheme 6. Compounds of formula 14 when treated with an amine of formula 15, provide compounds of formula 16. Compounds of formula 16 when treated with compounds of formula 8 provide compounds of formula 17.

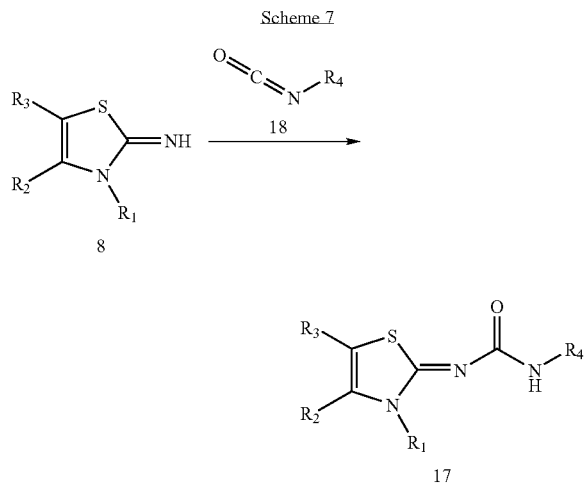

Alternatively, compounds of formula 17 may be prepared by treating compounds of formula 8 with an isocyanate of formula 18.

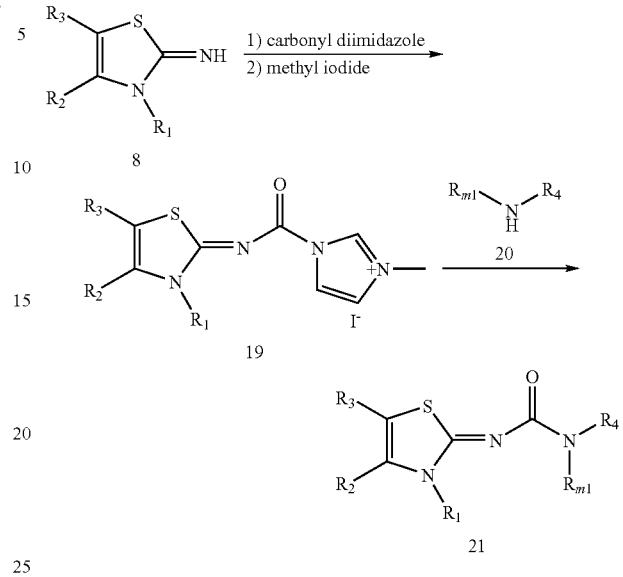

Another general synthetic method for the preparation of compounds of formula 4 wherein $L_2$ is $NR_{m1}$ is shown in Scheme 8. Compounds of formula 8 when treated with carbonyl diimidazole, followed by treatment with methyl iodide, provide the imidazolide compounds of formula 19. Compounds of formula 19 when treated with amines of formula 20, provide compounds of formula 21.

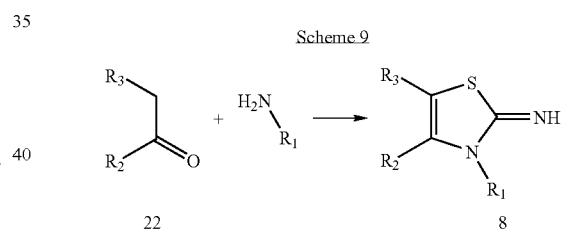

Compounds of formula 8 may be prepared according to the sequence outlined in Scheme 9. Carbonyl compounds 22 can be reacted at room temperature with amino compounds of formula $R_1$—$NH_2$ in a solvent such as, but not limited to, acetonitrile, tetrahydrofuran or methylene chloride for about 1-24 hours in the presence of a dehydrating agent such as, but not limited to, 4 Å molecular sieves, followed by the addition of potassium thiocyanate and iodine with heating to about 50° C. for about 4-24 hours to provide compounds of formula 8.

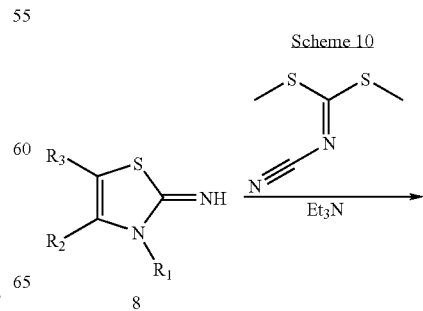

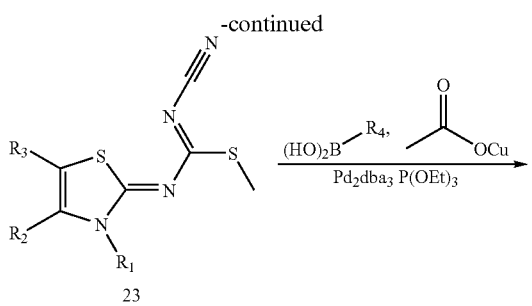

Compounds of formula (I) wherein A is CN and $L_2$ is a bond can be prepared according to the method outlined in Scheme 10. Reaction of compounds of formula 8 with commercially available dimethyl N-cyanodithioiminocarbonate in an aprotic solvents, like THF, dioxane, acetonitrile, etc. in the presence of base, like triethylamine, N-methylmorpholine, NaH, etc. at temperatures ranging from about room temperature to about 50° C. for about 8-24 hours affords the intermediates 23. The intermediates 23 were treated with a boronic acid $(HO)_2B$—$R_4$ in the presence of copper carboxylates (like commercially available copper acetate or copper 2-thiophenecarboxylate), a trialkylphosphite (e.g., triethylphosphite) and tris(dibenzylideneacetone)dipalladium(0) or other selected Pd(0) catalysts, in dimethoxyethane (or other aprotic solvents) at about 80-100° C. for about 12-24 hours to give the products of formula 24.

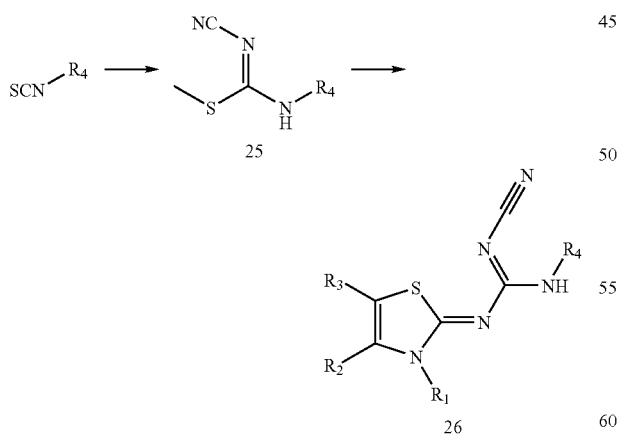

Compounds of formula (I) wherein A is CN and $L_2$ is NH, can be prepared using the general method shown in Scheme 11. The isothiocyanate of formula $R_4$—NCS can be reacted with sodium cyanamide in a solvent such as DMF at temperatures from about room temperature to about 50° C., followed by addition of iodomethane at temperatures from about 0° C. to about room temperature and further allowing the reaction to proceed at room temperature to provide the intermediates 25. This intermediate, in turn, can be converted to compounds of formula 26 by reaction with an imine of general formula 8, in the presence of mercuric acetate, in a solvent such as, but not limited to, tetrahydrofuran or dimethylformamide at temperatures from about room temperature to about 100° C.

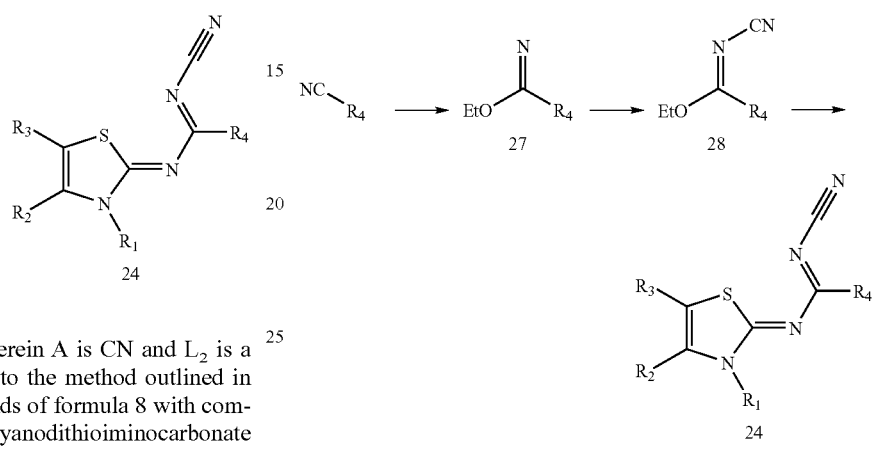

Compounds of general formula (I) wherein $L_2$ is a bond and A is CN, can be prepared using the general method shown in Scheme 12. The nitrile of formula $R_4$—CN can be reacted with an alcohol (e.g., methanol or ethanol) and HCl in a solvent such as dichloromethane at about 0° C. to about room temperature to form the intermediate iminoethers 27. The iminoethers 27 in a solvent such as acetonitrile can be treated with a solution of sodium phosphate monobasic monohydrate, sodium phosphate dibasic heptahydrate and cyanamide in water at about room temperature for about 12-24 hours to produce the intermediate cyanoiminoethers 28. The cyanoiminoethers 28 can be reacted with compounds of formula 8 either neat or in a solvent such as toluene, tetrahydrofuran, acetonitrile or dimethylformamide, at temperatures from about room temperature to about 100° C. for 8-24 hours to produce compounds of general formula 24.

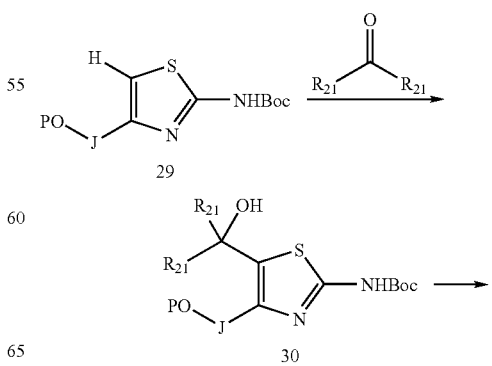

-continued

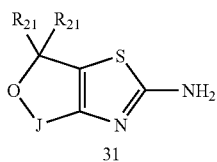

31

Thiazoles of formula 31 wherein J is alkylene or substituted alkylene can be prepared using the 2 steps method as illustrated in Scheme 13. Thiazoles of formula 29 wherein the P is an oxygen protecting group such as, but not limited to, tetrahydropyranyl, t-butyldimethylsilyl, triisopropylsilyl, or methoxymethyl, can be converted to compounds of formula 30 by (a) reacting with excess (at least 2 equivalents) lithium diisopropylamide in a solvent such as tetrahydrofuran or diethyl ether; and (b) treating the intermediate obtained from step (a) with an appropriate aldehyde ($R_{21}$CHO) or ketone of formula $R_{21}C(O)R_{21}$, wherein each $R_{21}$ can be the same or different, and are independently alkyl and haloalkyl; or together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl. Treatment of 30 with an acid such as, but not limited to, hydrochloric acid at a temperature from about room temperature to about 100° C. removes the nitrogen and oxygen protecting groups and leads to the cyclization of the intermediates formed, providing thiazoles of formula 31. Alternatively, 30 can be converted to 31 by a stepwise reaction wherein the oxygen protecting group is first removed, followed by activation of the oxygen as the corresponding halide or mesylate prior to cyclization. Another alternative would be to conduct the cyclization using Mitsunobu or with dicyclohexylcarbodiimide conditions that are well known to those skilled in the art.

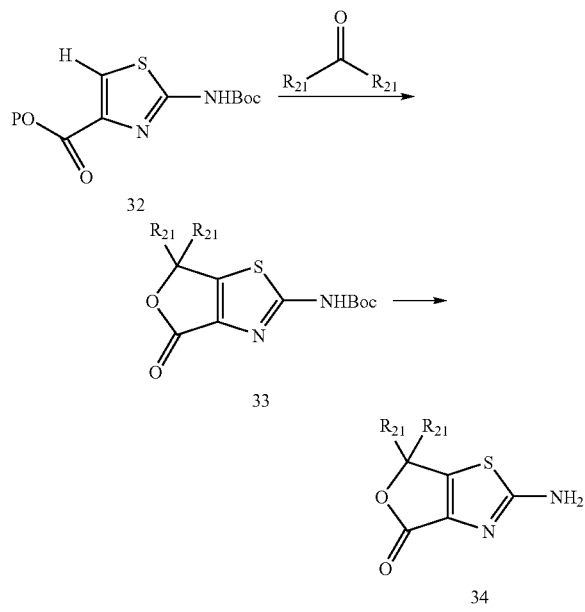

Thiazole intermediates of formula 34 can be prepared using the 2-step method illustrated in Scheme 14. Thiazoles of formula 32 wherein P is alkyl, benzyl, or allyl can be reacted with excess (at least 2 equivalents) lithium diisopropylamide in a solvent such as tetrahydrofuran or diethyl ether, followed by reaction with an appropriate aldehyde ($R_{21}$CHO) or ketone of formula $R_{21}C(O)R_{21}$ (wherein each $R_{21}$ can be the same or different, and are independently alkyl and haloalkyl; or together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl), to generate intermediates of formula 33. Deprotection of this intermediate with an acid such as but not limited to hydrochloric acid or trifluoroacetic acid at about room temperature provides thiazoles of formula 34.

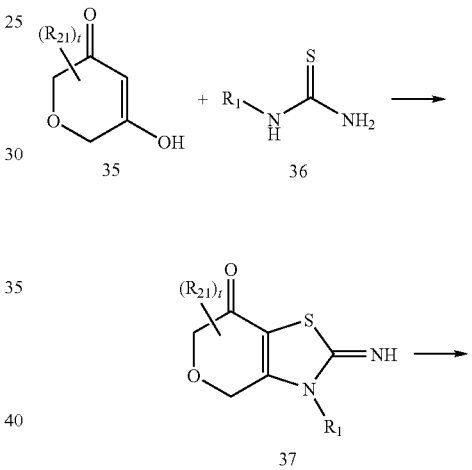

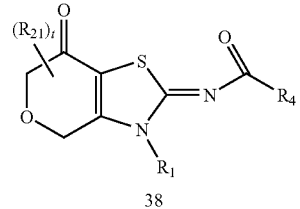

5-Hydroxy-2H-pyran-3(6H)-ones of formula 35 or the corresponding salts, (e.g., sodium salts) wherein $R_{21}$ is alkyl, halo, hydroxy, alkoxy, or haloalkyl, and t is 0, 1, 2, or 3 or the corresponding salts such as sodium salt, can be treated with thioureas of formula 36, in the presence of DMSO/hydrochloric acid, at a temperature ranging from about room temperature to about 120° C., to provide compounds of formula 37. The reaction can be conducted in a solvent such as, but not limited to, dioxane or tetrahydrofuran, or mixture thereof. Conversion of 37 to 38 can be accomplished using reaction conditions as described in Scheme 4.

Scheme 16

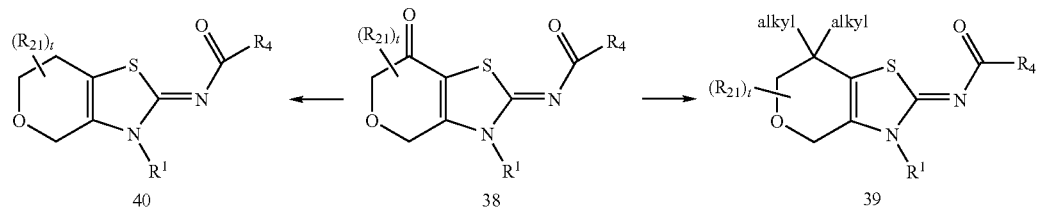

Compounds of formula 38 wherein $R_{21}$ and t are as disclosed in Scheme 15, can be treated with titanium tetrachloride and dialkylzinc to provide compounds of formula 39. The conversion can be conducted in a solvent, for example, in dichloromethane, and at a temperature ranging from about 0° C. to about 50° C. Compounds of formula 38 when treated with triethylsilane and trifluoroacetic acid, at a temperature from about room temperature to about 120° C., provide compounds of formula 40.

Scheme 17

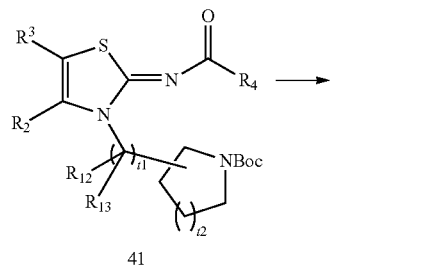

41

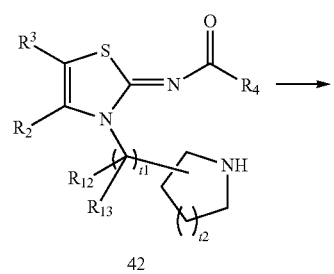

42

-continued

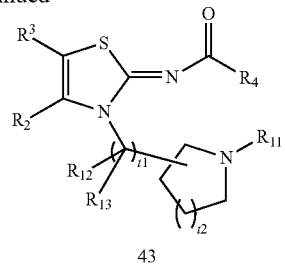

43

Amine compounds of formulae 42 and 43 wherein t1 is 1, 2, 3, or 4; t2 is 0, 1, 2, or 3; $R_{11}$ is alkyl, haloalkyl, alkoxyalkyl, cyanoalkyl, alkylsulfonyl, cycloalkylsulfonyl, $C(O)NZ_3Z_4$, alkylcarbonyl, alkoxycarbonyl or alkylcarbonylalkyl; $R_{12}$ and $R_{13}$ are each independently hydrogen or alkyl can be prepared according to the sequence outlined in Scheme 17. Compounds 41, prepared by the methods outlined herein above, can be converted to compounds 42 by treatment with an acid such as, but not limited to, trifluoroacetic acid or hydrochloric acid, in a solvent such as but not limited to methylene chloride at temperatures from about 0° C. to about room temperature. Amine compounds 42 can be converted to amine compounds 43 wherein $R_{11}$ is alkyl by reactions known in the art. For example, the conversion can be achieved via reductive amination reaction with an aldehyde or ketone in the presence of a reducing agent such as sodium triacetoxyhydroborate or sodium cyanoborohydride, in a solvent such as acetonitrile. When treated with reagents of formula $ClSO_2R_{14}$ ($R_{14}$ is alkyl or cycloalkyl) in a solvent such as, but not limited to, tetrahydrofuran or methylene chloride, and in the presence of a base such as triethylamine, diisopropylethylamine, or DBU, at temperatures from about 0° C. to about room temperature, compound 42 can be transformed into compounds 43 wherein $R_{11}$ is $SO_2R_{14}$.

Scheme 18

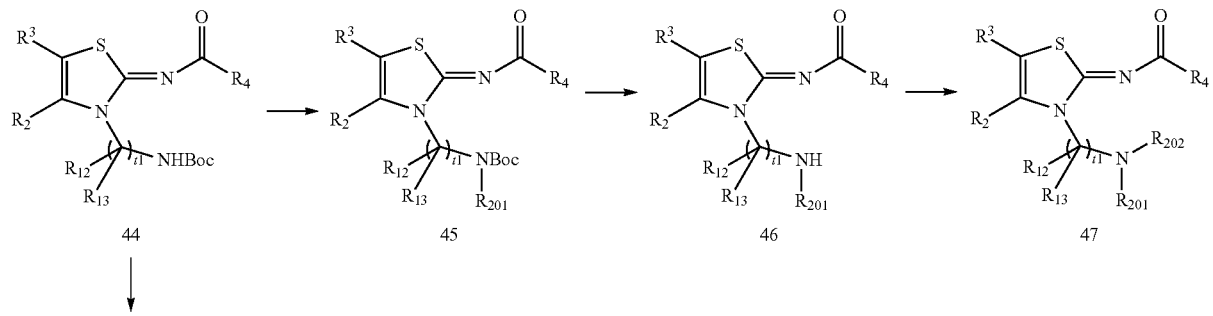

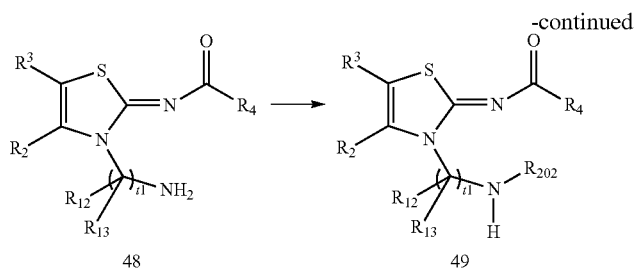

Compounds of formula 46, 47, 48, and 49 may be prepared according to the sequences outlined in Scheme 18. Compounds 44 can be converted to compounds 45 by reaction with a reagent $R_{201}$—$X_{201}$, wherein $R_{201}$ is $R_{z2}$ or $R_{m1}$, provided that $R_{z2}$ and $R_{m1}$ are not hydrogen, and $X_{201}$ is Cl, Br, I, OTs, or OMs, in a solvent such as, but not limited to, tetrahydrofuran, or dimethylformamide, and in the presence of a base such as, but not limited to, sodium hydride, potassium carbonate, or potassium tert-butoxide. Compounds 45 can be transformed to compounds 46 by treatment with an acid such as, but not limited to, trifluoroacetic acid or hydrochloric acid, in solvents such as, but not limited to, methylene chloride at temperatures ranging from about 0° C. to about room temperature.

Compounds 44 can be transformed to compounds 48 by removal of the Boc protecting group using similar conditions to those described for the conversion of compounds 45 to compounds 46.

Compounds 46 and 48 can be converted to compounds 47 and 49 wherein $R_{202}$ is —$SO_2R_{14}$ ($R_{14}$ is alkyl or cycloalkyl), respectively, by treatment with reagents $ClSO_2R_{14}$ in solvents such as, but not limited to, tetrahydrofuran or methylene chloride in the presence of a base such as triethylamine, diisopropylethylamine, or DBU, at temperatures ranging from about 0° C. to about room temperature.

Similarly, compounds 46 and 48 can be converted to compounds 47 and 49 wherein $R_{202}$ is —$COR_{14}$ or —$CONR_{j1}R_{k1}$, respectively, by reacting with reagents such as $ClCOR_{14}$, $ClCONR_{j1}R_{k1}$, or O=C=$NR_{j1}$.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which may be found in T. Greene and P. Wuts, Protecting Groups in Chemical Synthesis ($3^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

Following Examples may be used for illustrative purposes and should not be deemed to narrow the scope of the invention.

g. Examples

Example 1

N-[(2Z)-3-butyl-4,5-dimethyl-1,3-thiazol-2(3H)-ylidene]-5-chloro-2-methoxybenzenecarbothioamide Example 1A 3-butyl-4,5-dimethyl-1,3-thiazol-2(3H)-imine hydroiodide A mixture of 2-amino-4,5-dimethylthiazole (2.56 g, 20 mmol) and iodobutane (2.6 mL, 22 mmol) in toluene (20 mL) was refluxed at 80° C. for 48 hours. The mixture was cooled to room temperature and the precipitated solid was filtered, washed with toluene and dried under reduced pressure to provide 2.7 g of crude product as the hydroiodide salt; MS (ESI+) m/z 185 (M+H)$^+$.

Example 1B

N-[(2Z)-3-butyl-4,5-dimethyl-1,3-thiazol-2(3H)-ylidene]-5-chloro-2-methoxybenzamide To a solution of Example 1A (312 mg, 1 mmol) and triethylamine (0.42 mL, 3 mmol) in CH$_2$Cl$_2$ (15 mL) at 0° C. was added 5-chloro-2-methoxybenzoyl chloride (Waterstone, 205 mg, 1 mmol), the mixture was allowed to warm to room temperature and was stirred for 14 hours. The solution was washed sequentially with water, brine, dried with anhydrous MgSO$_4$, filtered and concentrated under reduced pressure. The residue was purified by column chromatography to afford the title compound. $^1$H NMR (300 MHz, DMSO-d$_6$) δ: 0.93 (t, J=7 Hz, 3H), 1.35 (sextet, J=7 Hz, 2H), 1.68 (quintet, J=7 Hz, 2H), 2.21 (s, 3H), 2.26 (s, 3H), 3.78 (s, 3H), 4.26 (t, J=7 Hz, 2H), 7.10 (d, J=9 Hz, 1H), 7.44 (d-d, J=9 Hz, 3 Hz, 1H), 7.70 (d, J=3 Hz, 1H); MS (ESI+) m/z 353 (M+H)$^+$.

Example 1C

N-[(2Z)-3-butyl-4,5-dimethyl-1,3-thiazol-2(3H)-ylidene]-5-chloro-2-methoxybenzenecarbothioamide To a solution of Example 1B (342 mg, 1 mmol) in toluene (15 mL) was added Lawesson's reagent (404 mg, 1 mmol) and the reaction mixture was refluxed at 80° C. for 45 min. After cooling to room temperature, the mixture was diluted with EtOAc, washed with 10% solution of sodium bicarbonate, brine and dried with anhydrous MgSO$_4$. Purification by column chromatography (1:1 Hexane-EtOAc) provided 350 mg (95%) of the desired thioamide. $^1$H NMR (300 MHz, DMSO-d$_6$) δ: 0.88 (t, J=7 Hz, 3H), 1.30 (sextet, J=7 Hz, 2H), 1.68 (quintet, J=7 Hz, 2H), 2.30 (s, 3H), 2.35 (s, 3H), 3.74 (s, 3H), 4.26 (t, J=7 Hz, 2H), 7.05 (d, J=9 Hz, 1H), 7.33 (d-d, J=9 Hz, 3 Hz, 1H), 7.39 (d, J=3 Hz, 1H); MS (ESI+) m/z 369 (M+H)$^+$. Anal. calcd for C$_{17}$H$_{21}$ClN$_2$OS$_2$.0.25H$_2$O: C, 54.68; H, 5.62; N, 7.18. Found: C, 54.68; H, 5.80; N, 7.50.

Example 2

N-[(2Z)-3-butyl-4,5-dimethyl-1,3-thiazol-2(3H)-ylidene]-5-chloro-2-methoxybenzenecarboximidamide Example 1C (55 mg, 0.15 mmol) in dioxane (10 mL) was treated with concentrated NH$_4$OH (1 mL) and Hg(OAc)$_2$ (64 mg, 0.2 mmol) and the resulting mixture was refluxed at 80° C. for 1 hour. The mixture was then concentrated under reduced pressure, the residue was dissolved in CH$_2$Cl$_2$, dried with anhydrous MgSO$_4$, filtered and concentrated under reduced pressure. Purification by column chromatography (9:1 CH$_2$Cl$_2$-MeOH) afforded the title compound. $^1$H NMR (300 MHz, DMSO-d$_6$) δ: 0.96 (t, J=7 Hz, 3H), 1.38 (sextet, J=7 Hz, 2H), 1.68 (m, 2H), 2.13 (s, 3H), 2.35 (s, 3H), 3.73 (s, 3H), 4.25 (t, J=7 Hz, 2H), 7.23 (d, J=9 Hz, 1H), 7.58 (m, 1H), 7.70 (d-d, J=9 Hz, 3 Hz, 1H), 9.36 (broad s, 1H), 9.50 (broad s, 1H); MS (ESI+) m/z 352 (M+H)$^+$. Anal. calcd for C$_{17}$H$_{23}$Cl$_2$N$_3$OS.0.3H$_2$O: C, 51.86; H, 6.04; N, 10.67. Found: C, 51.59; H, 6.16; N, 10.82.

Example 3

N-[(2Z)-3-butyl-4,5-dimethyl-1,3-thiazol-2(3H)-ylidene]-5-chloro-2-methoxy-N'-methylbenzenecarboximidamide Example 1C (37 mg, 0.1 mmol) in dioxane (25 mL) was treated with N-methylamine hydrochloride (13 mg, 2 mmol), triethylamine (0.28 mL, 2 mmol) and Hg(OAc)$_2$ (32 mg, 0.1 mmol) and the resulting mixture was refluxed at 80° C. for 4 hours. The mixture was concentrated under reduced pressure and the residue was dissolved in CH$_2$Cl$_2$, dried with anhydrous MgSO$_4$, filtered and concentrated under reduced pressure. Purification by column chromatography (9:1 CH$_2$Cl$_2$-MeOH) afforded the title compound. $^1$H NMR (300 MHz, DMSO-d$_6$) δ: 0.97 (t, J=7 Hz, 3H), 1.40 (sextet, J=7 Hz, 2H), 1.71 (m, 2H), 2.13 (s, 3H), 2.37 (s, 3H), 3.07 (s, 3H), 3.71 (s, 3H), 4.22 (t, J=7 Hz, 2H), 7.24 (d, J=9 Hz, 1H), 7.53 (d, J=3 Hz, 1H), 7.71 (d-d, J=9 Hz, 3 Hz, 1H), 9.90 (broad s, 1H); MS (ESI+) m/z 366 (M+H)$^+$. Anal. calcd for C$_{18}$H$_{25}$Cl$_2$N$_3$OS.1.25H$_2$O: C, 50.88; H, 6.52; N, 9.89. Found: C, 50.95; H, 6.51; N, 9.58.

Example 4

N-[(2Z)-3-butyl-4,5-dimethyl-1,3-thiazol-2(3H)-ylidene]-5-chloro-N',2-dimethoxybenzenecarboximidamide The desired material was prepared in 71% yield according to the procedure described in Example 3 substituting N-methoxyamine hydrochloride for N-methylamine hydrochloride. $^1$H NMR (300 MHz, DMSO-d$_6$) δ: 0.85 (t, J=7 Hz, 3H), 1.23 (sextet, J=7 Hz, 2H), 1.55 (m, 2H), 2.15 (s, 6H), 3.67 (s, 3H), 3.72 (s, 3H), 3.90 (t, J=7 Hz, 2H), 7.07 (m, 2H), 7.36 (d-d, J=9 Hz, 3 Hz, 1H); MS (ESI+) m/z 382 (M+H)$^+$. Anal. calcd for C$_{18}$H$_{21}$ClN$_3$O$_2$S.0.8H$_2$O: C, 54.55; H, 6.51; N, 10.60. Found: C, 54.24; H, 5.90; N, 10.31.

Example 5

N-[(2Z)-3-butyl-4,5-dimethyl-1,3-thiazol-2(3H)-ylidene]-5-chloro-N'-cyano-2-methoxybenzenecarboximidamide The desired material was prepared according to the procedure described in Example 3 substituting cyanamide for N-methylamine hydrochloride. $^1$H NMR (300 MHz, DMSO-d$_6$) δ: 0.88 (t, J=7 Hz, 3H), 1.27 (sextet, J=7 Hz, 2H), 1.65 (m, 2H), 2.30 (s, 6H), 3.81 (s, 3H), 4.21 (t, J=7 Hz, 2H), 7.20 (d, J=9 Hz, 1H), 7.36 (d, J=3 Hz, 1H), 7.51 (d-d, J=9 Hz, 3 Hz, 1H); MS (ESI+) m/z 377 (M+H)$^+$. Anal. calcd for C$_{18}$H$_{21}$ClN$_4$OS: C, 57.36; H, 5.62; N, 14.86. Found: C, 57.56; H, 5.90; N, 13.76.

Example 6

N-[(2Z)-3-butyl-5-tert-butyl-1,3-thiazol-2(3H)-ylidene]-5-chloro-2-methoxybenzenecarbothioamide

Example 6A 3-butyl-5-tert-butyl-1,3-thiazol-2(3H)-imine hydroiodide

A mixture of Example 74A (630 mg, 4 mmol) and iodobutane (1.14 mL, 10 mmol) in toluene (10 mL) was refluxed for 24 hours. The mixture was concentrated under reduced pressure to provide 1.4 g of the title compound. MS (ESI+) m/z 213 (M+H)$^+$.

Example 6B

N-[(2Z)-3-butyl-5-tert-butyl-1,3-thiazol-2(3H)-ylidene]-5-chloro-2-methoxybenzamide To a solution of Example 6A (1.4 g, ~4 mmol) and triethylamine (1.4 mL, 10 mmol) in $CH_2Cl_2$ (35 mL) at 0° C. was added 5-chloro-2-methoxy-benzoyl chloride (820 mg, 4 mmol), the mixture was allowed to warm to room temperature was stirred for 14 hours. The mixture was washed sequentially with water, brine, dried with anhydrous $MgSO_4$, filtered and concentrated under reduced pressure. The residue was purified by chromatography (6:2:2 Hexane-EtOAc-$CH_2Cl_2$) to provide the title compound. $^1$H NMR (300 MHz, DMSO-$d_6$) δ: 0.94 (t, J=7 Hz, 3H), 1.30 (m+s, 11H), 1.75 (m, 2H), 3.77 (s, 3H), 4.14 (t, J=7 Hz, 2H), 7.10 (d, J=9 Hz, 1H), 7.31 (s, 1H), 7.43 (d-d, J=9 Hz, 3 Hz, 1H), 7.65 (d, J=3 Hz, 1H); MS (ESI+) m/z 381 (M+H)$^+$.

Example 6C

N-[(2Z)-3-butyl-5-tert-butyl-1,3-thiazol-2(3H)-ylidene]-5-chloro-2-methoxybenzenecarbothioamide To a solution of Example 6B (1.4 g, 3.7 mmol) in toluene (50 mL) was added Lawesson's reagent (1.6 g, 4 mmol) and the mixture was refluxed at 80° C. for 30 minutes. After cooling to room temperature, the mixture was diluted with EtOAc, washed with 10% solution of bicarbonate, brine and dried with anhydrous $MgSO_4$, filtered and concentrated under reduced pressure. Purification by column chromatography (2:1 Hexane-EtOAc) provided the title compound. $^1$H NMR (300 MHz, DMSO-$d_6$) δ: 0.89 (t, J=7 Hz, 3H), 1.25 (sextet, J=7 Hz, 2H), 1.36 (s, 9H), 1.76 (m, 2H), 3.74 (s, 3H), 4.25 (t, J=7 Hz, 2H), 7.06 (d, J=9 Hz, 1H), 7.35 (m, 2H), 7.45 (s, 1H); MS (ESI+) m/z 397 (M+H)$^+$. Anal. calcd for $C_{19}H_{25}ClN_2OS_2$: C, 57.48; H, 6.35; N, 7.06. Found: C, 57.26; H, 6.17; N, 6.79.

Example 7

N-[(2Z)-3-butyl-5-tert-butyl-1,3-thiazol-2(3H)-ylidene]-5-chloro-N'-cyano-2-methoxybenzenecarboximidamide Example 6C (230 mg, 0.58 mmol) in acetonitrile (30 mL) was treated with cyanamide (52 mg, 1.2 mmol), triethylamine (0.22 mL, 1.6 mmol) and Hg(OAc)$_2$ (252 mg, 0.8 mmol) and the resulting mixture was refluxed at 80° C. for 45 minutes. The mixture was concentrated under reduced pressure and the residue was dissolved in $CH_2Cl_2$, dried with anhydrous $MgSO_4$, filtered and concentrated under reduced pressure. Purification by column chromatography (1:1 Hexane-EtOAc) afforded the title compound. $^1$H NMR (300 MHz, DMSO-$d_6$) δ: 0.88 (t, J=7 Hz, 3H), 1.27 (sextet, J=7 Hz, 2H), 1.35 (s, 9H), 1.73 (m, 2H), 2.30 (s, 6H), 3.81 (s, 3H), 4.20 (t, J=7 Hz, 2H), 7.20 (d, J=9 Hz, 1H), 7.35 (d, J=3 Hz, 1H), 7.50 (d-d, J=9 Hz, 3 Hz, 1H), 7.60 (s, 1H); MS (ESI+) m/z 405 (M+H). Anal. calcd for $C_{20}H_{25}ClN_4OS$: C, 59.32; H, 6.22; N, 13.84. Found: C, 59.35; H, 6.29; N, 13.71.

Example 8

N-[(2Z)-3-butyl-5-tert-butyl-1,3-thiazol-2(3H)-ylidene]-5-chloro-N',2-dimethoxybenzenecarboximidamide The title compound was prepared according to the procedure described in Example 7 by substituting N-methoxyamine hydrochloride for cyanamide. $^1$H NMR (300 MHz, DMSO-$d_6$) δ: 0.85 (t, J=7 Hz, 3H), 1.23 (sextet, J=7 Hz, 2H), 1.28 (s, 9H), 1.62 (m, 2H), 3.68 (s, 3H), 3.72 (s, 3H), 3.88 (t, J=7 Hz, 2H), 7.00 (s, 1H), 7.05 (m, 2H), 7.35 (d-d, J=9 Hz, 3 Hz, 1H); MS (ESI+) m/z 410 (M+H)$^+$.

Example 9

N-[(2Z)-3-butyl-4,5-dimethyl-1,3-thiazol-2(3H)-ylidene]-5-chloro-N'-ethoxy-2-methoxybenzenecarboximidamide The title compound was prepared according to the procedure described in Example 3 by substituting N-ethoxyamine hydrochloride for N-methylamine hydrochloride. $^1$H NMR (300 MHz, DMSO-$d_6$) δ: 0.85 (t, J=7 Hz, 3H), 1.18 (t, J=7 Hz, 3H), 1.23 (sextet, J=7 Hz, 2H), 1.56 (m, 2H), 2.17 (s, 6H), 3.73 (s, 3H), 3.92 (m, 4H), 7.05 (m, 2H), 7.35 (d-d, J=9 Hz, 3 Hz, 1H); MS (ESI+) m/z 396 (M+H). Anal. calcd for $C_{19}H_{26}ClN_3O_2S$: C, 57.64; H, 6.62; N, 10.61. Found: C, 57.94; H, 6.85; N, 10.11.

Example 10

N'-(allyloxy)-N-[(2Z)-3-butyl-4,5-dimethyl-1,3-thiazol-2(3H)-ylidene]-5-chloro-2-methoxybenzenecarboximidamide The title compound was prepared according to the procedure described in Example 3 by substituting N-allyloxyamine hydrochloride for N-methylamine hydrochloride. $^1$H NMR (300 MHz, DMSO-$d_6$) δ: 0.85 (t, J=7 Hz, 3H), 1.18 (t, J=7 Hz, 3H), 1.23 (sextet, J=7 Hz, 2H), 1.56 (m, 2H), 2.15 (s, 6H), 3.73 (s, 3H), 3.92 (t, J=7 Hz, 2H), 4.40 (m, 2H), 5.18 (m, 2H), 5.98 (m, 1H), 7.05 (m, 2H), 7.35 (d-d, J=9 Hz, 3 Hz, 1H); MS (ESI+) m/z 408 (M+H)$^+$.

Example 11 tert-butyl 2-[{[(2Z)-3-butyl-4,5-dimethyl-1,3-thiazol-2(3H)-ylidene]amino}(5-chloro-2-methoxyphenyl)methylene]hydrazinecarboxylate To the mixture of Example 1C (50 mg, 0.13 mmol), t-butyl carbazate (26 mg, 0.2 mmol) and Hg(OAc)$_2$ (90 mg, 0.3 mmol) in dioxane (10 mL) was added acetic acid (5 drops) and the mixture was heated at 40° C. for 1 hour. The mixture was concentrated under reduced pressure and the residue was dissolved in ethyl acetate. The mixture was then washed with saturated NaHCO$_3$, brine and dried with anhydrous MgSO$_4$, filtered and concentrated under reduced pressure. Column chromatography (EtOAc) provided the title compound as well as Example 12.

Example 11: $^1$H NMR (300 MHz, DMSO-d$_6$) δ: 0.93 (t, J=7 Hz, 3H), 1.36 (s+m, 11H), 1.66 (m, 2H), 2.21 (s, 3H), 2.25 (s, 3H), 3.78 (s, 3H), 4.15 (m, 2H), 7.10 (d, J=9 Hz, 1H), 7.44 (d-d, J=9 Hz, 3 Hz, 1H), 7.70 (d, J=3 Hz, 1H), 7.83 (broad s, 1H); MS (ESI+) m/z 467 (M+H)$^+$. Anal. calcd for C$_{22}$H$_{31}$ClN$_4$O$_3$S: C, 56.58; H, 6.69; N, 12.00. Found: C, 56.17; H, 6.86; N, 11.67.

Example 12 tert-butyl 2-[{[(2Z)-3-butyl-4,5-dimethyl-1,3-thiazol-2(3H)-ylidene]amino}(5-chloro-2-methoxyphenyl)methylene]hydrazinecarboxylate The title compound was obtained from chromatographic separation of Example 11. Example 12: $^1$H NMR (300 MHz, DMSO-d$_6$) δ: 0.99 (t, J=7 Hz, 3H), 1.41 (s+m, 11H), 1.63 (m, 2H), 1.95 (s, 3H), 2.08 (s, 3H), 3.66 (s, 3H), 3.95 (m, 2H), 7.05 (d, J=9 Hz, 1H), 7.23 (d-d, J=9 Hz, 3 Hz, 1H), 7.48 (d, J=3 Hz, 1H), 8.96 (broad s, 1H); MS (ESI+) m/z 467 (M+H)$^+$.

Example 13

N-[(2Z)-3-butyl-4,5-dimethyl-1,3-thiazol-2(3H)-ylidene]-5-chloro-2-methoxy-N'-(3-methylphenyl)benzenecarboximidamide The title compound was prepared according to the procedure described in Example 3 by substituting m-toluidine for N-methylamine hydrochloride. $^1$H NMR (300 MHz, DMSO-d$_6$) δ: 0.90 (t, J=7 Hz, 3H), 1.20 (sextet, J=7 Hz, 2H), 1.66 (m, 2H), 2.15 (2s, 6H), 2.22 (s, 3H), 3.42 (s, 3H), 4.08 (t, J=7 Hz, 2H), 6.30 (m, 1H), 6.47 (m, 1H), 6.62 (m, 1H), 6.85 (d, J=9 Hz, 1H), 6.91 (t, J=7 Hz, 1H), 7.16 (d, J=3 Hz, 1H), 7.25 (d-d, J=9 Hz, 3 Hz, 1H); MS (ESI+) m/z 442 (M+H)$^+$.

Example 14

N'-(tert-butoxy)-N-[(2Z)-3-butyl-4,5-dimethyl-1,3-thiazol-2(3H)-ylidene]-5-chloro-2-methoxybenzenecarboximidamide The title compound was prepared according to the procedure described in Example 3 by substituting N-t-butoxyamine hydrochloride for N-methylamine hydrochloride. $^1$H NMR (300 MHz, DMSO-d$_6$) δ: 0.86 (t, J=7 Hz, 3H), 1.23 (s+m, 11H), 1.58 (m, 2H), 2.14 (s, 6H), 3.71 (s, 3H), 3.88 (t, J=7 Hz, 2H), 7.05 (m, 2H), 7.33 (d-d, J=9 Hz, 3 Hz, 1H); MS (ESI+) m/z 424 (M+H)$^+$.

Example 15 tert-butyl 2-[{[(2Z)-3-butyl-5-tert-butyl-1,3-thiazol-2(3H)-ylidene]amino}(5-chloro-2-methoxyphenyl)methylene]hydrazinecarboxylate The title compound was prepared according to the procedure described in Example 7 by substituting t-butyl carbazate for cyanamide. $^1$H NMR (300 MHz, DMSO-d$_6$) δ: 0.97 (t, J=7 Hz, 3H), 1.06 (s, 9H), 1.36 (m, 2H), 1.43 (s, 9H), 1.69 (m, 2H), 3.63 (s, 3H), 3.91 (t, J=7 Hz, 2H), 6.93s, 1H), 7.06 (d, J=9 Hz, 1H), 7.27 (d, 3 Hz, 1H), 7.50 (d-d, J=9 Hz, 3 Hz, 1H), 8.97 (broad s, 1H); MS (DCI/NH$_3$) m/z 495 (M+H)$^+$. Anal. calcd for C$_{24}$H$_{35}$ClN$_4$O$_3$S: C, 58.23; H, 7.13; N, 11.32. Found: C, 57.94; H, 7.19; N, 10.98.

Example 16

N-[(2Z)-5-tert-butyl-3-isobutyl-1,3-thiazol-2(3H)-ylidene]-5-chloro-N'-cyano-2-methoxybenzenecarboximidamide Example 16A 5-tert-butyl-3-isobutylthiazol-2(3H)-imine Example 74A (1.6 g, 10 mmol) and 1-bromo-2-methylpropane (1.2 mL, 11 mmol) were combined and heated at 85° C. for 18 hours. Additional 1-bromo-2-methylpropane (2.2 mL, 20 mmol) was added and the mixture was stirred at 85° C. for an additional 24 hours. Additional 1-bromo-2-methylpropane (2.2 mL, 20 mmol) was added and the mixture was stirred for 24 hours at 85° C. The mixture was then cooled to ambient temperature, concentrated under reduced pressure and purified by column chromatography (SiO$_2$, 10% MeOH in EtOAc, then 9:1:0.1 CH$_2$Cl$_2$:MeOH:NH$_4$OH) to provide the title compound. MS (DCI/NH$_3$) m/z 213 (M+H)$^+$.

Example 16B 5-chloro-2-methoxybenzoyl chloride

A mixture of 5-chloro-2-methoxybenzoic acid (1.5 g, 8.2 mmol) and thionyl chloride (10 mL) was heated to reflux and allowed to stir for 2 hours. The mixture was then concentrated under reduced pressure. The crude material was dissolved in 10 mL toluene and concentrated under reduced pressure (3×) to give the title compound, which was used without purification.

Example 16C

N-[(2Z)-5-tert-butyl-3-isobutyl-1,3-thiazol-2(3H)-ylidene]-5-chloro-2-methoxybenzamide To the product of Example 16A (1.8 g, 8.2 mmol) in 25 mL THF was added triethylamine (3.5 mL, 25 mmol). The product of Example 16B in 5 mL THF was added rapidly via cannula. This mixture was warmed to 50° C. and allowed to stir for 16 hours. The mixture was cooled to ambient temperature, quenched with 10 mL saturated, aqueous NH$_4$Cl, and the layers were separated. The aqueous layer was extracted with EtOAc (3×10 mL) and the combined organic extracts were dried over anhydrous Na$_2$SO$_4$, filtered and concentrated under reduced pressure. Purification by column chromatography (SiO$_2$, 60% hexanes in EtOAc) provided the title compound. $^1$H NMR (300 MHz, CD$_3$OD) δ ppm 0.97 (d, J=6.8 Hz, 6H) 1.38 (s, 9H) 2.24-2.41 (m, 1H) 3.86 (s, 3H) 4.07 (d, J=7.5 Hz, 2H) 7.07 (d, J=8.8 Hz, 1H) 7.13 (s, 1H) 7.39 (dd, J=8.8, 2.7 Hz, 1H) 7.82 (d, J=2.7 Hz, 1H); MS (DCI/NH$_3$) m/z 381 (M+H)$^+$. Anal. calculated for C$_{19}$H$_{25}$ClN$_2$O$_2$S: C, 59.91; H, 6.61; N, 7.35. Found: C, 60.03; H, 6.76; N, 7.29.

Example 16D

N-[(2Z)-5-tert-butyl-3-isobutyl-1,3-thiazol-2(3H)-ylidene]-5-chloro-2-methoxybenzenecarbothioamide To a solution of the product of Example 16C (0.21 g, 0.54 mmol) in toluene (7 mL) was added 2,4-bis-(4-methoxyphenyl)-1,3-dithia-2,4-diphosphetane 2,4-disulfide (Lawesson's reagent, 0.22 g, 0.54 mmol). This mixture was warmed to 80° C. and allowed to stir for 45 minutes. The mixture was cooled to ambient temperature, concentrated under reduced pressure and purified by column chromatography ($SiO_2$, 60% hexanes in EtOAc) to provide the title compound. $^1$H NMR (300 MHz, $CDCl_3$) δ ppm 0.94 (d, J=6.8 Hz, 6H) 1.41 (s, 9H) 2.22-2.37 (m, 1H) 3.79 (s, 3H) 4.07 (d, J=7.5 Hz, 2H) 6.82 (s, 1H) 6.84 (d, J=8.8 Hz, 1H) 7.22 (dd, J=8.8, 2.7 Hz, 1H) 7.54 (d, J=2.7 Hz, 1H); MS (DCI/$NH_3$) m/z 397 (M+H)$^+$. Anal. calculated for $C_{19}H_{25}ClN_2OS_2 \cdot 0.4H_2O$: C, 56.46; H, 6.43; N, 6.93. Found: C, 56.86; H, 6.40; N, 6.55.

Example 16E

N-[(2Z)-5-tert-butyl-3-isobutyl-1,3-thiazol-2(3H)-ylidene]-5-chloro-N'-cyano-2-methoxybenzenecarboximidamide To the product of Example 16D (0.16 g, 0.40 mmol) in acetonitrile (20 mL) was added triethylamine (0.15 mL, 1.1 mmol) followed by cyanamide (34 mg, 0.81 mmol) and Hg(OAc)$_2$ (0.17 g, 0.52 mmol). This mixture was heated to reflux and allowed to stir for 2 hours. The mixture was cooled to ambient temperature and filtered through silica gel and Celite with 20 mL EtOAc. The filtrate was concentrated under reduced pressure and the residue was purified by column chromatography ($SiO_2$, 50% hexanes in EtOAc) to provide the title compound. $^1$H NMR (300 MHz, $CDCl_3$) δ ppm 0.95 (d, J=6.8 Hz, 6H) 1.38 (s, 9H) 2.15-2.31 (m, 1H) 3.92 (s, 3H) 4.02 (d, J=7.5 Hz, 2H) 6.73 (s, 1H) 6.94 (d, J=8.8 Hz, 1H) 7.32-7.38 (m, 2H); MS (DCI/$NH_3$) m/z 405 (M+H)$^+$. Anal. calculated for $C_{20}H_{25}ClN_4OS$: C, 59.06; H, 6.24; N, 13.77. Found: C, 59.27; H, 6.29; N, 13.39.

Example 17

N-[(2Z)-5-tert-butyl-3-[(2R)-tetrahydrofuran-2-ylmethyl]-1,3-thiazol-2(3H)-ylidene]-5-chloro-N'-cyano-2-methoxybenzenecarboximidamide

Example 17A (R)-(tetrahydrofuran-2-yl)methyl 4-methylbenzenesulfonate

To a solution of the (R)-(tetrahydrofuran-2-yl)methanol (Aldrich, 12 g, 0.12 mol) in 40 mL $CH_2Cl_2$ and 40 mL pyridine was added 4-dimethylaminopyridine (DMAP, 0.72 g, 5.9 mmol). This mixture was cooled to 0° C. and p-toluenesulfonyl chloride (23.5 g, 0.123 mol) was added portionwise over 20 minutes. The mixture stirred at ambient temperature for 16 hours, then quenched with excess 5% aqueous HCl. The layers were separated and the aqueous layer was extracted with $CH_2Cl_2$ (3×10 mL). The combined organic extracts were dried over anhydrous $Na_2SO_4$, filtered and concentrated under reduced pressure. Purification by column chromatography ($SiO_2$, 65% hexanes in EtOAc) provided the title compound. MS (DCI/$NH_3$) m/z 257 (M+H)$^+$; m/z 274 (M+$NH_4$)$^+$.

Example 17B 5-tert-butyl-3-[(2R)-tetrahydrofuran-2-ylmethyl]-1,3-thiazol-2(3H)-imine p-toluenesulfonic acid To a solution of Example 74A (9.8 g, 63 mmol) in 35 mL DMF was added the product of Example 17A (23.5 g, 91.7 mmol) and n-Bu$_4$NI (11.6 g, 31.4 mmol). This mixture was warmed to 90° C. and was allowed to stir for 72 hours. The mixture was cooled to ambient temperature and diluted with 30 mL saturated, aqueous NaHCO$_3$. The layers were separated and the aqueous layer was extracted with $CH_2Cl_2$ (3×10 mL). The combined organic layers were dried over anhydrous Na$_2$SO$_4$, filtered, concentrated under reduced pressure and purified by column chromatography ($SiO_2$, 10% MeOH in EtOAc then 9:1:0.1 $CH_2Cl_2$:MeOH:NH$_4$OH) to provide the title compound. MS (DCI/NH$_3$) m/z 341 (M+H-p-TsOH)$^+$.

Example 17C

N-[(2Z)-5-tert-butyl-3-[(2R)-tetrahydrofuran-2-ylmethyl]-1,3-thiazol-2(3H)-ylidene]-5-chloro-2-methoxybenzamide To a solution of the product of Example 17B (13.9 g, 33.7 mmol) in 125 mL THF was added triethylamine (19 mL, 0.14 mmol) and 4-dimethylaminopyridine (DMAP, 0.41 g, 3.4 mmol). A solution of 5-chloro-2-methoxy-benzoyl chloride (7.6 g, 37 mmol) in 25 mL THF was added rapidly via cannula. This mixture was warmed to 60° C. and allowed to stir for 16 hours. The mixture was cooled to ambient temperature and quenched with 30 mL saturated, aqueous NaHCO$_3$. The layers were separated and the aqueous phase was extracted with EtOAc (3×25 mL). The combined organic extracts were dried over anhydrous Na$_2$SO$_4$, filtered and concentrated under reduced pressure. Purification by column chromatography ($SiO_2$, 60% hexanes in EtOAc) provided the title compound. $^1$H NMR (300 MHz, CDCl$_3$) δ (m, 3H) 4.18-4.34 (m, 2H) 4.36-4.45 (m, 1H) 6.86 (s, 1H) 6.90 (d, J=9.2 Hz, 1H) 7.32 (dd, J=9.0, 2.9 Hz, 1H) 7.95 (d, J=3.1 Hz, 1H); MS (DCI/NH$_3$) m/z 409 (M+H)$^+$. Anal. calculated for $C_{20}H_{25}ClN_2O_3S$: C, 58.74; H, 6.16; N, 6.85. Found: C, 58.74; H, 6.27; N, 6.81.

Example 17D

N-[(2Z)-5-tert-butyl-3-[(2R)-tetrahydrofuran-2-ylmethyl]-1,3-thiazol-2(3H)-ylidene]-5-chloro-2-methoxybenzenecarbothioamide To a solution of the product of Example 17C (0.14 g, 0.33 mmol) in toluene (7 mL) was added 2,4-bis-(4-methoxyphenyl)-1,3-dithia-2,4-diphosphetane 2,4-disulfide (Lawesson's reagent, 80 mg, 0.20 mmol). This mixture was heated to 80° C. and allowed to stir for 45 minutes. The mixture was cooled to ambient temperature, concentrated under reduced pressure and purified by column chromatography ($SiO_2$, 60% hexanes in EtOAc) to provide the title compound. $^1$H NMR (300 MHz, CDCl$_3$) δ ppm 1.41 (s, 9H) 1.57-1.93 (m, 3H) 1.94-2.10 (m, 1H) 3.70-3.88 (m, 2H) 3.79 (s, 3H) 4.21-4.34 (m, 2H) 4.46-4.56 (m, 1H) 6.84 (d, J=8.8 Hz, 1H) 7.08 (s, 1H) 7.22 (dd, J=8.5, 2.7 Hz, 1H) 7.51 (d, J=2.7 Hz, 1H); MS (DCI/NH$_3$) m/z 425 (M+H)$^+$. Anal. calculated for $C_{20}H_{25}ClN_2O_2S_2$: C, 56.52; H, 5.93; N, 6.59. Found: C, 56.56; H, 5.51; N, 6.45.

Example 17E

N-[(2Z)-5-tert-butyl-3-[(2R)-tetrahydrofuran-2-ylmethyl]-1,3-thiazol-2(3H)-ylidene]-5-chloro-N'-cyano-2-methoxybenzenecarboximidamide A mixture of the product of Example 17D (0.14 g, 0.33 mmol), triethylamine (0.13 mL, 0.89 mmol), cyanamide (28 mg, 0.66 mmol) and Hg(OAc)$_2$ (0.14 g, 0.43 mmol) in CH₃CN (15 mL) was heated to reflux and allowed to stir for 2 hours. The mixture was cooled to ambient temperature, filtered through silica gel and Celite with EtOAc (15 mL). The filtrate was concentrated under reduced pressure and the residue was purified by column chromatography (SiO$_2$, 40% hexanes in EtOAc) to provide the title compound. $^1$H NMR (300 MHz, CDCl$_3$) δ ppm 1.38 (s, 9H) 1.55-1.65 (m, 1H) 1.71-1.96 (m, 2H) 1.99-2.13 (m, 1H) 3.73-3.88 (m, 2H) 3.92 (s, 3H) 4.14-4.27 (m, 2H) 4.40-4.51 (m, 1H) 6.94 (d, J=8.8 Hz, 1H) 7.01 (s, 1H) 7.30-7.38 (m, 2H); MS (DCI/NH$_3$) m/z 433 (M+H)$^+$. Anal. calculated for C$_{21}$H$_{25}$ClN$_4$O$_2$S: C, 58.25; H, 5.82; N, 12.94. Found: C, 58.32; H, 5.46; N, 12.74.

Example 18

N-[(2Z)-5-tert-butyl-3-propyl-1,3-thiazol-2(3H)-ylidene]-5-chloro-N'-cyano-2-methoxybenzenecarboximidamide

Example 18A 5-tert-butyl-3-propylthiazol-2(3H)-imine

A mixture of 3,3-dimethylbutanal (5 mL, 40 mmol), propan-1-amine (3.0 mL, 36 mmol), and 4 g of 4 Å molecular sieves (8-12 mesh beads) in acetonitrile (40 mL) was stirred at ambient temperature for 16 h. The material was filtered through Celite® with acetonitrile (additional 25 mL) then potassium thiocyanate (4.7 g, 48 mmol) was added and the mixture was warmed to 50° C. Iodine (18 g, 72 mmol) was added and the mixture was stirred at 50° C. for 16 h then was cooled to ambient temperature. The mixture was then stirred with 75 mL of 20% aqueous sodium metabisulfite for 1 h. The layers were separated and the aqueous layer was extracted with 3×10 mL CH$_2$Cl$_2$. The combined organics were dried over anhydrous Na$_2$SO$_4$, filtered and concentrated under reduced pressure to give the title compound (7.1 g, 36 mmol, 99% yield) which was carried on without further purification. MS (DCI/NH$_3$) m/z 199 (M+H)$^+$.

Example 18B 5-chloro-2-methoxybenzoyl chloride

A mixture of the 5-chloro-2-methoxybenzoic acid (0.94 g, 5.0 mmol) and SOCl$_2$ (10 mL) was warmed to reflux and was allowed to stir for 2 h. The mixture was cooled to ambient temperature, concentrated under reduced pressure and diluted with 10 mL toluene. This material was again concentrated under reduced pressure and was again diluted with 10 mL toluene. This concentration and dilution was repeated for an addition time and the crude material was carried on without further purification or characterization.

Example 18C (Z)-N-(5-tert-butyl-3-propylthiazol-2(3H)-ylidene)-5-chloro-2-methoxybenzamide To a solution of the product of Example 18A (1.0 g, 5.0 mmol) in THF (30 mL) was added triethylamine (2.1 mL, 15 mmol) followed by Example 18B in 20 mL toluene via cannula. This mixture was warmed to 50° C. and was allowed to stir for 4 h. The mixture was cooled to ambient temperature and was quenched with saturated, aqueous NH$_4$Cl (5 mL). The layers were separated and the aqueous layer was extracted with EtOAc (3×5 mL). The combined organics were dried over anhydrous Na$_2$SO$_4$, filtered and concentrated under reduced pressure. The crude material was purified by column chromatography (SiO$_2$, 60% hexanes in EtOAc) to give the title compound (1.0 g, 2.8 mmol, 55% yield). MS (DCI/NH$_3$) m/z 367 (M+H)$^+$.

Example 18D (Z)-N-(5-tert-butyl-3-propylthiazol-2(3H)-ylidene)-5-chloro-2-methoxybenzothioamide The product of Example 18C (0.87 g, 2.4 mmol) and 2,4-bis-(4-methoxyphenyl)-1,3-dithia-2,4-diphosphetane 2,4-disulfide (Lawesson's reagent, 0.96 g, 2.4 mmol) in toluene (20 mL) were processed as described in Example 16D to give the title compound (0.68 g, 1.8 mmol, 75% yield). MS (DCI/NH$_3$) m/z 383 (M+H)$^+$.

Example 18E

N-[(2Z)-5-tert-butyl-3-propyl-1,3-thiazol-2(3H)-ylidene]-5-chloro-N'-cyano-2-methoxybenzenecarboximidamide The product of Example 18D (0.65 g, 1.7 mmol), triethylamine (0.64 mL, 4.6 mmol), cyanamide (0.14 g, 3.4 mmol) and Hg(OAc)$_2$ (0.70 g, 2.2 mmol) in acetonitrile (20 mL) were processed as described in Example 16E to provide the title compound (0.55 g, 1.4 mmol, 83% yield). $^1$H NMR (300 MHz, CDCl$_3$) δ ppm 0.96 (t, J=7.3 Hz, 3H), 1.38 (s, 9H), 1.77-1.94 (m, 2H), 3.93 (s, 3H), 4.17 (dd, J=7.1 Hz, 2H), 6.76 (s, 1H), 6.90-6.99 (m, 1H), 7.32-7.38 (m, 2H); MS (DCI/NH$_3$) m/z 391 (M+H)$^+$. Anal. calculated for C$_{19}$H$_{23}$ClN$_4$OS: C, 58.37; H, 5.93; N, 14.33. Found: C, 58.19; H, 6.13; N, 14.42.

Example 19

N-[(2Z)-5-tert-butyl-3-(3-methylbutyl)-1,3-thiazol-2(3H)-ylidene]-5-chloro-N'-cyano-2-methoxybenzenecarboximidamide

Example 19A 5-tert-butyl-3-isopentylthiazol-2(3H)-imine

A mixture of 3,3-dimethylbutanal (3.0 mL, 24 mmol), 3-methylbutan-1-amine (2.5 mL, 22 mmol), 4 Å molecular sieves (3 g, 8-12 mesh beads), potassium thiocyanate (2.8 g, 29 mmol) and iodine (11 g, 44 mmol) in acetonitrile (40 mL) were processed as described in Example 18A to provide the title compound (4.9 g, 23 mol, 99% yield). MS (DCI/NH$_3$) m/z 227 (M+H)$^+$.

Example 19B (Z)-N-(5-tert-butyl-3-isopentylthiazol-2(3H)-ylidene)-5-chloro-2-methoxybenzamide The product of Example 19A (1.0 g, 4.4 mmol), 5-chloro-2-methoxybenzoic acid (0.82 g, 4.4 mmol), thionyl chloride (10 mL) and triethylamine (1.9 mL, 13 mmol) in THF (30 mL) were processed as described in Example 18B and

Example 19C (Z)-N-(5-tert-butyl-3-isopentylthiazol-2(3H)-ylidene)-5-chloro-2-methoxybenzothioamide The product of Example 19B (0.75 g, 1.9 mmol) and 2,4-bis-(4-methoxyphenyl)-1,3-dithia-2,4-diphosphetane 2,4-disulfide (Lawesson's reagent, 0.77 g, 1.9 mmol) in toluene (15 mL) were processed as described in Example 16D to give the title compound (0.72 g, 1.8 mmol, 92% yield). MS (DCI/NH$_3$) m/z 411 (M+H)$^+$.

Example 19D

N-[(2Z)-5-tert-butyl-3-(3-methylbutyl)-1,3-thiazol-2(3H)-ylidene]-5-chloro-N'-cyano-2-methoxybenzenecarboximidamide The product of Example 19C (0.69 g, 1.7 mmol), triethylamine (0.63 mL, 4.5 mmol), cyanamide (0.14 g, 3.4 mmol) and Hg(OAc)$_2$ (0.70 g, 2.2 mmol) in acetonitrile (25 mL) were processed as described in Example 16E to provide the title compound (0.58 g, 1.4 mmol, 82% yield). $^1$H NMR (300 MHz, CDCl$_3$) δ ppm 0.97 (d, J=5.8 Hz, 6H), 1.38 (s, 9H), 1.56-1.65 (m, 1H), 1.65-1.76 (m, 2H), 3.93 (s, 3H), 4.21 (dd, J=6.8 Hz, 2H), 6.76 (d, J=0.7 Hz, 1H), 6.90-6.98 (m, 1H), 7.32-7.39 (m, 2H); MS (DCI/NH$_3$) m/z 419 (M+H)$^+$. Anal. calculated for C$_{21}$H$_{27}$ClN$_4$OS: C, 60.20; H, 6.50; N, 13.37. Found: C, 60.45; H, 6.61; N, 13.08.

Example 20

1-{[(2Z)-5-tert-butyl-2-{[(5-chloro-2-methoxyphenyl)(cyanoimino)methyl]imino}-1,3-thiazol-3(2H)-yl]methyl}cyclohexyl acetate

Example 20A 1-((5-tert-butyl-2-iminothiazol-3(2H)-yl)methyl)cyclohexanol

A mixture of 3,3-dimethylbutanal (3.0 mL, 24 mmol), 1-(aminomethyl)cyclohexanol, hydrochloric acid (3.6 g, 22 mmol), triethylamine (3.0 mL, 22 mmol), and 3 g of 4 Å molecular sieves (8-12 mesh beads) in acetonitrile (25 mL) was stirred at ambient temperature for 20 h. The material was filtered through Celite® with acetonitrile (additional 20 mL) then potassium thiocyanate (2.8 g, 29 mmol) was added and the mixture was warmed to 50° C. Iodine (5.5 g, 22 mmol) was added and the mixture was stirred at 50° C. for 16 h then was cooled to ambient temperature. The mixture was then stirred with 50 mL of 20% aqueous sodium metabisulfite for 1 h then the layers were separated and the aqueous layer was extracted with 3×10 mL CH$_2$Cl$_2$. The combined organics were dried over anhydrous Na$_2$SO$_4$, filtered and concentrated under reduced pressure to give the title compound which was carried on without further purification. MS (DCI/NH$_3$) m/z 269 (M+H)$^+$.

Example 20B (Z)-N-(5-tert-butyl-3-((1-hydroxycyclohexyl)methyl)thiazol-2(3H)-ylidene)-5-chloro-2-methoxybenzamide The product of Example 20A (1.3 g, 3.7 mmol), 5-chloro-2-methoxybenzoic acid (0.70 g, 3.7 mmol), thionyl chloride (10 mL) and triethylamine (1.6 mL, 11 mmol) in THF (25 mL) were processed as described in Example 18B and Example 18C to provide the title compound (0.82 g, 1.9 mmol, 50% yield). MS (DCI/NH$_3$) m/z 437 (M+H)$^+$.

Example 20C (Z)-1-((5-tert-butyl-2-(5-chloro-2-methoxybenzoylimino)thiazol-3(2H)-yl)methyl)cyclohexyl acetate To the product of Example 20B (0.94 g, 2.2 mmol) in pyridine (10 mL) was added N,N-dimethylpyridin-4-amine (DMAP, 26 mg, 0.22 mmol) followed by acetic anhydride (0.30 mL, 3.2 mmol). This mixture stirred at ambient temperature for 72 hours then was quenched with 10 mL 5% aqueous HCl, diluted with 10 mL EtOAc and the layers were separated. The aqueous layer was extracted with EtOAc (3×5 mL), and the combined organics were dried over anhydrous Na$_2$SO$_4$, filtered and concentrated under reduced pressure. The crude material was purified by column chromatography (SiO$_2$, 60% hexanes in EtOAc) to give the title compound (0.85 g, 1.8 mmol, 82% yield). MS (DCI/NH$_3$) m/z 479 (M+H)$^+$.

Example 20D (Z)-1-((5-tert-butyl-2-(5-chloro-2-methoxyphenylcarbonothioylimino)thiazol-3(2H)-yl)methyl)cyclohexyl acetate The product of Example 20C (0.75 g, 1.6 mmol) and 2,4-bis-(4-methoxyphenyl)-1,3-dithia-2,4-diphosphetane 2,4-disulfide (Lawesson's reagent, 0.63 g, 1.6 mmol) in toluene (15 mL) were processed as described in Example 16D to give the title compound (0.60 g, 1.2 mmol, 77% yield). MS (DCI/NH$_3$) m/z 495 (M+H)$^+$.

Example 20E

1-{[(2Z)-5-tert-butyl-2-{[(5-chloro-2-methoxyphenyl)(cyanoimino)methyl]imino}-1,3-thiazol-3(2H)-yl]methyl}cyclohexyl acetate The product of Example 20D (0.57 g, 1.2 mmol), triethylamine (0.43 mL, 3.1 mmol), cyanamide (97 mg, 2.3 mmol) and Hg(OAc)$_2$ (0.48 g, 1.5 mmol) in acetonitrile (15 mL) were processed as described in Example 16E to provide the title compound (0.50 g, 1.0 mmol, 86% yield). $^1$H NMR (300 MHz, CDCl$_3$) δ ppm 1.38 (s, 9H), 1.40-1.52 (m, 6H), 1.56-1.66 (m, 2H), 2.03 (s, 3H), 2.10-2.20 (m, 2H), 3.91 (s, 3H), 4.71 (s, 2H), 6.69 (s, 1H), 6.94 (d, J=8.8 Hz, 1H), 7.30 (d, J=2.7 Hz, 1H), 7.36 (dd, J=8.8, 2.7 Hz, 1H); MS (DCI/NH$_3$) m/z 503 (M+H)$^+$. Anal. calculated for C$_{25}$H$_{31}$ClN$_4$O$_3$S: C, 59.69; H, 6.21; N, 11.14. Found: C, 59.76; H, 6.22; N, 11.05.

Example 18C to provide the title compound (0.88 g, 2.2 mmol, 50% yield). MS (DCI/NH$_3$) m/z 395 (M+H)$^+$.

Example 21

N-[(2Z)-5-tert-butyl-3-[(1-hydroxycyclohexyl)methyl]-1,3-thiazol-2(3H)-ylidene]-5-chloro-N'-cyano-2-methoxybenzenecarboximidamide To the product of Example 20E (0.40 g, 0.8 mmol) in CH$_3$OH (10 mL) and H$_2$O (1 mL) was added K$_2$CO$_3$ (1.0 g, 7.2 mmol). The mixture was warmed to 50° C. and was allowed to stir for 2 h. The reaction mixture was cooled to ambient temperature, diluted with EtOAc (10 mL) and brine (5 mL) and the layers were separated. The aqueous layer was extracted with EtOAc (2×5 mL) and the combined organics were dried over anhydrous Na$_2$SO$_4$, filtered and concentrated under reduced pressure. The crude material was purified by column chromatography (SiO$_2$, 60% hexanes in EtOAc) to give the title compound (0.25 g, 0.54 mmol, 68% yield). $^1$H NMR (300 MHz, CDCl$_3$) δ ppm 1.27-1.66 (m, 10H), 1.39 (s, 9H), 3.43 (s, 1H), 3.89 (s, 3H), 4.22 (s, 2H), 6.87 (s, 1H), 6.90-6.96 (m, 1H), 7.32-7.39 (m, 2H); MS (DCI/NH$_3$) m/z 461 (M+H)$^+$. Anal. calculated for C$_{23}$H$_{29}$ClN$_4$O$_2$S: C, 59.92; H, 6.34; N, 12.15. Found: C, 59.74; H, 6.22; N, 12.03.

Example 22

2-[(2Z)-5-tert-butyl-2-{[(5-chloro-2-methoxyphenyl)(cyanoimino)methyl]imino}-1,3-thiazol-3(2H)-yl]-1,1-dimethylethyl acetate

Example 22A 1-(5-tert-butyl-2-iminothiazol-3(2H)-yl)-2-methylpropan-2-ol

A mixture of 3,3-dimethylbutanal (7.7 mL, 62 mmol), 1-amino-2-methylpropan-2-ol (5.0 g, 56 mmol), 4 Å molecular sieves (5 g, 8-12 mesh beads), potassium thiocyanate (7.3 g, 75 mmol) and iodine (14 g, 56 mmol) in acetonitrile (100 mL) were processed as described in Example 18A to provide the title compound (12 g, 53 mmol, 94% yield). MS (DCI/NH$_3$) m/z 229 (M+H)$^+$.

Example 22B (Z)-N-(5-tert-butyl-3-(2-hydroxy-2-methylpropyl)thiazol-2(3H)-ylidene)-5-chloro-2-methoxybenzamide The product of Example 22A (6.0 g, 26 mmol), 5-chloro-2-methoxybenzoic acid (4.9 g, 26 mmol), thionyl chloride (20 mL) and triethylamine (11 mL, 79 mmol) in THF (100 mL) were processed as described in Example 18B and Example 18C to provide the title compound (6.0 g, 15 mmol, 58% yield). MS (DCI/NH$_3$) m/z 397 (M+H)$^+$.

Example 22C (Z)-1-(5-tert-butyl-2-(5-chloro-2-methoxybenzoylimino)thiazol-3(2H)-yl)-2-methylpropan-2-yl acetate The product of Example 22B (5.8 g, 15 mmol), N,N-dimethylpyridin-4-amine (DMAP, 0.18 g, 1.5 mmol) and acetic anhydride (2.1 mL, 22 mmol) in pyridine (40 mL) were processed as described in Example 20C to provide the title compound (5.5 g, 13 mmol, 86% yield). MS (DCI/NH$_3$) m/z 439 (M+H)$^+$.

Example 22D (Z)-1-(5-tert-butyl-2-(5-chloro-2-methoxyphenylcarbonothioylimino)thiazol-3(2H)-yl)-2-methylpropan-2-yl acetate The product of Example 22C (2.7 g, 6.2 mmol) and 2,4-bis-(4-methoxyphenyl)-1,3-dithia-2,4-diphosphetane 2,4-disulfide (Lawesson's reagent, 2.5 g, 6.2 mmol) in toluene (40 mL) were processed as described in Example 16D to give the title compound (3.6 g, 4.7 mmol, 76% yield). MS (DCI/NH$_3$) m/z 455 (M+H)$^+$.

Example 22E

2-[(2Z)-5-tert-butyl-2-{[(5-chloro-2-methoxyphenyl)(cyanoimino)methyl]imino}-1,3-thiazol-3(2H)-yl]-1,1-dimethylethyl acetate The product of Example 22D (3.5 g, 4.6 mmol), triethylamine (1.7 mL, 12 mmol), cyanamide (0.38 g, 9.1 mmol) and Hg(OAc)$_2$ (1.9 g, 5.9 mmol) in acetonitrile (30 mL) were processed as described in Example 16E to provide the title compound (2.05 g, 4.4 mmol, 97% yield). $^1$H NMR (300 MHz, CDCl$_3$) δ ppm 1.39 (s, 9H), 1.50 (s, 6H), 2.01 (s, 3H), 3.90 (s, 3H), 4.51 (s, 2H), 6.85 (s, 1H), 6.94 (d, J=8.7 Hz, 1H), 7.28 (d, J=2.4 Hz, 1H), 7.36 (dd, J=8.7, 2.8 Hz, 1H); MS (DCI/NH$_3$) m/z 463 (M+H)$^+$. Anal. calculated for C$_{22}$H$_{27}$ClN$_4$O$_3$S: C, 57.07; H, 5.88; N, 12.10. Found: C, 57.09; H, 6.05; N, 11.80.

Example 23

N-[(2Z)-5-tert-butyl-3-(2-hydroxy-2-methylpropyl)-1,3-thiazol-2(3H)-ylidene]-5-chloro-N'-cyano-2-methoxybenzenecarboximidamide The product of Example 22E (1.8 g, 3.8 mmol) and K$_2$CO$_3$ (2.6 g, 19 mmol) in CH$_3$OH (20 mL) and H$_2$O (3 mL) were processed as described in Example 21 to provide the title compound (1.5 g, 3.6 mmol, 94% yield). $^1$H NMR (300 MHz, CDCl$_3$) δ ppm 1.26 (s, 6H), 1.39 (s, 9H), 3.54 (s, 1H), 3.88 (s, 3H), 4.23 (s, 2H), 6.88 (s, 1H), 6.93 (d, J=8.8 Hz, 1H), 7.30-7.39 (m, 2H); MS (DCI/NH$_3$) m/z 421 (M+H)$^+$. Anal. calculated for C$_{20}$H$_{25}$ClN$_4$O$_2$S: C, 57.06; H, 5.99; N, 13.31. Found: C, 57.01; H, 6.05; N, 13.19.

Example 24

1-{[(2Z)-5-tert-butyl-2-{[(5-chloro-2-methoxyphenyl)(cyanoimino)methyl]imino}-1,3-thiazol-3(2H)-yl]methyl}cyclopentyl acetate

Example 24A 1-((5-tert-butyl-2-iminothiazol-3(2H)-yl)methyl)cyclopentanol

A mixture of 1-(aminomethyl)cyclopentanol (prepared from cyclopentanone as described in WO 2006/100208) (3.5 g, 30 mmol), 3,3-dimethylbutanal (3.4 g, 33 mmol), 4 Å molecular sieves (4 g, 8-12 mesh beads), potassium thiocyanate (3.9 g, 40 mmol) and iodine (7.7 g, 30 mmol) in acetonitrile (50 mL) were processed as described in Example 18A to provide the title compound (5.6 g, 22 mmol, 72% yield). MS (DCI/NH$_3$) m/z 255 (M+H)$^+$.

Example 24B (Z)-N-(5-tert-butyl-3-((1-hydroxycyclopentyl)methyl)thiazol-2(3H)-ylidene)-5-chloro-2-methoxybenzamide The product of Example 24A (2.0 g, 7.9 mmol), 5-chloro-2-methoxybenzoic acid (1.5 g, 7.9 mmol), thionyl chloride (10 mL) and triethylamine (3.3 mL, 23.6 mmol) in THF (40 mL) were processed as described in Example 18B and 18C to provide the title compound (2.2 g, 5.2 mmol, 66% yield). MS (DCI/NH$_3$) m/z 423 (M+H)$^+$.

Example 24C (Z)-1-((5-tert-butyl-2-(5-chloro-2-methoxybenzoylimino)thiazol-3(2H)-yl)methyl)cyclopentyl acetate The product of Example 24B (2.1 g, 4.9 mmol), N,N-dimethylpyridin-4-amine (DMAP, 60 mg, 0.49 mmol) and acetic anhydride (0.7 mL, 7.3 mmol) in pyridine (20 mL) were processed as described in Example 20C to provide the title compound (1.6 g, 3.5 mmol, 72% yield). MS (DCI/NH$_3$) m/z 465 (M+H)$^+$.

Example 24D (Z)-1-((5-tert-butyl-2-(5-chloro-2-methoxyphenylcarbonothioylimino)thiazol-3(2H)-yl)methyl)cyclopentyl acetate The product of Example 24C (1.5 g, 3.2 mmol) and 2,4-bis-(4-methoxyphenyl)-1,3-dithia-2,4-diphosphetane 2,4-disulfide (Lawesson's reagent, 1.3 g, 3.2 mmol) in toluene (15 mL) were processed as described in Example 16D to give the title compound (1.8 g, 3.7 mmol, 116% yield). This impure material was carried on without further purification. MS (DCI/NH$_3$) m/z 481 (M+H)$^+$.

Example 24E

1-{[(2Z)-5-tert-butyl-2-{[(5-chloro-2-methoxyphenyl)(cyanoimino)methyl]imino}-1,3-thiazol-3(2H)-yl]methyl}cyclopentyl acetate The product of Example 24D (1.6 g, 3.2 mmol), triethylamine (1.8 mL, 13 mmol), cyanamide (0.40 g, 9.7 mmol) and Hg(OAc)$_2$ (2.0 g, 6.5 mmol) in acetonitrile (20 mL) were processed as described in Example 16E to provide the title compound (1.2 g, 2.4 mmol, 74% yield). $^1$H NMR (300 MHz, CDCl$_3$) δ ppm 1.34-1.40 (m, 9H), 1.65-1.84 (m, 4H), 1.86-2.09 (m, 4H), 2.00-2.02 (m, 3H), 3.91 (s, 3H), 4.72 (s, 2H), 6.70 (s, 1H), 6.94 (d, J=9.1 Hz, 1H), 7.28 (d, J=2.4 Hz, 1H), 7.35 (dd, J=8.7, 2.8 Hz, 1H); MS (DCI/NH$_3$) m/z 489 (M+H)$^+$. Anal. calculated for C$_{24}$H$_{29}$ClN$_4$O$_3$S: C, 58.94; H, 5.98; N, 11.46. Found: C, 58.88; H, 5.86; N, 11.32.

Example 25

N-[(2Z)-5-tert-butyl-3-[(1-hydroxycyclopentyl)methyl]-1,3-thiazol-2(3H)-ylidene]-5-chloro-N'-cyano-2-methoxybenzenecarboximidamide The product of Example 24E (1.0 g, 2.1 mmol) and K$_2$CO$_3$ (1.5 g, 11 mmol) in CH$_3$OH (10 mL) and H$_2$O (2 mL) were processed as described in Example 21 to provide the title compound (0.95 g, 2.1 mmol, 100% yield). $^1$H NMR (300 MHz, CDCl$_3$) δ ppm 1.39 (s, 9H), 1.60-1.74 (m, 6H), 1.79-1.90 (m, 2H), 3.48 (s, 1H), 3.88 (s, 3H), 4.35 (s, 2H), 6.90 (s, 1H), 6.93 (d, J=8.5 Hz, 1H), 7.31-7.39 (m, 2H); MS (DCI/NH$_3$) m/z 447 (M+H)$^+$. Anal. calculated for C$_{22}$H$_{27}$ClN$_4$O$_2$S: C, 59.11; H, 6.09; N, 12.53. Found: C, 58.88; H, 5.80; N, 12.49.

Example 26

N-[(2Z)-5-tert-butyl-3-propyl-1,3-thiazol-2(3H)-ylidene]-N',5-dicyano-2-methoxybenzenecarboximidamide

Example 26A

Methyl 5-cyano-2-methoxybenzoate

A mixture of 3-bromo-4-methoxybenzonitrile (20 g, 94 mmol), PdCl$_2$(dppf)CH$_2$Cl$_2$ (2 g) and Et$_3$N (25 mL, 179 mmol) in methanol (200 mL) were shaken under a 60 psi atmosphere of CO at 100° C. for 4 h. The mixture was cooled to ambient temperature, filtered and concentrated under reduced pressure. The crude material was purified via column chromatography (SiO$_2$, 50% hexanes in EtOAc) to provide the title compound (16.7 g, 87 mmol, 93% yield). MS (DCI/NH$_3$) m/z 192 (M+H)$^+$.

Example 26B 5-cyano-2-methoxybenzoic acid

To a solution of the product of Example 26A (16.7 g, 87 mmol) in EtOH (300 mL) was added KOH (30% aqueous solution, 80 mL). The mixture was warmed to 45° C. and was allowed to stir for 2 h until all solids had dissolved. The mixture was cooled to ambient temperature and was partially concentrated under reduced pressure. The material was diluted with EtOAc (100 mL) and acidified with 10% aqueous HCl. The layers were separated and the aqueous layer was extracted with EtOAc (3×20 mL). The combined organics were dried over Na$_2$SO$_4$, filtered and concentrated under reduced pressure to give the title compound (15.2 g, 86 mmol, 98% yield). MS (DCI/NH$_3$) m/z 195 (M+NH$_4$)$^+$.

Example 26C (Z)-N-(5-tert-butyl-3-propylthiazol-2(3H)-ylidene)-5-cyano-2-methoxybenzamide The product of Example 18A (0.50 g, 2.5 mmol), the product of Example 26B (0.49 g, 2.5 mmol), thionyl chloride (10 mL) and triethylamine (1.9 mL, 13 mmol) in THF (30 mL) were processed as described in Example 18B and Example 18C to provide the title compound (0.49 g, 1.4 mmol, 54% yield). MS (DCI/NH$_3$) m/z 358 (M+H)$^+$.

Example 26D (Z)-N-(5-tert-butyl-3-propylthiazol-2(3H)-ylidene)-5-cyano-2-methoxybenzothioamide The product of Example 26C (0.35 g, 0.98 mmol) and 2,4-bis-(4-methoxyphenyl)-1,3-dithia-2,4-diphosphetane 2,4-disulfide (Lawesson's reagent, 0.40 g, 0.98 mmol) in toluene (10 mL) were processed as described in Example 16D

Example 26E

N-[(2Z)-5-tert-butyl-3-propyl-1,3-thiazol-2(3H)-ylidene]-N',5-dicyano-2-methoxybenzenecarboximidamide The product of Example 24D (0.30 g, 0.80 mmol), triethylamine (0.30 mL, 2.2 mmol), cyanamide (70 mg, 1.6 mmol) and Hg(OAc)$_2$ (0.33 g, 1.0 mmol) in acetonitrile (10 mL) were processed as described in Example 16E to provide the title compound (0.23 g, 0.59 mmol, 73% yield). $^1$H NMR (300 MHz, CDCl$_3$) δ ppm 0.97 (t, J=7.3 Hz, 3H), 1.39 (s, 9H), 1.79-1.92 (m, 2H), 4.00 (s, 3H), 4.17 (dd, J=7.4 Hz, 2H), 6.79 (s, 1H), 7.08 (d, J=8.5 Hz, 1H), 7.64-7.75 (m, 2H); MS (DCI/NH$_3$) m/z 382 (M+H)$^+$. Anal. calculated for C$_{20}$H$_{23}$N$_5$OS: C, 62.97; H, 6.08; N, 18.36. Found: C, 62.82; H, 5.91; N, 18.26.

Example 27

1-{[(2Z)-5-tert-butyl-2-{[(5-chloro-2-methoxyphenyl)(cyanoimino)methyl]imino}-1,3-thiazol-3(2H)-yl]methyl}cyclobutyl acetate

Example 27A 1-((5-tert-butyl-2-iminothiazol-3(2H)-yl)methyl)cyclobutanol

A mixture of 1-(aminomethyl)cyclobutanol (prepared from cyclobutanone as described in WO 2006/100208) (7.2 g, 71 mmol), 3,3-dimethylbutanal (9.8 mL, 78 mmol), 4 Å molecular sieves (10 g, 8-12 mesh beads), potassium thiocyanate (9.2 g, 95 mmol) and iodine (18 g, 71 mmol) in acetonitrile (100 mL) were processed as described in Example 18A to provide the title compound (5.5 g, 23 mmol, 32% yield). MS (DCI/NH$_3$) m/z 241 (M+H)$^+$.

Example 27B (Z)-N-(5-tert-butyl-3-((1-hydroxycyclobutyl)methyl)thiazol-2(3H)-ylidene)-5-chloro-2-methoxybenzamide The product of Example 27A (2.0 g, 8.3 mmol), 5-chloro-2-methoxybenzoic acid (1.7 g, 8.3 mmol), thionyl chloride (10 mL) and triethylamine (3.5 mL, 25.0 mmol) in THF (40 mL) were processed as described in Example 18B and Example 18C to provide the title compound (1.8 g, 4.4 mmol, 53% yield). MS (DCI/NH$_3$) m/z 409 (M+H)$^+$.

Example 27C (Z)-1-((5-tert-butyl-2-(5-chloro-2-methoxybenzoylimino)thiazol-3(2H)-yl)methyl)cyclobutyl acetate The product of Example 27B (1.6 g, 3.8 mmol), N,N-dimethylpyridin-4-amine (DMAP, (47 mg, 0.38 mmol) and acetic anhydride (0.54 mL, 5.7 mmol) in pyridine (20 mL) were processed as described in Example 20C to provide the title compound (1.3 g, 2.8 mmol, 74% yield). MS (DCI/NH$_3$) m/z 451 (M+H)$^+$.

Example 27D (Z)-1-((5-tert-butyl-2-(5-chloro-2-methoxyphenylcarbonothioylimino)thiazol-3(2H)-yl)methyl)cyclobutyl acetate The product of Example 27C (1.15 g, 2.6 mmol) and 2,4-bis-(4-methoxyphenyl)-1,3-dithia-2,4-diphosphetane 2,4-disulfide (Lawesson's reagent, 1.0 g, 2.6 mmol) in toluene (25 mL) were processed as described in Example 16D to give the title compound. This impure material was carried on without further purification. MS (DCI/NH$_3$) m/z 467 (M+H)$^+$.

Example 27E

1-{[(2Z)-5-tert-butyl-2-{[(5-chloro-2-methoxyphenyl)(cyanoimino)methyl]imino}-1,3-thiazol-3(2H)-yl]methyl}cyclobutyl acetate The product of Example 27D (1.2 g, 2.6 mmol), triethylamine (1.4 mL, 10 mmol), cyanamide (0.32 g, 7.7 mmol) and Hg(OAc)$_2$ (1.6 g, 5.1 mmol) in acetonitrile (20 mL) were processed as described in Example 16E to provide the title compound (0.93 g, 2.0 mmol, 77% yield). $^1$H NMR (300 MHz, CDCl$_3$) δ ppm 1.38 (s, 9H), 1.73-1.96 (m, 2H), 1.99 (s, 3H), 2.22-2.46 (m, 4H), 3.91 (s, 3H), 4.76 (s, 2H), 6.63 (s, 1H), 6.94 (d, J=8.8 Hz, 1H), 7.31-7.39 (m, 2H); MS (DCI/NH$_3$) m/z 475 (M+H)$^+$. Anal. calculated for C$_{23}$H$_{27}$ClN$_4$O$_3$S: C, 58.16; H, 5.73; N, 11.80. Found: C, 58.16; H, 5.66; N, 11.85.

Example 28

1-{[(2Z)-5-tert-butyl-2-{[(cyanoimino)(5-cyano-2-methoxyphenyl)methyl]imino}-1,3-thiazol-3(2H)-yl]methyl}cyclobutyl acetate

Example 28A (Z)-N-(5-tert-butyl-3-((1-hydroxycyclobutyl)methyl)thiazol-2(3H)-ylidene)-5-cyano-2-methoxybenzamide The product of Example 27A (1.0 g, 4.2 mmol), the product of Example 26B (0.74 g, 4.2 mmol), thionyl chloride (10 mL) and triethylamine (1.7 mL, 12.5 mmol) in THF (40 mL) were processed as described in Example 18B and Example 18C to provide the title compound (0.76 g, 1.9 mmol, 46% yield). MS (DCI/NH$_3$) m/z 409 (M+H)$^+$.

Example 28B (Z)-1-((5-tert-butyl-2-(5-cyano-2-methoxybenzoylimino)thiazol-3(2H)-yl)methyl)cyclobutyl acetate The product of Example 28A (0.67 g, 1.7 mmol), N,N-dimethylpyridin-4-amine (DMAP, 20 mg, 0.17 mmol) and acetic anhydride (0.40 mL, 4.2 mmol) in pyridine (20 mL) were processed as described in Example 20C to provide the title compound (0.71 g, 1.6 mmol, 96% yield). MS (DCI/NH$_3$) m/z 442 (M+H)$^+$.

Example 28C (Z)-1-((5-tert-butyl-2-(5-cyano-2-methoxyphenylcarbonothioylimino)thiazol-3(2H)-yl)methyl)cyclobutyl acetate The product of Example 28B (0.63 g, 1.4 mmol) and 2,4-bis-(4-methoxyphenyl)-1,3-dithia-2,4-diphosphetane 2,4-disulfide (Lawesson's reagent, 0.60 g, 1.4 mmol) in toluene (15 mL) were processed as described in Example 16D to give the title compound (0.55 g, 1.2 mmol, 84% yield). MS (DCI/NH$_3$) m/z 458 (M+H)$^+$.

Example 28D

1-{[(2Z)-5-tert-butyl-2-{[(cyanoimino)(5-cyano-2-methoxyphenyl)methyl]imino}-1,3-thiazol-3(2H)-yl]methyl}cyclobutyl acetate The product of Example 28C (0.55 g, 1.2 mmol), triethylamine (0.67 mL, 4.8 mmol), cyanamide (0.15 g, 3.6 mmol) and Hg(OAc)$_2$ (0.77 g, 2.4 mmol) in acetonitrile (10 mL) were processed as described in Example 16E to provide the title compound (0.51 g, 1.1 mmol, 91% yield). $^1$H NMR (300 MHz, CDCl$_3$) δ ppm 1.39 (s, 9H), 1.70-1.84 (m, 1H), 1.86-1.98 (m, 1H), 1.99 (s, 3H), 2.23-2.43 (m, 4H), 3.98 (s, 3H), 4.76 (s, 2H), 6.67 (s, 1H), 7.08 (d, J=8.5 Hz, 1H), 7.65 (d, J=2.0 Hz, 1H), 7.72 (dd, J=8.6, 2.2 Hz, 1H); MS (DCI/NH$_3$) m/z 466 (M+H)$^+$. Anal. calculated for C$_{24}$H$_{27}$N$_5$O$_3$S: C, 61.92; H, 5.85; N, 15.04. Found: C, 61.91; H, 5.88; N, 14.93.

Example 29

N-[(2Z)-5-tert-butyl-3-[(1-hydroxycyclobutyl)methyl]-1,3-thiazol-2(3H)-ylidene]-5-chloro-N'-cyano-2-methoxybenzenecarboximidamide The product of Example 27E (0.85 g, 1.8 mmol) and K$_2$CO$_3$ (1.2 g, 9.0 mmol) in CH$_3$OH (10 mL) and H$_2$O (2 mL) were processed as described in Example 21 to provide the title compound (0.72 g, 1.7 mmol, 93% yield). $^1$H NMR (300 MHz, CDCl$_3$) δ ppm 1.39 (s, 9H), 1.55-1.70 (m, 1H), 1.74-1.89 (m, 1H), 2.04-2.15 (m, 4H), 3.88 (s, 3H), 4.21 (s, 1H), 4.40 (s, 2H), 6.90 (s, 1H), 6.93 (d, J=8.7 Hz, 1H), 7.31-7.38 (m, 2H); MS (DCI/NH$_3$) m/z 433 (M+H)$^+$. Anal. calculated for C$_{21}$H$_{25}$ClN$_4$O$_2$S: C, 58.25; H, 5.82; N, 12.94. Found: C, 58.24; H, 5.62; N, 12.75.

Example 30

N-[(2Z)-5-tert-butyl-3-[(1-hydroxycyclobutyl)methyl]-1,3-thiazol-2(3H)-ylidene]-N',5-dicyano-2-methoxybenzenecarboximidamide The product of Example 28D (0.46 g, 0.99 mmol) and K$_2$CO$_3$ (0.68 g, 4.9 mmol) in CH$_3$OH (8 mL) and H$_2$O (1.5 mL) were processed as described in Example 21 to provide the title compound (0.29 g, 0.69 mmol, 69% yield). $^1$H NMR (300 MHz, CDCl$_3$) δ ppm 1.40 (s, 9H), 1.55-1.68 (m, 1H), 1.74-1.90 (m, 1H), 2.01-2.20 (m, 4H), 3.96 (s, 1H), 3.96 (s, 3H), 4.41 (s, 2H), 6.95 (s, 1H), 7.07 (d, J=8.7 Hz, 1H), 7.65 (d, J=2.4 Hz, 1H), 7.71 (dd, J=8.7, 2.0 Hz, 1H); MS (DCI/NH$_3$) m/z 424 (M+H)$^+$. Anal. calculated for C$_{22}$H$_{25}$N$_5$O$_2$S: C, 62.39; H, 5.95; N, 16.54. Found: C, 62.00; H, 6.06; N, 16.16.

Example 31

N-[(2Z)-5-tert-butyl-3-isobutyl-1,3-thiazol-2(3H)-ylidene]-N'-cyano-2-methoxy-5-(trifluoromethyl)benzenecarboximidamide

Example 31A (Z)-N-(5-tert-butyl-3-isobutylthiazol-2(3H)-ylidene)-2-methoxy-5-(trifluoromethyl)benzamide The product of Example 16A (0.60 g, 2.8 mmol), 2-methoxy-5-(trifluoromethyl)benzoic acid (0.62 g, 2.8 mmol), thionyl chloride (10 mL) and triethylamine (1.2 mL, 8.5 mmol) in THF (20 mL) were processed as described in Example 18B and Example 18B to provide the title compound (0.68 g, 1.6 mmol, 58% yield). MS (DCI/NH$_3$) m/z 415 (M+H)$^+$.

Example 31B (Z)-N-(5-tert-butyl-3-isobutylthiazol-2(3H)-ylidene)-2-methoxy-5-(trifluoromethyl)benzothioamide The product of Example 31A (0.6 g, 1.5 mmol) and 2,4-bis-(4-methoxyphenyl)-1,3-dithia-2,4-diphosphetane 2,4-disulfide (Lawesson's reagent, 0.59 g, 1.5 mmol) in toluene (10 mL) were processed as described in Example 16D to give the title compound (0.62 g, 1.44 mmol, 99% yield). MS (DCI/NH$_3$) m/z 431 (M+H)$^+$.

Example 31C

N-[(2Z)-5-tert-butyl-3-isobutyl-1,3-thiazol-2(3H)-ylidene]-N'-cyano-2-methoxy-5-(trifluoromethyl)benzenecarboximidamide The product of Example 31B (0.62 g, 1.4 mmol), triethylamine (0.54 mL, 3.9 mmol), cyanamide (0.12 g, 2.9 mmol) and Hg(OAc)$_2$ (0.60 g, 1.9 mmol) in acetonitrile (10 mL) were processed as described in Example 16E to provide the title compound (0.44 g, 1.0 mmol, 70% yield). $^1$H NMR (300 MHz, CDCl$_3$) δ ppm 0.95 (d, J=6.7 Hz, 6H), 1.39 (s, 9H), 2.14-2.31 (m, 1H), 4.00 (s, 3H), 4.02 (d, J=7.1 Hz, 2H), 6.75 (s, 1H), 7.09 (d, J=8.7 Hz, 1H), 7.62-7.71 (m, 2H); MS (DCI/NH$_3$) m/z 439 (M+H)$^+$. Anal. calculated for C$_{21}$H$_{25}$F$_3$N$_4$OS: C, 57.52; H, 5.75; N, 12.78. Found: C, 57.42; H, 5.80; N, 12.68.

Example 32

1-{[(2Z)-5-tert-butyl-2-{[(5-chloro-2-methoxyphenyl)(cyanoimino)methyl]imino}-1,3-thiazol-3(2H)-yl]methyl}cyclopropyl acetate

Example 32A 1-((5-tert-butyl-2-iminothiazol-3(2H)-yl)methyl)cyclopropanol

A mixture of 1-(aminomethyl)cyclopropanol (ChemPacific, 1.0 g, 11.5 mmol), 3,3-dimethylbutanal (1.6 mL, 12.6 mmol), 4 Å molecular sieves (3 g, 8-12 mesh beads), potassium thiocyanate (1.5 g, 15 mmol) and iodine (2.9 g, 11.5 mmol) in acetonitrile (25 mL) were processed as described in Example 18A to provide the title compound (2.5 g, 11 mmol, 95% yield). MS (DCI/NH$_3$) m/z 227 (M+H)$^+$.

Example 32B (Z)-N-(5-tert-butyl-3-((1-hydroxycyclopropyl)methyl)thiazol-2(3H)-ylidene)-5-chloro-2-methoxybenzamide The product of Example 32A (1.2 g, 5.3 mmol), 5-chloro-2-methoxybenzoic acid (0.99 g, 5.3 mmol), thionyl chloride (10 mL) and triethylamine (2.2 mL, 16 mmol) in THF (20 mL) were processed as described in Example 18B and Example 18C to provide the title compound (0.63 g, 1.6 mmol, 30% yield). MS (DCI/NH$_3$) m/z 395 (M+H)$^+$.

Example 32C (Z)-1-((5-tert-butyl-2-(5-chloro-2-methoxybenzoylimino)thiazol-3(2H)-yl)methyl)cyclopropyl acetate The product of Example 32B (0.54 g, 1.4 mmol), N,N-dimethylpyridin-4-amine (DMAP, (17 mg, 0.14 mmol) and acetic anhydride (0.39 mL, 4.1 mmol) in pyridine (10 mL) were processed as described in Example 20C to provide the title compound (0.48 g, 1.1 mmol, 80% yield). MS (DCI/NH$_3$) m/z 437 (M+H)$^+$.

Example 32D (Z)-1-((5-tert-butyl-2-(5-chloro-2-methoxyphenylcarbonothioylimino)thiazol-3(2H)-yl)methyl)cyclopropyl acetate The product of Example 32C (0.43 g, 0.98 mmol) and 2,4-bis-(4-methoxyphenyl)-1,3-dithia-2,4-diphosphetane 2,4-disulfide (Lawesson's reagent, 0.40 g, 0.98 mmol) in toluene (10 mL) were processed as described in Example 16D to give the title compound (0.38 g, 0.84 mmol, 85% yield). MS (DCI/NH$_3$) m/z 453 (M+H)$^+$.

Example 32E

1-{[(2Z)-5-tert-butyl-2-{[(5-chloro-2-methoxyphenyl)(cyanoimino)methyl]imino}-1,3-thiazol-3(2H)-yl]methyl}cyclopropyl acetate The product of Example 32D (0.38 g, 0.84 mmol), triethylamine (0.32 mL, 2.3 mmol), cyanamide (71 mg, 1.7 mmol) and Hg(OAc)$_2$ (0.35 g, 1.1 mmol) in acetonitrile (10 mL) were processed as described in Example 16E to provide the title compound (0.35 g, 0.76 mmol, 91% yield). $^1$H NMR (300 MHz, CDCl$_3$) δ ppm 0.95-1.09 (m, 4H), 1.39 (s, 9H), 1.91 (s, 3H), 3.91 (s, 3H), 4.56 (s, 2H), 6.74 (s, 1H), 6.93 (d, J=8.8 Hz, 1H), 7.31 (d, J=2.4 Hz, 1H), 7.35 (dd, J=8.8, 2.7 Hz, 1H); MS (DCI/NH$_3$) m/z 461 (M+H)$^+$. Anal. calculated for C$_{22}$H$_{25}$ClN$_4$O$_3$S: C, 57.32; H, 5.47; N, 12.15. Found: C, 57.22; H, 5.54; N, 12.07.

Example 33

N-[(2Z)-5-tert-butyl-3-[(1-hydroxycyclopropyl)methyl]-1,3-thiazol-2(3H)-ylidene]-5-chloro-N'-cyano-2-methoxybenzenecarboximidamide The product of Example 32E (0.29 g, 0.63 mmol) and K$_2$CO$_3$ (0.44 g, 3.2 mmol) in CH$_3$OH (5 mL) and H$_2$O (1 mL) were processed as described in Example 21 to provide the title compound (0.21 g, 0.50 mmol, 80% yield). $^1$H NMR (300 MHz, CDCl$_3$) δ ppm 0.70-0.77 (m, 2H), 0.88-0.94 (m, 2H), 1.40 (s, 9H), 3.88 (s, 3H), 4.17 (s, 1H), 4.33 (s, 2H), 6.83 (s, 1H), 6.93 (d, J=8.5 Hz, 1H), 7.32-7.38 (m, 2H); MS (DCI/NH$_3$) m/z 419 (M+H)$^+$. Anal. calculated for C$_{20}$H$_{23}$ClN$_4$O$_2$S.0.1C$_4$H$_8$O$_2$ (EtOAc): C, 57.28; H, 5.61; N, 13.10. Found: C, 57.44; H, 5.77; N, 12.73.

Example 34

1-{[(2Z)-5-tert-butyl-2-({(cyanoimino)[2-methoxy-5-(trifluoromethyl)phenyl]methyl}imino)-1,3-thiazol-3(2H)-yl]methyl}cyclobutyl acetate

Example 34A (Z)-N-(5-tert-butyl-3-((1-hydroxycyclobutyl)methyl)thiazol-2(3H)-ylidene)-2-methoxy-5-(trifluoromethyl)benzamide The product of Example 27A (1.2 g, 5.1 mmol), 2-methoxy-5-(trifluoromethyl)benzoic acid (1.1 g, 5.1 mmol), thionyl chloride (6 mL) and triethylamine (2.1 mL, 15 mmol) in THF (25 mL) were processed as described in Example 18B and Example 18C to provide the title compound (1.2 g, 2.7 mmol, 53% yield). MS (DCI/NH$_3$) m/z 443 (M+H)$^+$.

Example 34B (Z)-1-((5-tert-butyl-2-(2-methoxy-5-(trifluoromethyl)benzoylimino)thiazol-3(2H)-yl)methyl)cyclobutyl acetate The product of Example 34A (1.1 g, 2.5 mmol), N,N-dimethylpyridin-4-amine (DMAP, (30 mg, 0.25 mmol) and acetic anhydride (0.70 mL, 7.5 mmol) in pyridine (15 mL) were processed as described in Example 20C to provide the title compound (1.0 g, 2.1 mmol, 84% yield). MS (DCI/NH$_3$) m/z 485 (M+H)$^+$.

Example 34C (Z)-1-((5-tert-butyl-2-(2-methoxy-5-(trifluoromethyl)phenylcarbonothioylimino)thiazol-3(2H)-yl)methyl)cyclobutyl acetate The product of Example 34B (0.94 g, 1.9 mmol) and 2,4-bis-(4-methoxyphenyl)-1,3-dithia-2,4-diphosphetane 2,4-disulfide (Lawesson's reagent, 0.79 g, 1.9 mmol) in toluene (10 mL) were processed as described in Example 16D to give the title compound (1.1 g, 2.2 mmol, 111% yield). This impure material was carried on without further purification. MS (DCI/NH$_3$) m/z 501 (M+H)$^+$.

Example 34D

1-{[(2Z)-5-tert-butyl-2-({(cyanoimino)[2-methoxy-5-(trifluoromethyl)phenyl]methyl}imino)-1,3-thiazol-3(2H)-yl]methyl}cyclobutyl acetate The product of Example 34C (0.97 g, 1.9 mmol), triethylamine (1.1 mL, 7.8 mmol), cyanamide (0.25 g, 5.8 mmol) and Hg(OAc)$_2$ (1.2 g, 3.9 mmol) in acetonitrile (15 mL) were processed as described in Example 16E to provide the title compound (0.84 g, 1.7 mmol, 85% yield). $^1$H NMR (300 MHz, CDCl$_3$) δ ppm 1.38 (s, 9H), 1.73-1.86 (m, 1H), 1.85-1.98 (m, 1H), 2.01 (s, 3H), 2.21-2.48 (m, 4H), 3.98 (s, 3H), 4.77 (s, 2H), 6.63 (s, 1H), 7.09 (d, J=8.5 Hz, 1H), 7.60-7.71

(m, 2H); MS (DCI/NH$_3$) m/z 509 (M+H)$^+$. Anal. calculated for C$_{24}$H$_{27}$F$_3$N$_4$O$_3$S; C, 56.68; H, 5.35; N, 11.02. Found: C, 56.50; H, 5.10; N, 10.67.

Example 35

N-[(2Z)-5-tert-butyl-3-[(1-hydroxycyclobutyl)methyl]-1,3-thiazol-2(3H)-ylidene]-N'-cyano-2-methoxy-5-(trifluoromethyl)benzenecarboximidamide The product of Example 34D (0.75 g, 1.5 mmol) and K$_2$CO$_3$ (1.0 g, 7.4 mmol) in CH$_3$OH (10 mL) and H$_2$O (2 mL) were processed as described in Example 21 to provide the title compound (0.64 g, 1.4 mmol, 93% yield). $^1$H NMR (300 MHz, CDCl$_3$) δ ppm 1.40 (s, 9H), 1.57-1.70 (m, 1H), 1.73-1.89 (m, 1H), 2.00-2.22 (m, 4H), 3.83 (s, 1H), 3.96 (s, 3H), 4.42 (s, 2H), 6.94 (s, 1H), 7.08 (d, J=8.7 Hz, 1H), 7.58-7.72 (m, 2H); MS (DCI/NH$_3$) m/z 467 (M+H)$^+$. Anal. calculated for C$_{22}$H$_{25}$F$_3$N$_4$O$_2$S: C, 56.64; H, 5.40; N, 12.01. Found: 56.62; H, 5.38; N, 12.00.

Example 36

N-[(2Z)-5-tert-butyl-3-[(2R)-tetrahydrofuran-2-ylmethyl]-1,3-thiazol-2(3H)-ylidene]-N'-cyano-2-ethoxy-5-(trifluoromethyl)benzenecarboximidamide

Example 36A (R,Z)-N-(5-tert-butyl-3-((tetrahydrofuran-2-yl)methyl)thiazol-2(3H)-ylidene)-2-fluoro-5-(trifluoromethyl)benzamide To a solution of the product of Example 17B (0.62 g, 2.6 mmol) in THF (15 mL) was added triethylamine (1.1 mL, 7.7 mmol) followed by 2-fluoro-5-(trifluoromethyl)benzoyl chloride (0.39 mL, 2.6 mmol) in 5 mL THF via cannula. This mixture was warmed to 50° C. and was allowed to stir for 4 h. The mixture was quenched with saturated, aqueous NH$_4$Cl (5 mL) and diluted with EtOAc (10 mL). The layers were separated and the aqueous layer was extracted with EtOAc (3×5 mL). The combined organics were dried over anhydrous Na$_2$SO$_4$, filtered and concentrated under reduced pressure. The crude material was purified by column chromatography (SiO$_2$, 60% hexanes in EtOAc) to give the title compound (0.44 g, 1.0 mmol, 40% yield). MS (DCI/NH$_3$) m/z 431 (M+H)$^+$.

Example 36B (R,Z)-N-(5-tert-butyl-3-((tetrahydrofuran-2-yl)methyl)thiazol-2(3H)-ylidene)-2-ethoxy-5-(trifluoromethyl)benzamide To ethanol (0.13 mL, 2.1 mmol) in THF (5 mL) was added KOt-Bu (0.23 g, 2.0 mmol). The mixture stirred at ambient temperature for 20 min then the product of Example 36A (0.44 g, 1.0 mmol) in THF (10 mL) was added via cannula. The mixture stirred for 1 h at ambient temperature then was quenched with saturated, aqueous NH$_4$Cl (5 mL) and diluted with EtOAc (10 mL). The layers were separated and the aqueous layer was extracted with EtOAc (3×10 mL). The combined organics were dried over anhydrous Na$_2$SO$_4$, filtered and concentrated under reduced pressure. The crude material was purified by column chromatography (SiO$_2$, 60% hexanes in EtOAc) to give the title compound (0.45 g, 0.99 mmol, 96% yield). MS (DCI/NH$_3$) m/z 457 (M+H)$^+$.

Example 36C (R,Z)-N-(5-tert-butyl-3-((tetrahydrofuran-2-yl)methyl)thiazol-2(3H)-ylidene)-2-ethoxy-5-(trifluoromethyl)benzothioamide The product of Example 36B (0.25 g, 0.55 mmol) and 2,4-bis-(4-methoxyphenyl)-1,3-dithia-2,4-diphosphetane 2,4-disulfide (Lawesson's reagent, 0.22 g, 0.55 mmol) in toluene (10 mL) were processed as described in Example 16D to give the title compound (0.3 g, 0.66 mmol, 116% yield). This impure material was carried on without further purification. MS (DCI/NH$_3$) m/z 473 (M+H)$^+$.

Example 36D

N-[(2Z)-5-tert-butyl-3-[(2R)-tetrahydrofuran-2-ylmethyl]-1,3-thiazol-2(3H)-ylidene]-N'-cyano-2-ethoxy-5-(trifluoromethyl)benzenecarboximidamide The product of Example 36C (0.26 g, 0.55 mmol), triethylamine (0.21 mL, 1.5 mmol), cyanamide (50 mg, 1.1 mmol) and Hg(OAc)$_2$ (0.23 g, 0.71 mmol) in acetonitrile (10 mL) were processed as described in Example 16E to provide the title compound (0.84 g, 1.7 mmol, 85% yield). $^1$H NMR (300 MHz, CDCl$_3$) δ ppm 1.39 (s, 9H), 1.49 (t, J=6.8 Hz, 3H), 1.56-1.66 (m, 1H), 1.77-1.95 (m, 2H), 1.98-2.12 (m, 1H), 3.73-3.89 (m, 2H), 4.13-4.28 (m, 4H), 4.40-4.52 (m, 1H), 7.01 (s, 1H), 7.06 (d, J=8.1 Hz, 1H), 7.58-7.66 (m, 2H); MS (DCI/NH$_3$) m/z 481 (M+H)$^+$. Anal. calculated for C$_{23}$H$_{27}$F$_3$N$_4$O$_2$S: C, 57.49; H, 5.66; N, 11.66. Found: C, 57.38; H, 5.59; N, 11.60.

Example 37

N-[(2Z)-5-tert-butyl-3-{[1-(cyclopropylsulfonyl)azetidin-3-yl]methyl}-1,3-thiazol-2(3H)-ylidene]-N'-cyano-2-methoxy-5-(trifluoromethyl)benzenecarboximidamide

Example 37A

N-[(2Z)-5-tert-butyl-3-{[1-(cyclopropylsulfonyl)azetidin-3-yl]methyl}-1,3-thiazol-2(3H)-ylidene]-2-methoxy-5-(trifluoromethyl)benzamide To a solution of the product of Example 38D (0.35 g, 0.66 mmol) and Et$_3$N (0.27 mL, 2.0 mmol) in THF (10 mL) at 0° C. was added cyclopropanesulfonyl chloride (0.080 mL, 0.79 mmol). The mixture was stirred at 0° C. for 10 minutes and then was allowed to warm to ambient temperature and was stirred for 2 h. The mixture was quenched with 5 mL saturated, aqueous NaHCO$_3$, the layers were separated and the aqueous layer was extracted with 3×5 mL EtOAc. The combined organics were dried over Na$_2$SO$_4$, filtered and concentrated under reduced pressure. The crude material was purified by column chromatography (SiO$_2$, 60% hexanes in EtOAc) to give the title compound (0.25 g, 0.47 mmol, 72% yield). $^1$H NMR (300 MHz, CDCl$_3$) δ ppm 0.90-1.00 (m, 2H), 1.06-1.17 (m, 2H), 1.35 (s, 9H), 2.22-2.36 (m, 1H), 3.17-3.33 (m, 1H), 3.85 (dd, J=8.1, 5.8 Hz, 2H), 3.97 (s, 3H), 4.06 (t, J=8.1 Hz, 2H), 4.42 (d, J=7.1 Hz, 2H), 6.64 (s, 1H), 7.05 (d, J=8.8 Hz, 1H), 7.64 (dd, J=9.0, 2.9 Hz, 1H), 8.21 (d, J=2.4 Hz, 1H)); MS (DCI/NH$_3$) m/z 532 (M+H)$^+$; Anal. calculated for $C_{23}H_{28}F_3N_3O_4S_2 \cdot 0.1C_4H_8O_2$; C, 52.01; H, 5.37; N, 7.78. Found: C, 52.01; H, 4.98; N, 7.43.

Example 37B (Z)-N-(5-tert-butyl-3-((1-(cyclopropylsulfonyl)azetidin-3-yl)methyl)thiazol-2(3H)-ylidene)-2-methoxy-5-(trifluoromethyl)benzothioamide The product of Example 37A (0.21 g, 0.40 mmol) and 2,4-bis-(4-methoxyphenyl)-1,3-dithia-2,4-diphosphetane 2,4-disulfide (Lawesson's reagent, 0.16 g, 0.40 mmol) in toluene (7 mL) were processed as described in Example 16D to give the title compound (40 mg, 0.073 mmol, 18.5% yield). MS (DCI/NH$_3$) m/z 548 (M+H)$^+$.

Example 37C

N-[(2Z)-5-tert-butyl-3-{[1-(cyclopropylsulfonyl)azetidin-3-yl]methyl}-1,3-thiazol-2(3H)-ylidene]-N'-cyano-2-methoxy-5-(trifluoromethyl)benzenecarboximidamide The product of Example 37B (40 mg, 0.073 mmol), triethylamine (0.027 mL, 0.20 mmol), cyanamide (6.1 mg, 0.15 mmol) and Hg(OAc)$_2$ (30 mg, 0.095 mmol) in acetonitrile (5 mL) were processed as described in Example 16E to provide the title compound (35 mg, 0.063 mmol, 86% yield). $^1$H NMR (300 MHz, CDCl$_3$) δ ppm 0.79-0.90 (m, 1H), 0.91-0.98 (m, 2H), 1.06-1.13 (m, 2H), 1.39 (s, 9H), 3.08-3.25 (m, 1H), 3.78 (dd, J=8.3, 5.6 Hz, 2H), 3.99 (s, 3H), 4.03 (t, J=8.3 Hz, 2H), 4.44 (d, J=7.1 Hz, 2H), 6.78 (s, 1H), 7.10 (d, J=8.7 Hz, 1H), 7.60 (d, J=2.4 Hz, 1H), 7.68 (dd, J=9.1, 2.0 Hz, 1H); MS (DCI/NH$_3$) m/z 556 (M+H)$^+$. Anal. calculated for $C_{24}H_{28}F_3N_5O_3S_2 \cdot 0.1H_2O$; C, 51.71; H, 5.10; N, 12.56. Found: C, 51.43; H, 4.97; N, 12.32.

Example 38

N-[(2Z)-5-tert-butyl-3-{[1-(methylsulfonyl)azetidin-3-yl]methyl}-1,3-thiazol-2(3H)-ylidene]-N'-cyano-2-methoxy-5-(trifluoromethyl)benzenecarboximidamide

Example 38A tert-butyl 3-((5-tert-butyl-2-iminothiazol-3(2H)-yl)methyl)azetidine-1-carboxylate A mixture of 3,3-dimethylbutanal (3.7 mL, 30 mmol), tert-butyl 3-(aminomethyl)azetidine-1-carboxylate (Astatech, 5 g, 27 mmol), and 8 g of 4 Å molecular sieves (8-12 mesh beads) in acetonitrile (50 mL) was stirred at ambient temperature for 72 h. The material was filtered through Celite with acetonitrile (additional 25 mL) then potassium thiocyanate (3.5 g, 35 mmol) was added and the mixture was warmed to 50° C. Iodine (6.81 g, 26.8 mmol) was added and the mixture stirred at 50° C. for 16 h then was cooled to ambient temperature. The mixture was stirred with 75 mL of 20% aqueous sodium metabisulfite for 1 h then the layers were separated and the aqueous layer was extracted with 3×10 mL CH$_2$Cl$_2$. The combined organics were dried over anhydrous Na$_2$SO$_4$, filtered and concentrated under reduced pressure to give the crude title compound (6.3 g, 19 mmol, 72% yield) which was carried on without further purification. MS (DCI/NH$_3$) m/z 326 (M+H)$^+$.

Example 38B 2-methoxy-5-(trifluoromethyl)benzoyl chloride

A solution of the 2-methoxy-5-(trifluoromethyl)benzoic acid (0.68 g, 3.1 mmol) in thionyl chloride (10 mL) was warmed to reflux and was allowed to stir for 2 h. The mixture was cooled to ambient temperature, concentrated under reduced pressure and diluted with 10 mL toluene. This material was again concentrated under reduced pressure and was again diluted with 10 mL toluene. This concentration and dilution was repeated for an additional time and the crude acid chloride was carried on.

Example 38C (Z)-tert-butyl 3-((5-tert-butyl-2-(2-methoxy-5-(trifluoromethyl)benzoylimino)thiazol-3(2H)-yl)methyl)azetidine-1-carboxylate To a solution of the product of Example 38A (1.0 g, 3.1 mmol) in THF (20 mL) was added triethylamine (1.3 mL, 9.2 mmol) and Example 38B (3.1 mmol) in 5 mL THF via cannula. This mixture was warmed to 50° C. and was allowed to stir for 4 h. The mixture was then stirred at ambient temperature for 72 h. The reaction mixture was quenched with 10 mL saturated, aqueous NH$_4$Cl and the layers were separated. The aqueous layer was extracted with 3×10 mL EtOAc and the combined organics were dried over anhydrous Na$_2$SO$_4$, filtered and concentrated under reduced pressure. The crude material was purified by column chromatography (SiO$_2$, 60% hexanes in EtOAc) to give the title compound (0.55 g, 1.0 mmol, 34% yield). MS (DCI/NH$_3$) m/z 528 (M+H)$^+$.

Example 38D (Z)-N-(3-(azetidin-3-ylmethyl)-5-tert-butylthiazol-2(3H)-ylidene)-2-methoxy-5-(trifluoromethyl)benzamide To a solution of the product of Example 38C (1.8 g, 3.4 mmol) in CH$_2$Cl$_2$ (25 mL) at 0° C. was added trifluoroacetic acid (12 mL, 156 mmol) dropwise over 15 min. The mixture was allowed to warm to ambient temperature and was allowed to stir for 3 h. The mixture was concentrated under reduced pressure and purified by column chromatography (SiO$_2$, 100% CH$_2$Cl$_2$ then 9:1:0.1 CH$_2$Cl$_2$:MeOH:NH$_4$OH) to give the title compound (1.8 g, 3.4 mmol, 97% yield). MS (DCI/NH$_3$) m/z 428 (M+H)$^+$.

Example 38E

N-[(2Z)-5-tert-butyl-3-{[1-(methylsulfonyl)azetidin-3-yl]methyl}-1,3-thiazol-2(3H)-ylidene]-2-methoxy-5-(trifluoromethyl)benzamide To a solution of the product of Example 38D (0.35 g, 0.66 mmol) and Et$_3$N (0.27 mL, 2.0 mmol) in THF (10 mL) at 0° C. was added methanesulfonyl chloride (0.061 mL, 0.79 mmol). The mixture was stirred at 0° C. for 10 min and then was allowed to warm to ambient temperature and was stirred for 1 h. The reaction mixture was quenched with 5 mL saturated, aqueous NaHCO$_3$, the layers were separated and the aqueous layer was extracted with 3×5 mL EtOAc. The combined organics were dried over anhydrous $Na_2SO_4$, filtered and concentrated under reduced pressure. The crude material was purified by column chromatography ($SiO_2$, 60% hexanes in EtOAc) to give the title compound (0.22 g, 0.44 mmol, 66% yield). $^1$H NMR (300 MHz, $CDCl_3$) δ ppm 1.35 (s, 9H), 2.83 (s, 3H), 3.15-3.34 (m, 1H), 3.84 (dd, J=8.1, 5.8 Hz, 2H), 3.97 (s, 3H), 4.04 (t, J=8.3 Hz, 2H), 4.42 (d, J=7.5 Hz, 2H), 6.64 (s, 1H), 7.06 (d, J=8.7 Hz, 1H), 7.65 (dd, J=8.7, 2.0 Hz, 1H), 8.22 (d, J=2.4 Hz, 1H); MS ($DCI/NH_3$) m/z 506 $(M+H)^+$; Anal. calculated for $C_{21}H_{26}F_3N_3O_4S_2$; Calc: C, 49.89; H, 5.18; N, 8.31. Found: C, 49.93; H, 5.16; N, 8.05.

Example 38F (Z)-N-(5-tert-butyl-3-((1-(methylsulfonyl)azetidin-3-yl)methyl)thiazol-2(3H)-ylidene)-2-methoxy-5-(trifluoromethyl)benzothioamide The product of Example 38E (0.25 g, 0.49 mmol) and 2,4-bis-(4-methoxyphenyl)-1,3-dithia-2,4-diphosphetane 2,4-disulfide (Lawesson's reagent, 0.20 g, 0.49 mmol) in toluene (10 mL) were processed as described in Example 16D to give the title compound (40 mg, 0.077 mmol, 16% yield). MS ($DCI/NH_3$) m/z 522 $(M+H)^+$.

Example 38G

N-[(2Z)-5-tert-butyl-3-{[1-(methylsulfonyl)azetidin-3-yl]methyl}-1,3-thiazol-2(3H)-ylidene]-N'-cyano-2-methoxy-5-(trifluoromethyl)benzenecarboximidamide The product of Example 38F (40 mg, 0.077 mmol), triethylamine (0.029 mL, 0.21 mmol), cyanamide (6.5 mg, 0.15 mmol) and $Hg(OAc)_2$ (32 mg, 0.10 mmol) in acetonitrile (5 mL) were processed as described in Example 16E to provide the title compound (13 mg, 0.025 mmol, 32% yield). $^1$H NMR (300 MHz, $CDCl_3$) δ ppm 1.39 (s, 9H), 2.80 (s, 3H), 3.09-3.22 (m, 1H), 3.77 (dd, J=8.3, 5.6 Hz, 2H), 4.01 (t, J=8.3 Hz, 2H), 3.99 (s, 3H), 4.43 (d, J=7.5 Hz, 2H), 6.77 (s, 1H), 7.10 (d, J=8.8 Hz, 1H), 7.57-7.61 (m, 1H), 7.66-7.72 (m, 1H); MS ($DCI/NH_3$) m/z 530 $(M+H)^+$.

Example 39

N'-(aminocarbonyl)-N-[(2Z)-3-butyl-4,5-dimethyl-1,3-thiazol-2(3H)-ylidene]-5-chloro-2-methoxybenzenecarbohydrazonamide A mixture of Example 1 (72 mg, 0.2 mmol), semicarbazide (38 mg, 0.5 mmol) and triethylamine (0.7 ml, 0.5 mmol) in dioxane (15 mL) was refluxed at 50° C. for 2 h. The mixture was concentrated under reduced pressure and the residue was purified by chromatography (EtOAc-EtOH 9:1) to afford 35 mg of the title compound. $^1$H NMR (300 MHz-DMSO-$d_6$) δ: 0.97 (t, J=7 Hz, 3H), 1.38 (sextet, J=7 Hz, 2H), 1.64 (m, 2H), 1.93 (s, 3H), 2.09 (s, 3H), 3.65 (s, 3H), 3.97 (t, J=7 Hz, 2H), 6.16 (broad s, 2H), 7.04 (d, J=9 Hz, 1H), 7.32 (d, J=3 Hz, 1H), 7.46 (d-d, J=9 Hz, 3 Hz, 1H), 8.48 (s, 1H); MS ($DCI/NH_3$) m/z 410 $(M+H)^+$.

Example 40 Teodozyj Kolasa

N-[(2Z)-5-acetyl-3-(cyclobutylmethyl)-4-methyl-1,3-thiazol-2(3H)-ylidene]-5-chloro-N'-cyano-2-methoxybenzenecarboximidamide Example 40A N-(5-acetyl-4-methylthiazol-2-yl)-5-chloro-2-methoxybenzamide To a solution of 5-acetyl-2-amino-4-methylthiazole (5.0 g, 32 mmol) in 50 mL of tetrahydrofuran was added triethylamine (13.4 mL, 96 mmol) followed by Example 18B (32 mmol) in 10 mL of tetrahydrofuran via cannula. The mixture was warmed to 50° C. and was allowed to stir for 18 hours. The mixture was cooled to ambient temperature quenched with 15 mL of $NH_4Cl$ and diluted with 15 mL of ethyl acetate. The layers were separated and the aqueous layer was extracted with three 10 mL portions of ethyl acetate. The combined organic extracts were dried over anhydrous $Na_2SO_4$, filtered and concentrated under reduced pressure. The residue was washed with ethyl acetate and the remaining solids were pure title compound. MS ($DCI/NH_3$) m/z 325 $(M+H)^+$.

Example 40B (Z)-N-(5-acetyl-3-(cyclobutylmethyl)-4-methylthiazol-2(3H)-ylidene)-5-chloro-2-methoxybenzamide To Example 40A (97 mg, 0.3 mmol), cyclobutylmethanol (0.04 mL, 0.4 mmol) and $Ph_3P$ (262 mg, 1 mmol) in anhydrous chloroform (25 mL) at −20° C. was added dropwise within 30 seconds a solution of DIAD (0.21 mL, 1 mmol) in $CHCl_3$ (5 mL) and the mixture was allowed to warm to ambient temperature for 1 h. The mixture was then concentrated under reduced pressure and the residue was purified by chromatography (hexane-EtOAc 1:1) to afford 54 mg of the title compound. $^1$H NMR (300 MHz-DMSO-$d_6$) δ: 1.92 (m, 6H), 2.49 (s, 3H), 2.82 (s+m, 4H), 3.82 (s, 3H), 4.37 (d, J=7 Hz, 2H), 7.16 (d, J=9 Hz, 1H), 7.50 (d-d, J=9 Hz, 3 Hz, 1H), 7.80 (d, J=3 Hz, 1H); MS ($DCI/NH_3$) m/z 393 $(M+H)^+$.

Example 40C (Z)-N-(5-acetyl-3-(cyclobutylmethyl)-4-methylthiazol-2(3H)-ylidene)-5-chloro-2-methoxybenzothioamide A mixture of Example 40B (190 mg, 0.5 mmol) and Lawesson's reagent (290 mg, 0.7 mmol) in toluene (15 mL) was refluxed at 60° C. for 3 h. The mixture was then concentrated under reduced pressure and the residue was purified by chromatography (EtOAc) to provide 75 mg of the title compound. $^1$H NMR (300 MHz-DMSO-$d_6$) δ: 1.88 (m, 6H), 2.55 (s, 3H), 2.78 (s+m, 4H), 3.78 (s, 3H), 4.46 (d, J=7 Hz, 2H), 7.15 (m, 1H), 7.40 (m, 2H); MS ($DCI/NH_3$) m/z 409 $(M+H)^+$. Anal calcd for $C_{19}H_{21}ClN_2O_2S_2.0.5H_2O$: C, 54.60; H, 5.31; N, 6.70. Found: C, 54.79; H, 4.65; N, 6.62.

Example 40D

N-[(2Z)-5-acetyl-3-(cyclobutylmethyl)-4-methyl-1,3-thiazol-2(3H)-ylidene]-5-chloro-N'-cyano-2-methoxybenzenecarboximidamide Example 40C (53 mg, 0.13 mmol) in dioxane (10 mL) was treated with cyanamide (98.4 mg, 0.2 mmol) and $Hg(OAc)_2$ (48 mg, 0.15 mmol) at 80° C. for 1 h. The mixture was then concentrated under reduced pressure and the residue was purified by chromatography (hexane-EtOAc 1:2) to afford 40 mg of the title compound. $^1$H NMR (300 MHz-DMSO-$d_6$) δ:1.80 (m, 4H), 1.96 (m, 2H), 2.56 (s, 3H), 2.73 (s+m, 3H), 3.82 (s, 3H), 4.40 (d, J=7 Hz, 2H), 7.23 (d, J=9 Hz, 1H), 7.40 (d, J=3 Hz, 1H), 7.56 (d-d, J=9 Hz, 3 Hz, 1H); MS (DCI/NH$_3$) m/z 417 (M+H)$^+$. Anal calcd for $C_{20}H_{21}ClN_4O_2S.0.25H_2O$: C, 57.00; H, 5.14; N, 13.29. Found: C, 57.26; H, 5.12; N, 12.63.

Example 41

N'-(anilinocarbonyl)-N-[(2Z)-3-butyl-4,5-dimethyl-1,3-thiazol-2(3H)-ylidene]-5-chloro-2-methoxybenzenecarbohydrazonamide A mixture of Example 1C (46 mg, 0.125 mmol), N-phenylhydrazinecarboxamide (76 mg, 0.5 mmol) and $Hg(OAc)_2$ (48 mg, 0.15 mmol) in dioxane (15 mL0 and AcOH (1 mL) was refluxed at 60° C. for 1 h. The mixture was then concentrated under reduced pressure, the residue was redissolved in EtOAc and washed with 10% NaHCO$_3$, brine, dried with anhydrous MgSO$_4$ and concentrated under reduced pressure. Purification by chromatography (EtOAc) afforded 27 mg of the title compound. $^1$H NMR (300 MHz-DMSO-$d_6$) δ: 0.98 (t, J=7 Hz, 4H), 1.40 (sextet, J=7 Hz, 2H), 1.65 (m, 2H), 1.93 (s, 3H), 2.10 (s, 3H), 3.86 (s, 3H), 4.03 (t, J=7 Hz, 2H), 6.96 (m, 1H), 7.05 (d, J=9 Hz, 1H), 7.25 (t, J=9 Hz, 2H), 7.40 (d, J=3 Hz, 1H), 7.49 (d-d, J=9 Hz, 3 Hz, 1H), 7.57 (m, 2H), 8.70 (s, 1H), 8.98 (s, 1H); MS (DCI/NH$_3$) m/z 486 (M+H)$^+$. Anal calcd for $C_{24}H_{28}ClN_5O_2S$: C, 59.31; H, 5.81; N, 14.41. Found: C, 59.53; H, 5.84; N, 14.00.

Example 42

2-{{[(2Z)-3-butyl-5-tert-butyl-1,3-thiazol-2(3H)-ylidene]amino}[(phenoxycarbonyl)imino]methyl}-4-chlorophenyl acetate

Example 42A (Z)-N-(5-tert-butyl-3-butylthiazol-2(3H)-ylidene)-5-chloro-2-hydroxybenzothioamide To a solution of Example 6C (212 mg, 0.534 mmol) in CH$_2$Cl$_2$ (20 mL) at 0° C. was added IM BBr$_3$ in CH$_2$Cl$_2$ (1.6 mL, 1.6 mmol) and the reaction was allowed to warm to room temperature for 3 h. Saturated sodium bicarbonate was added, and the organic layer was separated, washed with brine, dried with anhydrous MgSO$_4$ and concentrated under reduced pressure to provide quantitatively of the title compound. $^1$H NMR (300 MHz-DMSO-$d_6$) δ: 0.95 (t, J=7 Hz, 4H), 1.37 (s+m, 11H), 1.82 (m, 2H), 4.30 (t, J=7 Hz, 2H), 6.95 (d, J=9 Hz, 1H), 7.40 (d-d, J=9 Hz, 3 Hz, 1H), 7.80 (s, 1H), 8.37 (d, J=3 Hz, 1H), 13.62 (s, 1H); MS (DCI/NH$_3$) m/z 383 (M+H)$^+$.

Example 42B

2-{{[(2Z)-3-butyl-5-tert-butyl-1,3-thiazol-2(3H)-ylidene]amino}[(phenoxycarbonyl)imino]methyl}-4-chlorophenyl acetate A mixture of Example 42A (29 mg, 0.076 mmol, phenyl carbamate (10 mg, 0.073 mmol and triethylamine (0.021 mL, 0.15 mmol) in acetonitrile (20 mL) was treated with $Hg(OAc)_2$ (26 mg, 0.08 mmol) at 80° C. for 45 min. The mixture was then concentrated under reduced pressure and the residue was purified by chromatography to afford 5 mg of the title compound. $^1$H NMR (300 MHz-DMSO-$d_6$) δ: 0.95 (t, J=7 Hz, 4H), 1.37 (s+m, 12H), 1.82 (m, 2H), 4.30 (t, J=7 Hz, 2H), 7.00 (d, J=9 Hz, 2H), 7.20 (t, J=9 Hz, 1H), 7.28 (d, J=9 Hz, 1H), 7.40 (m, 2H), 7.60 (m, 2H); MS (DCI/NH$_3$) m/z 528 (M+H)$^+$.

Example 43

N-[(2Z)-5-tert-butyl-3-[(2R)-tetrahydrofuran-2-ylmethyl]-1,3-thiazol-2(3H)-ylidene]-3,5-dichloro-N'-cyanobenzenecarboximidamide

Example 43A (NZ,N'Z)-methyl N-5-tert-butyl-3-(((S)-tetrahydrofuran-2-yl)methyl)thiazol-2(3H)-ylidene-N'-cyano-carbamimidothioate A mixture of Example 17B (as a free base) (0.361 g, 1.5 mmol) and dimethyl cyanocarbonimidodithioate (0.219 g, 1.5 mmol) in THF (35 mL) was treated with Et$_3$N (0.21 mL, 1.5 mmol) and the resulting mixture was stirred at 45° C. for 12 h. The mixture was concentrated under reduced pressure and the residue was purified by chromatography (hexane-EtOAc 1:1) to afford 430 mg of the title compound. $^1$H NMR (300 MHz-DMSO-$d_6$) δ 1.31 (s, 9H), 1.60 (m, 1H), 1.82 (quintet, J=7 Hz, 2H), 1.95 (m, 1H), 2.53 (s, 3H), 3.65 (m, 1H), 3.75 (m, 1H), 4.26 (m, 3H), 7.43 (s, 1H); MS (DCI/NH$_3$) m/z 339 (M+H)$^+$.

Example 43B

N-[(2Z)-5-tert-butyl-3-[(2R)-tetrahydrofuran-2-ylmethyl]-1,3-thiazol-2(3H)-ylidene]-3,5-dichloro-N'-cyanobenzenecarboximidamide To a mixture of Example 43A (0.102 g, 0.3 mmol), 3,5-dichlorophenylboronic acid (0.152 g, 0.8 mmol) and copper (I) acetate (0.123 g, 1 mmol) in DME (25 mL) were added tris(dibenzylideneacetone)dipalladium(0) 0.045 g, 0.05 mmol) and triethylphosphite (0.024 mg, 0.14 mmol) and the mixture was refluxed for 16 h. The mixture was then concentrated under reduced pressure and the residue was chromatographed (hexane-EtOAc 1:1) to afford 123 mg of the title compound. $^1$H NMR (300 MHz-DMSO-$d_6$) δ 1.36 (s, 9H), 1.62 (m, 1H), 1.84 (m, 2H), 1.95 (m, 1H), 3.65 (m, 1H), 3.78 (m, 1H), 4.34 (m, 3H), 7.58 (s, 1H), 7.87 (m, 1H), 7.95 (m, 2H); MS (DCI/NH$_3$) m/z 437 (M+H)$^+$. Anal calcd for $C_{20}H_{22}Cl_2N_4OS \cdot 0.25H_2O$: C, 54.36; H, 5.13; N, 12.68. Found: C, 54.33; H, 4.85; N, 12.14.

Example 44

N-[(2Z)-5-tert-butyl-3-[(2R)-tetrahydrofuran-2-ylmethyl]-1,3-thiazol-2(3H)-ylidene]-N'-cyano-2-formylbenzenecarboximidamide To a mixture of Example 43A (0.102 g, 0.3 mmol), 5-chloro-2-formylphenylboronic acid (0.184 g, 1 mmol) and copper(I) acetate (0.123 g, 1 mmol) in DME (25 mL) were added tris(dibenzylideneacetone)dipalladium(0) 0.045 g, 0.05 mmol) and triethylphosphite (0.024 mg, 0.14 mmol) and the mixture was refluxed for 16 h. The mixture was then concentrated under reduced pressure and the residue was chromatographed (hexane-EtOAc 1:1) to afford 50 mg of the title compound. $^1$H NMR (300 MHz-DMSO-$d_6$) δ 1.33 (s, 9H), 1.62 (m, 1H), 1.84 (m, 2H), 1.99 (m, 1H), 3.65 (m, 1H), 3.80 (m, 1H), 4.26 (m, 3H), 7.36 (s, 1H), 7.70 (m, 2H), 8.06 (d, J=3 Hz, 1H), 10.53 (s, 1H); MS (DCI/NH$_3$) m/z 407 (M+H)$^+$.

Example 45

N-[(2Z)-5-tert-butyl-3-[(2R)-tetrahydrofuran-2-ylmethyl]-1,3-thiazol-2(3H)-ylidene]-N'-cyano-2,5-difluorobenzenecarboximidamide The title compound was prepared as described in Example 44 by substituting 2-formylboronic acid with 2,5-difluorophenylboronic acid. $^1$H NMR (300 MHz-DMSO-$d_6$) δ 1.33 (s, 9H), 1.60 (m, 1H), 1.80 (m, 2H), 1.92 (m, 1H), 3.65 (m, 1H), 3.75 (m, 1H), 4.26 (m, 3H), 7.25 (s, 1H), 7.44 (m, 1H), 7.55 (s, 1H), 7.66 (m, 1H); MS (DCI/NH$_3$) m/z 405 (M+H)$^+$.

Example 46

N-[(2Z)-5-tert-butyl-3-[(2R)-tetrahydrofuran-2-ylmethyl]-1,3-thiazol-2(3H)-ylidene]-N'-cyano-2-[(hydroxyimino)methyl]benzenecarboximidamide A mixture of Example 44 (40 mg, 0.1 mmol) and hydroxylamine hydrochloride (7 mg, 0.1 mmol) in pyridine (7 mL) was stirred at ambient temperature for 8 h and then was concentrated under reduced pressure. The residue was dissolved in ethyl acetate and was washed with water, brine, dried with anhydrous MgSO$_4$ and concentrated under reduced pressure. The residue was chromatographed (EtOAc) to afford 20 mg of the title compound. $^1$H NMR (300 MHz-DMSO-$d_6$) δ 1.36 (s, 9H), 1.52 (m, 1H), 1.80 (m, 2H), 1.92 (m, 1H), 3.65 (m, 1H), 3.75 (m, 1H), 4.23 (m, 3H), 7.50 (m, 4H), 7.84 (m, 1H), 8.06 (s, 1H), 11.37 (s, 1H); MS (DCI/NH$_3$) m/z 412 (M+H)$^+$.

Example 47

N-[(2Z)-3-butyl-4,5-dimethyl-1,3-thiazol-2(3H)-ylidene]-2,5-difluoro-N'-methoxybenzenecarboximidamide

Example 47A 2,5-difluoro-N-methoxybenzamide

To a mixture of 2,5-difluorobenzoyl chloride (1.77 g, 10 mmol) and O-methylhydroxylamine hydrochloride (830 mg, 10 mmol) in methylene chloride (25 mL) at 0° C. was added dropwise triethylamine (2.8 mL, 20 mmol) and the mixture was stirred at room temperature for 8 h. The mixture was then washed with water, brine, dried with MgSO$_4$ and concentrated under reduced pressure. The residue was chromatographed (hexane-EtOAc 2:1) to afford 1.4 g of the title compound. $^1$H NMR (300 MHz-DMSO-$d_6$) δ 3.70 (s, 3H), 7.42 (m, 3H), 11.64 (s, 1H); MS (DCI/NH$_3$) m/z 188 (M+H)$^+$, 205 (M+NH$_4$)$^+$.

Example 47B 2,5-difluoro-N-methoxybenzimidoyl bromide

The compound 47A (1.4 g, 7.5 mmol) was dissolved in acetonitrile (25 mL) and triphenylphosphine (3.15 g, 12 mmol) followed by perbromomethane (3.98 g, 12 mmol) were added. The resulting mixture was refluxed for 2 h and then cooled to ambient temperature. The mixture was concentrated under reduced pressure and the residue was purified by chromatography (hexane-EtOAc 4:1) to afford 2.3 g of the title compound. $^1$H NMR (300 MHz-DMSO-$d_6$) δ 4.08 (s, 3H), 7.46 (m, 3H); MS (DCI/NH$_3$) m/z 250 (M+H)$^+$.

Example 47C

N-[(2Z)-3-butyl-4,5-dimethyl-1,3-thiazol-2(3H)-ylidene]-2,5-difluoro-N'-methoxybenzenecarboximidamide A mixture of compound 47B (250 mg, 1 mmol), 3-butyl-4,5-dimethylthiazol-2(3H)-imine (Example 1A) (374 mg, 2.03 mmol), potassium carbonate (553 mg, 4 mmol) and copper(II) oxide (8 mg, 0.1 mmol) in DMF (10 mL) was refluxed for 16 h. The mixture was brought to room temperature, water was added and the mixture was extracted with EtOAc. The acetate layer was washed with water, brine, dried with MgSO$_4$ and concentrated under reduced pressure. Purification by chromatography (hexane-Et$_2$O 2:1) afforded 20 mg of the title compound. $^1$H NMR (300 MHz-DMSO-$d_6$) δ: 0.88 (t, J=7 Hz, 3H), 1.25 (m, 2H), 1.60 (m, 2H), 2.15 (s, 6H), 3.73 (s, 3H), 3.95 (m, 2H), 7.14 (m, 1H), 7.25 (m, 2 Hz, 1H); MS (DCI/NH$_3$) m/z 354 (M+H)$^+$.

Example 48

N-[(2Z)-3-butyl-5-tert-butyl-4-methyl-1,3-thiazol-2(3H)-ylidene]-5-chloro-N',2-dimethoxybenzenecarboximidamide

Example 48A

N-(5-tert-butyl-4-methylthiazol-2-yl)-5-chloro-2-methoxybenzamide

To a mixture of 5-tert-butyl-4-methylthiazol-2-amine (500 mg, 2.94 mmol) and Example 18B (615 mg, 3 mmol) in anhydrous CH$_2$Cl$_2$ (50 mL) at 0° C. was added dropwise triethylamine (0.56 mL, 4 mmol) and the mixture was allowed to warm to ambient temperature for 12 h. The mixture was then washed with water, brine, dried with anhydrous MgSO$_4$ and concentrated under reduced pressure. The residue was purified by chromatography (hexane-EtOAc 1:1) to afford 525 mg of the title compound. MS (DCI/NH$_3$) m/z 339 (M+H)$^+$.

Example 48B (Z)-N-(5-tert-butyl-3-butyl-4-methylthiazol-2(3H)-ylidene)-5-chloro-2-methoxybenzamide The compound 48A (840 mg, 2.5 mmol), 1-iodobutane (1840 mg, 10 mmol), potassium carbonate (829 mg, 6 mmol), tetrabutylammonium iodide (15 mg, 0.041 mmol), tetrabutylammonium hydrogen sulfate (15 mg, 0.044 mmol) and tetraethylammonium iodide (15 mg, 0.05 mmol) were combined in toluene (50 mL) and the mixture was refluxed for 48 h. The mixture was then washed with water, brine, dried with MgSO$_4$ and concentrated under reduced pressure to afford 540 mg of the title compound. $^1$H NMR (300 MHz-DMSO-d$_6$) δ: 0.94 (t, J=7 Hz, 4H), 1.37 (s+m, 11H), 1.66 (m, 2H), 2.40 (s, 3H), 3.78 (s, 3H), 4.17 (t, J=7 Hz, 2H), 7.10 (d, J=9 Hz, 1H), 7.43 (d-d, J=9 Hz, 3 Hz, 1H), 7.68 (d, J=3 Hz, 1H); MS (DCI/NH$_3$) m/z 395 (M+H)$^+$.

Example 48C (Z)-N-(5-tert-butyl-3-butyl-4-methylthiazol-2(3H)-ylidene)-5-chloro-2-methoxybenzothioamide To Example 48B (540 mg, 1.4 mmol) in toluene was added Lawesson's Reagent (553 mg, 1.4 mmol) and the mixture was refluxed for 1 h. The mixture was concentrated under reduced pressure and the residue was chromatographed (hexane-EtOAc 2:1) to afford 400 mg of the title compound. $^1$H NMR (300 MHz-DMSO-d$_6$) δ: 0.89 (t, J=7 Hz, 4H), 1.30 (quintet, J=7 Hz, 2H), 1.42 (s, 9H), 1.66 (m, 2H), 2.46 (s, 3H), 3.72 (s, 3H), 4.28 (t, J=7 Hz, 2H), 7.05 (d, J=9 Hz, 1H), 7.34 (m, 2H); MS (DCI/NH$_3$) m/z 411 (M+H)$^+$.

Example 48D

N-[(2Z)-3-butyl-5-tert-butyl-4-methyl-1,3-thiazol-2(3H)-ylidene]-5-chloro-N',2-dimethoxybenzenecarboximidamide Example 48C was dissolved in dioxane (40 mL) and O-methylhydroxylamine hydrochloride (580 mg, 7 mmol) and Hg(OAc)$_2$ (436 mg, 1.4 mmol) were added followed by slow addition of triethylamine (1.25 mL, 9 mmol). The resulting mixture was refluxed at 80° C. for 12 h. The mixture was washed with water, brine, dried with MgSO$_4$ and concentrated under reduced pressure. The residue was purified by chromatography (hexane-Et$_2$O 2:1) to afford 350 mg of the title compound. $^1$H NMR (300 MHz-DMSO-d$_6$) δ 0.85 (t, J=7 Hz, 3H), 1.24 (m, 2H), 1.35 (s, 9H), 1.55 (m, 2H), 2.29 (s, 3H), 3.66 (s, 3H), 3.72 (3, 3H), 3.90 (t, J=7 Hz, 2H), 7.04 (m, 2H), 7.34 (d-d, J=9 Hz, 3 Hz, 1H); MS (DCI/NH$_3$) m/z 424 (M+H)$^+$. Anal calcd for C$_{21}$H$_{30}$ClN$_3$O$_2$S: C, 59.49; H, 7.13; N, 9.91. Found: C, 59.50; H, 7.22; N, 9.64.

Example 49 ethyl 2-[{[(2Z)-3-butyl-5-tert-butyl-1,3-thiazol-2(3H)-ylidene]amino}(5-chloro-2-methoxyphenyl)methylene]hydrazinecarboxylate A mixture of Example 6 (190 mg, 0.48 mmol), ethyl hydrazinecarboxylate (100 mg, 0.96 mmol), Hg(OAc)$_2$ (153 mg, 0.48 mmol) and acetic acid (0.03 mL, 0.48 mmol) in dioxane (30 mL) was heated at 80° C. for 2 h and then was concentrated under reduced pressure. The residue was partitioned between ethyl acetate and saturated sodium bicarbonate. The organic layer was washed with brine, dried with MgSO$_4$ and concentrated under reduced pressure. The residue was purified by chromatography (CH$_2$Cl$_2$-Et$_2$O 1:1, 1:2) to afford 22 mg of the title compound as the less polar isomer. $^1$H NMR (300 MHz-DMSO-d$_6$) δ 0.90 (t, J=7 Hz, 3H), 1.18 (s+m, 12H), 1.30 (m, 2H), 1.62 (m, 2H), 3.98 (s+m, 5H), 4.20 (q, J=7 Hz, 2H), 7.22 (d, J=9 Hz, 1H), 7.50 (d-d, J=9 Hz, 3 Hz, 1H), 7.58 (s, 1H), 7.96 (d, J=3 Hz, 1H), 13.30 (s, 1H); MS (DCI/NH$_3$) m/z 467 (M+H)$^+$.

Example 50 ethyl 2-[{[(2Z)-3-butyl-5-tert-butyl-1,3-thiazol-2(3H)-ylidene]amino}(5-chloro-2-methoxyphenyl)methylene]hydrazinecarboxylate The title compound was obtained as a second product (more polar) from the reaction in Example 49. $^1$H NMR (300 MHz-DMSO-d$_6$) δ 0.95 (t, J=7 Hz, 3H), 1.05 (s, 9H), 1.20 (t, J=7 Hz, 3H), 1.33 (quintet, J=7 Hz, 2H), 1.69 (m, 2H), 3.62 (s, 3H), 3.95 (t, J=7 Hz, 2H), 4.10 (q, J=7 Hz, 2H), 6.92 (s, 1H), 7.05 (d, J=9 Hz, 1H), 7.26 (d, J=3 Hz, 1H), 7.50 (d-d, J=9 Hz, 3 Hz, 1H), 9.18 (s, 1H); MS (DCI/NH$_3$) m/z 467 (M+H)$^+$. Anal calcd for C$_{22}$H$_{31}$ClN$_4$O$_3$S: C, 56.58; H, 6.69; N, 12.00. Found: C, 56.45; H, 6.73; N, 11.82.

Example 51

N-[(2Z)-5-tert-butyl-3-isobutyl-1,3-thiazol-2(3H)-ylidene]-5-chloro-N'-cyano-2-(2-methoxyethoxy)benzenecarboximidamide

Example 51A (Z)-N-(5-tert-butyl-3-isobutylthiazol-2(3H)-ylidene)-5-chloro-2-fluorobenzamide 5-tert-Butyl-3-isobutylthiazol-2(3H)-imine (Example 16A, 1.5 g, 7.1 mmol) was dissolved in 10 mL of THF. 5-Chloro-2-fluorobenzoyl chloride (1.4 g, 7.1 mmol) was added then triethylamine (3 mL, 21.6 mmol) and the mixture stirred at room temperature for 3 hours. The reaction was diluted with EtOAc, washed with water, brine, dried over MgSO$_4$, filtered and concentrated under reduced pressure. Purification by flash chromatography using a gradient from 0 to 40% EtOAc in hexanes afforded the title compound. $^1$H NMR (300 MHz, CHLOROFORM-D) δ ppm 0.98 (d, J=6.74 Hz, 6H) 1.36 (s, 9H) 2.19-2.39 (m, 1H) 4.01 (d, J=7.14 Hz, 2H) 6.63 (s, 1H) 7.05 (dd, J=10.31, 8.72 Hz, 1H) 7.35 (ddd, J=8.73, 3.97, 2.78 Hz, 1H) 8.10 (dd, J=6.74, 2.78 Hz, 1H). MS (DCI/NH$_3$) m/z 369.2 (M+H)$^+$.

Example 51B (Z)-N-(5-tert-butyl-3-isobutylthiazol-2(3H)-ylidene)-5-chloro-2-(2-methoxyethoxy)benzamide 1M Potassium tert-butoxide in THF (2.7 mL, 2.7 mmol) and 2-methoxyethanol (0.22 g, 2.9 mmol) were mixed for 10 minutes at ambient temperature. Example 51A (0.5 g, 1.4 mmol) in 0.5 mL of THF was added and the reaction stirred at ambient temperature for 18 hours. The reaction was diluted with 50 mL of EtOAc and washed with aqueous NH$_4$Cl, brine (2×), dried over MgSO₄, filtered and the solvent removed under reduced pressure. The final product was purified by flash chromatography with a gradient from 0 to 50% EtOAc in hexane. ¹H NMR (300 MHz, CHLOROFORM-D) δ ppm 0.97 (d, J=6.74 Hz, 6H) 1.35 (s, 9H) 2.21-2.35 (m, 1H) 3.42 (s, 3H) 3.76-3.80 (m, 2H) 3.98 (d, J=7.54 Hz, 2H) 4.19-4.24 (m, 2H) 6.59 (s, 1H) 6.97 (d, J=9.12 Hz, 1H) 7.29 (dd, J=8.73, 2.78 Hz, 1H) 7.91 (d, J=2.78 Hz, 1H). MS (DCI/NH₃) m/z 425.2 (M+H)⁺.

Example 51C (Z)-N-(5-tert-butyl-3-isobutylthiazol-2(3H)-ylidene)-5-chloro-2-(2-methoxyethoxy)benzothioamide The title compound was prepared according to the procedure described in Example 16D by substituting the product of Example 51B for the product of Example 16C. ¹H NMR (300 MHz, CHLOROFORM-D) δ ppm 0.93 (d, J=6.78 Hz, 6H) 1.41 (s, 9H) 2.27 (m, 1H) 3.34 (s, 3H) 3.62-3.67 (m, 2H) 4.06-4.15 (m, 4H) 6.82 (s, 1H) 6.90 (d, J=8.82 Hz, 1H) 7.20 (dd, J=8.82, 2.71 Hz, 1H) 7.50 (d, J=2.71 Hz, 1H). MS (DCI/NH₃) m/z 441.2 (M+H)⁺.

Example 51D

N-[(2Z)-5-tert-butyl-3-isobutyl-1,3-thiazol-2(3H)-ylidene]-5-chloro-N'-cyano-2-(2-methoxyethoxy)benzenecarboximidamide The title compound was prepared according to the procedure described in Example 16E by substituting the product of Example 5° C. for the product of Example 16D. ¹H NMR (300 MHz, CHLOROFORM-D) δ ppm 0.95 (d, J=6.74 Hz, 6H) 1.39 (s, 9H) 2.16-2.30 (m, 1H) 3.40 (s, 3H) 3.81-3.86 (m, 2H) 4.01 (d, J=7.54 Hz, 2H) 4.24-4.29 (m, 2H) 6.73 (s, 1H) 6.96-7.01 (m, 1H) 7.31-7.35 (m, 2H). MS (DCI/NH₃) m/z 449.2 (M+H)⁺. Anal. Calc. for C₂₂H₂₉ClN₄O₂S: C, 58.85; H, 6.51; N, 12.48. Found: C, 58.83; H, 6.44; N, 12.38.

Example 52

N-[(2Z)-5-tert-butyl-3-isobutyl-1,3-thiazol-2(3H)-ylidene]-5-chloro-N'-cyano-2-(2,2,2-trifluoroethoxy)benzenecarboximidamide Example 52A (Z)-N-(5-tert-butyl-3-isobutylthiazol-2(3H)-ylidene)-5-chloro-2-(2,2,2-trifluoroethoxy)benzamide The title compound was prepared according to the procedure described in Example 51B by substituting 2,2,2-trifluoroethanol for 2-methoxyethanol. ¹H NMR (300 MHz, CHLOROFORM-D) δ ppm 0.97 (d, J=6.74 Hz, 6H) 1.36 (s, 9H) 2.20-2.34 (m, 1H) 4.00 (d, J=7.14 Hz, 2H) 4.48 (q, J=8.46 Hz, 2H) 6.63 (s, 1H) 7.02 (d, J=8.72 Hz, 1H) 7.33 (dd, J=8.72, 2.78 Hz, 1H) 8.01 (d, J=2.78 Hz, 1H). MS (DCI/NH₃) m/z 449.2 (M+H)⁺.

Example 52B (Z)-N-(5-tert-butyl-3-isobutylthiazol-2(3H)-ylidene)-5-chloro-2-(2,2,2-trifluoroethoxy)benzothioamide The title compound was prepared according to the procedure described in Example 16D by substituting the product of Example 52A for the product of Example 16C. ¹H NMR (300 MHz, CHLOROFORM-D) δ ppm 0.92 (d, J=6.74 Hz, 6H) 1.42 (s, 9H) 2.25 (m, 1H) 4.08 (d, J=7.54 Hz, 2H) 4.30 (q, J=8.59 Hz, 2H) 6.85 (s, 1H) 6.93 (d, J=8.73 Hz, 1H) 7.23 (dd, J=8.72, 2.78 Hz, 1H) 7.58 (d, J=2.78 Hz, 1H). MS (DCI/NH₃) m/z 465.1 (M+H)⁺.

Example 52C

N-[(2Z)-5-tert-butyl-3-isobutyl-1,3-thiazol-2(3H)-ylidene]-5-chloro-N'-cyano-2-(2,2,2-trifluoroethoxy)benzenecarboximidamide The title compound was prepared according to the procedure described in Example 16E by substituting the product of Example 52B for the product of Example 16D. ¹H NMR (300 MHz, CHLOROFORM-D) δ ppm 0.95 (d, J=6.78 Hz, 6H) 1.40 (s, 9H) 2.15-2.29 (m, 1H) 4.02 (d, J=7.46 Hz, 2H) 4.54 (q, J=8.36 Hz, 2H) 6.76 (s, 1H) 6.95-7.00 (m, 1H) 7.35-7.40 (m, 2H). MS (DCI/NH₃) m/z 473.2 (M+H)⁺. Anal. Calc. for C₂₁H₂₄ClF₃N₄OS: C, 53.33; H, 5.11; N, 11.85. Found: C, 53.24; H, 4.96; N, 11.68.

Example 53

N-[(2Z)-5-tert-butyl-3-isobutyl-1,3-thiazol-2(3H)-ylidene]-2,3-dichloro-N'-cyanobenzenecarboximidamide Example 53A (Z)-N-(5-tert-butyl-3-isobutylthiazol-2(3H)-ylidene)-2,3-dichlorobenzamide The title compound was prepared according to the procedure in Example 51A by substituting 2,3-dichlorobenzoyl chloride for 5-chloro-2-fluorobenzoyl chloride. ¹H NMR (300 MHz, CHLOROFORM-D) δ ppm 0.96 (d, J=6.78 Hz, 6H) 1.37 (s, 9H) 2.27 (m, 1H) 3.98 (d, J=7.46 Hz, 2H) 6.64 (s, 1H) 7.23 (t, J=7.80 Hz, 1H) 7.49 (dd, J=7.80, 1.70 Hz, 1H) 7.76 (dd, J=7.80, 1.70 Hz, 1H). MS (DCI/NH₃) m/z 385.1 (M+H)⁺.

Example 53B (Z)-N-(5-tert-butyl-3-isobutylthiazol-2(3H)-ylidene)-2,3-dichlorobenzothioamide The title compound was prepared according to the procedure described in Example 16D by substituting the product of Example 53A for the product of Example 16C. ¹H NMR (300 MHz, CHLOROFORM-D) δ ppm 0.93 (d, J=6.44 Hz, 6H) 1.40-1.43 (m, 9H) 2.25 (m, 1H) 4.10 (d, J=7.46 Hz, 2H) 6.86 (s, 1H) 7.18 (t, J=7.80 Hz, 1H) 7.39 (dd, J=8.14, 1.70 Hz, 1H) 7.46 (dd, J=7.46, 1.70 Hz, 1H). MS (DCI/NH₃) m/z 401.1 (M+H)⁺.

Example 53C

N-[(2Z)-5-tert-butyl-3-isobutyl-1,3-thiazol-2(3H)-ylidene]-2,3-dichloro-N'-cyanobenzenecarboximidamide The title compound was prepared according to the procedure described in Example 16E by substituting the product of Example 53B for the product of Example 16D. ¹H NMR (300 MHz, CHLOROFORM-D) δ ppm 0.92 (d, J=6.74 Hz, 6H)

1.40 (s, 9H) 2.19 (m, 1H) 4.00 (d, J=7.54 Hz, 2H) 6.77 (s, 1H) 7.28-7.35 (m, 2H) 7.50-7.54 (m, 1H). MS (DCI/NH$_3$) m/z 409.1 (M+H)$^+$. Anal. Calc. for C$_{19}$H$_{22}$Cl$_2$N$_4$S: C, 55.74; H, 5.42; N, 13.69. Found: C, 55.46; H, 5.17; N, 13.39.

Example 54

N-[(2Z)-5-tert-butyl-3-isobutyl-1,3-thiazol-2(3H)-ylidene]-N',5-dicyano-2-methoxybenzenecarboximidamide

Example 54A (Z)-N-(5-tert-butyl-3-isobutylthiazol-2(3H)-ylidene)-5-cyano-2-methoxybenzamide Example 26B (0.22 g, 1.2 mmol) was suspended in 0.6 mL of CH$_2$Cl$_2$. Oxalyl chloride in CH$_2$Cl$_2$ (2M, 1.8 mL, 3.6 mmol) was added, then 10 µL of dimethylformamide. The reaction was stirred at ambient temperature for 1 hour. The solvent was removed under reduced pressure and the residue dried twice by addition and evaporation of 5 mL of toluene. The acid chloride was dissolved in 2 mL of THF and Example 16A (0.26 g, 1.2 mmol) and triethylamine (0.5 mL, 3.6 mmol) were added and the mixture was stirred at ambient temperature for 3 hours. The reaction was diluted with EtOAc, washed with water, brine, dried over MgSO$_4$, filtered and the solvent removed under reduced pressure. Final product was purified by flash chromatography using a gradient from 0 to 50% EtOAc in hexane to provide the title compound. $^1$H NMR (300 MHz, CHLOROFORM-D) δ ppm 0.98 (d, J=6.74 Hz, 6H) 1.35 (s, 9H) 2.21-2.35 (m, 1H) 3.97 (s, 3H) 4.00 (d, J=7.14 Hz, 2H) 6.63 (s, 1H) 7.02 (d, J=8.72 Hz, 1H) 7.67 (dd, J=8.72, 1.98 Hz, 1H) 8.30 (d, J=1.98 Hz, 1H). MS (DCI/NH$_3$) m/z 372.2 (M+H)$^+$.

Example 54B (Z)-N-(5-tert-butyl-3-isobutylthiazol-2(3H)-ylidene)-5-cyano-2-methoxybenzothioamide The title compound was prepared according to the procedure described in Example 16D by substituting the product of Example 54A for the product of Example 16C. $^1$H NMR (300 MHz, CHLOROFORM-D) δ ppm 0.94 (d, J=6.74 Hz, 6H) 1.41 (s, 9H) 2.21-2.35 (m, 1H) 3.86 (s, 3H) 4.07 (d, J=7.54 Hz, 2H) 6.84 (s, 1H) 6.96 (d, J=8.73 Hz, 1H) 7.58 (dd, J=8.72, 2.38 Hz, 1H) 7.82 (d, J=2.38 Hz, 1H). MS (DCI/NH$_3$) m/z 388.2 (M+H)$^+$.

Example 54C

N-[(2Z)-5-tert-butyl-3-isobutyl-1,3-thiazol-2(3H)-ylidene]-N',5-dicyano-2-methoxybenzenecarboximidamide zimidamide The title compound was prepared according to the procedure described in Example 16E by substituting the product of Example 54B for the product of Example 16D. $^1$H NMR (300 MHz, CHLOROFORM-D) δ ppm 0.95 (d, J=6.78 Hz, 6H) 1.39 (s, 9H) 2.22 (m, 1H) 4.00 (s, 3H) 4.02 (d, J=7.46 Hz, 2H) 6.76 (s, 1H) 7.08 (d, J=8.48 Hz, 1H) 7.66 (d, J=2.37 Hz, 1H) 7.69-7.73 (m, 1H). MS (DCI/NH$_3$) m/z 396.2 (M+H)$^+$. Anal. Calc. for C$_{21}$H$_{25}$N$_5$OS: C, 63.77; H, 6.37; N, 17.71. Found: C, 63.40; H, 6.17; N, 17.36.

Example 55

N-[(2Z)-5-tert-butyl-3-isobutyl-1,3-thiazol-2(3H)-ylidene]-N'-cyano-2-ethoxypyridine-3-carboximidamide

Example 55A (Z)-N-(5-tert-butyl-3-isobutylthiazol-2(3H)-ylidene)-2-ethoxynicotinamide The title compound was prepared according to the procedure described in Example 54A by substituting 2-ethoxynicotinic acid (ALFA) for Example 26B. $^1$H NMR (300 MHz, CHLOROFORM-D) δ ppm 0.97 (d, J=6.78 Hz, 6H) 1.35 (s, 9H) 1.45 (t, J=7.12 Hz, 3H) 2.24-2.38 (m, 1H) 3.99 (d, J=7.46 Hz, 2H) 4.53 (q, J=7.12 Hz, 2H) 6.59 (s, 1H) 6.90 (dd, J=7.29, 4.92 Hz, 1H) 8.20 (dd, J=4.75, 2.03 Hz, 1H) 8.33 (dd, J=7.46, 2.03 Hz, 1H). MS (DCI/NH$_3$) m/z 362.2 (M+H)$^+$.

Example 55B (Z)-N-(5-tert-butyl-3-isobutylthiazol-2(3H)-ylidene)-2-ethoxypyridine-3-carbothioamide The title compound was prepared according to the procedure described in Example 16D by substituting the product of Example 55A for the product of Example 16C. $^1$H NMR (300 MHz, CHLOROFORM-D) δ ppm 0.94 (d, J=6.74 Hz, 6H) 1.35 (t, J=7.14 Hz, 3H) 1.41 (s, 9H) 2.34 (m, 1H) 4.09 (d, J=7.54 Hz, 2H) 4.43 (q, J=7.01 Hz, 2H) 6.82 (s, 1H) 6.88 (dd, J=7.34, 4.96 Hz, 1H) 7.97 (dd, J=7.14, 1.98 Hz, 1H) 8.12 (dd, J=5.16, 1.98 Hz, 1H). MS (DCI/NH$_3$) m/z 378.2 (M+H)$^+$.

Example 55C

N-[(2Z)-5-tert-butyl-3-isobutyl-1,3-thiazol-2(3H)-ylidene]-N'-cyano-2-ethoxypyridine-3-carboximidamide The title compound was prepared according to the procedure described in Example 16E by substituting the product of Example 55B for the product of Example 16D. $^1$H NMR (300 MHz, CHLOROFORM-D) δ ppm 0.95 (d, J=6.78 Hz, 6H) 1.39 (s, 9H) 1.44 (t, J=6.95 Hz, 3H) 2.18-2.32 (m, 1H) 4.00 (d, J=7.46 Hz, 2H) 4.50 (q, J=7.12 Hz, 2H) 6.73 (s, 1H) 6.93 (dd, J=7.29, 4.92 Hz, 1H) 7.71 (dd, J=7.46, 2.03 Hz, 1H) 8.24 (dd, J=5.09, 2.03 Hz, 1H). MS (DCI/NH$_3$) m/z 386.2 (M+H)$^+$. Anal. Calc. for: C$_{20}$H$_{27}$N$_5$OS: C, 62.31; H, 7.06; N, 18.17. Found: C, 62.19; H, 7.19; N, 17.96.

Example 56

N-[(2Z)-5-tert-butyl-3-(3-methylbut-2-enyl)-1,3-thiazol-2(3H)-ylidene]-5-chloro-N'-cyano-2-methoxybenzenecarboximidamide

Example 56A 5-tert-butyl-3-(3-methylbut-2-enyl)thiazol-2(3H)-imine 3,3-Dimethylbutanal (0.95 g, 9.1 mmol), 3-methylbut-2-enyl-amine hydrochloride (1.1 g, 9.1 mmol), and triethylamine (1.3 mL, 9.1 mmol) were mixed in 9 mL of dry MeCN with 2 g of 4 Å (8-12 mesh beads) molecular sieves and stirred for 20 hours at room temperature. The reaction was filtered through Celite and washed with 8 mL of MeCN. KSCN (1.2 g, 12.3 mmol) was added and the mixture warmed to 50° C. Iodine (2.3 g, 9.1 mmol) was added and the reaction stirred at 50° C. for 6 hours. 20% $Na_2S_2O_5$ was added, stirred for 30 minutes and the organic layer separated, dried with $Na_2SO_4$ and the solvent removed. The resulting solid was used without further purification. LC/MS m/z 225.3 $(M+H)^+$.

Example 56B (Z)-N-(5-tert-butyl-3-(3-methylbut-2-enyl)thiazol-2 (3H)-ylidene)-5-chloro-2-methoxybenzamide The title compound was prepared according to the procedure described in Example 54A substituting 5-chloro-2-methoxybenzoic acid for Example 26B and Example 56A for Example 16A. $^1$H NMR (300 MHz, CHLOROFORM-D) δ ppm 1.34 (s, 9H) 1.82 (d, J=6.78 Hz, 6H) 3.90 (s, 3H) 4.78 (d, J=7.12 Hz, 2H) 5.31-5.40 (m, 1H) 6.61 (s, 1H) 6.90 (d, J=8.82 Hz, 1H) 7.32 (dd, J=8.82, 3.05 Hz, 1H) 8.01 (d, J=2.71 Hz, 1H). MS $(DCI/NH_3)$ m/z 393.2 $(M+H)^+$.

Example 56C (Z)-N-(5-tert-butyl-3-(3-methylbut-2-enyl)thiazol-2 (3H)-ylidene)-5-chloro-2-methoxybenzothioamide The title compound was prepared according to the procedure described in Example 16D by substituting the product of Example 56B for the product of Example 16C. $^1$H NMR (300 MHz, CHLOROFORM-D) δ ppm 1.40 (s, 9H) 1.77 (d, J=8.33 Hz, 6H) 3.81 (s, 3H) 4.86 (d, J=7.14 Hz, 2H) 5.31-5.40 (m, 1H) 6.82-6.87 (m, 2H) 7.19-7.24 (m, 1H) 7.50 (d, J=2.78 Hz, 1H). MS $(DCI/NH_3)$ m/z 409.1 $(M+H)^+$.

Example 56D

N-[(2Z)-5-tert-butyl-3-(3-methylbut-2-enyl)-1,3-thiazol-2(3H)-ylidene]-5-chloro-N'-cyano-2-methoxybenzenecarboximidamide The title compound was prepared according to the procedure described in Example 16E by substituting the product of Example 56C for the product of Example 16D. $^1$H NMR (300 MHz, CHLOROFORM-D) δ ppm 1.37 (s, 9H) 1.79 (d, J=8.33 Hz, 6H) 3.93 (s, 3H) 4.78 (d, J=7.14 Hz, 2H) 5.27-5.34 (m, 1H) 6.74 (s, 1H) 6.91-6.97 (m, 1H) 7.32-7.37 (m, 2H). MS $(DCI/NH_3)$ m/z 417.1 $(M+H)^+$. Anal. Calc. for $C_{21}H_{25}ClN_4OS$: C, 60.49; H, 6.04; N, 13.44. Found: C, 60.38; H, 6.01; N, 13.36.

Example 57

N-[(2Z)-5-tert-butyl-3-(3,3,3-trifluoropropyl)-1,3-thiazol-2(3H)-ylidene]-5-chloro-N'-cyano-2-methoxybenzenecarboximidamide

Example 57A 5-tert-butyl-3-(3,3,3-trifluoropropyl)thiazol-2(3H)-imine

The title compound was prepared according to the procedure described in Example 56A by substituting 3,3,3-trifluoropropan-1-amine hydrochloride (Oakwood) for 3-methylbut-2-en-1-amine hydrochloride. $^1$H NMR (500 MHz, ACETONITRILE-D3) δ ppm 1.30 (s, 9H) 2.72-2.84 (m, 2H) 4.28 (t, J=6.87 Hz, 2H) 6.92 (s, 1H). MS $(DCI/NH_3)$ m/z 253.0 $(M+H)^+$.

Example 57B (Z)-N-(5-tert-butyl-3-(3,3,3-trifluoropropyl)thiazol-2 (3H)-ylidene)-5-chloro-2-methoxybenzamide The title compound was prepared according to the procedure described in Example 54A by substituting 5-chloro-2-methoxybenzoic acid for Example 26B and Example 57A for Example 16A. $^1$H NMR (300 MHz, CHLOROFORM-D) δ ppm 1.35 (s, 9H) 2.70-2.89 (m, 2H) 3.90 (s, 3H) 4.36 (t, J=6.94 Hz, 2H) 6.62 (s, 1H) 6.92 (d, J=8.73 Hz, 1H) 7.35 (dd, J=8.72, 2.78 Hz, 1H) 7.98 (d, J=2.78 Hz, 1H). MS $(DCI/NH_3)$ m/z 421.1 $(M+H)^+$.

Example 57C (Z)-N-(5-tert-butyl-3-(3,3,3-trifluoropropyl)thiazol-2 (3H)-ylidene)-5-chloro-2-methoxybenzothioamide The title compound was prepared according to the procedure described in Example 16D by substituting the product of Example 57B for the product of Example 16C. $^1$H NMR (300 MHz, CHLOROFORM-D) δ ppm 1.40 (s, 9H) 2.74-2.92 (m, 2H) 3.78 (s, 3H) 4.41 (t, J=6.78 Hz, 2H) 6.85 (d, 1H) 6.83 (s, 1H) 7.22-7.28 (m, 1H) 7.62 (d, J=2.71 Hz, 1H). MS $(DCI/NH_3)$ m/z 437.1 $(M+H)^+$.

Example 57D

N-[(2Z)-5-tert-butyl-3-(3,3,3-trifluoropropyl)-1,3-thiazol-2(3H)-ylidene]-5-chloro-N'-cyano-2-methoxybenzenecarboximidamide The title compound was prepared according to the procedure described in Example 16E by substituting the product of Example 57C for the product of Example 16D. $^1$H NMR (300 MHz, CHLOROFORM-D) δ ppm 1.38 (s, 9H) 2.62-2.80 (m, 2H) 3.92 (s, 3H) 4.39 (t, J=6.78 Hz, 2H) 6.75 (s, 1H) 6.95 (d, J=8.48 Hz, 1H) 7.32-7.41 (m, 2H). MS $(DCI/NH_3)$ m/z 445.1 $(M+H)^+$. Anal. Calc. for $C_{19}H_{20}ClF_3N_4OS$: C, 51.29; H, 4.53; N, 12.59. Found: C, 51.04; H, 4.40; N, 12.23.

Example 58

N-[(2Z)-5-tert-butyl-3-(3,3,3-trifluoropropyl)-1,3-thiazol-2(3H)-ylidene]-N',5-dicyano-2-(2-methoxyethoxy)benzenecarboximidamide

Example 58A

Methyl 5-cyano-2-(2-methoxyethoxy)benzoate

Methyl 5-cyano-2-hydroxybenzoate (Astatech, 3.0 g, 16.9 mmol), 1-bromo-2-methoxyethane (2.6 g, 18.6 mmol), and $K_2CO_3$ (2.3 g, 16.9 mmol) were mixed in 25 mL of DMF and heated at 60° C. for 48 hours. The reaction was diluted with 100 mL of EtOAc washed with water, brine, dried with $MgSO_4$ and the solvent removed to provide the title compound. $^1$H NMR (300 MHz, CHLOROFORM-D) δ ppm 3.46 (s, 3H) 3.79-3.84 (m, 2H) 3.90 (s, 3H) 4.23-4.28 (m, 2H) 7.07 (d, J=8.82 Hz, 1H) 7.72 (dd, J=8.65, 2.20 Hz, 1H) 8.11 (d, J=2.37 Hz, 1H). MS $(DCI/NH_3)$ m/z 236.0 $(M+H)^+$.

Example 58B 5-cyano-2-(2-methoxyethoxy)benzoic acid

2N LiOH (15 mL) was added to Example 58A in 20 mL of EtOH and stirred at ambient temperature for 24 hours. The reaction was diluted with EtOAc and acidified to pH 1 with 2N HCl. The organic phase was washed with water, brine, dried with $MgSO_4$ and the solvent removed. $^1$H NMR (300 MHz, CHLOROFORM-D) δ ppm 3.47 (s, 3H) 3.81-3.86 (m, 2H) 4.40-4.45 (m, 2H) 7.15 (d, J=8.48 Hz, 1H) 7.79-7.84 (m, 1H) 8.45 (d, J=2.37 Hz, 1H). MS (DCI/$NH_3$) m/z 239.0 (M+NH4)$^+$.

Example 58C (Z)-N-(5-tert-butyl-3-(3,3,3-trifluoropropyl)thiazol-2 (3H)-ylidene)-5-cyano-2-(2-methoxyethoxy)benzamide The title compound was prepared according to the procedure described in Example 54A substituting Example 58B for Example 26B and Example 57A for Example 16A. $^1$H NMR (300 MHz, CHLOROFORM-D) δ ppm 1.36 (s, 9H) 2.75 (m, 2H) 3.41 (s, 3H) 3.78-3.83 (m, 2H) 4.25-4.31 (m, 2H) 4.38 (t, J=6.74 Hz, 2H) 6.63 (s, 1H) 7.09 (d, J=8.73 Hz, 1H) 7.65 (dd, J=8.53, 2.18 Hz, 1H) 8.24 (d, J=1.98 Hz, 1H). MS (DCI/$NH_3$) m/z 456.2 (M+H)$^+$.

Example 58D (Z)-N-(5-tert-butyl-3-(3,3,3-trifluoropropyl)thiazol-2 (3H)-ylidene)-5-cyano-2-(2-methoxyethoxy)benzothioamide The title compound was prepared according to the procedure described in Example 16D by substituting the product of Example 58C for the product of Example 16C. $^1$H NMR (300 MHz, CHLOROFORM-D) δ ppm 1.41 (s, 9H) 2.75 (m, 2H) 3.31 (s, 3H) 3.65-3.69 (m, 2H) 4.16-4.21 (m, 2H) 4.46 (t, J=6.74 Hz, 2H) 6.85 (s, 1H) 7.01 (d, J=8.73 Hz, 1H) 7.57 (dd, J=8.72, 2.38 Hz, 1H) 7.87 (d, J=2.38 Hz, 1H). MS (DCI/$NH_3$) m/z 472.0 (M+H)$^+$.

Example 58E

N-[(2Z)-5-tert-butyl-3-(3,3,3-trifluoropropyl)-1,3-thiazol-2(3H)-ylidene]-N',5-dicyano-2-(2-methoxyethoxy)benzenecarboximidamide The title compound was prepared according to the procedure described in Example 16E by substituting the product of Example 58D for the product of Example 16D $^1$H NMR (300 MHz, CHLOROFORM-D) δ ppm 1.39 (s, 9H) 2.62-2.77 (m, 2H) 3.40 (s, 3H) 3.83-3.88 (m, 2H) 4.32-4.37 (m, 2H) 4.41 (t, J=6.61 Hz, 2H) 6.78 (s, 1H) 7.14 (d, J=9.16 Hz, 1H) 7.67-7.72 (m, 2H). MS (DCI/$NH_3$) m/z 480.1 (M+H)$^+$. Anal. Calc. for $C_{22}H_{24}F_3N_5O_2S$: C, 55.10; H, 5.04; N, 14.60. Found: C, 55.12; H, 4.82; N, 14.43.

Example 59

N-[(2Z)-5-tert-butyl-3-isobutyl-1,3-thiazol-2(3H)-ylidene]-N',5-dicyano-2-(2-methoxyethoxy)benzenecarboximidamide

Example 59A (Z)-N-(5-tert-butyl-3-isobutylthiazol-2(3H)-ylidene)-5-cyano-2-(2-methoxyethoxy)benzamide The title compound was prepared according to the procedure described in Example 54A by substituting Example 58B for Example 26B. $^1$H NMR (300 MHz, CHLOROFORM-D) δ ppm 0.98 (d, J=6.78 Hz, 6H) 1.36 (s, 9H) 2.20-2.34 (m, 1H) 3.42 (s, 3H) 3.79-3.84 (m, 2H) 3.99 (d, J=7.46 Hz, 2H) 4.26-4.31 (m, 2H) 6.62 (s, 1H) 7.08 (d, J=8.48 Hz, 1H) 7.63 (dd, J=8.65, 2.20 Hz, 1H) 8.24 (d, J=2.37 Hz, 1H). MS (DCI/$NH_3$) m/z 416.2 (M+H)$^+$.

Example 59B (Z)-N-(5-tert-butyl-3-isobutylthiazol-2(3H)-ylidene)-5-cyano-2-(2-methoxyethoxy)benzothioamide The title compound was prepared according to the procedure described in Example 16D by substituting the product of Example 59A for the product of Example 16C. $^1$H NMR (300 MHz, CHLOROFORM-D) δ ppm 0.93 (d, J=6.78 Hz, 6H) 1.41 (s, 9H) 2.19-2.33 (m, 1H) 3.34 (s, 3H) 3.67-3.72 (m, 2H) 4.08 (d, J=7.46 Hz, 2H) 4.18-4.22 (m, 2H) 6.84 (s, 1H) 7.01 (d, J=8.81 Hz, 1H) 7.53-7.57 (m, 1H) 7.79 (d, J=2.37 Hz, 1H). MS (DCI/$NH_3$) m/z 432.1 (M+H)$^+$.

Example 59C

N-[(2Z)-5-tert-butyl-3-isobutyl-1,3-thiazol-2(3H)-ylidene]-N',5-dicyano-2-(2-methoxyethoxy)benzenecarboximidamide The title compound was prepared according to the procedure described in Example 16E by substituting the product of Example 59B for the product of Example 16D. $^1$H NMR (300 MHz, CHLOROFORM-D) δ ppm 0.96 (d, J=6.44 Hz, 6H) 1.40 (s, 9H) 2.16-2.30 (m, 1H) 3.40 (s, 3H) 3.84-3.89 (m, 2H) 4.01 (d, J=7.46 Hz, 2H) 4.32-4.37 (m, 2H) 6.76 (s, 1H) 7.13 (ddd, J=9.32, 1.36, 1.19 Hz, 1H) 7.66-7.71 (m, 2H). MS (DCI/$NH_3$) m/z 440.2 (M+H)$^+$. Anal. Calc. for $C_{23}H_{29}N_5O_2S$: C, 62.84; H, 6.65; N, 15.93. Found: C, 62.74; H, 6.62; N, 15.99.

Example 60

N-[(2Z)-5-tert-butyl-3-isobutyl-1,3-thiazol-2(3H)-ylidene]-5-chloro-N'-cyano-2-ethoxybenzenecarboximidamide

Example 60A (Z)-N-(5-tert-butyl-3-isobutylthiazol-2(3H)-ylidene)-5-chloro-2-ethoxybenzamide The title compound was prepared according to the procedure described in Example 54A by substituting 5-chloro-2-ethoxybenzoic acid for Example 26B. $^1$H NMR (300 MHz, CHLOROFORM-D) δ ppm 0.97 (d, J=6.74 Hz, 6H) 1.35 (s, 9H) 1.44 (t, J=6.94 Hz, 3H) 2.22-2.36 (m, 1H) 3.98 (d, J=7.14

Hz, 2H) 4.13 (q, J=7.14 Hz, 2H) 6.59 (s, 1H) 6.89 (d, J=8.72 Hz, 1H) 7.28 (dd, J=8.72, 2.78 Hz, 1H) 7.93 (d, J=2.78 Hz, 1H). MS (DCI/NH$_3$) m/z 395.2 (M+H)$^+$.

Example 60B (Z)-N-(5-tert-butyl-3-isobutylthiazol-2(3H)-ylidene)-5-chloro-2-ethoxybenzothioamide The title compound was prepared according to the procedure described in Example 16D by substituting the product of Example 60A for the product of Example 16C. $^1$H NMR (300 MHz, CHLOROFORM-D) δ ppm 0.93 (d, J=6.78 Hz, 6H) 1.32 (t, 3H) 1.41 (s, 9H) 2.21-2.39 (m, 1H) 4.04 (q, J=6.78 Hz, 2H) 4.08 (d, J=7.46 Hz, 2H) 6.82 (s, 1H) 6.84 (d, J=8.82 Hz, 1H) 7.19 (dd, J=8.82, 2.71 Hz, 1H) 7.51 (d, J=2.71 Hz, 1H). MS (DCI/NH$_3$) m/z 411.1 (M+H)$^+$.

Example 60C

N-[(2Z)-5-tert-butyl-3-isobutyl-1,3-thiazol-2(3H)-ylidene]-5-chloro-N'-cyano-2-ethoxybenzenecarboximidamide The title compound was prepared according to the procedure described in Example 16E by substituting the product of Example 60B for the product of Example 16D. $^1$H NMR (300 MHz, CHLOROFORM-D) δ ppm 0.96 (d, J=6.74 Hz, 6H) 1.39 (s, 9H) 1.46 (t, J=6.94 Hz, 3H) 2.16-2.30 (m, 1H) 4.01 (d, J=7.54 Hz, 2H) 4.16 (q, J=6.74 Hz, 2H) 6.73 (s, 1H) 6.89-6.94 (m, 1H) 7.30-7.35 (m, 2H). MS (DCI/NH$_3$) m/z 419.1 (M+H)$^+$. Anal. Calc. for C$_{21}$H$_{27}$ClN$_4$OS: C, 60.20; H, 6.50; N, 13.37. Found: C, 60.01; H, 6.58; N, 13.12.

Example 61

N-[(2Z)-5-tert-butyl-3-isobutyl-1,3-thiazol-2(3H)-ylidene]-5-chloro-N'-cyano-2-(cyclopropyloxy)benzenecarboximidamide

Example 61A 5-chloro-2-cyclopropoxybenzoic acid

Methyl 5-chloro-2-cyclopropoxybenzoate was obtained from methyl-5-chlorosalicylate as described by Maligres, P. E. et al. J. Org. Chem., 2002, 67, 1093-1101. The methyl ester was hydrolyzed with 40% aqueous KOH in EtOH.

Example 61B (Z)-N-(5-tert-butyl-3-isobutylthiazol-2(3H)-ylidene)-5-chloro-2-cyclopropoxybenzamide The title compound was prepared according to the procedure described in Example 54A by substituting 5-chloro-2-cyclopropoxybenzoic acid (Example 61A) for Example 26B. $^1$H NMR (300 MHz, CHLOROFORM-D) δ ppm 0.75-0.82 (m, 2H) 0.82-0.91 (m, 2H) 0.97 (d, J=6.78 Hz, 6H) 1.34 (s, 9H) 2.19-2.39 (m, 1H) 3.71-3.84 (m, 1H) 3.97 (d, J=7.46 Hz, 2H) 6.58 (s, 1H) 7.27-7.39 (m, 2H) 7.90-7.97 (m, 1H). MS (DCI/NH$_3$) m/z 407.1 (M+H)$^+$.

Example 61C (Z)-N-(5-tert-butyl-3-isobutylthiazol-2(3H)-ylidene)-5-chloro-2-cyclopropoxybenzothioamide The title compound was prepared according to the procedure described in Example 16D by substituting the product of Example 61B for the product of Example 16C. $^1$H NMR (300 MHz, CHLOROFORM-D) δ ppm 0.70-0.74 (m, 4H) 0.93 (d, J=6.78 Hz, 6H) 1.40 (s, 9H) 2.33 (m, 1H) 3.68-3.74 (m, 1H) 4.04 (d, J=7.46 Hz, 2H) 6.81 (s, 1H) 7.21-7.23 (m, 2H) 7.56 (dd, J=2.03, 0.68 Hz, 1H). MS (DCI/NH$_3$) m/z 423.1 (M+H)$^+$.

Example 61D

N-[(2Z)-5-tert-butyl-3-isobutyl-1,3-thiazol-2(3H)-ylidene]-5-chloro-N'-cyano-2-(cyclopropyloxy)benzenecarboximidamide The title compound was prepared according to the procedure described in Example 16E by substituting the product of Example 61C for the product of Example 16D. $^1$H NMR (300 MHz, CHLOROFORM-D) δ ppm 0.74-0.82 (m, 2H) 0.95 (d, J=6.74 Hz, 6H) 0.98-1.05 (m, 2H) 1.38 (s, 9H) 2.15-2.29 (m, 1H) 3.77-3.84 (m, 1H) 4.00 (d, J=7.14 Hz, 2H) 6.72 (s, 1H) 7.29-7.38 (m, 3H). MS (DCI/NH$_3$) m/z 431.2 (M+H)$^+$. Anal. Calc. for C$_{22}$H$_{27}$ClN$_4$OS: C, 61.31; H, 6.31; N, 13.00. Found: C, 61.27; H, 6.33; N, 12.92.

Example 62

N-[(2Z)-5-tert-butyl-3-isobutyl-1,3-thiazol-2(3H)-ylidene]-N',5-dicyano-2-ethoxybenzenecarboximidamide

Example 62A 3-bromo-4-ethoxybenzonitrile

Title compound was prepared according to the procedure described in Example 64A by substituting ethyl iodide for bromocyclobutane. $^1$H NMR (300 MHz, CHLOROFORM-D) δ ppm 1.51 (t, J=6.95 Hz, 3H) 4.17 (q, J=6.89 Hz, 2H) 6.91 (d, J=8.82 Hz, 1H) 7.57 (dd, J=8.48, 2.03 Hz, 1H) 7.83 (d, J=2.03 Hz, 1H). MS (DCI/NH$_3$) m/z 225.9 (M+H)$^+$.

Example 62B

Methyl 5-cyano-2-ethoxybenzoate

Title compound was prepared according to the procedure described in Example 64B by substituting the product of Example 62A for the product of Example 64A. $^1$H NMR (300 MHz, CHLOROFORM-D) δ ppm 1.50 (t, J=6.95 Hz, 3H) 3.91 (s, 3H) 4.19 (q, J=6.89 Hz, 2 H) 7.02 (d, J=8.82 Hz, 1H) 7.72 (dd, J=8.82, 2.37 Hz, 1H) 8.08 (d, J=2.37 Hz, 1H). MS (DCI/NH$_3$) m/z 205.9 (M+H)$^+$.

Example 62C 5-cyano-2-ethoxybenzoic acid

Title compound was prepared according to the procedure described in Example 64C by substituting the product of Example 62B for the product of Example 64B.

Example 62D (Z)-N-(5-tert-butyl-3-isobutylthiazol-2(3H)-ylidene)-5-cyano-2-ethoxybenzamide The title compound was prepared according to the procedure described in Example 54A by substituting 5-cyano-2-ethoxybenzoic acid (Example 62C) for Example 26B. $^1$H NMR (300 MHz, CHLOROFORM-D) δ ppm 0.98 (d, J=6.74 Hz, 6H) 1.36 (s, 9H) 1.48 (t, J=6.94 Hz, 3H) 2.28 (m, 1H) 3.99 (d, J=7.54 Hz, 2H) 4.22 (q, J=7.14 Hz, 2H) 6.62 (s, 1H) 7.00 (d, J=8.73 Hz, 1H) 7.63 (dd, J=8.72, 1.98 Hz, 1H) 8.25 (d, J=2.38 Hz, 1H). MS (DCI/NH$_3$) m/z 386.2 (M+H)$^+$.

Example 62E (Z)-N-(5-tert-butyl-3-isobutylthiazol-2(3H)-ylidene)-5-cyano-2-ethoxybenzothioamide The title compound was prepared according to the procedure described in Example 16D by substituting the product of Example 62D for the product of Example 16C. $^1$H NMR (300 MHz, CHLOROFORM-D) δ ppm 0.94 (d, J=6.44 Hz, 6H) 1.37 (t, J=6.95 Hz, 3H) 1.42 (s, 9H) 2.17-2.38 (m, 1H) 4.02-4.19 (m, 4H) 6.84 (s, 1H) 6.95 (d, J=8.82 Hz, 1H) 7.54 (dd, J=8.48, 2.03 Hz, 1H) 7.79 (d, J=1.70 Hz, 1H). MS (DCI/NH$_3$) m/z 402.2 (M+H)$^+$.

Example 62F

N-[(2Z)-5-tert-butyl-3-isobutyl-1,3-thiazol-2(3H)-ylidene]-N',5-dicyano-2-ethoxybenzenecarboximidamide The title compound was prepared according to the procedure described in Example 16E by substituting the product of Example 62E for the product of Example 16D. $^1$H NMR (300 MHz, CHLOROFORM-D) δ ppm 0.96 (d, J=6.78 Hz, 6H) 1.40 (s, 9H) 1.51 (t, J=6.95 Hz, 3H) 2.15-2.32 (m, 1H) 4.02 (d, J=7.46 Hz, 2H) 4.24 (q, J=6.78 Hz, 2H) 6.76 (s, 1H) 7.05 (d, J=8.48 Hz, 1H) 7.65-7.70 (m, 2H). MS (DCI/NH$_3$) m/z 410.2 (M+H)$^+$. Anal. Calc. for $C_{22}H_{27}N_5OS$: C, 64.52; H, 6.64; N, 17.10. Found: C, 64.47; H, 6.72; N, 16.97.

Example 63

N-[(2Z)-5-tert-butyl-3-{[1-(methylsulfonyl)azetidin-3-yl]methyl}-1,3-thiazol-2(3H)-ylidene]-5-chloro-N'-cyano-2-methoxybenzenecarboximidamide

Example 63A tert-butyl 3-((5-tert-butyl-2-iminothiazol-3(2H)-yl)methyl)azetidine-1-carboxylate The title compound is prepared according to the procedure described in Example 56A by substituting tert-butyl 3-(aminomethyl)azetidine-1-carboxylate for 3-methylbut-2-en-1-amine hydrochloride. LCMS m/z 326.3 (M+H)$^+$.

Example 63B (Z)-tert-butyl 3-((5-tert-butyl-2-(5-chloro-2-methoxybenzoylimino)thiazol-3(2H)-yl)methyl)azetidine-1-carboxylate The title compound was prepared according to the procedure described in Example 54A by substituting 5-chloro-2-methoxybenzoic acid for Example 26B and the product of Example 63A for Example 16A. $^1$H NMR (300 MHz, CHLOROFORM-D) δ ppm 1.34 (s, 9H) 1.44 (s, 9H) 3.10-3.30 (m, 1H) 3.77 (dd, J=9.12, 5.16 Hz, 2H) 3.90 (s, 3H) 4.05 (t, J=8.53 Hz, 2H) 4.37 (s, 2H) 6.63 (s, 1H) 6.91 (d, J=8.73 Hz, 1H) 7.33 (dd, J=8.72, 2.78 Hz, 1H) 7.89 (d, J=2.78 Hz, 1H). MS (DCI/NH$_3$) m/z 494.2 (M+H)$^+$.

Example 63C (Z)-N-(3-(azetidin-3-ylmethyl)-5-tert-butylthiazol-2(3H)-ylidene)-5-chloro-2-methoxybenzamide Example 63B (0.3 g, 0.6 mmol) was dissolved in 2 mL TFA and stirred at ambient temperature for 15 minutes. The reaction was dissolved in 100 mL of EtOAc, washed with saturated NaHCO$_3$, water and brine. The organic phase was dried with MgSO$_4$ and the solvent removed to provide the title compound, which was used without further purification. LCMS m/z 394.1 (M+H)$^+$

Example 63D (Z)-N-(5-tert-butyl-3-((1-(methylsulfonyl)azetidin-3-yl)methyl)thiazol-2(3H)-ylidene)-5-chloro-2-methoxybenzamide The TFA salt of Example 63C (0.25 g, 0.64 mmol) was dissolved in 3 mL of THF. The mixture was cooled to 0° C. and triethylamine (0.27 mL, 1.9 mmol) was added. Methanesulfonyl chloride (0.1 ml, 1.3 mMol) was added dropwise and the reaction was stirred at 0° C. for 30 minutes. The reaction was diluted with EtOAc, washed with water, brine, dried with MgSO$_4$ and the solvent removed. Final product was purified by flash chromatography using a gradient from 0 to 100% EtOAc in hexane over 300 mL. $^1$H NMR (300 MHz, CHLOROFORM-D) δ ppm 1.35 (s, 9H) 2.85 (s, 3H) 3.16-3.30 (m, 1H) 3.84 (dd, J=8.14, 5.76 Hz, 2H) 3.90 (s, 3H) 4.04 (t, J=8.31 Hz, 2H) 4.42 (d, J=7.46 Hz, 2H) 6.63 (s, 1H) 6.92 (d, J=9.16 Hz, 1H) 7.34 (dd, J=8.82, 2.71 Hz, 1H) 7.91 (d, J=2.71 Hz, 1H). MS (DCI/NH$_3$) m/z 472.1 (M+H)$^+$.

Example 63E (Z)-N-(5-tert-butyl-3-((1-(methylsulfonyl)azetidin-3-yl)methyl)thiazol-2(3H)-ylidene)-5-chloro-2-methoxybenzothioamide The title compound was prepared according to the procedure described in Example 16D by substituting the product of Example 63D for the product of Example 16C. $^1$H NMR (300 MHz, CHLOROFORM-D) δ ppm 1.40 (s, 9H) 2.78 (s, 3H) 3.09-3.33 (m, 1H) 3.76-3.84 (m, 2H) 3.81 (s, 3H) 3.98 (t, J=8.13 Hz, 2H) 4.48 (d, J=7.54 Hz, 2H) 6.82-6.88 (m, 2H) 7.21-7.25 (m, 1H) 7.48 (d, J=2.78 Hz, 1H). MS (DCI/NH$_3$) m/z 488.1 (M+H)$^+$.

Example 63F

N-[(2Z)-5-tert-butyl-3-{[1-(methylsulfonyl)azetidin-3-yl]methyl}-1,3-thiazol-2(3H)-ylidene]-5-chloro-N'-cyano-2-methoxybenzenecarboximidamide The title compound was prepared according to the procedure described in Example 16E by substituting the product of Example 63E for the product of Example 16D. $^1$H NMR (300 MHz, CHLOROFORM-D) δ ppm 1.38 (s, 9H) 2.82 (s, 3H) 3.10-3.23 (m, 1H) 3.77 (dd, J=8.48, 5.76 Hz, 2H) 3.92 (s, 3H) 4.01 (t, J=8.31 Hz, 2H) 4.43 (d, J=7.46 Hz, 2H) 6.76 (s, 1H) 6.96 (d, J=8.82 Hz, 1H) 7.30 (d, J=2.37 Hz, 1H) 7.37 (dd, J=8.82, 2.71 Hz, 1H). MS (DCI/NH$_3$) m/z 496.1 (M+H)$^+$. Anal. Calc. for $C_{21}H_{26}ClN_5O_3S_2$: C, 50.85; H, 5.28; N, 14.12. Found: C, 50.67; H, 5.32; N, 13.38.

Example 64

N-[(2Z)-5-tert-butyl-3-isobutyl-1,3-thiazol-2(3H)-ylidene]-N',5-dicyano-2-(cyclobutyloxy)benzenecarboximidamide

Example 64A 3-bromo-4-cyclobutoxybenzonitrile

3-Bromo-4-hydroxybenzonitrile (2.0 g, 10.1 mmol), bromocyclobutane (2.7 g, 20.2 mmol), and K$_2$CO$_3$ (2.8 g, 20.2 mmol) were mixed in 5 mL of DMF and heated at 60° C. for 72 hours. The reaction was diluted with EtOAc washed with water, brine dried with MgSO$_4$ and the solvent was removed. The product was purified by flash chromatography using a gradient from 0 to 30% EtOAc in hexane to provide the title compound. $^1$H NMR (300 MHz, CHLOROFORM-D) δ ppm 1.69-1.82 (m, 1H) 1.87-2.00 (m, 1H) 2.21-2.35 (m, 2H) 2.45-2.57 (m, 2H) 4.69-4.79 (m, 1H) 6.76 (d, J=8.48 Hz, 1H) 7.53 (dd, J=8.48, 2.03 Hz, 1H) 7.82 (d, J=2.03 Hz, 1H). MS (DCI/NH$_3$) m/z 251.9 (M+H)$^+$.

Example 64B

Methyl 5-cyano-2-cyclobutoxybenzoate

Example 64A (2.2 g, 8.73 mmol) in MeOH (20 ml) was added to Pd-dppf (0.178 g, 0.218 mmol) and Et$_3$N (2.433 mL, 17.45 mmol) in a 50 mL vessel. The mixture was pressurized with carbon monoxide (60 psi), and stirred 3 hr at 100° C. $^1$H NMR (300 MHz, CHLOROFORM-D) δ ppm 1.67-1.82 (m, 1H) 1.86-1.99 (m, 1H) 2.20-2.34 (m, 2H) 2.45-2.56 (m, 2H) 3.91 (s, 3H) 4.71-4.81 (m, 1H) 6.85 (d, J=8.73 Hz, 1H) 7.68 (dd, J=8.72, 2.38 Hz, 1H) 8.09 (d, J=2.38 Hz, 1H). MS (DCI/NH$_3$) m/z 232.0 (M+H)$^+$.

Example 64C 5-cyano-2-cyclobutoxybenzoic acid

Example 64B (0.45 g, 1.9 mmol) was dissolved in 6 mL of EtOH and 3 mL of 2N LiOH was added and the reaction stirred at ambient temperature for 6 hours. Reaction was diluted with EtOAc and washed with 2N HCl, water and brine. The organic phase dried with MgSO$_4$ and the solvent removed to provide the title compound. $^1$H NMR (300 MHz, CHLOROFORM-D) δ ppm 1.77-1.90 (m, 1H) 1.96-2.09 (m, 1H) 2.27-2.41 (m, 2H) 2.55-2.66 (m, 2H) 4.94 (m, 1H) 6.97 (d, J=8.73 Hz, 1H) 7.79 (dd, J=8.73, 2.38 Hz, 1H) 8.47 (d, J=1.98 Hz, 1H). MS (DCI/NH$_3$) m/z 218.0 (M+H)$^+$.

Example 64D (Z)-N-(5-tert-butyl-3-isobutylthiazol-2(3H)-ylidene)-5-cyano-2-cyclobutoxybenzamide The title compound was prepared according to the procedure described in Example 54A by substituting Example 64C for Example 26B. $^1$H NMR (300 MHz, CHLOROFORM-D) δ ppm 0.98 (d, J=6.74 Hz, 6H) 1.36 (s, 9H) 1.63-1.76 (m, 1H) 1.81-1.94 (m, 1H) 2.23-2.38 (m, 3H) 2.43-2.55 (m, 2H) 3.99 (d, J=7.54 Hz, 2H) 4.71-4.82 (m, 1H) 6.62 (s, 1H) 6.83 (d, J=8.72 Hz, 1H) 7.60 (dd, J=8.53, 2.18 Hz, 1H) 8.26 (d, J=2.38 Hz, 1H). MS (DCI/NH$_3$) m/z 412.2 (M+H)$^+$.

Example 64E (Z)-N-(5-tert-butyl-3-isobutylthiazol-2(3H)-ylidene)-5-cyano-2-cyclobutoxybenzothioamide The title compound was prepared according to the procedure described in Example 16D by substituting the product of Example 64D for the product of Example 16C. $^1$H NMR (300 MHz, CHLOROFORM-D) δ ppm 0.94 (d, J=6.74 Hz, 6H) 1.42 (s, 9H) 1.61-1.73 (m, 1H) 1.75-1.88 (m, 1H) 2.08-2.22 (m, 2H) 2.27-2.37 (m, 1H) 2.38-2.47 (m, 2H) 4.07 (d, J=7.14 Hz, 2H) 4.66-4.76 (m, 1H) 6.78 (d, J=8.73 Hz, 1H) 6.84 (s, 1H) 7.51 (dd, J=8.53, 2.18 Hz, 1H) 7.84 (d, J=2.38 Hz, 1H). MS (DCI/NH$_3$) m/z 428.2 (M+H)$^+$.

Example 64F

N-[(2Z)-5-tert-butyl-3-isobutyl-1,3-thiazol-2(3H)-ylidene]-N',5-dicyano-2-(cyclobutyloxy)benzenecarboximidamide The title compound was prepared according to the procedure described in Example 16E by substituting the product of Example 64E for the product of Example 16D. $^1$H NMR (300 MHz, CHLOROFORM-D) δ ppm 0.96 (d, J=6.74 Hz, 6H) 1.40 (s, 9H) 1.60-1.78 (m, 1H) 1.86-1.99 (m, 1H) 2.17-2.30 (m, 1H) 2.36-2.51 (m, 4H) 4.01 (d, J=7.14 Hz, 2H) 4.74-4.84 (m, 1H) 6.76 (s, 1H) 6.86-6.90 (m, 1H) 7.61-7.67 (m, 2H). MS (DCI/NH$_3$) m/z 436.2 (M+H)$^+$. Anal. Calc. for $C_{24}H_{29}N_5OS$: C, 66.18; H, 6.71; N, 16.08. Found: C, 65.81; H, 6.85; N, 15.59.

Example 65

N-[(2Z)-5-tert-butyl-3-(3,3,3-trifluoropropyl)-1,3-thiazol-2(3H)-ylidene]-N',5-dicyano-2-(cyclobutyloxy)benzenecarboximidamide

Example 65A (Z)-N-(5-tert-butyl-3-(3,3,3-trifluoropropyl)thiazol-2(3H)-ylidene)-5-cyano-2-cyclobutoxybenzamide The title compound was prepared according to the procedure described in Example 54A by substituting Example 64C for Example 26B and Example 57A for Example 16A. $^1$H NMR (300 MHz, CHLOROFORM-D) δ ppm 1.36 (s, 9H) 1.66-1.79 (m, 1H) 1.81-1.94 (m, 1H) 2.21-2.36 (m, 2H) 2.44-2.55 (m, 2H) 2.69-2.84 (m, 2H) 4.37 (t, J=6.94 Hz, 2H)

4.72-4.82 (m, 1H) 6.63 (s, 1H) 6.84 (d, J=8.72 Hz, 1H) 7.62 (dd, J=8.72, 2.38 Hz, 1H) 8.24 (d, J=1.98 Hz, 1H). MS (DCI/NH$_3$) m/z 452.2 (M+H)$^+$.

Example 65B (Z)-N-(5-tert-butyl-3-(3,3,3-trifluoropropyl)thiazol-2 (3H)-ylidene)-5-cyano-2-cyclobutoxybenzothioamide The title compound was prepared according to the procedure described in Example 16D by substituting the product of Example 65A for the product of Example 16C. $^1$H NMR (300 MHz, CHLOROFORM-D) δ ppm 1.42 (s, 9H) 1.56-1.74 (m, 2H) 2.02-2.25 (m, 2H) 2.33-2.52 (m, 2H) 2.69-2.90 (m, 2H) 4.43 (t, J=6.94 Hz, 2H) 4.65-4.78 (m, 1H) 6.79 (d, J=8.72 Hz, 1H) 6.86 (s, 1H) 7.53 (dd, J=8.72, 2.38 Hz, 1H) 7.89 (d, J=2.38 Hz, 1H). MS (DCI/NH$_3$) m/z 438.2 (M+H)$^+$.

Example 65C

N-[(2Z)-5-tert-butyl-3-(3,3,3-trifluoropropyl)-1,3-thiazol-2(3H)-ylidene]-N',5-dicyano-2-(cyclobutyloxy)benzenecarboximidamide The title compound was prepared according to the procedure described in Example 16E by substituting the product of Example 65B for the product of Example 16D. $^1$H NMR (300 MHz, CHLOROFORM-D) δ ppm 1.39 (s, 9H) 1.62-1.76 (m, 1H) 1.86-2.00 (m, 1H) 2.31-2.43 (m, 2H) 2.43-2.54 (m, 2H) 2.70 (qt, J=10.48, 6.65 Hz, 2H) 4.40 (t, J=6.61 Hz, 2H) 4.79 (qd, J=7.18, 6.95 Hz, 1H) 6.77 (s, 1H) 6.87-6.92 (m, 1H) 7.64-7.67 (m, 1H) 7.67 (s, 1H). MS (DCI/NH$_3$) m/z 476.2 (M+H)$^+$. Anal. Calc. for C$_{23}$H$_{24}$F$_3$N$_5$OS: C, 58.09; H, 5.09; N, 14.73. Found: C, 58.07; H, 5.08; N, 14.30.

Example 66

N-[(2Z)-5-tert-butyl-3-isobutyl-1,3-thiazol-2(3H)-ylidene]-N'-cyano-2-fluoro-3-(trifluoromethyl)benzenecarboximidamide

Example 66A (Z)-N-(5-tert-butyl-3-isobutylthiazol-2(3H)-ylidene)-2-fluoro-3-(trifluoromethyl)benzamide The title compound was prepared according to the procedure described in Example 51A by substituting 2-fluoro-3-(trifluoromethyl)benzoyl chloride for 5-chloro-2-fluorobenzoyl chloride. $^1$H NMR (300 MHz, CHLOROFORM-D) δ ppm 0.98 (d, J=6.78 Hz, 6H) 1.37 (s, 9H) 2.23-2.37 (m, 1H) 4.02 (d, J=7.46 Hz, 2H) 6.65 (s, 1H) 7.24-7.30 (m, 1H) 7.64-7.70 (m, 1H) 8.27-8.33 (m, J=7.29, 7.29, 1.70 Hz, 1H). MS (DCI/NH$_3$) m/z 403.2 (M+H)$^+$.

Example 66B (Z)-N-(5-tert-butyl-3-isobutylthiazol-2(3H)-ylidene)-2-fluoro-3-(trifluoromethyl)benzothioamide The title compound was prepared according to the procedure described in Example 16D by substituting the product of Example 66A for the product of Example 16C. $^1$H NMR (300 MHz, CHLOROFORM-D) δ ppm 0.95 (d, J=6.78 Hz, 6H) 1.42 (s, 9H) 2.23-2.37 (m, 1H) 4.12 (d, J=7.12 Hz, 2H) 6.87 (s, 1H) 7.19-7.26 (m, 1H) 7.55-7.62 (m, 1H) 8.19 (m, 1H). MS (DCI/NH$_3$) m/z 419.1 (M+H)$^+$.

Example 66C

N-[(2Z)-5-tert-butyl-3-isobutyl-1,3-thiazol-2(3H)-ylidene]-N'-cyano-2-fluoro-3-(trifluoromethyl)benzenecarboximidamide The title compound was prepared according to the procedure described in Example 16E by substituting the product of Example 66B for the product of 16D. $^1$H NMR (300 MHz, CHLOROFORM-D) δ ppm 0.94 (d, J=6.35 Hz, 6H) 1.40 (s, 9H) 2.23 (m, 1H) 4.02 (d, J=7.54 Hz, 2H) 6.78 (s, 1H) 7.34 (t, J=7.73 Hz, 1H) 7.68-7.75 (m, 1H) 7.80-7.86 (m, 1H). MS (DCI/NH$_3$) m/z 427.1 (M+H)$^+$. Anal. Calc. for C$_{20}$H$_{22}$F$_4$N$_4$S: C, 56.33; H, 5.20; N, 13.14. Found: C, 56.27; H, 5.20; N, 12.98.

Example 67

N-[(2Z)-5-tert-butyl-3-isobutyl-1,3-thiazol-2(3H)-ylidene]-N',5-dicyano-2-(2,2,2-trifluoroethoxy)benzenecarboximidamide

Example 67A 3-bromo-4-(2,2,2-trifluoroethoxy)benzonitrile

The title compound was prepared according to the procedure described in Example 64A by substituting 1,1,1-trifluoro-2-iodoethane for bromocyclobutane. $^1$H NMR (300 MHz, CHLOROFORM-D) δ ppm 4.42-4.51 (m, 2H) 6.96 (d, J=8.72 Hz, 1H) 7.63 (dd, J=8.33, 1.98 Hz, 1H) 7.89 (d, J=1.98 Hz, 1H). MS (DCI/NH$_3$) m/z 279.9 (M+H)$^+$.

Example 67B

Methyl 5-cyano-2-(2,2,2-trifluoroethoxy)benzoate

The title compound was prepared according to the procedure described in Example 64B by substituting the product of 67A for 3-bromo-4-cyclobutoxybenzonitrile. $^1$H NMR (300 MHz, CHLOROFORM-D) δ ppm 3.93 (s, 3H) 4.48 (q, J=7.80 Hz, 2H) 7.05 (d, J=8.82 Hz, 1H) 7.79 (dd, J=8.65, 2.20 Hz, 1H) 8.17 (d, J=2.03 Hz, 1H). MS (DCI/NH$_3$) m/z 277.0 (M+NH$_4$)$^+$.

Example 67C 5-cyano-2-(2,2,2-trifluoroethoxy)benzoic acid

The title compound was prepared according to the procedure described in Example 64C by substituting the product of 67B for Example 64B. $^1$H NMR (300 MHz, CHLOROFORM-D) δ ppm 4.56 (q, J=7.80 Hz, 2H) 7.10 (d, J=8.82 Hz, 1H) 7.85 (dd, J=8.65, 2.20 Hz, 1H) 8.36 (d, J=2.03 Hz, 1H). MS (DCI/NH$_3$) m/z 263.0 (M+NH$_4$)$^+$.

Example 67D (Z)-N-(5-tert-butyl-3-isobutylthiazol-2(3H)-ylidene)-5-cyano-2-(2,2,2-trifluoroethoxy)benzamide The title compound was prepared according to the procedure described in Example 54A by substituting Example 67C for Example 26B. $^1$H NMR (300 MHz, CHLOROFORM-D)

δ ppm 0.97 (d, J=6.44 Hz, 6H) 1.37 (s, 9H) 2.26 (m, 1H) 4.00 (d, J=7.46 Hz, 2H) 4.53 (q, J=8.48 Hz, 2H) 6.65 (s, 1H) 7.10 (d, J=8.82 Hz, 1H) 7.67 (dd, J=8.48, 2.03 Hz, 1H) 8.32 (d, J=2.03 Hz, 1H). MS (DCI/NH$_3$) m/z 440.2 (M+H)$^+$.

Example 67E (Z)-N-(5-tert-butyl-3-isobutylthiazol-2(3H)-ylidene)-5-cyano-2-(2,2,2-trifluoroethoxy)benzothioamide The title compound was prepared according to the procedure described in Example 16D by substituting the product of Example 67D for the product of 16C. $^1$H NMR (300 MHz, CHLOROFORM-D) δ ppm 0.92 (d, J=6.74 Hz, 6H) 1.42 (s, 9H) 2.17-2.31 (m, 1H) 4.08 (d, J=7.54 Hz, 2H) 4.40 (q, J=8.33 Hz, 2H) 6.87 (s, 1H) 7.01 (d, J=8.33 Hz, 1H) 7.58 (dd, J=8.53, 2.18 Hz, 1H) 7.89 (d, J=1.98 Hz, 1H). MS (DCI/NH$_3$) m/z 456.1 (M+H)$^+$.

Example 67F

N-[(2Z)-5-tert-butyl-3-isobutyl-1,3-thiazol-2(3H)-ylidene]-N',5-dicyano-2-(2,2,2-trifluoroethoxy)benzenecarboximidamide The title compound was prepared according to the procedure described in Example 16E by substituting the product of Example 67E for the product of Example 16D. $^1$H NMR (300 MHz, CHLOROFORM-D) δ ppm 0.95 (d, J=6.44 Hz, 6H) 1.40 (s, 9H) 2.15-2.29 (m, 1H) 4.02 (d, J=7.46 Hz, 2H) 4.62 (q, J=7.91 Hz, 2H) 6.78 (s, 1H) 7.10 (d, J=8.81 Hz, 1H) 7.69-7.76 (m, 2H). MS (DCI/NH$_3$) m/z 464.2 (M+H)$^+$.

Example 68

N-[(2Z)-5-tert-butyl-3-(3,3,3-trifluoropropyl)-1,3-thiazol-2(3H)-ylidene]-N',5-dicyano-2-(2,2,2-trifluoroethoxy)benzenecarboximidamide

Example 68A (Z)-N-(5-tert-butyl-3-(3,3,3-trifluoropropyl)thiazol-2(3H)-ylidene)-5-cyano-2-(2,2,2-trifluoroethoxy)benzamide The title compound was prepared according to the procedure described in Example 54A substituting Example 57A for Example 16A and Example 67C for Example 26B. $^1$H NMR (300 MHz, CHLOROFORM-D) δ ppm 1.37 (s, 9H) 2.72 (m, 2H) 4.38 (t, J=6.78 Hz, 2H) 4.52 (q, J=8.25 Hz, 2H) 6.66 (s, 1H) 7.08 (d, J=8.48 Hz, 1H) 7.69 (dd, J=8.65, 2.20 Hz, 1H) 8.30 (d, J=2.03 Hz, 1H). MS (DCI/NH$_3$) m/z 480.1 (M+H)$^+$.

Example 68B (Z)-N-(5-tert-butyl-3-(3,3,3-trifluoropropyl)thiazol-2(3H)-ylidene)-5-cyano-2-(2,2,2-trifluoroethoxy)benzothioamide The title compound was prepared according to the procedure described in Example 16D by substituting the product of Example 68A for the product of 16C. $^1$H NMR (300 MHz, CHLOROFORM-D) δ ppm 1.42 (s, 9H) 2.60-2.81 (m, 2H) 3.86-3.91 (m, 2H) 4.30-4.50 (m, 2H) 6.88 (s, 1H) 7.00 (d, J=8.73 Hz, 1H) 7.61 (dd, J=8.53, 2.18 Hz, 1H) 7.93 (d, J=1.98 Hz, 1H). MS (DCI/NH$_3$) m/z 496.1 (M+H)$^+$.

Example 68C

N-[(2Z)-5-tert-butyl-3-(3,3,3-trifluoropropyl)-1,3-thiazol-2(3H)-ylidene]-N',5-dicyano-2-(2,2,2-trifluoroethoxy)benzenecarboximidamide The title compound was prepared according to the procedure described in Example 16E by substituting the product of Example 68B for the product of Example 16D. $^1$H NMR (300 MHz, CHLOROFORM-D) δ ppm 1.40 (s, 9H) 2.69 (m, 2H) 4.41 (t, J=6.74 Hz, 2H) 4.62 (q, J=7.93 Hz, 2H) 6.81 (s, 1H) 7.11 (d, J=8.72 Hz, 1H) 7.75 (m, 2H). MS (DCI/NH$_3$) m/z 504.2 (M+H)$^+$.

Example 69

N-[(2Z)-5-tert-butyl-3-isobutyl-1,3-thiazol-2(3H)-ylidene]-N'-cyano-2-fluoro-5-(trifluoromethyl)benzenecarboximidamide

Example 69A (Z)-N-(5-tert-butyl-3-isobutylthiazol-2(3H)-ylidene)-2-fluoro-5-(trifluoromethyl)benzamide The title compound was prepared according to the procedure described in Example 51A by substituting 2-fluoro-5-(trifluoromethyl)benzoyl chloride for 5-chloro-2-fluorobenzoyl chloride. $^1$H NMR (300 MHz, CHLOROFORM-D) δ ppm 0.99 (d, J=6.44 Hz, 6H) 1.37 (s, 9H) 2.31 (m, 1H) 4.02 (d, J=7.46 Hz, 2H) 6.65 (s, 1H) 7.18-7.25 (m, 1H) 7.61-7.69 (m, 1H) 8.47 (dd, J=6.95, 2.54 Hz, 1H). MS (DCI/NH$_3$) m/z 403.2 (M+H)$^+$.

Example 69B (Z)-N-(5-tert-butyl-3-isobutylthiazol-2(3H)-ylidene)-2-fluoro-5-(trifluoromethyl)benzothioamide The title compound was prepared according to the procedure described in Example 16D by substituting the product of Example 69A for the product of Example 16C. $^1$H NMR (300 MHz, CHLOROFORM-D) δ ppm 0.96 (d, J=6.78 Hz, 6H) 1.42 (s, 9H) 2.16-2.40 (m, 1H) 4.12 (d, J=7.46 Hz, 2H) 6.86 (s, 1H) 7.10-7.21 (m, 1H) 7.54-7.61 (m, 1H) 8.29 (dd, J=6.95, 2.20 Hz, 1H). MS (DCI/NH$_3$) m/z 419.2 (M+H)$^+$.

Example 69C

N-[(2Z)-5-tert-butyl-3-isobutyl-1,3-thiazol-2(3H)-ylidene]-N'-cyano-2-fluoro-5-(trifluoromethyl)benzenecarboximidamide The title compound was prepared according to the procedure described in Example 16E by substituting the product of Example 69B for the product of Example 16D. $^1$H NMR (300 MHz, CHLOROFORM-D) δ ppm 0.95 (d, J=6.44 Hz, 6H) 1.40 (s, 9H) 2.15-2.30 (m, 1H) 4.03 (d, J=7.46 Hz, 2H) 6.79 (s, 1H) 7.31 (t, J=8.98 Hz, 1H) 7.69-7.75 (m, 1H) 7.83 (dd, J=5.93, 2.20 Hz, 1H). MS (DCI/NH$_3$) m/z 427.2 (M+H)$^+$. Anal. Calc. for $C_{20}H_{22}F_4N_4S$ C, 56.33; H, 5.20; N, 13.14. Found: C, 56.35; H, 5.36; N, 12.89.

Example 70

N-[(2Z)-5-tert-butyl-3-{2-[methyl(methylsulfonyl)amino]ethyl}-1,3-thiazol-2(3H)-ylidene]-5-chloro-N'-cyano-2-methoxybenzenecarboximidamide

Example 70A tert-butyl 2-(5-tert-butyl-2-iminothiazol-3(2H)-yl)ethylcarbamate The title compound was prepared according to the procedure described in Example 56A by substituting tert-butyl-2-aminoethylcarbamate for 3-methylbut-2-en-1-amine hydrochloride. $^1$H NMR (300 MHz, CHLOROFORM-D) δ ppm 1.31 (s, 9H) 1.42 (s, 9H) 3.57 (q, J=6.78 Hz, 2H) 4.26 (t, J=6.95 Hz, 2H) 5.63 (t, J=5.76 Hz, 1H) 6.58 (s, 1H). MS (DCI/NH$_3$) m/z 300.2 (M+H)$^+$.

Example 70B (Z)-tert-butyl 2-(5-tert-butyl-2-(5-chloro-2-methoxybenzoylimino)thiazol-3(2H)-yl)ethylcarbamate The title compound was prepared according to the procedure described in Example 54A by substituting 5-chloro-2-methoxybenzoic acid for Example 26B and the product of Example 70A for Example 16A. $^1$H NMR (300 MHz, CHLOROFORM-D) δ ppm 1.35 (s, 9H) 1.39 (s, 9H) 3.57 (q, J=5.82 Hz, 2H) 3.90 (s, 3H) 4.33 (t, J=5.75 Hz, 2H) 5.41 (s, 1H) 6.64 (s, 1H) 6.91 (d, J=9.12 Hz, 1H) 7.34 (dd, J=8.72, 2.78 Hz, 1H) 7.93 (d, J=2.78 Hz, 1H). MS (DCI/NH$_3$) m/z 468.2 (M+H)$^+$.

Example 70C (Z)-tert-butyl 2-(5-tert-butyl-2-(5-chloro-2-methoxybenzoylimino)thiazol-3(2H)-yl)ethyl(methyl)carbamate Example 70B (0.5 g, 1.1 mmol) was dissolved in 4 mL of DMF and cooled to 0° C., iodomethane (0.3 g, 2.1 mmol) was added then NaH (60%, 0.06 g, 1.4 mmol). The ice bath was removed and the reaction stirred for 1 hour. EtOAc was added and the reaction was washed with NH$_4$Cl, water, brine, dried with MgSO$_4$ and the solvent removed. LCMS m/z 482.2 (M+H)$^+$

Example 70D (Z)-N-(5-tert-butyl-3-(2-(methylamino)ethyl)thiazol-2(3H)-ylidene)-5-chloro-2-methoxybenzamide Example 70C (0.5 g, 1.0 mmol) was dissolved in 10 mL of CH$_2$Cl$_2$ and 2 mL of TFA was added the reaction was stirred at ambient temperature for 90 minutes. The solvent was removed and the residue was treated with CH$_2$Cl$_2$ and solvents removed (2×). The residue was dissolved in 5% MeOH/CH$_2$Cl$_2$ (0.1% NH$_4$OH) and filtered through silica and washed with 5% MeOH/CH$_2$Cl$_2$ (0.1% NH$_4$OH). $^1$H NMR (300 MHz, CHLOROFORM-D) δ ppm 1.37 (s, 9H) 2.54 (s, 3H) 3.47 (s, 2H) 3.92 (s, 3H) 4.54-4.62 (m, 2H) 6.82 (s, 1H) 6.98 (d, J=8.82 Hz, 1H) 7.43 (dd, J=8.81, 2.71 Hz, 1H) 7.80 (d, J=2.71 Hz, 1H) 10.89 (s, 1H). MS (DCI/NH$_3$) m/z 382.2 (M+H)$^+$.

Example 70E (Z)-N-(5-tert-butyl-3-(2-(N-methylmethylsulfonamido)ethyl)thiazol-2(3H)-ylidene)-5-chloro-2-methoxybenzamide The title compound was prepared according to the procedure described in Example 63D by substituting the product of Example 70D for the product of Example 63C. $^1$H NMR (300 MHz, CHLOROFORM-D) δ ppm 1.35 (s, 9H) 2.79 (s, 3H) 2.83 (s, 3H) 3.61 (t, J=6.44 Hz, 2H) 3.91 (s, 3H) 4.38 (t, J=6.27 Hz, 2H) 6.74 (s, 1H) 6.92 (d, J=8.82 Hz, 1H) 7.34 (dd, J=8.99, 2.88 Hz, 1H) 8.00 (d, J=2.71 Hz, 1H). MS (DCI/NH$_3$) m/z 460.1 (M+H)$^+$.

Example 70F (Z)-N-(5-tert-butyl-3-(2-(N-methylmethylsulfonamido)ethyl)thiazol-2(3H)-ylidene)-5-chloro-2-methoxybenzothioamide The title compound was prepared according to the procedure described in Example 16D by substituting the product of Example 70E for the product of Example 16C. $^1$H NMR (300 MHz, CHLOROFORM-D) δ ppm 1.41 (s, 9H) 2.74 (s, 3H) 2.78 (s, 3H) 3.61 (t, J=5.76 Hz, 2H) 3.81 (s, 3H) 4.37-4.55 (m, 2H) 6.85 (d, J=8.81 Hz, 1H) 6.94-7.02 (m, 1H) 7.21-7.26 (m, 1H) 7.51-7.57 (m, 1H). MS (DCI/NH$_3$) m/z 476.1 (M+H)$^+$.

Example 70G

N-[(2Z)-5-tert-butyl-3-{2-[methyl(methylsulfonyl)amino]ethyl}-1,3-thiazol-2(3H)-ylidene]-5-chloro-N'-cyano-2-methoxybenzenecarboximidamide The title compound was prepared according to the procedure described in Example 16E by substituting the product of Example 70F for the product of Example 16D. $^1$H NMR (300 MHz, CHLOROFORM-D) δ ppm 1.39 (s, 9H) 2.78 (s, 3H) 2.79 (s, 3H) 3.55 (t, J=6.15 Hz, 2H) 3.93 (s, 3H) 4.40 (t, J=6.15 Hz, 2H) 6.88 (s, 1H) 6.95 (d, J=8.72 Hz, 1H) 7.31-7.39 (m, 2H). MS (DCI/NH$_3$) m/z 484.1 (M+H)$^+$. Anal. Calc. for C$_{20}$H$_{26}$ClN$_5$O$_3$S$_2$: C, 49.63; H, 5.41; N, 14.47. Found: C, 49.39; H, 5.18; N, 14.32.

Example 71

N-[(2Z)-5-tert-butyl-3-isobutyl-1,3-thiazol-2(3H)-ylidene]-N'-cyano-2-ethoxy-5-(trifluoromethyl)benzenecarboximidamide

Example 71A (Z)-N-(5-tert-butyl-3-isobutylthiazol-2(3H)-ylidene)-2-ethoxy-5-(trifluoromethyl)benzamide The title compound was prepared according to the procedure described in Example 51B by substituting Example 69A for Example 51A and ethanol for 2-methoxyethanol. $^1$H NMR (300 MHz, CHLOROFORM-D) δ ppm 0.97 (d, J=6.78 Hz, 6H) 1.36 (s, 9H) 1.48 (t, J=6.95 Hz, 3H) 2.24-2.38 (m, 1H) 3.98 (d, J=7.46 Hz, 2H) 4.21 (q, J=7.12 Hz, 2H) 6.60 (s, 1H) 7.01 (d, J=8.82 Hz, 1H) 7.59 (dd, J=8.99, 2.20 Hz, 1H) 8.28 (d, J=2.37 Hz, 1H). MS (DCI/NH$_3$) m/z 429.2 (M+H)$^+$.

Example 71B (Z)-N-(5-tert-butyl-3-isobutylthiazol-2(3H)-ylidene)-2-ethoxy-5-(trifluoromethyl)benzothioamide The title compound was prepared according to the procedure described in Example 16D by substituting the product of Example 71A for the product of Example 16C. $^1$H NMR (300 MHz, CHLOROFORM-D) δ ppm 0.94 (d, J=6.74 Hz, 6H) 1.36 (t, J=6.94 Hz, 3H) 1.41 (s, 9H) 2.20-2.43 (m, 1H) 4.07 (d, J=7.14 Hz, 2H) 4.10-4.18 (m, 2H) 6.83 (s, 1H) 6.97 (d, J=8.72 Hz, 1H) 7.50 (dd, J=8.72, 2.38 Hz, 1H) 7.81 (d, J=2.38 Hz, 1H). MS (DCI/NH$_3$) m/z 445.2 (M+H)$^+$.

Example 71C

N-[(2Z)-5-tert-butyl-3-isobutyl-1,3-thiazol-2(3H)-ylidene]-N'-cyano-2-ethoxy-5-(trifluoromethyl)benzenecarboximidamide The title compound was prepared according to the procedure described in Example 16E by substituting the product of Example 71B for the product of Example 16D. $^1$H NMR (300 MHz, CHLOROFORM-D) δ ppm 0.96 (d, J=6.74 Hz, 6H) 1.39 (s, 9H) 1.51 (t, J=6.94 Hz, 3H) 2.17-2.31 (m, 1H) 4.02 (d, J=7.14 Hz, 2H) 4.24 (q, J=6.74 Hz, 2H) 6.74 (s, 1H) 7.06 (d, J=9.52 Hz, 1H) 7.61-7.66 (m, 2H). MS (DCI/NH$_3$) m/z 453.2 (M+H)$^+$. Anal. Calc. for C$_{22}$H$_{27}$F$_3$N$_4$OS: C, 58.39; H, 6.01; N, 12.38. Found: C, 58.30; H, 5.95; N, 12.33.

Example 72

N-[(2Z)-5-tert-butyl-3-isobutyl-1,3-thiazol-2(3H)-ylidene]-N'-cyano-2-(2,2,2-trifluoroethoxy)-5-(trifluoromethyl)benzenecarboximidamide

Example 72A (Z)-N-(5-tert-butyl-3-isobutylthiazol-2(3H)-ylidene)-2-(2,2,2-trifluoroethoxy)-5-(trifluoromethyl)benzamide The title compound was prepared according to the procedure described in Example 51B by substituting Example 69A for Example 51A and 2,2,2-trifluoroethanol for 2-methoxyethanol. $^1$H NMR (300 MHz, CHLOROFORM-D) δ ppm 0.97 (d, J=6.74 Hz, 6H) 1.37 (s, 9H) 2.28 (m, 1H) 4.00 (d, J=7.14 Hz, 2H) 4.53 (q, J=8.33 Hz, 2H) 6.64 (s, 1H) 7.13 (d, J=8.33 Hz, 1H) 7.63 (dd, J=8.73, 2.38 Hz, 1H) 8.35 (d, J=2.38 Hz, 1H). MS (DCI/NH$_3$) m/z 483.2 (M+H)$^+$.

Example 72B (Z)-N-(5-tert-butyl-3-isobutylthiazol-2(3H)-ylidene)-2-(2,2,2-trifluoroethoxy)-1-(trifluoromethyl)benzothioamide The title compound was prepared according to the procedure described in Example 16D by substituting the product of Example 72A for the product of 16C. $^1$H NMR (300 MHz, CHLOROFORM-D) δ ppm 0.92 (d, J=6.74 Hz, 6H) 1.42 (s, 9H) 2.18-2.33 (m, 1H) 4.08 (d, J=7.54 Hz, 2H) 4.39 (q, J=8.33 Hz, 2H) 6.85 (s, 1H) 7.04 (d, J=8.72 Hz, 1H) 7.54 (dd, J=8.13, 2.18 Hz, 1H) 7.89 (d, J=2.38 Hz, 1H). MS (DCI/NH$_3$) m/z 499.1 (M+H)$^+$.

Example 72C

N-[(2Z)-5-tert-butyl-3-isobutyl-1,3-thiazol-2(3H)-ylidene]-N'-cyano-2-(2,2,2-trifluoroethoxy)-5-(trifluoromethyl)benzenecarboximidamide The title compound was prepared according to the procedure described in Example 16E by substituting the product of Example 72B for the product of Example 16D. $^1$H NMR (300 MHz, CHLOROFORM-D) δ ppm 0.95 (d, J=6.78 Hz, 6H) 1.40 (s, 9H) 2.15-2.29 (m, 1H) 4.02 (d, J=7.46 Hz, 2H) 4.63 (q, J=8.14 Hz, 2H) 6.77 (s, 1H) 7.11 (d, J=8.48 Hz, 1H) 7.66-7.72 (m, 2H). MS (DCI/NH$_3$) m/z 507.2 (M+H)$^+$. Anal. Calc for C$_{22}$H$_{24}$F$_6$N$_4$OS: C, 52.17; H, 4.78; N, 11.06. Found: C, 52.30; H, 4.69; N, 11.04.

Example 73

N-[(2Z)-3-butyl-5-tert-butyl-1,3-thiazol-2(3H)-ylidene]-N'-1-naphthylpropanimidamide

Example 73A ethyl N-naphthalen-1-ylpropionimidate

The title compound was prepared from 1-aminonaphthalene and triethylorthopropionate according to the following procedure: DeWolfe, R. H. J. Org. Chem. 1962, 27, 490-493.

Example 73B

N-[(2Z)-3-butyl-5-tert-butyl-1,3-thiazol-2(3H)-ylidene]-N'-1-naphthylpropanimidamide To a 20-ml scintillation vial containing a magnetic stir bar were added the free base of Example 6A and the liquid imidate from Example 73A. Butanol was added to form a yellow solution. The reaction was heated to 85° C. in a heated shaker block and stirred for 48 h. The volatiles were removed by rotary evaporator to give a brown oil. Product purified by flash chromatography (silica gel: 5-40% ethyl acetate in hexanes) to give the title compound as a colorless oil. $^1$H NMR (DMSO-d$_6$) δ 0.96 (t, J=7.3 Hz, 3H), 1.04 (t, J=7.5 Hz, 3H), 1.24 (s, 9H) 1.29-1.42 (m, 2H), 1.73-1.83 (m, 2H), 2.18 (q, J=7.5 Hz, 2H), 4.13 (t, J=7.1 Hz, 2H), 6.76 (dd, J=7.3, 1.2 Hz, 1H), 7.13 (s, 1H), 7.38-7.55 (m, 4H), 7.83-7.88 (m, 2H). MS (ESI+) m/z 394 (M+H)$^+$.

Example 74

N-[(2Z)-5-tert-butyl-3-(tetrahydro-2H-pyran-4-ylmethyl)-1,3-thiazol-2(3H)-ylidene]-5-chloro-N'-cyano-2-methoxybenzenecarboximidamide

Example 74A 5-tert-butylthiazol-2-amine

To a flask equipped with a Dean-Stark trap was added 3,3-dimethylbutanal (Aldrich, 5.0 g, 50 mmol), pyrrolidine (Aldrich, 4.4 mL, 52 mmol) and p-toluenesulfonic acid monohydrate (10 mg) in cyclohexane (70 mL). The mixture was heated to reflux for 3 hours, the water was removed and the organic phase was concentrated under reduced pressure. The residue was dissolved in methanol (20 mL) and cooled to 0° C. Sulfur (Aldrich, 1.6 g, 50 mmol) and a solution of cyanamide (Aldrich, 2.1 g, 50 mmol) in methanol (5 mL) were added. The reaction mixture was allowed to warm to ambient temperature, stirred for 12 hours, and was concentrated under reduced pressure. The residue was purified by column chromatography (SiO$_2$, 2% methanol in CH$_2$Cl$_2$) to afford the title compound. MS (ESI$^+$) m/z 157 (M+H)$^+$.

Example 74B

N-(5-tert-butylthiazol-2-yl)-5-chloro-2-methoxybenzamide

To a solution of Example 74A (0.94 g, 6.0 mmol) in tetrahydrofuran (40 mL) was added Example 18B (1.23 g, 6.0 mmol), triethylamine (2.4 mL, 18 mmol), and 4-dimethylaminopyridine (7.5 mg, 0.06 mmol). The reaction mixture was stirred at 60° C. for 14 hours and then cooled to ambient temperature, diluted with saturated aqueous NaHCO$_3$ (20 mL) and extracted with ethyl acetate (3×30 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-100% ethyl acetate in hexanes) to afford the title compound. MS (ESI$^+$) m/z 325 (M+H)$^+$.

Example 74C

N-[(2Z)-5-tert-butyl-3-(tetrahydro-2H-pyran-4-ylmethyl)-1,3-thiazol-2(3H)-ylidene]-5-chloro-2-methoxybenzamide To a solution of Example 74B (1.0 g, 3.1 mmol) in 4:1 N,N-dimethylformamide/tetrahydrofuran (20 mL) were added potassium tert-butoxide (Aldrich, 0.42 g, 3.7 mmol) and 4-(iodomethyl)tetrahydro-2H-pyran (Maybridge, 0.97 g, 4.3 mmol). The reaction mixture was stirred at 80° C. for 16 hours, cooled to room temperature, quenched with saturated aqueous NaHCO$_3$ (20 mL) and extracted with ethyl acetate (3×20 mL). The combined organic extracts were dried over anhydrous Na$_2$SO$_4$, filtered and concentrated under reduced pressure. The residue was purified by column chromatography using an Analogix® Intelliflash280 ™ (SiO$_2$, 0-100% ethyl acetate in hexanes) to afford the title compound. $^1$H NMR (300 MHz, dimethylsulfoxide-d$_6$) δ ppm 1.21-1.51 (m, 4H), 1.32 (s, 9H), 2.06-2.35 (m, 1H), 3.20-3.30 (m, 2H), 3.79 (s, 3H), 3.80-3.91 (m, J=9.3, 2.2, 2.0 Hz, 2H), 4.06 (d, J=7.1 Hz, 2H), 7.11 (d, J=8.8 Hz, 1H), 7.30 (s, 1H), 7.45 (dd, J=8.8, 3.1 Hz, 1H), 7.64 (d, J=2.7 Hz, 1H); MS (ESI$^+$) m/z 423 (M+H)$^+$; Anal. Calculated for C$_{21}$H$_{27}$ClN$_2$O$_3$S: C, 59.63; H, 6.43; N, 6.62. Found: C, 59.66; H, 6.36; N, 6.56.

Example 74D (Z)-N-(5-tert-butyl-3-((tetrahydro-2H-pyran-4-yl)methyl)thiazol-2(3H)-ylidene)-5-chloro-2-methoxybenzothioamide The title compound was prepared from Example 74C according to the procedure described in Example 6C from Example 74C. $^1$H NMR (300 MHz, CHLOROFORM-D) δ ppm 1.38-1.46 (m, 9H), 1.51-1.66 (m, 4H), 2.16-2.35 (m, 1H), 3.26-3.44 (m, 2H), 3.81 (s, 3H), 3.92-4.04 (m, 2H), 4.17 (d, J=7.5 Hz, 2H), 6.77-6.91 (m, 2H), 7.19-7.27 (m, 1H), 7.53 (d, J=2.7 Hz, 1H). MS (DCI+) m/z 440 (M+H)$^+$.

Example 74E

N-[(2Z)-5-tert-butyl-3-(tetrahydro-2H-pyran-4-ylmethyl)-1,3-thiazol-2(3H)-ylidene]-5-chloro-N'-cyano-2-methoxybenzenecarboximidamide The title compound was prepared from Example 74D according to the procedure described in Example 7. $^1$H NMR (300 MHz, CHLOROFORM-D) δ ppm 1.36-1.42 (m, 9H), 1.47-1.60 (m, 2H), 2.10-2.28 (m, 1H), 3.28-3.46 (m, 2H), 3.91-3.96 (m, 3H), 3.95-4.04 (m, 2H), 3.95-4.06 (m, 2H), 4.03-4.16 (m, 2H), 6.72 (s, 1H), 6.95 (d, J=8.8 Hz, 1H), 7.29-7.44 (m, 2H). MS (DCI+) m/z 447 (M+H)$^+$.

Example 75

N-[(2Z)-3-butyl-5-tert-butyl-1,3-thiazol-2(3H)-ylidene]-5-chloro-N'-cyano-2-(2,2,2-trifluoroethoxy)benzenecarboximidamide Example 75A (Z)-N-(5-tert-butyl-3-butylthiazol-2(3H)-ylidene)-5-chloro-2-fluorobenzamide A mixture of 5-tert-butyl-3-butylthiazol-2(3H)-imine (free base of Example 6A, 500 mg, 2.4 mmol), 5-chloro-2-fluorobenzoic acid (670 mg, 2.8 mmol), EDCI (900 mg, 4.7 mmol), HOBt (635 mg, 4.7 mmol) and DMAP (36 mg, 0.3 mmol) in pyridine (20 mL) was stirred at room temperature for 2 hours. The solvent was removed, the mixture was diluted with water, and extracted with EtOAc. The organic extract was dried (Na$_2$SO$_4$), filtered and concentrated. The residue was triturated with EtOAc, to give 537 mg (61%) of the title compound. MS (ESI) m/z 369 (M+H)$^+$.

Example 75B (Z)-N-(5-tert-butyl-3-butylthiazol-2(3H)-ylidene)-5-chloro-2-(2,2,2-trifluoroethoxy)benzamide A mixture of the product from Example 75A (537 mg, 1.45 mmol), trifluoroethanol (87 µL, 2.18 mmol) and potassium 2-methylpropan-2-olate (2.18 mL, 2.18 mmol) in THF (10 mL) was stirred at room temperature for 3 hrs. The mixture was diluted with water and extracted with EtOAc. The organic extract was dried (Na$_2$SO$_4$), filtered and concentrated. The residue was purified by column chromatography using an Analogix® Intelliflash280 ™ (SiO$_2$, 0-50% Hexane in ethyl acetate) to afford 258 mg (40%) of the title compound. $^1$H NMR (500 MHz, CDCl$_3$) δ ppm 0.99 (t, J=7.32 Hz, 3H) 1.36 (s, 9H) 1.40 (dd, J=7.63 Hz, 2H) 1.82 (m, 2H) 4.19 (t, J=7.32 Hz, 2H) 4.48 (q, J=8.54 Hz, 2H) 6.65 (s, 1H) 7.02 (d, J=8.54 Hz, 1H) 8.03 (d, J=2.75 Hz, 1H). MS (DCI/NH$_4$) m/z 449 (M+H)$^+$.

Example 75C (Z)-N-(5-tert-butyl-3-butylthiazol-2(3H)-ylidene)-5-chloro-2-(2,2,2-trifluoroethoxy)benzothioamide The title compound was prepared from Example 75B according to the procedure described in Example 6C. $^1$H NMR (300 MHz, CDCl$_3$) δ ppm 0.94 (t, J=7.3 Hz, 3H), 1.25-1.40 (m, 2H), 1.38-1.46 (s, 9H), 1.71-1.89 (m, 2H), 4.20-4.44 (m, 4H), 6.92 (d, J=8.5 Hz, 2H), 7.22 (d, J=2.7 Hz, 1H), 7.60 (d, J=2.7 Hz, 1H). MS (DCI+) m/z 466 (M+H)$^+$.

Example 75D

N-[(2Z)-3-butyl-5-tert-butyl-1,3-thiazol-2(3H)-ylidene]-5-chloro-N'-cyano-2-(2,2,2-trifluoroethoxy)benzenecarboximidamide The title compound was prepared from Example 75C according to the procedure described in Example 7. $^1$H NMR (300 MHz, CDCl$_3$) δ ppm 0.96 (t, J=7.3 Hz, 3H), 1.29-1.38 (m, 2H), 1.37-1.43 (m, 9H), 1.54 (s, 2H), 1.67-1.92 (m, 2H), 4.55 (q, J=8.2 Hz, 2H), 6.78 (s, 1H), 6.91-7.03 (m, 1H), 7.33-7.43 (m, 2H). MS (DCI+) m/z 473 (M+H)$^+$.

Example 76

N-[(2Z)-5-tert-butyl-3-(cyclobutylmethyl)-1,3-thiazol-2(3H)-ylidene]-5-chloro-N'-cyano-2-methoxybenzenecarboximidamide

Example 76A 5-tert-butyl-3-(cyclobutylmethyl)thiazol-2(3H)-imine

A mixture of Example 74A (1.56 g, 10 mmol) and (bromomethyl)cyclobutane (1.1 mL, 10 mmol) was warmed to 85° C. and was allowed to stir for 18 h. The mixture was cooled to ambient temperature and the crude material was purified via column chromatography (SiO$_2$, 10% MeOH in EtOAc then 9:1:0.1 CH$_2$Cl$_2$: MeOH:NH$_4$OH) to provide the title compound (1.8 g, 80% yield). MS, DCI, m/z 225 (M+H)$^+$.

Example 76B (Z)-N-(5-tert-butyl-3-(cyclobutylmethyl)thiazol-2(3H)-ylidene)-5-chloro-2-methoxybenzamide To a solution of the product of Example 76A (0.26 g, 1.2 mmol) in THF (15 mL) was added Et$_3$N (0.50 mL, 3.6 mmol) followed by the product of Example 18B (1.2 mmol). This mixture was warmed to 50° C. and was allowed to stir for 4 h. The mixture was cooled to ambient temperature, quenched with saturated aqueous NaHCO$_3$ (5 mL) and diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc) to provide the title compound (161 mg, 40% yield). $^1$H NMR (300 MHz, CD$_3$OD) δ ppm 1.38 (s, 9H), 1.79-2.19 (m, 6H), 2.79-3.03 (m, 1H), 3.86 (s, 3H), 4.28 (d, J=7.1 Hz, 2H), 7.07 (d, J=9.2 Hz, 1H), 7.13 (s, 1H), 7.40 (dd, J=8.8, 2.7 Hz, 1H), 7.83 (d, J=3.1 Hz, 1H). MS, DCI, m/z 393 (M+H)$^+$.

Example 76C (Z)-N-(5-tert-butyl-3-(cyclobutylmethyl)thiazol-2(3H)-ylidene)-5-chloro-2-methoxybenzothioamide The title compound was prepared from Example 76B according to the procedure described in Example 6C. $^1$H NMR (300 MHz, CDCl$_3$) δ ppm 1.37-1.44 (m, 9H), 1.73-1.98 (m, 4H), 1.98-2.13 (m, 2H), 2.78-2.96 (m, 1H), 3.81 (s, 3H), 4.33 (d, J=7.5 Hz, 2H), 6.79-6.88 (m, 2H), 7.17-7.26 (m, 1H), 7.52 (d, J=2.7 Hz, 1H). MS, DCI, m/z 410 (M+H)$^+$.

Example 76D

N-[(2Z)-5-tert-butyl-3-(cyclobutylmethyl)-1,3-thiazol-2(3H)-ylidene]-5-chloro-N'-cyano-2-methoxybenzenecarboximidamide The title compound was prepared from example 76C according to the procedure described in Example 7. $^1$H NMR (300 MHz, DMSO-D$_6$) δ ppm 1.29-1.40 (m, 9H), 1.74-1.90 (m, 4H), 1.89-2.03 (m, 1H), 2.69-2.90 (m, 1H), 3.24-3.40 (m, 1H), 3.74-3.84 (m, 3H), 4.24 (d, J=7.5 Hz, 2H), 7.20 (d, J=8.7 Hz, 1H), 7.33 (d, J=2.8 Hz, 1H), 7.51 (dd, J=9.1, 2.8 Hz, 1H), 7.58 (s, 1H). MS, DCI, m/z 417 (M+H)$^+$.

Example 77

N-[(2Z)-5-tert-butyl-3-(4,4,4-trifluorobutyl)-1,3-thiazol-2(3H)-ylidene]-5-chloro-N'-cyano-2-methoxybenzenecarboximidamide

Example 77A 5-tert-butyl-3-(4,4,4-trifluorobutyl)thiazol-2(3H)-imine hydrobromide A mixture of the product of Example 74A (0.25 g, 1.6 mmol) and 1-bromo-4,4,4-trifluorobutane (336 mg, 1.8 mmol) was warmed to 85° C. and was stirred for 16 hours. The mixture was cooled to ambient temperature and the title compound (0.35 g, 63% yield) was isolated via filtration. MS (DCI/NH$_3$) m/z 267 (M+H)$^+$.

(Z)-N-(5-tert-butyl-3-(4,4,4-trifluorobutyl)thiazol-2(3H)-ylidene)-5-chloro-2-methoxybenzamide

Example 77B

To a solution of the product of Example 77A (0.35 g, 1.0 mmol) in THF (10 mL) and DMF (2 mL) was added Et$_3$N (0.55 mL, 4.0 mmol) followed by the product of Example 18B (1.0 mmol). This mixture was warmed to 50° C. and was allowed to stir for 3 hours. The mixture was cooled to ambient temperature, was quenched with saturated, aqueous NH$_4$Cl (5 mL) and was diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and recrystallized with 4:1 hexanes:EtOAc to provide the title compound (0.24 g, 0.56 mmol, 56% yield). MS (DCI/NH$_3$) m/z 435 (M+H)$^+$.

Example 77C (Z)-N-(5-tert-butyl-3-(4,4,4-trifluorobutyl)thiazol-2(3H)-ylidene)-5-chloro-2-methoxybenzothioamide The title compound was prepared from Example 77B according to the procedure described in Example 6C. $^1$H NMR (300 MHz, CDCl$_3$) δ ppm 1.38-1.47 (m, 9H), 2.15 (dd, J=8.6, 3.2 Hz, 4H), 3.78 (s, 3H), 4.34 (t, J=6.6 Hz, 2H), 6.78-6.91 (m, 2H), 7.18-7.27 (m, 1H), 7.52 (d, J=2.7 Hz, 1H). MS, DCI, m/z 451 (M+H)$^+$.

Example 77D

N-[(2Z)-5-tert-butyl-3-(4,4,4-trifluorobutyl)-1,3-thiazol-2(3H)-ylidene]-5-chloro-N'-cyano-2-methoxybenzenecarboximidamide The title compound was prepared from Example 77C according to the procedure described in Example 7. $^1$H NMR (300 MHz, CDCl$_3$) δ ppm 1.34-1.45 (m, 9H), 2.02-2.28 (m, 4H), 3.91 (s, 3H), 4.27 (t, J=6.9 Hz, 2H), 6.76 (s, 1H), 6.95 (d, J=8.7 Hz, 1H), 7.28-7.42 (m, 2H). MS, DCI, m/z 459 (M+H)$^+$.

Example 78

N-[(2Z)-5-tert-butyl-3-but-3-ynyl-1,3-thiazol-2(3H)-ylidene]-5-chloro-N'-cyano-2-methoxybenzenecarboximidamide

Example 78A but-3-ynyl 4-methylbenzenesulfonate

To a mixture of 3-butyn-1-ol (0.5 g, 8.3 mmol) in CH$_2$Cl$_2$ (20 mL) and pyridine (1.7 mL, 33.2 mmol) was added p-toluenesulfonyl chloride (1.7 g, 8.7 mmol). This mixture was stirred at ambient temperature for 16 h then diluted with CH$_2$Cl$_2$ (20 mL) and quenched with aqueous 1% HCl (5 mL). The layers were separated and the organic layer was washed with aqueous 1% HCl (5 mL) and brine (5 mL). The organic layer was dried over anhydrous Na$_2$SO$_4$, filtered, concentrated under reduced pressure and purified via column chromatography (4:1 hexanes:EtOAc) to provide the title compound (0.30 g, 1.3 mmol, 16% yield). MS (DCI/NH$_3$) m/z 242 (M+NH$_4$)$^+$.

Example 78B 3-(but-3-ynyl)-5-tert-butylthiazol-2(3H)-imine

A mixture of the product of Example 74A (0.20 g, 1.3 mmol), the product of Example 78A (0.29 g, 1.3 mmol), tetrabutylammonium iodide (0.24 g, 0.64 mmol) in DMF (1.5 mL) was warmed to 85° C. and stirred for 16 h. The mixture was cooled to ambient temperature and quenched with saturated aqueous NaHCO$_3$ (5 mL) and diluted with EtOAc (10 mL). The layers were separated and the aqueous layer was extracted with EtOAc (2×5 mL). The combined organics were dried over anhydrous Na$_2$SO$_4$, filtered, concentrated under reduced pressure and purified via flash column chromatography (SiO$_2$, 10% MeOH in EtOAc then 9:1:0.1 CH$_2$Cl$_2$:MeOH:NH$_4$OH) to provide the title compound (0.18 g, 0.84 mmol, 65% yield). MS (DCI/NH$_3$) m/z 209 (M+H)$^+$.

Example 78C (Z)-N-(3-(but-3-ynyl)-5-tert-butylthiazol-2(3H)-ylidene)-5-chloro-2-methoxybenzamide To a solution of the product of Example 78B (0.17 g, 0.81 mmol) in THF (10 mL) was added Et$_3$N (0.34 mL, 2.4 mmol) followed by the product of Example 18B (0.81 mmol). This mixture was warmed to 50° C. and was allowed to stir for 1 h. The mixture was cooled to ambient temperature, quenched with saturated, aqueous NH$_4$Cl (5 mL) and diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 60% hexanes/EtOAc) to provide the title compound (0.12 g, 0.32 mmol, 39% yield). MS (DCI/NH$_3$) m/z 377 (M+H)$^+$.

Example 78D (Z)-N-(3-(but-3-ynyl)-5-tert-butylthiazol-2(3H)-ylidene)-5-chloro-2-methoxybenzothioamide The title compound was prepared from Example 78C according to the procedure described in Example 6C. $^1$H NMR (300 MHz, DMSO-D$_6$) δ ppm 1.31-1.41 (m, 9H), 2.70-2.86 (m, 2H), 3.72-3.78 (m, 3H), 3.78-3.86 (m, 1H), 4.29-4.44 (m, 2H), 7.04-7.14 (m, 1H), 7.29-7.47 (m, 2H), 7.63-7.73 (m, 1H). MS, DCI, m/z 451 (M+H)$^+$. MS, DCI, m/z 393 (M+H)$^+$.

Example 78E

N-[(2Z)-5-tert-butyl-3-but-3-ynyl-1,3-thiazol-2(3H)-ylidene]-5-chloro-N'-cyano-2-methoxybenzenecarboximidamide The title compound was prepared from Example 78D according to the procedure described in Example 7. $^1$H NMR (300 MHz, DMSO-D$_6$) δ ppm 1.35 (s, 9H), 2.65-2.80 (m, J=2.4 Hz, 2H), 2.88-3.01 (m, 1H), 3.82 (s, 3H), 4.33 (t, J=6.8 Hz, 2H), 7.20 (d, J=9.2 Hz, 1H), 7.40 (d, J=2.7 Hz, 1H), 7.46-7.57 (m, 1H), 7.61 (s, 1H). MS, DCI, m/z 401 (M+H)$^+$. Anal. calcd for C$_{20}$H$_{21}$ClN$_4$OS: C, 59.91; H, 5.23; N, 13.97. Found: C, 59.60; H, 5.11; N, 13.63.

Example 79

5-chloro-N'-cyano-2-methoxy-N-[(2Z)-5-methyl-3-(1,3-thiazol-4-ylmethyl)-1,3-thiazol-2(3H)-ylidene]benzenecarboximidamide

Example 79A 5-chloro-2-methoxy-N-(5-methylthiazol-2-yl)benzamide

Commercially available 5-methylthiazol-2-amine and Example 18B were processed using the method described for Example 74B to afford the title compound. MS (DCI) m/z 283 (M+H)$^+$.

Example 79B 5-chloro-2-methoxy-N-[(2Z)-5-methyl-3-(1,3-thiazol-4-ylmethyl)-1,3-thiazol-2(3H)-ylidene]benzamide To a solution of Example 79A (2.65 g, 9.4 mmol) in DMF (20 mL) at 0° C. was added sodium hydride (60% dispersion in mineral oil, 0.247 g, 10.3 mmol). The reaction mixture was stirred for 30 min. and then treated with commercially available 4-(chloromethyl)thiazole (1.25 g, 9.4 mmol). The resulting mixture was stirred at room temperature for 18 hr, poured into water (100 mL) and extracted with EtOAc (2×100 mL). The organics were washed with water, brine (2×100 mL), dried over MgSO$_4$ and concentrated. The residue was purified by using an Analogix® Intelliflash280™ (SiO$_2$, 0-50% ethyl acetate in hexanes) to afford the title compound (2.56 g, 72% yield). ¹H NMR (300 MHz, DMSO-D6) δ ppm 2.28 (s, 3H), 3.77 (s, 3H), 5.50 (s, 2H), 7.10 (d, J=8.7 Hz, 1H), 7.31 (d, J=1.6 Hz, 1H), 7.38-7.52 (m, 2H), 7.63 (dd, J=14.5, 2.6 Hz, 1H), 9.09 (d, J=2.0 Hz, 1H). MS (DCI) m/z 398 (M+H)⁺; MS (DCI) m/z 380 (M+H)⁺. Anal. Calculated for $C_{16}H_{14}ClN_3O_2S_2$: C, 50.59; H, 3.71; N, 11.06. Found: C, 50.57; H, 3.02; N, 11.03.

Example 79C (Z)-5-chloro-2-methoxy-N-(5-methyl-3-(thiazol-4-ylmethyl)thiazol-2(3H)-ylidene)benzothioamide The title compound was prepared from Example 79B according to the procedure described in Example 6C. ¹H NMR (300 MHz, DMSO-D6) δ ppm 2.28-2.44 (m, 3H), 3.62-3.78 (m, 3H), 5.57-5.71 (m, 2H), 6.97-7.15 (m, 1H), 7.28-7.40 (m, 2H), 7.48-7.67 (m, 2H), 9.04-9.15 (m, 1H). MS, DCI, m/z 396 (M+H)⁺. Anal. calcd for $C_{16}H_{14}ClN_3OS_3$: C, 48.53; H, 3.56; N, 10.61. Found: C, 48.41; H, 3.49; N, 10.54.

Example 79D 5-chloro-N'-cyano-2-methoxy-N-[(2Z)-5-methyl-3-(1,3-thiazol-4-ylmethyl)-1,3-thiazol-2(3H)-ylidene] benzenecarboximidamide The title compound was prepared from Example 79C according to the procedure described in Example 7. ¹H NMR (300 MHz, DMSO-D6) δ ppm 2.29-2.43 (m, J=1.4 Hz, 3H), 3.81 (s, 3H), 5.55 (s, 2H), 7.11-7.30 (m, 2H), 7.45-7.58 (m, 2H), 7.61 (d, J=2.0 Hz, 1H), 9.09 (d, J=2.0 Hz, 1H). MS, DCI, m/z 404 (M+H)⁺. Anal. calcd for $C_{16}H_{14}ClN_3OS_3$: C, 50.55; H, 3.49; N, 17.34. Found: C, 50.65; H, 3.55; N, 17.12.

Example 80

5-chloro-N'-cyano-2-methoxy-N-[(2Z)-5-methyl-3-[(2R)-tetrahydrofuran-2-ylmethyl]-1,3-thiazol-2 (3H)-ylidene]benzenecarboximidamide

Example 80A (R)-(tetrahydrofuran-2-yl)methyl 4-methylbenzenesulfonate

To a solution of (R)-tetrahydrofurfuryl alcohol (Lancaster, 1.0 g, 9.8 mmol) in 5 mL of CH₂Cl₂ and 5 mL of pyridine was added p-toluenesulfonyl chloride (2.8 g, 14.7 mmol) in portions over 15 minutes. The mixture was stirred at ambient temperature for 3 hours and was quenched with 10 mL of saturated, aqueous NaHCO₃. The layers were separated and the aqueous layer was extracted with three 5 mL portions of CH₂Cl₂. The combined organic extracts were dried over anhydrous Na₂SO₄, filtered and concentrated under reduced pressure to afford the title compound. MS (DCI/NH₃) m/z 257 (M+H)⁺, 274 (M+NH₄)⁺.

Example 80B (R)-5-methyl-3-((tetrahydrofuran-2-yl)methyl)thiazol-2(3H)-imine A mixture of Example 80A (1.5 g, 5.9 mmol), 2-amino-5-methylthiazole (0.68 g, 5.9 mmol) and tetrabutylammonium iodide (1.1 g, 3.0 mmol) in 3 mL of N,N-dimethylformamide was warmed to 85° C. and was allowed to stir for 48 hours. The mixture was diluted with 10 mL of CH₂Cl₂ and the solution was quenched with 10 mL of saturated, aqueous NaHCO₃. The layers were separated and the aqueous layer was extracted twice with 10 mL portions of CH₂Cl₂. The combined organic extracts were dried over anhydrous Na₂SO₄, filtered and concentrated under reduced pressure. Purification via column chromatography (SiO₂, 10% methanol in ethyl acetate then 9:1:0.1 CH₂Cl₂:methanol NH₄OH) afforded the title compound. MS (DCI/NH₃) m/z 199 (M+H)⁺.

Example 80C 5-chloro-2-methoxy-N-[(2Z)-5-methyl-3-[(2R)-tetrahydrofuran-2-ylmethyl]-1,3-thiazol-2(3H)-ylidene] benzamide To a solution of Example 80B (0.23 g, 1.2 mmol) in 10 mL of tetrahydrofuran at ambient temperature was added triethylamine (0.49 mL, 3.5 mmol) followed by Example 18B (1.2 mmol) in 5 mL of tetrahydrofuran via cannula. This mixture was warmed to 50° C. and was allowed to stir for 3 hours and was quenched with 10 mL of NH₄Cl and diluted with 10 mL of CH₂Cl₂. The layers were separated and the aqueous layer was extracted with three 5 mL portions of CH₂Cl₂. The combined organic extracts were dried over anhydrous Na₂SO₄, filtered and concentrated under reduced pressure. Purification via flash column chromatography (SiO₂, 1:1:1 hexanes:ethyl acetate:CH₂Cl₂) afforded the title compound. ¹H NMR (300 MHz, CD₃OD) δ ppm 1.64-1.79 (m, 1H), 1.84-1.96 (m, 2H), 2.00-2.14 (m, 1H), 2.34 (d, J=1.4 Hz, 3H), 3.69-3.81 (m, 1H), 3.84-3.93 (m, 1H), 3.85 (s, 3H), 4.20-4.43 (m, 3H), 7.07 (d, J=8.8 Hz, 1H), 7.14 (q, J=1.1 Hz, 1H), 7.39 (dd, J=9.0, 2.9 Hz, 1H), 7.81 (d, J=2.7 Hz, 1H); MS (DCI/NH₃) m/z 367 (M+H)⁺. Anal. Calculated for $C_{17}H_{19}ClN_2O_3S$: C, 55.66; H, 5.22; N, 7.64. Found: C, 55.42; H, 5.08; N, 7.58.

Example 80D (R,Z)-5-chloro-2-methoxy-N-(5-methyl-3-((tetrahydrofuran-2-yl)methyl)thiazol-2(3H)-ylidene)benzothioamide The title compound was prepared from Example 80C according to the procedure described in Example 6C. ¹H NMR (300 MHz, DMSO-d₆) δ ppm 1.48-1.67 (m, 1H), 1.73-2.02 (m, 3H), 2.32-2.42 (m, 3H), 3.55-3.69 (m, 1H), 3.69-3.87 (m, 4H), 4.12-4.45 (m, 3H), 6.99-7.13 (m, 1H), 7.28-7.45 (m, 2H), 7.49-7.59 (m, 1H). MS, DCI, m/z 384 (M+H)⁺. Anal. calcd for $C_{17}H_{19}ClN_2O_2S_2$: C, 53.32; H, 5.00; N, 7.32. Found: C, 53.28; H, 4.84; N, 7.20.

Example 80E 5-chloro-N'-cyano-2-methoxy-N-[(2Z)-5-methyl-3-[(2R)-tetrahydrofuran-2-ylmethyl]-1,3-thiazol-2 (3H)-ylidene]benzenecarboximidamide The title compound was prepared from Example 80D according to the procedure described in Example 7. ¹H NMR (300 MHz, DMSO-d₆) δ ppm 1.49-1.69 (m, 1H), 1.71-2.02 (m, 3H), 2.30-2.41 (m, 3H), 3.57-3.70 (m, 1H), 3.71-3.87 (m, 4H), 4.12-4.36 (m, 3H), 7.12-7.26 (m, 1H), 7.31-7.42 (m, 1H), 7.45-7.60 (m, 2H). MS, DCI, m/z 391 (M+H)⁺. Anal. calcd for $C_{18}H_{19}N_4O_2S$: C, 55.31; H, 4.90; N, 14.33. Found: C, 55.25; H, 4.83; N, 14.51.

Example 81

N'-cyano-N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboximidamide

Example 81A

2-Oxa-tricyclo[3.3.1.1$^{3,7}$]decane-1-carboxylic acid methyl ester

The title compound was prepared according to the procedure as described in Partch, R.; Brewster W.; Stokes, B. *Croatia Chemical Acta* (1986), 58(4), 661-669. MS (ESI) m/z 197 (M+H)$^+$.

Example 81B

2-Oxa-tricyclo[3.3.1.1$^{3,7}$]decane-1-carboxylic acid

To a solution of Example 81A (2.5 g, 12.6 mmol) in methanol/water (1:1, 100 mL) was added 5 N aqueous NaOH (3.8 mL, 19 mmol). The mixture was stirred at room temperature for 3 hours and then extracted with methylene chloride to remove unreacted starting material. The aqueous layer was acidified (pH~2) with 6 N aqueous HCl and then extracted with methylene chloride. The combined acidic extracts were dried ($Na_2SO_4$), filtered and concentrated to afford 1.92 g of the title compound. MS (ESI$^+$) m/z 183 (M+H)$^+$.

Example 81C

2-Oxa-tricyclo[3.3.1.1$^{3,7}$]decane-1-carbonyl chloride

A solution of Example 81B (0.1 g, 0.55 mmol) in 5 mL of thionyl chloride was warmed to reflux and stirred for 2 hours. The mixture was cooled to ambient temperature and concentrated under reduced pressure. The residue was diluted with 5 mL of toluene and concentrated under reduced pressure three times to afford the title compound, which was used without additional purification or characterization.

Example 81D

N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboxamide Example 80B (0.11 g, 0.55 mmol), triethylamine (0.23 mL, 1.6 mmol) and Example 81C (0.55 mmol) were processed as described in Example 80C to afford the title compound. $^1$H NMR (300 MHz, CD$_3$OD) δ ppm 1.60-1.77 (m, 3H), 1.81-2.07 (m, 9H), 2.08-2.22 (m, 4H), 2.29 (d, J=1.4 Hz, 3H), 3.69-3.79 (m, 1H), 3.82-3.91 (m, 1H), 4.15-4.36 (m, 4H), 7.05 (q, J=1.4 Hz, 1H); MS (DCI/NH$_3$) m/z 363 (M+H)$^+$. Anal. Calculated for $C_{19}H_{26}N_2O_3S \cdot 0.2H_2O$: C, 62.34; H, 7.27; N, 7.65. Found: C, 62.25; H, 7.32; N, 7.67.

Example 81E

N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carbothioamide The title compound was prepared from Example 81D according to the procedure described in Example 6C. MS, DCI, m/z 379 (M+H)$^+$.

Example 81F

N'-cyano-N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboximidamide The title compound was prepared from Example 81E according to the procedure described in Example 7. $^1$H NMR (300 MHz, DMSO-d$_6$) δ ppm 1.49-1.71 (m, 3H), 1.75-2.11 (m, 11H), 2.13-2.26 (m, 2H), 2.28-2.36 (m, 3H), 3.54-3.83 (m, 2H), 4.08-4.19 (m, 1H), 4.18-4.30 (m, 3H), 7.35-7.45 (m, 1H). MS, DCI, m/z 387 (M+H)$^+$.

Example 82

N'-cyano-N-[(2Z)-3-(2-methoxyethyl)-4,5-dimethyl-1,3-thiazol-2(3H)-ylidene]-2,2,3,3-tetramethylcyclopropanecarboximidamide

Example 82A 2,2,3,3-tetramethylcyclopropanecarbonyl chloride

To a solution of 2,2,3,3-tetramethylcyclopropanecarboxylic acid (0.50 g, 3.5 mmol) in 18 mL of methylene chloride at 0° C. was added oxalyl chloride (0.61 mL, 7.0 mmol) and a catalytic amount of dimethylformamide (2 drops). The solution was stirred at ambient temperature for 1 hour, and then concentrated under reduced pressure to provide 0.56 g of the title compound.

Example 82B 3-(2-Methoxyethyl)-4,5-dimethyl-3H-thiazol-2-ylideneamine hydrobromide A mixture of 4,5-dimethylthiazol-2-ylamine (9.0 g, 70 mmol) and 2-bromoethyl methyl ether (7.9 mL, 84 mmol) were heated at 85° C. for 12 hours. The mixture was cooled to ambient temperature and then triturated with isopropanol. The solid was collected by filtration and dried under vacuum to provide 10 g (56%) of the title compound. $^1$H NMR (DMSO-d$_6$, 300 MHz) δ ppm 2.17 (s, 3H), 2.19 (s, 3H), 3.25 (s, 3H) 3.56 (t, J=5.1 Hz, 2H) 4.16 (t, J=5.1 Hz, 2H) 9.41 (s, 1H).

Example 82C

N-[(2Z)-3-(2-methoxyethyl)-4,5-dimethyl-1,3-thiazol-2(3H)-ylidene]-2,2,3,3-tetramethylcyclopropanecarboxamide Example 82B and Example 82A were processed using the methods described in Example 80C to provide the title compound. $^1$H NMR (DMSO-d$_6$, 300 MHz) δ ppm 1.16 (s, 6H), 1.23 (s, 6H), 1.44 (s, 1H), 2.13 (s, 3H), 2.19 (s, 3H), 3.24 (s, 3H), 3.61 (t, J=5.4 Hz, 2H), 4.21 (t, J=5.4 Hz, 2H); MS (DCI/NH$_3$) m/z 311 (M+H)$^+$. Anal. Calculated for $C_{16}H_{26}N_2O_2S$: C, 61.92; H, 8.44; N, 9.02. Found: C, 61.89; H, 8.38; N, 8.81.

Example 82D (Z)-N-(3-(2-methoxyethyl)-4,5-dimethylthiazol-2(3H)-ylidene)-2,2,3,3-tetramethylcyclopropanecarbothioamide The title compound was prepared from Example 82C according to the procedure described in Example 6C. $^1$H NMR (300 MHz, DMSO-$d_6$) δ ppm 1.12-1.24 (m, 6H), 1.24-1.34 (m, 6H), 2.11-2.18 (m, 1H), 2.20-2.26 (m, 3H), 2.27-2.37 (m, 3H), 3.18-3.27 (m, 3H), 3.53-3.66 (m, 2H), 4.33-4.46 (m, 2H). MS, DCI, m/z 327 (M+H)$^+$.

Example 82E

N'-cyano-N-[(2Z)-3-(2-methoxyethyl)-4,5-dimethyl-1,3-thiazol-2(3H)-ylidene]-2,2,3,3-tetramethylcyclopropanecarboximidamide The title compound was prepared from Example 82D according to the procedure described in Example 7. $^1$H NMR (300 MHz, DMSO-$d_6$) δ ppm 1.13-1.33 (m, 12H), 1.55-1.78 (m, 1H), 2.18-2.32 (m, 6H), 3.16-3.25 (m, 3H), 3.49-3.62 (m, 2H), 4.20-4.38 (m, 2H). MS, DCI, m/z 335 (M+H)$^+$. Anal. calcd for $C_{17}H_{26}N_4OS$: C, 61.04; H, 7.83; N, 16.75. Found: C, 60.98; H, 4.82; N, 16.43.

Example 83

5-chloro-N-[(2Z)-5-chloro-3-(1,3-thiazol-4-ylmethyl)-1,3-thiazol-2(3H)-ylidene]-N'-cyano-2-methoxybenzenecarboximidamide

Example 83A

N-(5-chlorothiazol-2-yl)-5-chloro-2-methoxybenzamide

Commercially available 5-chlorothiazol-2-amine and Example 18B were processed using the method described for Example 74B to afford the title compound. MS (DCI) m/z 304 (M+H)$^+$.

Example 83B 5-chloro-N-[(2Z)-5-chloro-3-(1,3-thiazol-4-ylmethyl)-1,3-thiazol-2(3H)-ylidene]-2-methoxybenzamide A mixture of Example 83A (1001 mg, 3.33 mmol), commercially available 4-(chloromethyl)thiazole (574 mg, 3.33 mmol), potassium t-butoxide (354 mg, 3.33 mmol) and tetrabutylammonium iodide (492 mg, 1.33 mmol) in anhydrous toluene (30 mL)/dioxane (10 mL) was refluxed for 15 h. The mixture was then cooled to room temperature, washed with water, brine, dried with anhydrous MgSO$_4$ and concentrated under reduced pressure. The residue was purified by using an Analogix® Intelliflash280 ™ (SiO$_2$, 0-70% ethyl acetate in hexanes) to afford the title compound. 800 mg, 60% yield. $^1$H NMR (300 MHz, DMSO-$d_6$) δ ppm 3.79 (s, 3H), 5.54 (s, 2H), 7.13 (d, J=8.7 Hz, 1H), 7.49 (dd, J=8.7, 2.8 Hz, 1H), 7.70 (dd, J=16.3, 2.4 Hz, 2H), 7.91 (s, 1H), 9.10 (d, J=2.0 Hz, 1H). MS (DCI) m/z 401 (M+H)$^+$; Anal. Calculated for $C_{15}H_{11}Cl_2N_3O_2S_2$: C, 45.01; H, 2.77; N, 10.50. Found: C, 44.83; H, 2.71; N, 10.16.

Example 83C (Z)-N-(5-chloro-3-(thiazol-4-ylmethyl)thiazol-2(3H)-ylidene)-5-chloro-2-methoxybenzothioamide The title compound was prepared from Example 83B according to the procedure described in Example 6C. $^1$H NMR (300 MHz, DMSO-$d_6$) δ ppm 3.69 (s, 3H), 5.67 (s, 2H), 7.08 (d, J=8.8 Hz, 1H), 7.30-7.45 (m, 2H), 7.61 (d, J=1.7 Hz, 1H), 8.22 (s, 1H), 9.10 (d, J=2.0 Hz, 1H). MS, DCI, m/z 417 (M+H)$^+$.

Example 83D 5-chloro-N-[(2Z)-5-chloro-3-(1,3-thiazol-4-ylmethyl)-1,3-thiazol-2(3H)-ylidene]-N'-cyano-2-methoxybenzenecarboximidamide The title compound was prepared from Example 83C according to the procedure described in Example 7. $^1$H NMR (300 MHz, DMSO-$d_6$) δ ppm 3.82 (s, 3H), 5.59 (s, 2H), 7.15-7.31 (m, 2H), 7.54 (dd, J=8.7, 2.8 Hz, 1H), 7.67 (d, J=2.0 Hz, 1H), 8.13 (s, 1H), 9.11 (d, J=2.0 Hz, 1H). MS, DCI, m/z 425 (M+H)$^+$. Anal. calcd for $C_{16}H_{11}N_5OSCl$: C, 45.29; H, 2.61; N, 16.05. Found: C, 45.07; H, 2.61; N, 16.01.

Example 84

N-[(2Z)-5-bromo-3-(1,3-thiazol-4-ylmethyl)-1,3-thiazol-2(3H)-ylidene]-5-chloro-N'-cyano-2-methoxybenzenecarboximidamide

Example 84A

N-(5-bromothiazol-2-yl)-5-chloro-2-methoxybenzamide

Commercially available 5-bromothiazol-2-amine and Example 18B were processed using the method described for Example 74B to afford the title compound. MS (DCI) m/z 348 (M+H)$^+$.

Example 84B

N-[(2Z)-5-bromo-3-(1,3-thiazol-4-ylmethyl)-1,3-thiazol-2(3H)-ylidene]-5-chloro-2-methoxybenzamide A mixture of Example 84A (1001 mg, 3.33 mmol) and commercially available 4-(bromomethyl)thiazole were processed using the method described for Example 83B to afford the title compound (660 mg, 52% yield). $^1$H NMR (300 MHz, DMSO-$d_6$) δ ppm 3.78 (s, 3H), 5.54 (s, 2H), 7.12 (d, J=9.2 Hz, 1H), 7.49 (dd, J=8.8, 2.7 Hz, 1H), 7.69 (dd, J=15.9, 2.4 Hz, 2H), 7.93 (s, 1H), 9.10 (d, J=2.0 Hz, 1H) MS (DCI) m/z 445 (M+H); Anal. Calculated for $C_{15}H_{11}BrClN_3O_2S_2$: C, 40.51; H, 2.49; N, 9.45. Found: C, 40.85; H, 2.90; N, 9.62.

Example 84C (Z)-N-(5-bromo-3-(thiazol-4-ylmethyl)thiazol-2 (3H)-ylidene)-5-chloro-2-methoxybenzothioamide The title compound was prepared from Example 84B according to the procedure described in Example 6C. $^1$H NMR (300 MHz, DMSO-$d_6$) δ ppm 3.69 (s, 3H), 5.67 (s, 2H), 7.08 (d, J=8.7 Hz, 1H), 7.28-7.45 (m, 2H), 7.60 (d, J=1.6 Hz, 1H), 8.24 (s, 1H), 9.10 (d, J=2.0 Hz, 1H). MS, DCI, m/z 461 (M+H)$^+$. Anal. calcd for $C_{15}H_{11}N_3OS_2Br$: C, 39.10; H, 2.41; N, 9.12. Found: C, 40.08; H, 2.56; N, 8.62.

Example 84D

N-[(2Z)-5-bromo-3-(1,3-thiazol-4-ylmethyl)-1,3-thiazol-2(3H)-ylidene]-5-chloro-N'-cyano-2-methoxybenzenecarboximidamide The title compound was prepared from Example 84C according to the procedure described in Example 7. $^1$H NMR (300 MHz, DMSO-$d_6$) δ ppm 3.81 (s, 3H), 5.59 (s, 2H), 7.07-7.32 (m, 2H), 7.54 (dd, J=9.1, 2.8 Hz, 1H), 7.66 (d, J=2.0 Hz, 1H), 8.15 (s, 1H), 9.10 (d, J=2.0 Hz, 1H). MS, DCI, m/z 469 (M+H)$^+$. Anal. calcd for $C_{16}H_{11}N_5OS_2Br$: C, 40.99; H, 2.37; N, 14.94. Found: C, 41.19; H, 2.56; N, 14.57.

Example 85

N-[(2Z)-5-tert-butyl-3-(1,3-thiazol-4-ylmethyl)-1,3-thiazol-2(3H)-ylidene]-5-chloro-N'-cyano-2-methoxybenzenecarboximidamide

Example 85A

N-[(2Z)-5-tert-butyl-3-(1,3-thiazol-4-ylmethyl)-1,3-thiazol-2(3H)-ylidene]-5-chloro-2-methoxybenzamide To a solution of Example 74B (0.75 g, 2.31 mmol) in DMF/THF (1:4, 20 mL) were added potassium tert-butoxide (0.77 g, 6.93 mmol), tetrabutylammonium iodide (0.09, 0.23 mmol) and the commercially available HCl salt of 4-(chloromethyl)thiazole (TCI-US, 0.59 g, 3.46 mmol). The reaction mixture was stirred at 80° C. for 16 hours, cooled, diluted with ethyl acetate (20 mL) and quenched with saturated aqueous NaHCO$_3$ (20 mL). The aqueous layer was extracted with ethyl acetate (2×20 mL). The combined organic layers were washed with water (1×25 mL). The combined organic extracts were dried over anhydrous Na$_2$SO$_4$, filtered and concentrated under reduced pressure. The residue was purified by column chromatography using an Analogix® Intelliflash280™ (SiO$_2$, 0-100% ethyl acetate in hexanes) to afford the title compound. $^1$H NMR (300 MHz, dimethylsulfoxide-$d_6$) δ ppm 1.32 (s, 9H), 3.76 (s, 3H), 5.49 (s, 2H), 7.09 (d, J=9.2 Hz, 1H), 7.36 (s, 1H), 7.44 (dd, J=9.0, 2.9 Hz, 1H), 7.57 (d, J=2.0 Hz, 1H), 7.61 (d, J=3.1 Hz, 1H), 9.10 (d, J=2.0 Hz, 1H); MS (ESI$^+$) m/z 422 (M+H)$^+$; Anal. Calculated for $C_{19}H_{20}ClN_3O_2S_2$: C, 54.08; H, 4.78; N, 9.96. Found: C, 54.10; H, 4.62; N, 9.81.

Example 85B (Z)-N-(5-tert-butyl-3-(thiazol-4-ylmethyl)thiazol-2 (3H)-ylidene)-5-chloro-2-methoxybenzothioamide The title compound was prepared from Example 85A according to the procedure described in Example 6C. $^1$H NMR (300 MHz, DMSO-$d_6$) δ ppm 1.30-1.43 (m, 9H), 3.68 (s, 3H), 5.62 (s, 2H), 7.05 (d, J=8.7 Hz, 1H), 7.23-7.40 (m, 2H), 7.51 (d, J=2.0 Hz, 1H), 7.69 (s, 1H), 9.09 (d, J=2.0 Hz, 1H). MS, DCI, m/z 439 (M+H)$^+$. Anal. calcd for $C_{19}H_{20}N_3OS_3Cl$: C, 52.10; H, 4.60; N, 9.59. Found: C, 52.00; H, 4.98; N, 9.58.

Example 85C

N-[(2Z)-5-tert-butyl-3-(1,3-thiazol-4-ylmethyl)-1,3-thiazol-2(3H)-ylidene]-5-chloro-N'-cyano-2-methoxybenzenecarboximidamide The title compound was prepared from Example 85B according to the procedure described in Example 7. $^1$H NMR (300 MHz, DMSO-$d_6$) δ ppm 1.30-1.43 (m, 9H), 3.68 (s, 3H), 5.62 (s, 2H), 7.05 (d, J=8.7 Hz, 1H), 7.23-7.40 (m, 2H), 7.51 (d, J=2.0 Hz, 1H), 7.69 (s, 1H), 9.09 (d, J=2.0 Hz, 1H). MS, DCI, m/z 446 (M+H)$^+$. Anal. calcd for $C_{19}H_{20}N_3OS_3Cl$: C, 52.10; H, 4.60; N, 9.59. Found: C, 52.00; H, 4.98; N, 9.58.

Example 86

N-[(2Z)-5-tert-butyl-3-[(2R)-tetrahydrofuran-2-ylmethyl]-1,3-thiazol-2(3H)-ylidene]-5-chloro-N'-cyano-2-[(Z)-(methoxyimino)methyl]benzenecarboximidamide

Example 86A (1E,NZ)-N-(5-tert-butyl-3-(((R)-tetrahydrofuran-2-yl)methyl)thiazol-2(3H)-ylidene)-5-chloro-N'-cyano-2-formylbenzimidamide The title compound was prepared according to the procedure described in Example 44, replacing 2-formylphenylboronic acid with 5-chloro-2-formylphenylboronic acid.

Example 86B

N-[(2Z)-5-tert-butyl-3-[(2R)-tetrahydrofuran-2-ylmethyl]-1,3-thiazol-2(3H)-ylidene]-5-chloro-N'-cyano-2-[(Z)-(methoxyimino)methyl]benzenecarboximidamide A mixture of Example 86A (62 mg, 0.1 mmol) and O-methylhydroxylamine hydrochloride (7 mg, 0.1 mmol) in pyridine (7 mL) was stirred at ambient temperature for 8 h and then was concentrated under reduced pressure. The residue was dissolved in ethyl acetate and was washed with water, brine, dried with anhydrous MgSO$_4$ and concentrated under reduced pressure. The residue was chromatographed (EtOAc) to afford 33 mg of the title product. $^1$H NMR (300 MHz, DMSO-$d_6$) δ ppm 1.37 (s, 9H), 1.45-1.67 (m, 2H), 1.68-1.98 (m, 3H), 3.54-3.83 (m, 2H), 3.84 (s, 3H), 4.11-4.31 (m, 3H), 7.55 (s, 1H), 7.58-7.67 (m, 1H), 7.79-7.91 (m, 1H), 8.11 (s, 1H). MS, DCI, m/z 460 (M+H)$^+$. Anal. calcd for $C_{19}H_{20}N_3OS_3Cl$: C, 57.44; H, 5.70; N, 15.22. Found: C, 57.28; H, 5.52; N, 14.05.

Example 87

5-chloro-N'-cyano-N-[(2Z)-3-(cyclobutylmethyl)-1,3-thiazol-2(3H)-ylidene]-2-methoxybenzenecarboximidamide

Example 87A 3-(cyclobutylmethyl)thiazol-2(3H)-imine

A mixture of 2-aminothiazole (1.0 g, 10 mmol) and (bromomethyl)cyclobutane (1.1 mL, 10 mmol) was warmed to 85° C. and was allowed to stir for 18 h. The mixture was cooled to ambient temperature and the crude material was purified via column chromatography (SiO$_2$, 10% MeOH in EtOAc then 9:1:0.1 CH$_2$Cl$_2$:MeOH:NH$_4$OH) to provide the title compound (1.4 g, 8.0 mmol, 80% yield). MS (DCI/NH$_3$) m/z 169 (M+H)$^+$.

Example 87B (Z)-5-chloro-N-(3-(cyclobutylmethyl)thiazol-2(3H)-ylidene)-2-methoxybenzamide To a solution of the product of Example 87A (0.20 g, 1.2 mmol) in THF (15 mL) was added Et$_3$N (0.50 mL, 3.6 mmol) followed by the product of Example 18B (1.2 mmol). This mixture was warmed to 50° C. and was allowed to stir for 4 h. The mixture was cooled to ambient temperature, was quenched with saturated, aqueous NaHCO$_3$ (5 mL) and was diluted with EtOAc (10 mL). The layers were separated and the aqueous layer was extracted with EtOAc (3×5 mL). The combined organics were dried over anhydrous Na$_2$SO$_4$, filtered, concentrated under reduced pressure and purified via column chromatography (SiO$_2$, 50% hexanes/EtOAc) to provide the title compound (0.16 g, 0.48 mmol, 40% yield). MS (DCI/NH$_3$) m/z 337 (M+H)$^+$.

Example 87C (Z)-5-chloro-N-(3-(cyclobutylmethyl)thiazol-2(3H)-ylidene)-2-methoxybenzothioamide The title compound was prepared from Example 87B according to the procedure described in Example 6C. $^1$H NMR (300 MHz, DMSO-d$_6$) δ ppm 1.65-2.04 (m, 6H), 2.77-3.02 (m, 1H), 3.76 (s, 3H), 4.36 (d, J=7.5 Hz, 2H), 7.07 (d, J=8.5 Hz, 1H), 7.24-7.46 (m, 3H), 7.89 (d, J=4.7 Hz, 1H). MS, DCI, m/z 353 (M+H)$^+$.

Example 87D 5-chloro-N'-cyano-N-[(2Z)-3-(cyclobutylmethyl)-1,3-thiazol-2(3H)-ylidene]-2-methoxybenzenecarboximidamide The title compound was prepared from Example 87C according to the procedure described in Example 7. $^1$H NMR (300 MHz, DMSO-d$_6$) δ ppm 1.68-2.02 (m, 6H), 2.67-2.92 (m, 1H), 3.82 (s, 3H), 4.30 (d, J=7.5 Hz, 2H), 7.21 (d, J=9.2 Hz, 1H), 7.30-7.45 (m, 2H), 7.52 (dd, J=9.0, 2.9 Hz, 1H), 7.82 (d, J=4.4 Hz, 1H). MS, DCI, m/z 361 (M+H)$^+$. Anal. calcd for C$_{17}$H$_{17}$N$_4$OSCl: C, 56.58; H, 4.75; N, 15.53. Found: C, 56.37; H, 4.57; N, 15.17.

Example 88

N-[(2Z)-5-tert-butyl-3-[(2-methyl-1,3-thiazol-4-yl)methyl]-1,3-thiazol-2(3H)-ylidene]-5-chloro-N'-cyano-2-methoxybenzenecarboximidamide

Example 88A (Z)-N-(5-tert-butyl-3-((2-methylthiazol-4-yl)methyl)thiazol-2(3H)-ylidene)-5-chloro-2-methoxybenzamide To a solution of Example 74B (0.79 g, 2.43 mmol) in N,N-dimethylformamide (20 mL) was added sodium hydride (Aldrich, 98 mg, 2.43 mmol) and the reaction mixture was stirred for 15 min and 4-(chloromethyl)-2-methylthiazole (0.36 g, 2.43 mmol) was added. The reaction mixture was stirred at room temperature for 18 hr, poured into water (75 mL) and then extracted with EtOAc (75 mL). The organic layer was washed with water (2×75 mL), dried over anhydrous MgSO$_4$, filtered and concentrated under reduced pressure to provide the title compound. MS, DCI, m/z 436 (M+H)$^+$.

Example 88B (Z)-N-(5-tert-butyl-3-((2-methylthiazol-4-yl)methyl)thiazol-2(3H)-ylidene)-5-chloro-2-methoxybenzothioamide The title compound was prepared from Example 88A according to the procedure described in Example 6C. $^1$H NMR (300 MHz, DMSO-d$_6$) δ ppm 1.29-1.44 (m, 9H), 2.58-2.68 (m, 3H), 3.69 (s, 3H), 5.52 (s, 2H), 7.05 (d, J=8.8 Hz, 1H), 7.24 (s, 1H), 7.28-7.39 (m, 2H), 7.67 (s, 1H). MS, DCI, m/z 453 (M+H)$^+$.

Example 88C

N-[(2Z)-5-tert-butyl-3-[(2-methyl-1,3-thiazol-4-yl)methyl]-1,3-thiazol-2(3H)-ylidene]-5-chloro-N'-cyano-2-methoxybenzenecarboximidamide The title compound was prepared from Example 88B according to the procedure described in Example 7. $^1$H NMR (300 MHz, DMSO-d$_6$) δ ppm 1.32-1.42 (m, 9H), 2.59-2.66 (m, 3H), 3.81 (s, 3H), 5.45 (s, 2H), 7.20 (d, J=9.2 Hz, 1H), 7.23-7.35 (m, 2H), 7.52 (dd, J=8.8, 2.7 Hz, 1H), 7.64 (s, 1H). MS, DCI, m/z 461 (M+H)$^+$. Anal. calcd for C$_{21}$H$_{22}$N$_5$OS$_2$Cl: C, 54.83; H, 4.82; N, 15.22. Found: C, 56.37; H, 4.57; N, 15.17.

Example 89

5-chloro-N'-cyano-N-[(2Z)-1-isobutyl-4,4-dimethyl-1,4,6,7-tetrahydro-2H-pyrano[4,3-d][1,3]thiazol-2-ylidene]-2-methoxybenzenecarboximidamide

Example 89A ethyl 2-(2-(tert-butoxycarbonylamino)thiazol-4-yl)acetate

The title compound was obtained from commercially available ethyl 2-(2-aminothiazol-4-yl)acetate (Aldrich) as per the procedure described in JP 06345736. The crude product was used in the next step without purification. MS (ESI+) m/z 287 (M+H)+

Example 89B tert-butyl 4-(2-hydroxyethyl)thiazol-2-ylcarbamate

To a cooled solution of the crude product of Example 89A in THF (100 mL) was added lithium borohydride (100 mL, 2M solution in THF) at 0° C. The reaction mixture was refluxed for overnight, then cooled on ice bath, quenched with water and extracted with ethyl acetate (3×100 mL). The combined organic extracts were dried ($Na_2SO_4$), filtered and concentrated. The residue was purified by column chromatography ($SiO_2$, 0-5% methanol in dichloromethane to afford 6.3 g (26%) of the title compound. MS (ESI+) m/z 245 (M+H)+

Example 89C tert-butyl 4-(2-(tetrahydro-2H-pyran-2-yloxy)ethyl)thiazol-2-ylcarbamate To a solution of Example 89B (6.3 g, 27.4 mmol) in dichloromethane (100 mL) were added commercially available 3,4-dihydro-2H-pyran (Aldrich) (21 g, 250 mmol) and pyridinium-p-toluenesulfonic acid (Aldrich) (3.5 g, 14.0 mmol). The reaction mixture was stirred for overnight at room temperature and then diluted with dichloromethane, washed with water, dried ($Na_2SO_4$), filtered and concentrated. The residue was purified by column chromatography ($SiO_2$, 0-100% ethyl acetate in hexanes) to afford 7.4 g (82%) of the title compound. MS (ESI+) m/z 329 (M+H)+

Example 89D tert-butyl 5-(2-hydroxypropan-2-yl)-4-(2-(tetrahydro-2H-pyran-2-yloxy)ethyl)thiazol-2-ylcarbamate To a solution of diisopropylamine (9.5 mL, 67.2 mmol) in THF (100 ml) was added butyllithium (42 mL, 1.6M in hexanes, 67.2 mmol) drop wise at −78° C. and stirred for 30 min. Thus obtained LDA solution was immediately added by cannulation to a solution of Example 89C (7.36 g, 22.4 mmol) in THF (100 ml) at −78° C. and stirred for 30 min at the same temperature. Then, dry acetone (8.2 ml, 112 mmol, Acros) was added slowly and the reaction mixture was removed from cold bath and allowed to reach room temperature for overnight while stirring. The reaction mixture was quenched with saturated aqueous $NH_4Cl$ solution (100 mL) and the aqueous layer was extracted with ethyl acetate (3×100 mL). The combined organic extracts were dried ($Na_2SO_4$), filtered and concentrated. The residue was purified by column chromatography ($SiO_2$, 0-100% ethyl acetate in hexanes) to afford 4.6 g (53%) of the title compound. MS (ESI+) m/z 387 (M+H)+

Example 89E 4,4-dimethyl-6,7-dihydro-4H-pyrano[4,3-d]thiazol-2-amine

To a solution of Example 89D (4.6 g, 11 mmol) in THF (90 mL) was added conc. HCl (6.9 mL). The reaction mixture was refluxed for overnight and then cooled. The mixture was basified with 5N NaOH ((17 mL) and extracted with ethyl acetate (3×50 mL). The combined organic extracts were dried ($Na_2SO_4$), filtered and concentrated. The residue was purified by column chromatography ($SiO_2$, 0-10% methanol in dichloromethane) to afford 1.04 g (51%) of the title compound. MS (ESI+) m/z 185 (M+H)+

Example 89F 5-chloro-N-(4,4-dimethyl-6,7-dihydro-4H-pyrano[4,3-d]thiazol-2-yl)-2-methoxybenzamide To a solution of Example 89E (1.0 g, 5.6 mmol) in THF (30 mL) were added 5-chloro-2-methoxy-benzoic acid (1.86 g, 10.0 mmol, Aldrich), N-(3-dimethylaminopropyl)-N-ethylcarbodiimide hydrochloride (1.91 g, 10.0 mmol, Aldrich), 1-hydroxybenzotriazole (1.35 g, 10.0 mmol) and triethylamine (3.5 mL, 3.5 mmol, Aldrich). The mixture was stirred overnight at room temperature. The reaction mixture was then diluted with 1 M aqueous $NaHCO_3$ (20 mL) and the aqueous layer was extracted with ethyl acetate (2×30 mL). The combined organic extracts were dried ($Na_2SO_4$), filtered and concentrated. The residue was purified by column chromatography ($SiO_2$, 0-5% methanol in dichloromethane to afford 1.55 g (78%) of the title compound. MS (ESI+) m/z 353 (M+H)+

Example 89G (Z)-5-chloro-N-(1-isobutyl-4,4-dimethyl-6,7-dihydro-1H-pyrano[4,3-d]thiazol-2(4H)-ylidene)-2-methoxybenzamide To a solution of Example 89F (1.0 g, 2.8 mmol) in DMF/THF (1:4, 20 mL) were added potassium tert-butoxide (0.35 g, 3.1 mmol, Aldrich), 1-bromo-2-methylpropane (0.43 g, 3.1 mmol, Aldrich) and tetrabutylammonium iodide (0.1 g, 0.3 mmol, Aldrich). The reaction mixture was stirred at 80° C. for 16 h, cooled to room temperature, quenched with saturated aqueous $NaHCO_3$ (20 mL). The aqueous layer was extracted with ethyl acetate (3×20 mL). The combined organic extracts were dried over anhydrous ($Na_2SO_4$), filtered and concentrated under reduced pressure. The residue was purified by column chromatography using an Analogix® Intelliflash280 ™ ($SiO_2$, 0-1% methanol in dichloromethane) to afford 90 mg (29%) of the title compound. MS (ESI+) m/z 409 (M+H)+

Example 89H (Z)-5-chloro-N-(1-isobutyl-4,4-dimethyl-6,7-dihydro-1H-pyrano[4,3-d]thiazol-2(4H)-ylidene)-2-methoxybenzothioamide To a solution of Example 89G (0.25 g, 0.61 mmol) in toluene (10 mL) was added Lawesson's Reagent (0.25 g, 0.61 mmol, Aldrich) and stirred at 80° C. for 2 hr. The reaction mixture was then cooled and concentrated. The residue was purified by column chromatography using an Analogix® Intelliflash280 ™ ($SiO_2$, 0-50% ethyl acetate in hexanes) to afford 0.18 g (70%) of the title compound. MS (ESI+) m/z 425 (M+H)+

Example 89I 5-chloro-N'-cyano-N-[(2Z)-1-isobutyl-4,4-dimethyl-1,4,6,7-tetrahydro-2H-pyrano[4,3-d][1,3]thiazol-2-ylidene]-2-methoxybenzenecarboximidamide To a solution of Example 89H (0.18 g, 0.42 mmol) in acetonitrile (10 mL) were added mercuric acetate (0.18 g, 0.55 mmol, Aldrich), triethylamine (0.18 mL, 1.27 mmol)

and cyanamide (0.04 g, 0.85 mmol, Aldrich). After stirring at 80° C. for 16 hr, the reaction mixture was cooled and quenched with saturated NaHCO$_3$ (20 mL). The aqueous layer was extracted with ethyl acetate (3×20 mL). The combined the organic extracts were washed with water (1×25 mL), dried (Na$_2$SO$_4$), filtered and concentrated. The residue was purified by column chromatography using an Analogix® Intelliflash280™ (SiO$_2$, 0-50% ethyl acetate in hexanes) and followed by crystallization from ethyl acetate/hexanes to afford 0.04 g (21%) of the title compound. $^1$H NMR (300 MHz, DMSO-d$_6$) δ ppm 0.86 (d, J=6.8 Hz, 6H), 1.51 (s, 6H), 2.06-2.35 (m, 1H), 2.66-2.87 (m, 2H), 3.81 (s, 3H), 3.94-4.14 (m, 4H), 7.21 (d, J=9.2 Hz, 1H), 7.33 (d, J=2.4 Hz, 1H), 7.52 (dd, J=9.2, 2.7 Hz, 1H); MS (ESI$^+$) m/z 433 (M+H)$^+$; Anal. Calculated C$_{21}$H$_{25}$ClN$_4$O$_2$S: C, 58.25; H, 5.82; N, 12.94. Found: C, 58.30; H, 5.79; N, 12.64.

Example 90

N-[(2Z)-3-butyl-7,7-dimethyl-6,7-dihydro-4H-pyrano[3,4-d][1,3]thiazol-2(3H)-ylidene]-5-chloro-N'-cyano-2-methoxybenzenecarboximidamide Example 90A (Z)-N-(3-butyl-7-oxo-3,4,6,7-tetrahydro-2H-pyrano[3,4-d]thiazol-2-ylidene)-5-chloro-2-methoxybenzamide To a mixture of sodium 5-oxo-5,6-dihydro-2H-pyran-3-olate (Li, Wenke; Wayne, Gregory S.; Lallaman, John E.; Wittenberger, Steven J. J. Org. Chem. (2006), 71, 1725-1727) (1.36 g, 10 mmol) and n-butylthiourea (Trans World) (1.32 g, 10 mmol) in tetrahydrofuran (15 mL) was added a mixture of DMSO/12 N HCl (1/1 molar ratio, 4.6 mL, 30 mmol). The reaction mixture was heated at 40° C. for overnight, and then cooled. The mixture was diluted with ethyl acetate and washed with aqueous sodium bicarbonate. The organic extract was dried (MgSO$_4$), filtered and concentrated. The residue was dried under vacuum for 12 h and dissolved in tetrahydrofuran (40 mL). To the solution was added 5-chloro-2-methoxy-benzoic acid (1.86 g, 10.0 mmol), N-(3-dimethylaminopropyl)-N-ethylcarbodimide hydrochloride (1.91 g, 10.0 mmol), 1-hydroxybenzotriazole (1.35 g, 10.0 mmol) and triethylamine (3.5 mL, 3.5 mmol). The mixture was stirred overnight at 80° C. and then cooled at room temperature. The mixture was diluted with ethyl acetate, washed with 1 M aqueous NaHCO$_3$, dried (Na$_2$SO$_4$), filtered and concentrated. The residue was purified by flash chromatography (SiO$_2$, 0-75% ethyl acetate in hexanes) to afford 412 mg of the title compound. MS (ESI$^+$) m/z 395 (M+H)$^+$ Example 90B (Z)-N-(3-butyl-7,7-dimethyl-3,4,6,7-tetrahydro-2H-pyrano[3,4-d]thiazol-2-ylidene)-5-chloro-2-methoxybenzamide To a solution of TiCl$_4$ (0.62 mL of 1M in dichloromethane, 0.62 mmol, Aldrich) in dichloromethane (4 mL) was added dimethylzinc (0.31 mL of 2M in toluene, 0.62 mmol, Aldrich) drop wise at −30° C. and stirred for 10 minutes at the same temperature. Then, a solution of Example 90A (82 mg, 0.21 mmol) in dichloromethane (2 mL) was added drop wise to the reaction mixture and the reaction was allowed reach room temperature slowly for overnight. The reaction mixture was then quenched with 5 mL of 2% NH$_4$OH aqueous solution, filtered through celite and washed with ethyl acetate (3×10 mL). To the filtrate 10 mL of saturated NaHCO$_3$ was added and layers were separated. The aqueous layer was extracted with ethyl acetate (15 mL). The combined organic extracts were dried (Na$_2$SO$_4$), filtered and concentrated. The residue was purified by column chromatography (SiO$_2$, 0-100% ethyl acetate in hexanes) to afford 52 mg (60%) of the title compound. MS (ESI$^+$) m/z 409 (M+H)$^+$ Example 90C (Z)-N-(3-butyl-7,7-dimethyl-3,4,6,7-tetrahydro-2H-pyrano[3,4-d]thiazol-2-ylidene)-5-chloro-2-methoxybenzothioamide Example 90B and Lawesson's reagent were processed as described for Example 89H to obtain the title compound. MS (ESI$^+$) m/z 425 (M+H)$^+$ Example 90D N-[(2Z)-3-butyl-7,7-dimethyl-6,7-dihydro-4H-pyrano[3,4-d][1,3]thiazol-2(3H)-ylidene]-5-chloro-N'-cyano-2-methoxybenzenecarboximidamide Example 90C, triethylamine, cyanamide and mercuric acetate were processed as described for example 89I to obtain the title compound. $^1$H NMR (300 MHz, DMSO-d$_6$) δ ppm 0.87 (t, J=7.3 Hz, 3H), 1.18-1.40 (m, 2H), 1.28 (s, 6H), 1.53-1.74 (m, 2H), 3.63 (s, 2H), 3.82 (s, 3H), 4.06 (t, J=7.3 Hz, 2H), 4.75 (s, 2H), 7.21 (d, J=8.8 Hz, 1H), 7.37 (d, J=2.7 Hz, 1H), 7.52 (dd, J=8.8, 2.7 Hz, 1H); MS (ESI$^+$) m/z 433 (M+H)$^+$; Anal. Calculated C$_{21}$H$_{25}$ClN$_4$O$_2$S: C, 58.25; H, 5.82; N, 12.94. Found: C, 58.31; H, 5.89; N, 12.80.

Example 91

5-chloro-N'-cyano-N-[(2Z)-3-isobutyl-4,4,6,6-tetramethyl-4,6-dihydrofuro[3,4-d][1,3]thiazol-2(3H)-ylidene]-2-methoxybenzenecarboximidamide Example 91A 3-isobutyl-4,4,6,6-tetramethyl-4,6-dihydrofuro[3,4-d]thiazol-2(3H)-imine To a solution of 2,2,5,5-tetramethyldihydrofuran-3(2H)-one (2.0 g, 14.1 mmol, Aldrich) in acetonitrile (10 mL) were added molecular sieves (2.0 g) and 2-methylpropan-1-amine (1.0 mL, 12.8 mmol, Aldrich). The reaction mixture was stirred at 60° C. for 48 hr and then filtered through celite. To the filtrate were added potassium thiocyanate (1.65 g, 17.0 mmol, Aldrich). The reaction mixture was stirred at 60° C. until the solids were dissolved and then iodine (6.5 g, 25.6 mmol, EMD chemicals) was added. The reaction mixture was stirred 60° C. for 48 hr, cooled, concentrated and dissolved in ethyl acetate (15 mL). The solution was washed with sodium metabisulfite 20% (35 mL) by mixing the layers for 30 min. The organic layer was washed twice with HCl 1N (35 mL). The aqueous layers (sodium metabisulfite and HCl) were combined and the pH was adjusted to pH 9 by adding NH$_4$OH and then extracted with ethyl acetate (4×40 mL). The combined organic extracts were dried (Na$_2$SO$_4$), filtered and concentrated to obtain the crude product (0.75 g) of the title compound. MS (ESI$^+$) m/z 255 (M+H)$^+$

Example 91B (Z)-5-chloro-N-(3-isobutyl-4,4,6,6-tetramethylfuro[3,4-d]thiazol-2(3H,4H,6H)-ylidene)-2-methoxybenzamide Example 91A, 5-chloro-2-methoxy-benzoic acid, N-(3-dimethylaminopropyl)-N-ethylcarbodimide hydrochloride, 1-hydroxybenzotriazole and triethylamine were processed as described for Example 89F to obtain the title compound. MS (ESI$^+$) m/z 423 (M+H)$^+$

Example 91C (Z)-5-chloro-N-(3-isobutyl-4,4,6,6-tetramethylfuro[3,4-d]thiazol-2(3H,4H,6H)-ylidene)-2-methoxybenzothioamide Example 91B and Lawesson's reagent were processed as described for Example 89H to obtain the title compound. LC/MS (ESI$^+$) m/z 439 (M+H)$^+$

Example 91D 5-chloro-N'-cyano-N-[(2Z)-3-isobutyl-4,4,6,6-tetramethyl-4,6-dihydrofuro[3,4-d][1,3]thiazol-2(3H)-ylidene]-2-methoxybenzenecarboximidamide Example 91C, triethylamine, cyanamide and mercuric acetate were processed as described for Example 89I to obtain the title compound. $^1$H NMR (300 MHz, DMSO-d$_6$) δ ppm 0.89 (d, J=6.8 Hz, 6H), 1.53 (s, 6H), 1.57 (s, 6H), 2.36-2.47 (m, 1H), 3.82 (s, 3H), 3.95 (d, J=7.5 Hz, 2H), 7.22 (d, J=9.2 Hz, 1H), 7.36 (d, J=2.7 Hz, 1H), 7.53 (dd, J=8.8, 2.7 Hz, 1H); MS (ESI$^+$) m/z 449 (M+H)$^+$; Anal. Calculated C$_{22}$H$_{27}$ClN$_4$O$_2$S.0.1CH$_2$Cl$_2$: C, 58.28; H, 6.02; N, 12.30. Found: C, 58.20; H, 6.02; N, 6.92

Example 92

5-chloro-N'-cyano-N-[(2Z)-3-(cyclobutylmethyl)-4,4,6,6-tetramethyl-4,6-dihydrofuro[3,4-d][1,3]thiazol-2(3H)-ylidene]-2-methoxybenzenecarboximidamide

Example 92A 3-(cyclobutylmethyl)-4,4,6,6-tetramethyl-4,6-dihydrofuro[3,4-d]thiazol-2(3H)-imine Commercially available 2,2,5,5-tetramethyldihydrofuran-3(2H)-one (Aldrich), triethylamine, cyclobutylmethanamine hydrochloride (prepared from cyclobutanecarbonitrile as described in WO2005075464), potassium thiocyanate (Aldrich) and iodine (EMD chemicals) were processed using the method described in Example 91A to afford the title compound. MS (ESI$^+$) m/z 267 (M+H)$^+$

Example 92B (Z)-5-chloro-N-(3-(cyclobutylmethyl)-4,4,6,6-tetramethylfuro[3,4-d]thiazol-2(3H,4H,6H)-ylidene)-2-methoxybenzamide Example 92A, 5-chloro-2-methoxy-benzoic acid, N-(3-dimethylaminopropyl)-N-ethylcarbodimide hydrochloride, 1-hydroxybenzotriazole and triethylamine were processed as described for Example 89F to obtain the title compound. MS (ESI$^+$) m/z 435 (M+H)$^+$

Example 92C (Z)-5-chloro-N-(3-(cyclobutylmethyl)-4,4,6,6-tetramethylfuro[3,4-d]thiazol-2(3H,4H,6H)-ylidene)-2-methoxybenzothioamide Example 92B and Lawesson's reagent were processed as described for Example 89H to obtain the title compound. $^1$H NMR (300 MHz, DMSO-d$_6$) δ ppm 1.52 (s, 6H), 1.60 (s, 6H), 1.68-1.81 (m, 2H), 1.81-1.98 (m, 4H), 3.78 (s, 3H), 3.79-3.83 (m, 1H), 4.21 (d, J=6.7 Hz, 2H), 7.09 (d, J=8.7 Hz, 1H), 7.32-7.40 (m, 2H).

Example 92D 5-chloro-N'-cyano-N-[(2Z)-3-(cyclobutylmethyl)-4,4,6,6-tetramethyl-4,6-dihydrofuro[3,4-d][1,3]thiazol-2(3H)-ylidene]-2-methoxybenzenecarboximidamide Example 92C, triethylamine, cyanamide and mercuric acetate were processed as described for Example 89I to obtain the title compound. $^1$H NMR (300 MHz, DMSO-d$_6$) δ ppm 1.52 (s, 6H), 1.56 (s, 6H), 1.65-1.82 (m, 2H), 1.82-2.03 (m, 4H), 2.72-2.87 (m, 1H), 3.82 (s, 3H), 4.17 (d, J=6.8 Hz, 2H), 7.22 (d, J=8.8 Hz, 1H), 7.36 (d, J=2.7 Hz, 1H), 7.53 (dd, J=9.2, 2.7 Hz, 1H); MS (ESI$^+$) m/z 459 (M+H)$^+$; Anal. Calculated C$_{23}$H$_{27}$ClN$_4$O$_2$S: C, 60.18; H, 5.93; N, 12.21. Found: C, 60.20; H, 5.80; N, 12.12

Example 93

5-chloro-N'-cyano-N-[(2Z)-5-cyclohexyl-3-(2-methoxyethyl)-1,3-thiazol-2(3H)-ylidene]-2-methoxybenzenecarboximidamide

Example 93A 2-cyclohexylacetaldehyde

The title compound was prepared from 2-cyclohexylethanol according to the procedure as described Tetrahedron Letters (1995), 36(17), 3019-22. $^1$H NMR (300 MHz, chloroform-d) δ ppm 0.87-1.08 (m, 2H), 1.13-1.41 (m, 3H), 1.61-1.80 (m, 5H), 1.81-1.99 (m, 1H), 2.29 (dd, J=6.8, 2.4 Hz, 2H), 9.76 (t, J=2.4 Hz, 1H).

Example 93B 5-cyclohexylthiazol-2-amine

To a solution of Example 93A (1.8 g, 16.0 mmol) in cyclohexanone (50 mL) were added pyrrolidine (1.4 mL, 17.0 mmol) and p-toluenesulfonic acid monohydrate (0.01 g). The reaction mixture was refluxed for 4 hr under Dean-Stark conditions, cooled and concentrated. The residue was dissolved in methanol (30 mL) and then sulfur (0.57 g, 16 mmol) was added. To the above mixture was added a solution of cyanamide (0.67 g, 16 mmol) in methanol (10 mL) at 0° C. The reaction mixture was stirred at room temperature for overnight, filtered, concentrated and purified by column chromatography (SiO$_2$, 0-100% ethyl acetate in hexanes) to afford 0.5 g (20%) of the title compound. MS (ESI$^+$) m/z 183 (M+H)$^+$.

Example 93C 5-cyclohexyl-3-(2-methoxyethyl)thiazol-2(3H)-imine hydrobromide

To Example 93B (0.5 g, 2.7 mmol) was added 1-bromo-2-methoxyethane (0.52 mL, 5.5 mmol) and heated at 85° C. for overnight. The reaction mixture was triturated in diethyl ether to afford 0.65 g (74%) of the title compound. MS (ESI$^+$) m/z 241 (M+H)$^+$.

Example 93D

Ethyl 5-chloro-2-methoxybenzimidate hydrochloride

A cooled solution of 5-chloro-2-methoxybenzonitrile (9.3 g, 0.056 mol, Maybridge) and ethanol (16.2 mL, 0.28 mol) in CH$_2$Cl$_2$ (40 mL) was bubbled with HCl gas at 0° C. for 30 min. The reaction mixture was kept in refrigerator for 5 days. The reaction mixture was then concentrated and triturated with diethyl ether to remove unreacted starting material. The precipitate was dried under reduced pressure to obtain 7.1 g (51%) of the title compound. MS (ESI$^+$) m/z 214 (M+H)$^+$.

Example 93E ethyl 5-chloro-N-cyano-2-methoxybenzimidate

A solution of ethyl 5-chloro-2-methoxybenzimidate (1.3 g, 6.2 mmol, obtained after aqueous bicarbonate wash of Example 93D) in acetonitrile (2 mL) was added to a solution of sodium phosphate monobasic monohydrate (3.4 g, 24.7 mmol), sodium phosphate dibasic heptahydrate (3.3 g, 12.4 mmol) and cyanamide (0.52 g, 12.4 mmol) in water (20 mL). The reaction mixture was stirred at room temperature for overnight and then extracted with CH$_2$Cl$_2$ (3×15 mL). The combined organic extracts were dried (Na$_2$SO$_4$), filtered and concentrated. The residue contained about 30% of starting material. The residue was reprocessed with half the amounts of the reagents to drive the reaction to completion and that yielded 1.32 g (90%) of the title compound. MS (ESI$^+$) m/z 239 (M+H)$^+$.

Example 93F 5-chloro-N'-cyano-N-[(2Z)-5-cyclohexyl-3-(2-methoxyethyl)-1,3-thiazol-2(3H)-ylidene]-2-methoxybenzenecarboximidamide A mixture of 5-cyclohexyl-3-(2-methoxyethyl)thiazol-2 (3H)-imine (120 mg, 0.5 mmol, obtained after aqueous bicarbonate wash of Example 93C) and Example 93E (119 mg, 0.5 mmol) was heated in a 20 mL scintillation vial at 100° C. for 16 hr. The residue was purified by column chromatography using an Analogix® Intelliflash280 ™ (SiO$_2$, 0-50% ethyl acetate in hexanes) to obtain 35 mg (17%) of the title compound. $^1$H NMR (300 MHz, DMSO-d$_6$) δ ppm 1.19-1.34 (m, 2H), 1.33-1.50 (m, 3H), 1.60-1.88 (m, 3H), 1.90-2.03 (m, 2H), 2.74-2.92 (m, 1H), 3.24 (s, 3H), 3.68 (t, J=5.3 Hz, 2H), 3.82 (s, 3H), 4.37 (t, J=5.3 Hz, 2H), 7.20 (d, J=9.2 Hz, 1H), 7.37 (d, J=2.7 Hz, 1H), 7.47-7.55 (m, 1H), 7.50 (s, 1H); MS (ESI$^+$) m/z 433 (M+H)$^+$; Anal. Calculated C$_{21}$H$_{25}$ClN$_4$O$_2$S: C, 58.25; H, 5.82; N, 12.94. Found: C, 58.32; H, 5.67; N, 12.67.

Example 94

5-chloro-N'-cyano-N-[(2Z)-1-isobutyl-1,4,6,7-tetrahydro-2H-pyrano[4,3-d][1,3]thiazol-2-ylidene]-2-methoxybenzenecarboximidamide Example 94A 1-isobutyl-6,7-dihydro-1H-pyrano[4,3-d]thiazol-2 (4H)-imine Commercially available dihydro-2H-pyran-4(3H)-one (Aldrich), 2-methylpropan-1-amine (Aldrich), potassium thiocyanate (Aldrich) and iodine (EMD chemicals) were processed using the method described in Example 91A to afford the title compound. MS (ESI$^+$) m/z 213 (M+H)$^+$.

Example 94B 5-chloro-N'-cyano-N-[(2Z)-1-isobutyl-1,4,6,7-tetrahydro-2H-pyrano[4,3-d][1,3]thiazol-2-ylidene]-2-methoxybenzenecarboximidamide A mixture of Example 94A (140 mg, 0.66 mmol) and Example 93E (105 mg, 0.44 mmol) in ethanol (1 mL) was heated in a 20 mL scintillation vial at 80° C. for 16 hr. The residue was purified by column chromatography using an Analogix® Intelliflash280 ™ (SiO$_2$, 0-100% ethyl acetate in hexanes) to afford 80 mg (50%) of the title compound. $^1$H NMR (300 MHz, DMSO-d$_6$) δ ppm 0.87 (d, J=6.4 Hz, 6H), 2.11-2.27 (m, 1H), 2.79 (t, J=5.3 Hz, 2H), 3.81 (s, 3H), 3.93-4.01 (m, 2H), 4.01 (d, J=6.8 Hz, 2H), 4.67 (s, 2H), 7.21 (d, J=9.2 Hz, 1H), 7.34 (d, J=2.7 Hz, 1H), 7.52 (dd, J=8.8, 2.7 Hz, 1H); MS (ESI$^+$) m/z 405 (M+H)$^+$; Anal. Calculated C$_{19}$H$_{21}$ClN$_4$O$_2$S.0.1C$_4$H$_8$O$_2$: C, 56.32; H, 5.31; N, 13.54. Found: C, 55.98; H, 5.04; N, 13.28.

Example 95

N-[(2Z)-3-butyl-4-tert-butyl-1,3-thiazol-2(3H)-ylidene]-5-chloro-N'-cyano-2-methoxybenzenecarboximidamide Example 95A 4-tert-butyl-3-butylthiazol-2(3H)-imine To a solution of 3,3-dimethylbutan-2-one (Aldrich) (3.35 g, 33.4 mmol) in acetonitrile (30 mL) was added 4 g of molecular sieves (4A beads, 8-12 mesh) and 2,2-butan-1-amine (Aldrich) (2.00 g, 27.3 mmol). The mixture was stirred for 12 h at room temperature. The mixture was filtered and to the filtrate was added potassium thiocyanate (3.93 g, 40.4 mmol). The temperature was adjusted at 50° C. and the mixture was stirred until all solids were dissolved then iodine (15.4 g, 60.8 mmol) was added. The reaction was stirred at 50° C. for 12 h. The reaction mixture was cooled to room temperature and diluted with ethyl acetate. The solution was washed with a solution of sodium metabisulfate. The aqueous layers was brought to pH=9 by adding NaOH (25%) and extracted with ethyl acetate. The Organic extracts were combined, dried over sodium sulfate and concentrated under reduced pressure. The residue was purified by flash chromatography on $SiO_2$ (hexanes-ethyl acetate, 50%, then dichloromethane-methaol, 10%) to afford the title compound. MS (ESI$^+$) m/z 213 (M+H)$^+$.

Example 95B (Z)-N-(4-tert-butyl-3-butylthiazol-2(3H)-ylidene)-5-chloro-2-methoxybenzamide Example 95A, triethylamine, dimethylaminopyridine, and example 16B were processed as described for example 17C to obtain the title compound. MS (ESI$^+$) m/z 381 (M+H)$^+$.

Example 95C (Z)-N-(4-tert-butyl-3-butylthiazol-2(3H)-ylidene)-5-chloro-2-methoxybenzothioamide Example 95B and Lawesson's reagent were processed as described for Example 89H to obtain the title compound. LC/MS (ESI$^+$) m/z 397 (M+H)$^+$.

Example 95D

N-[(2Z)-3-butyl-4-tert-butyl-1,3-thiazol-2(3H)-ylidene]-5-chloro-N'-cyano-2-methoxybenzenecarboximidamide Example 95C, triethylamine, cyanamide and mercuric acetate were processed as described for Example 89I to obtain the title compound. $^1$H NMR (300 MHz, DMSO-d$_6$) δ ppm 0.70-1.03 (m, 3H), 1.30-1.39 (m, 2H), 1.41 (s, 9H), 1.81 (dd, 2H), 3.83 (s, 3H), 4.17-4.56 (m, 2H), 7.07 (s, 1H), 7.21 (d, J=9.1 Hz, 1H), 7.41 (d, J=2.8 Hz, 1H), 7.52 (dd, J=8.7, 2.8 Hz, 1H); MS (ESI$^+$) m/z 405 (M+H)$^+$; Anal. Calculated $C_{20}H_{25}ClN_4OS$: C, 59.32; H, 6.22; N, 13.84. Found: C, 59.31; H, 6.17; N, 13.63.

Example 96

N-[(2Z)-3-butyl-6,7-dihydro-4H-pyrano[3,4-d][1,3]thiazol-2(3H)-ylidene]-5-chloro-N'-cyano-2-methoxybenzenecarboximidamide

Example 96A 6,7-dihydro-4H-pyrano[3,4-d]thiazol-2-amine

To a solution of lithium diisopropylamide (2.5 mL, 5.0 mmol, 2M in THF, Aldrich) in THF (20 mL) was added drop wise dihydro-2H-pyran-3(4H)-one (0.5 g, 5 mmol, Small Molecules Inc) in THF (2 mL) at −78° C. The reaction mixture was stirred at −45° C. for 2 hr and then cannulated to a solution of sulfur (0.16 g, 5.0 mmol) in THF (20 mL) at −45° C. The reaction mixture was warmed to 0° C. and a solution of cyanamide (0.42 g, 10.0 mmol) in THF (2 mL) was added. After stirring for overnight, the reaction mixture was quenched with saturated NaHCO$_3$ (10 mL). The aqueous layer was extracted with ethyl acetate (3×20 mL). The combined organic extracts were dried (Na$_2$SO$_4$), filtered and concentrated. The residue was purified by column chromatography using an Analogix® Intelliflash280 ™ (SiO$_2$, 0-5% methanol in dichloromethane) to afford 0.1 g (10%) of the title compound. MS (ESI$^+$) m/z 157 (M+H)$^+$.

Example 96B 3-butyl-3,4,6,7-tetrahydro-2H-pyrano[3,4-d]thiazol-2-imine

A mixture of Example 96A (290 mg, 1.86 mmol) and 1-bromobutane (220 µL, 2.0 mmol) in DMF (400 µL) was heated at 95° C. for 16 hr, cooled to room temperature and quenched with 5 mL of aqueous 1M NaHCO$_3$ solution. The aqueous layer was extracted with dichloromethane (3×5 mL). The combined organic extracts were dried (Na$_2$SO$_4$), filtered and concentrated to afford 0.4 g of the crude product of the title compound. LC/MS (ESI$^+$) m/z 213 (M+H)$^+$.

Example 96C

N-[(2Z)-3-butyl-6,7-dihydro-4H-pyrano[3,4-d][1,3]thiazol-2(3H)-ylidene]-5-chloro-N'-cyano-2-methoxybenzenecarboximidamide A mixture of Example 96B (0.4 g, 1.9 mmol, crude), Example 93E (0.45 g, 1.9 mmol), and triethylamine (0.5 mL, 3.8 mmol) in ethanol (0.5 mL) was heated in 20 mL scintillation vial at 80° C. for 16 hr. The reaction mixture was cooled, concentrated and then diluted with saturated NaHCO$_3$ (10 mL). The aqueous layer was extracted with ethyl acetate (3×15 mL). The combined organic extracts were dried (Na$_2$SO$_4$), filtered and concentrated. The residue was purified by column chromatography using an Analogix® Intelliflash280™ (SiO$_2$, 0-50% ethyl acetate in dichloromethane) to afford 115 mg (15%) of the title compound. $^1$H NMR (300 MHz, DMSO-d$_6$) δ ppm 0.87 (t, J=7.3 Hz, 3H), 1.20-1.37 (m, 2H), 1.57-1.77 (m, 2H), 2.77 (t, J=5.2 Hz, 2H), 3.82 (s, 3H), 3.93 (t, J=5.4 Hz, 2H), 4.08 (t, J=7.5 Hz, 2H), 4.75 (s, 2H), 7.21 (d, J=9.1 Hz, 1H), 7.38 (d, J=2.8 Hz, 1H), 7.52 (dd, J=8.7, 2.8 Hz, 1H); MS (ESI$^+$) m/z 405 (M+H)$^+$; Anal. Calculated $C_{19}H_{21}ClN_4O_2S$: C, 56.36; H, 5.23; N, 13.84. Found: C, 56.24; H, 5.29; N, 13.50.

Example 97

N-[(2Z)-5-tert-butyl-3-(2-morpholin-4-ylethyl)-1,3-thiazol-2(3H)-ylidene]-5-chloro-N'-cyano-2-methoxybenzenecarboximidamide

Example 97A 5-tert-butyl-3-(2-morpholinoethyl)thiazol-2(3H)-imine

Commercially available 3,3-dimethylbutanal (Aldrich), 2-morpholinoethanamine (Aldrich), potassium thiocyanate (Aldrich) and iodine (EMD chemicals) were processed using the method described in Example 91A to afford the crude product of the title compound. MS (ESI$^+$) m/z 270 (M+H)$^+$.

Example 97B

N-[(2Z)-5-tert-butyl-3-(2-morpholin-4-ylethyl)-1,3-thiazol-2(3H)-ylidene]-5-chloro-N'-cyano-2-methoxybenzenecarboximidamide Example 97A and Example 93E were processed as described for Example 96C to obtain the title compound. $^1$H NMR (300 MHz, DMSO-d$_6$) δ ppm 1.36 (s, 9H), 2.36-2.46 (m, J=4.4 Hz, 4H), 2.67 (t, J=6.3 Hz, 2H), 3.44-3.56 (m, J=4.4 Hz, 4H), 3.81 (s, 3H), 4.31 (t, J=6.3 Hz, 2H), 7.20 (d, J=9.2

Hz, 1H), 7.35 (d, J=2.7 Hz, 1H), 7.51 (dd, J=9.2, 2.7 Hz, 1H), 7.56 (s, 1H); MS (ESI+) m/z 462 (M+H)+; Anal. Calculated $C_{22}H_{28}ClN_5O_2S$: C, 57.19; H, 6.11; N, 15.16. Found: C, 56.94; H, 6.20; N, 14.95.

Example 98

N-[(2Z)-5-tert-butyl-3-neopentyl-1,3-thiazol-2(3H)-ylidene]-N'-(5-chloro-2-methoxyphenyl)-N''-cyanoguanidine Example 98A 5-tert-butyl-3-neopentylthiazol-2(3H)-imine To a solution of 3,3-dimethylbutanal (Aldrich) (3.99 g, 39.8 mmol) in of acetonitrile (40 mL) was added 4 g of molecular sieves (4A beads, 8-12 mesh) and 2,2-dimethyl-propan-1-amine (Aldrich) (3.16 g, 36.2 mmol). The mixture was stirred for 12 h at room temperature. The mixture was filtered and to the filtrate was successively added potassium thiocyanate (4.68 g, 48.1 mmol) and 1,4,7,10,13,16-hexaoxacyclooctadecane (1.24 g, 4.71 mmol). The temperature was adjusted at 50° C. and the mixture was stirred until all solids were dissolved then iodine (18.4 g, 72.4 mmol) was added. The reaction was stirred at 50° C. for 12 h. The reaction mixture was cooled to room temperature and diluted with EtOAc. The solution was washed with a solution of sodium metabisulfate. The aqueous layers was brought to pH=9 by adding NaOH (25%) and extracted with EtOAc. The Organic extracts were combined, dried over sodium sulfate and concentrated under reduced pressure. The residue was crystallized from EtOAc/Hexane to give 4.9 g of the title compound. MS (ESI+) m/z 227 (M+H)+.

Example 98B

Methyl N-5-chloro-2-methoxyphenyl-N'-cyanocarbamimidothioate

To a solution of 4-chloro-2-isothiocyanato-1-methoxybenzene (Maybridge) (250 mg, 1.25 mmol) in DMF (2 mL) was added sodium cyanamide (80.0 mg, 1.25 mmol). The reaction was stirred at room temperature for 1 h. Iodomethane (0.078 ml, 1.25 mmol) was added at 0° C. and the reaction was stirred at room temperature for 2 h. Water (5 mL) was added to the reaction mixture and the reaction was stirred for 20 min. The precipitate was filtered, washed with water and dried at 60° C. for 10 h to afford the title compound. MS (ESI+) m/z 256 (M+H)+.

Example 98C

N-[(2Z)-5-tert-butyl-3-neopentyl-1,3-thiazol-2(3H)-ylidene]-N'-(5-chloro-2-methoxyphenyl)-N''-cyanoguanidine A mixture of Example 98A (124 mg, 0.55 mmol), Example 98B (140 mg, 0.55 mmol) and mercuric acetate (174 mg, 0.55 mmol) in 10 ml of THF was heated at 70° C. for 12 h. The reaction was cooled at room temperature and filtered twice through Celite. The mixture was purified by flash chromatography on SiO2 (gradient hexane-EtOAc, 0 to 75%) to yield the title compound. 1H NMR (300 MHz, DMSO-d6) δ ppm 0.81 (s, 9H), 1.30 (s, 9H), 3.83 (s, 3H), 3.85 (s, 2H), 7.09 (d, J=8.8 Hz, 1H), 7.15 (s, 1H), 7.21 (dd, J=9.0, 2.7 Hz, 1H), 7.85 (d, J=2.7 Hz, 1H), 8.38 (s, 1H); MS (ESI+) m/z 434 (M+H)+.

Example 99

N-[(2Z)-5-tert-butyl-3-[(2R)-tetrahydrofuran-2-ylmethyl]-1,3-thiazol-2(3H)-ylidene]-N''-cyano-N'-(1,2-dimethylpropyl)guanidine Example 99A (R)-5-tert-butyl-3-((tetrahydrofuran-2-yl)methyl)thiazol-2(3H)-imine The title compound was obtained according to the procedure outlined in Example 98A substituting (R)-(tetrahydrofuran-2-yl)methanamine (Aldrich) for 2,2-dimethylpropan-1-amine. MS (ESI+) m/z 241 (M+H)+.

Example 99B

Methyl N'-cyano-N-(3-methylbutan-2-yl)carbamimidothioate

The title compound was obtained according to the procedure outlined in Example 98B substituting 3-methyl-2-butylisothiocyanate (Aldrich) for 4-chloro-2-isothiocyanato-1-methoxybenzene. MS (ESI+) m/z 186 (M+H)+.

Example 99C

N-[(2Z)-5-tert-butyl-3-[(2R)-tetrahydrofuran-2-ylmethyl]-1,3-thiazol-2(3H)-ylidene]-N''-cyano-N'-(1,2-dimethylpropyl)guanidine The title compound was obtained according to the procedure outlined in Example 98C substituting Example 99A for Example 98A and Example 99B for Example 98B. 1H NMR (300 MHz, DMSO-d6) δ ppm 0.86 (d, J=6.8 Hz, 6H), 1.09 (d, J=6.8 Hz, 3H), 1.27 (s, 9H), 1.50-1.66 (m, 1H), 1.75-1.94 (m, 4H), 3.60-3.69 (m, 1H), 3.71-3.90 (m, 2H), 3.98-4.13 (m, 2H), 4.15-4.29 (m, 1H), 6.89 (s, 1H), 7.10 (d, J=3.1 Hz, 1H); MS (ESI+) m/z 378 (M+H)+.

Example 100

N-[(2Z)-5-tert-butyl-3-neopentyl-1,3-thiazol-2(3H)-ylidene]-5-chloro-N'-cyano-2-methoxybenzenecarboximidamide Example 100A (Z)-N-(5-tert-butyl-3-neopentylthiazol-2(3H)-ylidene)-5-chloro-2-methoxybenzamide Example 98A (1.00 g, 4.42 mmol) was dissolved in tetrahydrofuran (20 mL). To the solution was added 5-chloro-2-methoxybenzoic acid (Aldrich) (0.82 g, 4.42 mmol), 1-(3-dimethylaminopropyl)-3-ethylcarbodiimide hydrochloride (0.85 g, 4.42 mmol), HOBT (0.68 g, 4.42 mmol) and triethylamine (0.93 ml, 6.63 mmol). The mixture was stirred overnight at 80° C. and then cooled at room temperature. The mixture was diluted with ethyl acetate, washed with 1 M aqueous NaHCO3, dried (Na2SO4), filtered and concentrated.

The residue was purified by flash chromatography (SiO$_2$, 0-75% ethyl acetate in hexanes) to afford the title compound. MS (ESI$^+$) m/z 395 (M+H)$^+$.

Example 100B (Z)-N-(5-tert-butyl-3-neopentylthiazol-2(3H)-ylidene)-5-chloro-2-methoxybenzothioamide The title compound was obtained according to the procedure outlined in Example 17D. MS (ESI$^+$) m/z 412 (M+H)$^+$.

Example 100C

N-[(2Z)-5-tert-butyl-3-neopentyl-1,3-thiazol-2(3H)-ylidene]-5-chloro-N'-cyano-2-methoxybenzenecarboximidamide The title compound was obtained according to the procedure outlined in Example 17E. $^1$H NMR (300 MHz, DMSO-d$_6$) δ ppm 0.93 (s, 9H), 1.36 (s, 9H), 3.79 (s, 3H), 4.09 (s, 2H), 7.20 (d, J=8.8 Hz, 1H), 7.27 (d, J=2.7 Hz, 1H), 7.46 (s, 1H), 7.51 (dd, J=8.8, 2.7 Hz, 1H); MS (ESI$^+$) m/z 419 (M+H)$^+$.

Example 101

N-2-adamantyl-N'-[(2Z)-5-tert-butyl-3-[(2R)-tetrahydrofuran-2-ylmethyl]-1,3-thiazol-2(3H)-ylidene]-N''-cyanoguanidine Example 101A Methyl N-2-adamantyl-N'-cyanocarbamimidothioate The title compound was obtained according to the procedure outlined in Example 98B substituting 2-adamantane isothiocyanate (Oakwood) for 4-chloro-2-isothiocyanato-1-methoxybenzene. MS (ESI$^+$) m/z 250 (M+H)$^+$.

Example 101B

N-2-adamantyl-N'-[(2Z)-5-tert-butyl-3-[(2R)-tetrahydrofuran-2-ylmethyl]-1,3-thiazol-2(3H)-ylidene]-N''-cyanoguanidine The title compound was obtained according to the procedure outlined in Example 98C substituting Example 99A for Example 98A and Example 101A for Example 98B. $^1$H NMR (300 MHz, CDCl$_3$) δ ppm 1.31 (s, 9H), 1.61-1.69 (m, 2H), 1.71-1.98 (m, 14H), 1.98-2.06 (m, 2H), 3.71-3.87 (m, 2H), 3.90-4.00 (m, 1H), 4.01-4.08 (m, 1H), 4.13-4.25 (m, 2H), 5.82 (d, J=7.1 Hz, 1H), 6.69 (s, 1H); MS (ESI$^+$) m/z 442 (M+H)$^+$.

Example 102

N-1-adamantyl-N'-[(2Z)-5-tert-butyl-3-[(2R)-tetrahydrofuran-2-ylmethyl]-1,3-thiazol-2(3H)-ylidene]-N''-cyanoguanidine Example 102A Methyl N-1-adamantyl-N'-cyanocarbamimidothioate The title compound was obtained according to the procedure outlined in Example 98B substituting 1-adamantane isothiocyanate (Aldrich) for 4-chloro-2-isothiocyanato-1-methoxybenzene. MS (ESI$^+$) m/z 250 (M+H)$^+$.

Example 102B N-1-adamantyl-N'-[(2Z)-5-tert-butyl-3-[(2R)-tetrahydrofuran-2-ylmethyl]-1,3-thiazol-2 (3H)-ylidene]-N''-cyanoguanidine The title compound was obtained according to the procedure outlined in Example 98C substituting Example 99A for Example 98A and Example 102A for Example 98B. $^1$H NMR (300 MHz, CDCl$_3$) δ ppm 1.31 (s, 9H), 1.61-1.77 (m, 7H), 1.81-2.03 (m, 3H), 2.06-2.16 (m, 9H), 3.71-3.88 (m, 2H), 3.97 (dd, J=13.7, 7.0 Hz, 1H), 4.09-4.24 (m, 1H), 4.31 (dd, J=13.7, 2.9 Hz, 1H), 5.31 (s, 1H), 6.71 (s, 1H); MS (ESI$^+$) m/z 442 (M+H)$^+$.

Example 103

N-[(1S,2S,4R)-bicyclo[2.2.1]hept-2-yl]-N'-[(2Z)-5-tert-butyl-3-[(2R)-tetrahydrofuran-2-ylmethyl]-1,3-thiazol-2(3H)-ylidene]-N''-cyanoguanidine Example 103A Methyl N-((1S,2S,4R)-bicyclo[2.2.1]heptan-2-yl)-N'-cyanocarbamimidothioate The title compound was obtained according to the procedure outlined in Example 98B substituting (1S,2S,4R)-2-isothiocyanatobicyclo[2.2.1]heptane (Aldrich) for 4-chloro-2-isothiocyanato-1-methoxybenzene. MS (ESI$^+$) m/z 210 (M+H)$^+$.

Example 103B

N-[(1S,2S,4R)-bicyclo[2.2.1]hept-2-yl]-N'-[(2Z)-5-tert-butyl-3-[(2R)-tetrahydrofuran-2-ylmethyl]-1,3-thiazol-2(3H)-ylidene]-N''-cyanoguanidine The title compound was obtained according to the procedure outlined in Example 98C substituting Example 99A for Example 98A and Example 103A for Example 98B. $^1$H NMR (300 MHz, CDCl$_3$) δ ppm 1.09-1.22 (m, 4H), 1.32 (s, 9H), 1.40-1.65 (m, 3H), 1.70-2.08 (m, 5H), 2.22-2.37 (m, 2H), 3.66-3.87 (m, 3H), 3.93-4.12 (m, 1H), 4.15-4.32 (m, 2H), 5.27 (d, J=5.2 Hz, 1H), 6.71 (s, 1H); MS (ESI$^+$) m/z 402 (M+H)$^+$.

Example 104

N-[(2Z)-5-tert-butyl-3-[(2R)-tetrahydrofuran-2-ylmethyl]-1,3-thiazol-2(3H)-ylidene]-N''-cyano-N'-[(1R)-1,2-dimethylpropyl]guanidine Example 104A (R)-methyl N'-cyano-N-(3-methylbutan-2-yl)carbamimidothioate The title compound was obtained according to the procedure outlined in Example 98B substituting (R)-2-isothiocyanato-3-methylbutane (Aldrich) for 4-chloro-2-isothiocyanato-1-methoxybenzene. MS (ESI$^+$) m/z 186 (M+H)$^+$.

Example 104B

N-[(2Z)-5-tert-butyl-3-[(2R)-tetrahydrofuran-2-ylmethyl]-1,3-thiazol-2(3H)-ylidene]-N''-cyano-N'-[(1R)-1,2-dimethylpropyl]guanidine The title compound was obtained according to the procedure outlined in Example 98C substituting Example 99A for Example 98A and Example 104A for Example 98B. $^1$H NMR (300 MHz, CDCl$_3$) δ ppm 0.91 (d, J=5.4 Hz, 3H), 0.93 (d, J=5.4 Hz, 3H), 1.13 (d, J=6.8 Hz, 3H), 1.32 (s, 9H), 1.57-1.66 (m, 1H), 1.71-2.06 (m, 4H), 3.70-3.85 (m, 2H), 3.88-4.08 (m, 2H), 4.13-4.26 (m, 2H), 5.34 (d, J=8.5 Hz, 1H), 6.70 (s, 1H). MS (ESI$^+$) m/z 378 (M+H)$^+$.

Example 105

N-[(2Z)-5-tert-butyl-3-[(2R)-tetrahydrofuran-2-ylmethyl]-1,3-thiazol-2(3H)-ylidene]-N''-cyano-N'-[(1S)-1,2-dimethylpropyl]guanidine

Example 105A (S)-methyl N'-cyano-N-(3-methylbutan-2-yl)carbamimidothioate

The title compound was obtained according to the procedure outlined in Example 98B substituting (S)-2-isothiocyanato-3-methylbutane (Aldrich) for 4-chloro-2-isothiocyanato-1-methoxybenzene. MS (ESI$^+$) m/z 186 (M+H)$^+$.

Example 105B

N-[(2Z)-5-tert-butyl-3-[(2R)-tetrahydrofuran-2-ylmethyl]-1,3-thiazol-2(3H)-ylidene]-N''-cyano-N'-[(1S)-1,2-dimethylpropyl]guanidine The title compound was obtained according to the procedure outlined in Example 98C substituting Example 99A for Example 98A and Example 105A for Example 98B. $^1$H NMR (300 MHz, CDCl$_3$) δ ppm 0.91 (d, J=5.4 Hz, 3H), 0.93 (d, J=5.4 Hz, 3H), 1.13 (d, J=6.8 Hz, 3H), 1.32 (s, 9H), 1.60-1.72 (m, 1H), 1.72-1.93 (m, 3H), 1.94-2.09 (m, 1H), 3.69-4.03 (m, 4H), 4.04-4.17 (m, 2H), 5.34 (d, J=8.1 Hz, 1H), 6.71 (s, 1H); MS (ESI$^+$) m/z 378 (M+H)$^+$.

Example 106

N-[(2Z)-5-bromo-3-(cyclobutylmethyl)-1,3-thiazol-2(3H)-ylidene]-5-chloro-N'-cyano-2-methoxybenzenecarboximidamide

Example 106A

N-(5-bromothiazol-2-yl)-5-chloro-2-methoxybenzamide

To a solution of 2-amino-5-bromothiazole (1220 mg, 6.81 mmol) in dichloromethane (10 ml) was added triethylamine (1.235 ml, 8.86 mmol) and 4-dimethylamino pyridine (83 mg, 0.681 mmol), followed by addition of 5-chloro-2-methoxybenzoyl chloride (1397 mg, 6.81 mmol) and stirred overnight. The reaction was concentrated and water was added to the residue. The mixture was sonicated and filtered to obtain the title compound as off-white solid (1.56 g, 66%). $^1$H NMR (300 MHz, DMSO-D6) δ ppm 3.88 (m, 3H) 7.23 (d, J=8.81 Hz, 1H) 7.58-7.67 (m, 3H) 12.32 (s, 1H); MS (DCI/NH$_3$) m/z 347 (M+H)$^+$.

Example 106B (Z)-N-(5-bromo-3-(cyclobutylmethyl)thiazol-2(3H)-ylidene)-5-chloro-2-methoxybenzamide To a solution of Example 106A (232 mg, 2.071 mmol) in toluene (18 mL) and dioxane (2 mL) was added potassium 2-methylpropan-2-olate (232 mg, 2.071 mmol) and stirred at rt for 0.5 hr, followed by addition of tetrabutylammonium iodide (255 mg, 0.690 mmol) and (bromomethyl)cyclobutane (0.194 ml, 1.726 mmol). The reaction was refluxed overnight. Water (15 mL) was added to the reaction and the mixture was extracted with ethyl acetate (3×15 mL). The organics were combined, washed with brine, dried and concentrated. The residue was purified by column chromatography using an Analogix® Intelliflash280 (SiO$_2$, 0-30% ethyl acetate in hexane) to afford the title compound (350 mg, 48.8%). $^1$H NMR (300 MHz, CHLOROFORM-D) δ ppm 1.82-1.98 (m, 4H) 2.06-2.17 (m, 2H) 2.85 (dt, J=15.17, 7.50 Hz, 1H) 3.91 (s, 3H) 4.24 (d, J=7.46 Hz, 2H) 6.92 (d, J=8.82 Hz, 1H) 6.97 (s, 1H) 7.36 (dd, J=8.98, 2.88 Hz, 1H) 8.02 (d, J=2.71 Hz, 1H); MS (DCI/NH$_3$) m/z 415 (M+H)$^+$.

Example 106C (Z)-N-(5-bromo-3-(cyclobutylmethyl)thiazol-2(3H)-ylidene)-5-chloro-2-methoxybenzothioamide The title compound was prepared and isolated as described in Example 1C, substituting Example 106B for Example 1B. $^1$H NMR (300 MHz, DMSO-D6) δ ppm 1.81 (m, 4H) 1.94 (m, 2H) 2.87 (m, 1H) 3.77 (s, 3H) 4.35 (d, J=7.54 Hz, 2H) 7.10 (d, J=8.72 Hz, 1H) 7.36-7.43 (m, 2H) 8.21 (s, 1H); MS (DCI/NH$_3$) m/z 431 (M+H)$^+$. Anal. calcd C$_{16}$H$_{16}$BrClN$_2$OS$_2$: C, 44.50; H, 3.73; N, 6.79. Found: C, 44.84; H, 3.38; N, 6.07.

Example 106D

N-[(2Z)-5-bromo-3-(cyclobutylmethyl)-1,3-thiazol-2(3H)-ylidene]-5-chloro-N'-cyano-2-methoxybenzenecarboximidamide The title compound was prepared and isolated as described in Example 2, substituting Example 106C for Example 1C, and cyanamide for N-methylamine hydrochloride. $^1$H NMR (300 MHz, CHLOROFORM-D) δ ppm 1.83 (m, 2H) 1.94 (m, 2H) 2.11 (m, 2H) 2.81 (m, 1H) 3.92 (s, 3H) 4.26 (d, J=7.46 Hz, 2H) 6.95 (d, J=8.81 Hz, 1H) 7.10 (s, 1H) 7.34-7.40 (m, 2H); MS (DCI/NH$_3$) m/z 439 (M+H)$^+$.

Example 107

5-chloro-N-[(2Z)-5-chloro-3-(cyclobutylmethyl)-1,3-thiazol-2(3H)-ylidene]-N'-cyano-2-methoxybenzenecarboximidamide

Example 107A 5-chloro-N-(5-chlorothiazol-2-yl)-2-methoxybenzamide

The title compound was prepared and isolated as described in Example 106A, substituting 2-amino-5-chlorothiazole for 2-amino-5-bromothiazole. $^1$H NMR (300 MHz, DMSO-D6) δ ppm 3.89 (s, 3H) 7.23 (d, J=9.16 Hz, 1H) 7.57-7.63 (m, 2H) 7.65 (d, J=2.71 Hz, 1H) 12.29 (s, 1H); MS (DCI/NH$_3$) m/z 303 (M+H)$^+$.

Example 107B (Z)-5-chloro-N-(5-chloro-3-(cyclobutylmethyl)thiazol-2(3H)-ylidene)-2-methoxybenzamide The title compound was prepared and isolated as described in Example 106B, substituting Example 107A for Example 106A. $^1$H NMR (300 MHz, DMSO-D6) δ ppm 1.78-1.93 (m, 4H) 1.94-2.03 (m, 2H) 2.79-2.92 (m, 1H) 3.81 (s, 3H) 4.23 (d, J=7.46 Hz, 2H) 7.14 (d, J=8.81 Hz, 1H) 7.50 (dd, J=8.98, 2.88 Hz, 1H) 7.73 (d, J=2.71 Hz, 1H) 7.88 (s, 1H); MS (DCI/NH$_3$) m/z 371 (M+H)$^+$.

Example 107C (Z)-5-chloro-N-(5-chloro-3-(cyclobutylmethyl)thiazol-2(3H)-ylidene)-2-methoxybenzothioamide The title compound was prepared and isolated as described in Example 1C, substituting Example 107B for Example 1B. $^1$H NMR (300 MHz, CHLOROFORM-D) δ ppm 1.81-1.97 (m, 4H) 2.03-2.14 (m, 2H) 2.82-2.93 (m, 1H) 3.81 (s, 3H) 4.33 (d, J=7.46 Hz, 2H) 6.87 (d, J=8.82 Hz, 1H) 7.11 (s, 1H) 7.28 (d, J=2.71 Hz, 1H) 7.56 (d, J=2.71 Hz, 1H); MS (DCI/NH$_3$) m/z 387 (M+H)$^+$.

Example 107D 5-chloro-N-[(2Z)-5-chloro-3-(cyclobutylmethyl)-1,3-thiazol-2(3H)-ylidene]-N'-cyano-2-methoxybenzenecarboximidamide The title compound was prepared and isolated as described in Example 2, substituting Example 107C for Example 1C, and cyanamide for N-methylamine hydrochloride. $^1$H NMR (300 MHz, CHLOROFORM-D) δ ppm 1.78-1.88 (m, 2H) 1.90-2.00 (m, 2H) 2.05-2.16 (m, 2H) 2.75-2.86 (m, 1H) 3.92 (s, 3H) 4.25 (d, J=7.46 Hz, 2H) 6.95 (d, J=8.48 Hz, 1H) 7.02 (s, 1H) 7.34-7.41 (m, 2H); MS (DCI/NH$_3$) m/z 395 (M+H)$^+$. Anal. calcd C$_{17}$H$_{16}$ClN$_4$OS: C, 51.65; H, 4.08; N, 14.17. Found: C, 51.40; H, 3.69; N, 13.85.

Example 108

N-[(2Z)-5-bromo-3-isobutyl-1,3-thiazol-2(3H)-ylidene]-5-chloro-N'-cyano-2-methoxybenzenecarboximidamide

Example 108A (Z)-N-(5-bromo-3-isobutylthiazol-2(3H)-ylidene)-5-chloro-2-methoxybenzamide The title compound was prepared and isolated as described in Example 106B, substituting 1-iodo-2-methylpropane for (bromomethyl)cyclobutane. $^1$H NMR (300 MHz, CHLOROFORM-D) δ ppm 1.00 (d, J=6.78 Hz, 6H) 2.23-2.36 (m, 1H) 3.91 (s, 3H) 4.02 (d, J=7.46 Hz, 2H) 6.92 (d, J=8.82 Hz, 1H) 6.98 (s, 1H) 7.36 (dd, J=8.82, 2.71 Hz, 1H) 8.02 (d, J=2.71 Hz, 1H); MS (DCI/NH$_3$) m/z 403 (M+H)$^+$.

Example 108B (Z)-N-(5-bromo-3-isobutylthiazol-2(3H)-ylidene)-5-chloro-2-methoxybenzothioamide The title compound was prepared and isolated as described in Example 1C, substituting Example 108A for Example 1B. $^1$H NMR (300 MHz, CHLOROFORM-D) δ ppm 1.00 (d, J=6.78 Hz, 6H) 2.23-2.36 (m, 1H) 3.91 (s, 3H) 4.02 (d, J=7.46 Hz, 2H) 6.92 (d, J=8.82 Hz, 1H) 6.98 (s, 1H) 7.36 (dd, J=8.82, 2.71 Hz, 1H) 8.02 (d, J=2.71 Hz, 1H); MS (DCI/NH$_3$) m/z 419 (M+H)$^+$.

Example 108C

N-[(2Z)-5-bromo-3-isobutyl-1,3-thiazol-2(3H)-ylidene]-5-chloro-N'-cyano-2-methoxybenzenecarboximidamide The title compound was prepared and isolated as described in Example 2, substituting Example 108B for Example 1C, and cyanamide for N-methylamine hydrochloride. $^1$H NMR (300 MHz, CHLOROFORM-D) δ ppm 0.97 (d, J=6.78 Hz, 6H) 2.16-2.30 (m, 1H) 3.92 (s, 3H) 4.05 (d, J=7.46 Hz, 2H) 6.95 (d, J=8.82 Hz, 1H) 7.10 (s, 1H) 7.37 (td, J=8.99, 2.71 Hz, 2H); MS (DCI/NH$_3$) m/z 427 (M+H)$^+$. Anal. calcd C$_{16}$H$_{16}$BrClN$_4$OS: C, 44.93; H, 3.77; N, 13.1. Found: C, 45.13; H, 3.44; N, 12.8.

Example 109

N-[(2Z)-5-tert-butyl-3-(2-cyanoethyl)-1,3-thiazol-2(3H)-ylidene]-5-chloro-N'-cyano-2-methoxybenzenecarboximidamide

Example 109 A

N-(5-tert-butylthiazol-2-yl)-5-chloro-2-methoxybenzamide

The title compound was prepared and isolated as described in Example 106A, substituting 2-amino-5-t-butylthiazole for 2-amino-5-bromothiazole. $^1$H NMR (300 MHz, DMSO-D6) δ ppm 1.36 (s, 9H) 3.89 (s, 3H) 7.20-7.24 (m, 1H) 7.21 (s, 1H) 7.56-7.61 (m, 1H) 7.61-7.64 (m, 1H) 11.81 (s, 1H); MS (DCI/NH$_3$) m/z 325 (M+H)$^+$.

Example 109B (Z)-N-(5-tert-butyl-3-(2-cyanoethyl)thiazol-2(3H)-ylidene)-5-chloro-2-methoxybenzamide To a solution of Example 109A (65 mg, 0.200 mmol) in pyridine (1 mL) and water (1 mL) was added acrylonitrile (0.185 ml, 3.00 mmol) and the reaction heated at 90° C. for 7 hr. The reaction was concentrated and the residue was purified by column chromatography using an Analogix® Intelliflash280 ™ (SiO$_2$, 0-50% ethyl acetate in hexane) to afford the title compound (65 mg, 86%). $^1$H NMR (300 MHz, CHLOROFORM-D) δ ppm 1.36 (s, 9H) 3.05 (t, J=6.44 Hz, 2H) 3.90 (s, 3H) 4.40 (t, J=6.44 Hz, 2H) 6.74 (s, 1H) 6.92 (d, J=8.81 Hz, 1H) 7.35 (dd, J=8.81, 3.05 Hz, 1H) 7.90 (d, J=3.05 Hz, 1H); MS (DCI/NH$_3$) m/z 378 (M+H)$^+$. Anal. calcd C$_{18}$H$_{20}$ClN$_3$O$_2$S: C, 57.21; H, 5.33; N, 11.12. Found: C, 56.93; H, 5.42; N, 10.92.

Example 109C (Z)-N-(5-tert-butyl-3-(2-cyanoethyl)thiazol-2(3H)-ylidene)-5-chloro-2-methoxybenzothioamide The title compound was prepared and isolated as described in Example 1C, substituting Example 109B for Example 1B. $^1$H NMR (300 MHz, CHLOROFORM-D) δ ppm 1.42 (s, 9H) 3.08 (t, J=6.61 Hz, 2H) 3.80 (s, 3H) 4.45 (t, J=6.44 Hz, 2H) 6.85 (d, J=8.82 Hz, 1H) 6.94 (s, 1H) 7.27 (d, J=2.71 Hz, 1H) 7.58 (d, J=2.71 Hz, 1H); MS (DCI/NH$_3$) m/z 394 (M+H)$^+$.

Example 109D

N-[(2Z)-5-tert-butyl-3-(2-cyanoethyl)-1,3-thiazol-2(3H)-ylidene]-5-chloro-N'-cyano-2-methoxybenzenecarboximidamide The title compound was prepared and isolated as described in Example 2, substituting Example 109C for Example 1C, and cyanamide for N-methylamine hydrochloride. $^1$H NMR (300 MHz, CHLOROFORM-D) δ ppm 1.40 (s, 9H) 2.95 (t, J=6.27 Hz, 2H) 3.92 (s, 3H) 4.43 (t, J=6.44 Hz, 2H) 6.88 (s, 1H) 6.96 (d, J=8.82 Hz, 1H) 7.31 (d, J=2.71 Hz, 1H) 7.38 (dd, J=8.82, 2.71 Hz, 1H); MS (DCI/NH$_3$) m/z 402 (M+H)$^+$. Anal. calcd C$_{19}$H$_{20}$ClN$_5$OS: C, 56.78; H, 5.02; N, 17.42. Found: C, 56.54; H, 5.09; N, 17.17.

Example 110

5-chloro-N'-cyano-N-[(2Z)-3-(cyclobutylmethyl)-4-methyl-1,3-thiazol-2(3H)-ylidene]-2-methoxybenzenecarboximidamide

Example 110A 5-chloro-2-methoxy-N-(4-methylthiazol-2-yl)benzamide

The title compound was prepared and isolated as described in Example 106A, substituting 2-amino-4-methylthiazole for 2-amino-5-bromothiazole. $^1$H NMR (300 MHz, DMSO-D6) δ ppm 2.28 (s, 3H) 3.89 (s, 3H) 6.84 (s, 1H) 7.24 (d, J=8.72 Hz, 1H) 7.57-7.62 (m, 1H) 7.67 (d, J=2.78 Hz, 1H) 11.87 (s, 1H); MS (DCI/NH$_3$) m/z 283 (M+H)$^+$.

Example 110B (Z)-5-chloro-N-(3-(cyclobutylmethyl)-4-methylthiazol-2(3H)-ylidene)-2-methoxybenzamide The title compound was prepared and isolated as described in Example 106B, substituting Example 110A for Example 106 A. $^1$H NMR (300 MHz, CHLOROFORM-D) δ ppm 1.86-1.98 (m, 4H) 1.99-2.12 (m, 2H) 2.33 (s, 3H) 2.79-2.94 (m, 1H) 3.91 (s, 3H) 4.28 (d, J=7.14 Hz, 2H) 6.28 (s, 1H) 6.91 (d, J=9.12 Hz, 1H) 7.33 (dd, J=8.92, 2.97 Hz, 1H) 8.05 (d, J=2.78 Hz, 1H); MS (DCI/NH$_3$) m/z 351 (M+H)$^+$.

Example 110C (Z)-5-chloro-N-(3-(cyclobutylmethyl)-4-methylthiazol-2(3H)-ylidene)-2-methoxybenzothioamide The title compound was prepared and isolated as described in Example 1C, substituting Example 110B for Example 1B. $^1$H NMR (300 MHz, CHLOROFORM-D) δ ppm 1.81-1.92 (m, 4H) 1.96-2.05 (m, 2H) 2.43 (s, 3H) 2.85-2.89 (m, 1H) 3.81 (s, 3H) 4.36 (d, J=7.12 Hz, 2H) 6.47 (d, J=1.36 Hz, 1H) 6.85 (d, J=8.81 Hz, 1H) 7.23 (dd, J=8.81, 2.71 Hz, 1H) 7.53 (d, J=2.71 Hz, 1H); MS (DCI/NH$_3$) m/z 367 (M+H)$^+$.

Example 110D 5-chloro-N'-cyano-N-[(2Z)-3-(cyclobutylmethyl)-4-methyl-1,3-thiazol-2(3H)-ylidene]-2-methoxybenzenecarboximidamide The title compound was prepared and isolated as described in Example 2, substituting Example 110C for Example 1C, and cyanamide for N-methylamine hydrochloride. $^1$H NMR (300 MHz, CHLOROFORM-D) δ ppm 1.81-1.93 (m, 4H) 1.97-2.09 (m, 2H) 2.34 (s, 3H), 2.72-2.86 (m, 1H) 3.91 (s, 3H) 4.29 (d, J=7.12 Hz, 2H) 6.53 (s, 1H) 6.91-6.97 (m, 1H) 7.31-7.39 (m, 2H); MS (DCI/NH$_3$) m/z 375 (M+H)$^+$. Anal. calcd C$_{18}$H$_{19}$ClN$_4$OS.0.2 CH$_3$CN.90.5H$_2$O: C, 56.36; H, 5.30; N, 15.00. Found: C, 56.77; H, 5.02; N, 15.38.

Example 111

5-chloro-N'-cyano-N-[(2Z)-3-(cyclobutylmethyl)-5-(1-hydroxy-1-methylethyl)-4-methyl-1,3-thiazol-2(3H)-ylidene]-2-methoxybenzenecarboximidamide To a solution of Example 110D (101 mg, 0.269 mmol) in anhydrous tetrahydrofuran (4 mL) at −78° C. was added lithium diisopropylamide (2 M, 0.404 mL). After 5 min acetone (46.9 mg, 0.808 mmol) was added and the reaction was stirred for 0.5 hrs. Saturated ammonium chloride solution (2 mL) was added to quench the reaction at this temperature. The reaction mixture was diluted with water and extracted with ethyl acetate (3×10 mL). The organic layers were combined, washed with brine, dried with sodium sulfate and concentrated in vacuo. The residue was purified by column chromatography using an Analogix® Intelliflash280™ (SiO$_2$, 0-20% ethyl acetate in hexane) to afford the title compound (65 mg, 86%). $^1$H NMR (300 MHz, CHLOROFORM-D) δ ppm 1.67 (s, 6H) 1.81-1.94 (m, 4H) 2.00-2.08 (m, 2H) 2.50 (s, 3H) 2.68-2.81 (m, 1H) 3.91 (s, 3H) 4.30 (d, J=7.12 Hz, 2H) 6.91-6.96 (m, 1H) 7.33-7.38 (m, 2H); MS (DCI/NH$_3$) m/z 433 (M+H)$^+$. Anal. calcd C$_{21}$H$_{25}$ClN$_4$O$_2$S 90.6 EtOH: C, 57.95; H,6.19; N, 12.24. Found: C, 57.86; H, 6.13; N, 11.85.

Example 112

N-[(2Z)-5-tert-butyl-3-[(2R)-piperidin-2-ylmethyl]-1,3-thiazol-2(3H)-ylidene]-5-chloro-N'-cyano-2-methoxybenzenecarboximidamide

Example 112A (R)-tert-butyl 2-((5-tert-butyl-2-iminothiazol-3(2H)-yl)methyl)piperidine-1-carboxylate To a solution of 3,3-dimethylbutanal (439 mg, 4.39 mmol) in acetonitrile (8 mL) was added molecular sieves (4A beads, 8-12 mesh, 0.7 g) and (R)-tert-butyl 2-(aminomethyl)piperidine-1-carboxylate (940 mg, 4.39 mmol). The mixture was stirred for 12 hr at room temperature, filtered and washed with acetonitrile (5 mL). To this solution was added potassium thiocyanate (567 mg, 5.83 mmol) and the temperature was adjusted at 50° C. The reaction was stirred until all solids were dissolved then iodine (1.13 g, 4.39 mmol) was added. The reaction was stirred at 50° C. for 12 hr. The mixture was then stirred with 20% sodium metabisulfite for 1 hr. Then the organic layer was separated and the aqueous layer was extracted with dichloromethane (3×10 mL). The combined organics were dried over sodium sulfate, filtered and concentrated under reduced pressure to give the crude product. This intermediate was used without further purification. MS (DCI/NH$_3$) m/z 354 (M+H)$^+$.

Example 112B (R,Z)-tert-butyl 2-((5-tert-butyl-2-(5-chloro-2-methoxybenzoylimino)thiazol-3(2H)-yl)methyl)piperidine-1-carboxylate The title compound was prepared and purified as described in Example 106A, substituting Example 112A for 5-bromo-2-aminothiazole. $^1$H NMR (300 MHz, DMSO-D6) δ ppm 1.14-1.28 (m, 9H) 1.29 (s, 9H) 1.52-1.64 (m, 4H) 1.67-1.72 (m, 2H) 3.33-3.38 (m, 1H) 3.78 (s, 3H) 3.83-3.90 (m, 1H) 4.00-4.04 (m, 1H) 4.57-4.61 (m, 1H) 4.70-4.74 (m, 1H) 7.07-7.11 (m, 1H) 7.16-7.22 (m, 1H) 7.41-7.45 (m, 1H) 7.65-7.71 (m, 1H); MS (DCI/NH$_3$) m/z 522 (M+H)$^+$.

Example 112C (R,Z)-tert-butyl 2-((5-tert-butyl-2-(5-chloro-2-methoxyphenylcarbonothioylimino)thiazol-3(2H)-yl)methyl)piperidine-1-carboxylate The title compound was prepared and isolated as described in Example 1C, substituting Example 112B for Example 1B. $^1$H NMR (300 MHz, CHLOROFORM-D) δ ppm 1.22-1.26 (m, 2H) 1.36 (m, 1H) 1.38 (s, 9H) 1.54 (s, 9H) 1.68 (m, 3H) 2.91 (s, 1H) 3.80 (s, 3H) 4.06-4.16 (m, 2H) 4.47 (m, 1H) 4.79 (m, 1H) 6.84 (d, J=9.16 Hz, 1H) 7.22 (dd, J=8.82, 2.71 Hz, 2H) 7.52 (s, 1H); MS (DCI/NH$_3$) m/z 538 (M+H)$^+$.

Example 112D (R,Z)-N-(5-tert-butyl-3-(piperidin-2-ylmethyl)thiazol-2(3H)-ylidene)-5-chloro-2-methoxybenzothioamide To a solution of Example 112C (160 mg, 0.306 mmol) in methyl alcohol (2 mL) added hydrogen chloride (4 M) in dioxane (1 mL) and stirred at rt for 2 hr. The reaction concentrated to give the title compound as HCl salt. $^1$H NMR (300 MHz, CHLOROFORM-D) δ ppm 1.27 (m, 1H) 1.34-1.38 (m, 1H) 1.40 (s, 9H) 1.61 (m, 2H) 1.81 (m, 2H) 2.53-2.63 (m, 1H) 3.02 (m, 1H) 3.13 (m, 1H) 3.81 (s, 3H) 4.03-4.09 (m, 1H) 4.33 (m, 1H) 6.85 (d, J=8.73 Hz, 1H) 6.93 (s, 1H) 7.21-7.24 (m, 1H) 7.53 (d, J=2.78 Hz, 1H); MS (DCI/NH$_3$) m/z 438 (M+H)$^+$.

Example 112E

N-[(2Z)-5-tert-butyl-3-[(2R)-piperidin-2-ylmethyl]-1,3-thiazol-2(3H)-ylidene]-5-chloro-N'-cyano-2-methoxybenzenecarboximidamide The title compound was prepared and isolated as described in Example 2, substituting Example 112D for Example 1C, and cyanamide for N-methylamine hydrochloride. $^1$H NMR (300 MHz, CHLOROFORM-D) δ ppm 1.10-1.22 (m, 1H) 1.23-1.33 (m, 1H) 1.38 (s, 9H) 1.60-1.66 (m, 3H) 1.80-1.84 (m, 1H) 2.55-2.65 (m, 1H) 3.01-3.10 (m, 2H) 3.93 (s, 3H) 3.94-4.03 (m, 1H) 4.19-4.25 (m, 1H) 6.84 (s, 1H) 6.95 (d, J=8.72 Hz, 1H) 7.32-7.38 (m, 2H); MS (DCI/NH$_3$) m/z 446 (M+H)$^+$. Anal. calcd for C$_{22}$H$_{28}$ClN$_5$OS.0.4 EtOAc.0.1 CH$_2$Cl$_2$: C, 58.26; H, 6.36; N, 14.83. Found: C, 57.90; H, 6.02; N, 14.45.

What is claimed:

1. A compound having formula (I)

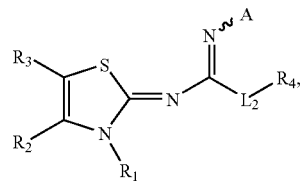

or a pharmaceutically acceptable salt, prodrug, salt of a prodrug, or a combination thereof, wherein A is OR$_b$, CN, NR$_c$R$_d$, NR$_c$C(O)R$_d$, NR$_c$C(S)R$_d$, C(O)OR$_{w1}$, or C(O)R$_{w2}$;

R$_1$ is C$_2$-C$_{10}$ alkyl, aryl, arylalkyl, cycloalkyl, cycloalkylalkyl, heteroaryl, heteroarylalkyl, heterocycle, heterocyclealkyl, R$_{g1}$R$_{h1}$N—C(O)—, R$_{g1}$R$_{h1}$N—C(O)-alkyl, alkenyl, alkoxycarbonylalkyl, alkylcarbonylalkyl, alkylsulfinylalkyl, alkylsulfonylalkyl, alkynyl, carboxyalkyl, cyanoalkyl, R$_{n1}$O—N=CR$_z$—, R$_{n1}$O—N=CR$_z$-alkyl-, R$_{o1}$R$_{p1}$N—N=CR$_z$—, R$_{o1}$R$_{p1}$N—N=CR$_z$-alkyl-, alkoxyalkyl, alkylthioalkyl, aryloxyalkyl, arylalkoxyalkyl, alkoxyalkoxyalkyl, haloalkyl, haloalkoxyalkyl, heteroaryloxyalkyl, heterocycleoxyalkyl, hydroxyalkyl, R$_{e1}$R$_{f1}$N-alkyl, R$_{j1}$R$_{k1}$N—C(O)—NR$_{m1}$-alkyl, R$_z$C(O)—O—C$_2$-C$_6$ alkyl-, R$_{z1}$SO$_2$NR$_{z2}$-alkyl-, R$_{z1}$C(O)NR$_{z2}$-alkyl-, R$_{j1}$R$_{k1}$N—SO$_2$—NR$_{m1}$-alkyl-, or R$_{g1}$R$_{h1}$NSO$_2$-alkyl-;

R$_2$ and R$_3$ are each independently hydrogen, alkenyl, alkoxy, alkoxyalkyl, alkoxycarbonyl, alkoxycarbonylalkyl, alkyl, alkynyl, alkylcarbonyl, alkylsulfinyl, alkylsulfonyl, alkylthio, aryl, arylalkyl, arylalkenyl, azidoalkyl, cyano, cycloalkyl, formyl, halo, haloalkyl, heteroaryl, heterocycle, hydroxyalkyl, R$_{e2}$R$_{f2}$N—, R$_{e2}$R$_{f2}$Nalkyl-, R$_{g2}$R$_{h2}$N—C(O)—, R$_{j2}$R$_{k2}$N—C(O)—NR$_{m2}$—, R$_{n2}$O—N=CR$_z$-alkyl-, R$_n$O—N=CR$_z$—, or R$_{o2}$R$_{p2}$N—N=CR$_z$-alkyl-; or R$_2$ and R$_3$, taken together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or R$_2$ and R$_3$, taken together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl;

$R_4$ is alkyl, alkenyl, alkynyl, aryl, cycloalkyl, cycloalkenyl, heteroaryl, heterocycle, arylalkyl, cycloalkylalkyl, cycloalkenylalkyl, heteroarylalkyl, or heterocyclealkyl;

$L_2$ is a bond or —$NR_{m1}$—; $R_b$ is alkyl, alkenyl, alkoxyalkyl, or arylalkyl;

$R_c$ and $R_d$ are each independently alkyl, arylalkyl, or heteroarylalkyl, or $R_c$ and $R_d$ taken together with the nitrogen atom to which they are attached form a 5-7 membered heterocyclic ring;

$R_{c'}$, at each occurrence, is independently hydrogen or alkyl $R_{d'}$, at each occurrence, is independently alkyl, alkoxy, amino, alkylamino, dialkylamino, arylamino, heteroarylamino, cycloalkylamino, heterocycleamino, or heterocycle:

$R_{e1}$ and $R_{f1}$ are each independently hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;

$R_{g1}$ and $R_{h1}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclalkyl, hydroxyalkyl, nitroalkyl, cycloalkyl, or haloalkoxyalkyl; or $R_{g1}$ and $R_{h1}$ together with the nitrogen atom to which they are attached form a 5-7 membered heterocyclic ring;

$R_{j1}$ and $R_{k1}$, at each occurrence, are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclalkyl; cycloalkyl, or haloalkoxyalkyl; or $R_{j1}$ and $R_{k1}$ together with the nitrogen atom to which they are attached form a 5-7 membered heterocyclic ring;

$R_{m1}$, at each occurrence, is independently hydrogen, alkyl, cycloalkyl, haloalkyl, alkoxyalkyl, or haloalkoxyalkyl;

$R_{n1}$, at each occurrence, is independently hydrogen, alkyl, alkenyl, alkoxyalkyl, alkynyl, arylalkyl, cyanoalkyl, cycloalkylalkyl, heteroarylalkyl, heterocyclalkyl, haloalkyl, hydroxyalkyl, or nitroalkyl;

$R_{o1}$ and $R_{p1}$, at each occurrence, are each independently hydrogen, alkyl, alkenyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{o1}$ and $R_{p1}$ together with the nitrogen atom to which they are attached form a 5-7 membered heterocyclic ring;

$R_{e2}$ and $R_{f2}$, at each occurrence, are each independently hydrogen, alkyl, alkylcarbonyl, alkylsulfonyl, alkoxycarbonyl, aryl, arylalkyl, cycloalkyl, cycloalkylalkyl, heteroaryl, heteroarylalkyl, heterocycle, or heterocyclealkyl;

$R_{g2}$ and $R_{h2}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{g2}$ and $R_{h2}$ together with the nitrogen atom to which they are attached form a 5-7 membered heterocyclic ring;

$R_{j2}$ and $R_{k2}$ are each independently hydrogen, alkyl, alkenyl, alkoxycarbonyl, alkoxyalkyl, alkynyl, arylalkyl, cyanoalkyl, cycloalkylalkyl, haloalkyl, heteroarylalkyl, or heterocyclalkyl;

$R_{m2}$ is hydrogen or alkyl;

$R_{n2}$, at each occurrence, is independently hydrogen, alkyl, alkenyl, alkoxyalkyl, alkynyl, arylalkyl, cyanoalkyl, cycloalkylalkyl, heteroarylalkyl, heterocyclalkyl, haloalkyl, hydroxyalkyl, or nitroalkyl;

$R_{o2}$ and $R_{p2}$, at each occurrence, are each independently hydrogen, alkyl, alkenyl, alkoxyalkyl, alkynyl, arylalkyl, cyanoalkyl, cycloalkylalkyl, haloalkyl, heteroarylalkyl, heterocyclalkyl, hydroxyalkyl, or nitroalkyl; or $R_{o2}$ and $R_{p2}$ together with the nitrogen atom to which they are attached form a 5-7 membered heterocyclic ring;

$R_z$ is hydrogen or alkyl;

$R_{z1}$, at each occurrence, is independently alkyl, cycloalkyl, cycloalkylalkyl, alkoxyalkyl, haloalkyl, or cyanoalkyl;

$R_{z2}$, at each occurrence, is independently hydrogen, alkyl, cycloalkyl, haloalkyl, alkoxyalkyl, or haloalkoxyalkyl; and $R_{w1}$ and $R_{w2}$ are each independently alkyl, haloalkyl, aryl, cycloalkyl, or alkoxyalkyl.

2. The compound according to claim 1 or a pharmaceutically acceptable salt thereof, wherein A is $OR_b$, CN, $NR_cC(O)R_{d'}$, or $C(O)OR_{w1}$.

3. The compound according to claim 1 or a pharmaceutically acceptable salt thereof, wherein A is CN.

4. The compound according to claim 1 or a pharmaceutically acceptable salt thereof, wherein $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

5. The compound according to claim 1 or a pharmaceutically acceptable salt thereof, wherein $R_2$ is hydrogen or alkyl, and $R_3$ is hydrogen, alkyl, alkylcarbonyl, halo, cycloalkyl, or hydroxyalkyl.

6. The compound according to claim 1 or a pharmaceutically acceptable salt thereof, wherein $R_4$ is alkyl, aryl, cycloalkyl, heterocycle, or heteroaryl.

7. The compound according to claim 1 or a pharmaceutically acceptable salt thereof, wherein A is $OR_b$, CN, $NR_cC(O)R_{d'}$, or $C(O)OR_1$, and $L_2$ is a bond.

8. The compound according to claim 1 or a pharmaceutically acceptable salt thereof, wherein A is $OR_b$, CN, $NR_cC(O)R_{d'}$, or $C(O)OR_{w1}$, $L_2$ is a bond, and $R_4$ is alkyl, aryl, cycloalkyl, heterocycle, or heteroaryl.

9. The compound according to claim 1 or a pharmaceutically acceptable salt thereof, wherein A is $OR_b$, CN, $NR_cC(O)R_{d'}$, or $C(O)OR_{w1}$, $L_2$ is a bond, and $R_4$ is aryl or heteroaryl.

10. The compound according to claim 1 or a pharmaceutically acceptable salt thereof, wherein A is $OR_b$, CN, $NR_cC(O)R_{d'}$, or $C(O)OR_{w1}$, $L_2$ is a bond, $R_4$ is alkyl, aryl, cycloalkyl, heterocycle, or heteroaryl, and $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

11. The compound according to claim 1 or a pharmaceutically acceptable salt thereof, wherein A is $OR_b$, CN, $NR_cC(O)R_{d'}$, or $C(O)OR_{w1}$, $L_2$ is a bond, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, $R_2$ is hydrogen or alkyl, and $R_3$ is hydrogen, alkyl, alkylcarbonyl, halo, cycloalkyl, or hydroxyalkyl.

12. The compound according to claim 1 or a pharmaceutically acceptable salt thereof, wherein A is $OR_b$, CN, $NR_cC(O)R_{d'}$, or $C(O)OR_{w1}$, $L_2$ is a bond, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, and $R_2$ and $R_3$, taken together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R_2$ and $R_3$, taken together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl.

13. The compound according to claim 12 or a pharmaceutically acceptable salt thereof wherein A is CN.

14. The compound according to claim 12 or a pharmaceutically acceptable salt thereof wherein A is CN, and $R_4$ is aryl or heteroaryl.

15. The compound according to claim 12 or a pharmaceutically acceptable salt thereof wherein A is CN, $R_4$ is aryl or heteroaryl, and $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, or $R_{z1}SO_2NR_{z2}$-alkyl-.

16. The compound according to claim 1 or a pharmaceutically acceptable salt thereof wherein A is CN and $L_2$ is a bond.

17. The compound according to claim 1 or a pharmaceutically acceptable salt thereof wherein A is CN, $L_2$ is a bond, and $R_4$ is alkyl, aryl, cycloalkyl, heterocycle, or heteroaryl.

18. The compound according to claim 1 or a pharmaceutically acceptable salt thereof wherein A is CN, $L_2$ is a bond, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, $R_2$ is hydrogen or alkyl, and $R_3$ is hydrogen, alkyl, alkylcarbonyl, halo, cycloalkyl, or hydroxyalkyl.

19. The compound according to claim 1 or a pharmaceutically acceptable salt thereof wherein A is CN and $L_2$ is $NR_{m1}$.

20. The compound according to claim 1 or a pharmaceutically acceptable salt thereof wherein A is CN, $L_2$ is $NR_{m1}$, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, $R_2$ is hydrogen or alkyl, and $R_3$ is hydrogen, alkyl, alkylcarbonyl, halo, cycloalkyl, or hydroxyalkyl.

21. The compound according to claim 1 or a pharmaceutically acceptable salt thereof wherein A is CN, $L_2$ is $NR_{m1}$, $R_4$ is alkyl, aryl, cycloalkyl, heterocycle, or heteroaryl, $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-, and $R_2$ and $R_3$, taken together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R_2$ and $R_3$, taken together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl.

22. The compound according to claim 1 having formula (XII) or a pharmaceutically acceptable salt thereof

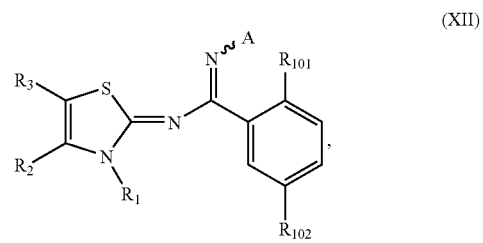

wherein
A is $OR_b$, CN, $NR_cC(O)R_d$, or $C(O)OR_{w1}$;
$R_{101}$ and $R_{102}$ are each independently alkyl, alkoxy, alkoxyalkoxy, cycloalkyloxy, cyano, formyl, halogen, alkylcarbonyloxy, haloalkyl, haloalkoxy, hydroxy, $NH_2$, or —$CR_z$(=N—$OR_{n1}$), and $R_b$, $R_c$, $R_d$, $R_{w1}$, $R_z$, $R_{n1}$, $R_1$, $R_2$, and $R_3$ are as defined in claim 1.

23. The compound according to claim 22 having formula (XII) or a pharmaceutically acceptable salt thereof, wherein A is CN, $R_2$ is hydrogen or alkyl, and $R_3$ is hydrogen, alkyl, alkylcarbonyl, halo, cycloalkyl, or hydroxyalkyl.

24. The compound according to claim 22 having formula (XII) or a pharmaceutically acceptable salt thereof, wherein A is CN, $R_2$ is hydrogen or alkyl, $R_3$ is hydrogen, alkyl, alkylcarbonyl, halo, cycloalkyl, or hydroxyalkyl, and $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

25. The compound according to claim 22 having formula (XII) or a pharmaceutically acceptable salt thereof wherein A is CN, and $R_2$ and $R_3$, taken together with the carbon atoms to which they are attached, optionally form a 4-, 5-, 6-, or 7-membered monocyclic ring, said monocyclic ring contains zero or one additional double bond, zero or one oxygen atom, and zero or one nitrogen atom as ring atoms; two non-adjacent atoms of said monocyclic ring can be optionally linked by an alkenylene bridge of 2, 3, or 4 carbon atoms, or optionally linked by an alkylene bridge of 1, 2, 3, or 4 carbon atoms, said monocyclic ring is independently unsubstituted or substituted with 1, 2, 3, 4, or 5 substituents independently selected from the group consisting of oxo, alkyl, halo, hydroxy, alkoxy, and haloalkyl; two substituents on the same carbon atom of said monocyclic ring, together with the carbon atom to which they are attached, optionally form a 3-, 4-, 5-, or 6-membered monocyclic cycloalkyl ring, wherein the monocyclic cycloalkyl ring is optionally substituted with 1, 2, 3, 4, 5, or 6 substituents independently selected from the group consisting of alkyl and haloalkyl; or $R_2$ and $R_3$, taken together with the carbon atoms to which they are attached, optionally form a 6-membered monocyclic ring, said monocyclic ring contains two additional double bonds, zero or one nitrogen atom as ring atoms; said monocyclic ring is independently unsubstituted or substituted with 1, 2, 3 or 4 substituents independently selected from the group consisting of alkyl, halo, cyano, hydroxy, alkoxy, and haloalkyl.

26. The compound according to claim 25 having formula (XII) or a pharmaceutically acceptable salt thereof, wherein $R_1$ is $C_2$-$C_{10}$ alkyl, cycloalkylalkyl, haloalkyl, heteroarylalkyl, heterocyclealkyl, alkenyl, alkynyl, cyanoalkyl, alkoxyalkyl, hydroxyalkyl, $R_zC(O)$—O—$C_2$-$C_6$ alkyl- or $R_{z1}SO_2NR_{z2}$-alkyl-.

27. The compound according to claim 1 selected from the group consisting of

N-[(2Z)-3-butyl-4,5-dimethyl-1,3-thiazol-2(3H)-ylidene]-5-chloro-N',2-dimethoxybenzenecarboximidamide;

N-[(2Z)-3-butyl-4,5-dimethyl-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N',2-dimethoxybenzenecarboximidamide;

N-[(2Z)-3-butyl-4,5-dimethyl-1,3-thiazol-2(3H)-ylidene]-5-chloro-N'-ethoxy-2-methoxybenzenecarboximidamide;

N'-(allyloxy)-N-[(2Z)-3-butyl-4,5-dimethyl-1,3-thiazol-2(3H)-ylidene]-5-chloro-2-methoxybenzenecarboximidamide;

tert-butyl (2Z)-2-[{[(2Z)-3-butyl-4,5-dimethyl-1,3-thiazol-2(3H)-ylidene]amino}(5-chloro-2-methoxyphenyl)methylene]hydrazinecarboxylate;

N'-(tert-butoxy)-N-[(2Z)-3-butyl-4,5-dimethyl-1,3-thiazol-2(3H)-ylidene]-5-chloro-2-methoxybenzenecarboximidamide;

tert-butyl 2-[{[(2Z)-3-butyl-5-tert-butyl-1,3-thiazol-2(3H)-ylidene]amino}(5-chloro-2-methoxyphenyl)methylene]hydrazinecarboxylate;

N-[(2Z)-5-tert-butyl-3-isobutyl-1,3-thiazol-2(3H)-ylidene]-5-chloro-N'-cyano-2-methoxybenzenecarboximidamide;

N-[(2Z)-5-tert-butyl-3-[(2R)-tetrahydrofuran-2-ylmethyl]-1,3-thiazol-2(3H)-ylidene]-5-chloro-N'-cyano-2-methoxybenzenecarboximidamide;

N-[(2Z)-5-tert-butyl-3-propyl-1,3-thiazol-2(3H)-ylidene]-5-chloro-N'-cyano-2-methoxybenzenecarboximidamide;

N-[(2Z)-5-tert-butyl-3-(3-methylbutyl)-1,3-thiazol-2(3H)-ylidene]-5-chloro-N'-cyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclohexyl acetate;

N-[(2Z)-5-tert-butyl-3-[(1-hydroxycyclohexyl)methyl]-1,3-thiazol-2(3H)-ylidene]-5-chloro-N'-cyano-2-methoxybenzenecarboximidamide;

2-[(2Z)-5-tert-butyl-2-{[(5-chloro-2-methoxyphenyl)(cyanoimino)methyl]imino}-1,3-thiazol-3(2H)-yl]-1,1-dimethylethyl acetate;

N-[(2Z)-5-tert-butyl-3-(2-hydroxy-2-methylpropyl)-1,3-thiazol-2(3H)-ylidene]-5-chloro-N'-cyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclopentyl acetate;

N-[(2Z)-5-tert-butyl-3-[(1-hydroxycyclopentyl)methyl]-1,3-thiazol-2(3H)-ylidene]-5-chloro-N'-cyano-2-methoxybenzenecarboximidamide;

N-[(2Z)-5-tert-butyl-3-propyl-1,3-thiazol-2(3H)-ylidene]-N',5-dicyano-2-methoxybenzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclobutyl acetate;

1-{[(2Z)-5-tert-butyl-2-{[(cyanoimino)(5-cyano-2-methoxyphenyl)methyl]imino}-1,3-thiazol-3(2H)-yl]methyl}cyclobutyl acetate;

N-[(2Z)-5-tert-butyl-3-[(1-hydroxycyclobutyl)methyl]-1,3-thiazol-2(3H)-ylidene]-5-chloro-N'-cyano-2-methoxybenzenecarboximidamide;

N-[(2Z)-5-tert-butyl-3-[(1-hydroxycyclobutyl)methyl]-1,3-thiazol-2(3H)-ylidene]-N',5-dicyano-2-methoxybenzenecarboximidamide;

N-[(2Z)-5-tert-butyl-3-isobutyl-1,3-thiazol-2(3H)-ylidene]-N'-cyano-2-methoxy-5-(trifluoromethyl)benzenecarboximidamide;

1-{[(2Z)-5-tert-butyl-2-{[(5-chloro-2-methoxyphenyl)(cyanoimino)methyl]imino}-1,3-thiazol-3(2H)-yl]methyl}cyclopropyl acetate;

N-[(2Z)-5-tert-butyl-3-[(1-hydroxycyclopropyl)methyl]-1,3-thiazol-2(3H)-ylidene]-5-chloro-N'-cyano-2-methoxybenzenecarboximidamide;

1-{[(2Z)-5-tert-butyl-2-({(cyanoimino)[2-methoxy-5-(trifluoromethyl)phenyl]methyl}imino)-1,3-thiazol-3(2H)-yl]methyl}cyclobutyl acetate;

N-[(2Z)-5-tert-butyl-3-[(1-hydroxycyclobutyl)methyl]-1,3-thiazol-2(3H)-ylidene]-N'-cyano-2-methoxy-5-(trifluoromethyl)benzenecarboximidamide;

N-[(2Z)-5-tert-butyl-3-[(2R)-tetrahydrofuran-2-ylmethyl]-1,3-thiazol-2(3H)-ylidene]-N'-cyano-2-ethoxy-5-(trifluoromethyl)benzenecarboximidamide;

N-[(2Z)-5-tert-butyl-3-{[1-(cyclopropylsulfonyl)azetidin-3-yl]methyl}-1,3-thiazol-2(3H)-ylidene]-N'-cyano-2-methoxy-5-(trifluoromethyl)benzenecarboximidamide;

N-[(2Z)-5-tert-butyl-3-{[1-(methylsulfonyl)azetidin-3-yl]methyl}-1,3-thiazol-2(3H)-ylidene]-N'-cyano-2-methoxy-5-(trifluoromethyl)benzenecarboximidamide;

N'-(aminocarbonyl)-N-[(2Z)-3-butyl-4,5-dimethyl-1,3-thiazol-2(3H)-ylidene]-5-chloro-2-methoxybenzenecarbohydrazonamide;

N-[(2Z)-5-acetyl-3-(cyclobutylmethyl)-4-methyl-1,3-thiazol-2(3H)-ylidene]-5-chloro-N'-cyano-2-methoxybenzenecarboximidamide;

N'-(anilinocarbonyl)-N-[(2Z)-3-butyl-4,5-dimethyl-1,3-thiazol-2(3H)-ylidene]-5-chloro-2-methoxybenzenecarbohydrazonamide;

2-{{[(2Z)-3-butyl-5-tert-butyl-1,3-thiazol-2(3H)-ylidene]amino}[(phenoxycarbonyl)imino]methyl}-4-chlorophenyl acetate;

N-[(2Z)-5-tert-butyl-3-[(2R)-tetrahydrofuran-2-ylmethyl]-1,3-thiazol-2(3H)-ylidene]-3,5-dichloro-N'-cyanobenzenecarboximidamide;

N-[(2Z)-5-tert-butyl-3-[(2R)-tetrahydrofuran-2-ylmethyl]-1,3-thiazol-2(3H)-ylidene]-N'-cyano-2-formylbenzenecarboximidamide;

N-[(2Z)-5-tert-butyl-3-[(2R)-tetrahydrofuran-2-ylmethyl]-1,3-thiazol-2(3H)-ylidene]-N'-cyano-2,5-difluorobenzenecarboximidamide;

N-[(2Z)-5-tert-butyl-3-[(2R)-tetrahydrofuran-2-ylmethyl]-1,3-thiazol-2(3H)-ylidene]-N'-cyano-2-[(hydroxyimino)methyl]benzenecarboximidamide;

N-[(2Z)-3-butyl-4,5-dimethyl-1,3-thiazol-2(3H)-ylidene]-2,5-difluoro-N'-methoxybenzenecarboximidamide;

N-[(2Z)-3-butyl-5-tert-butyl-4-methyl-1,3-thiazol-2(3H)-ylidene]-5-chloro-N',2-dimethoxybenzenecarboximidamide;

ethyl 2-[{[(2Z)-3-butyl-5-tert-butyl-1,3-thiazol-2(3H)-ylidene]amino}(5-chloro-2-methoxyphenyl)methylene]hydrazinecarboxylate;

N-[(2Z)-5-tert-butyl-3-isobutyl-1,3-thiazol-2(3H)-ylidene]-5-chloro-N'-cyano-2-(2-methoxyethoxy)benzenecarboximidamide;

N-[(2Z)-5-tert-butyl-3-isobutyl-1,3-thiazol-2(3H)-ylidene]-5-chloro-N'-cyano-2-(2,2,2-trifluoroethoxy)benzenecarboximidamide;

N-[(2Z)-5-tert-butyl-3-isobutyl-1,3-thiazol-2(3H)-ylidene]-2,3-dichloro-N'-cyanobenzenecarboximidamide;

N-[(2Z)-5-tert-butyl-3-isobutyl-1,3-thiazol-2(3H)-ylidene]-N',5-dicyano-2-methoxybenzenecarboximidamide;

N-[(2Z)-5-tert-butyl-3-isobutyl-1,3-thiazol-2(3H)-ylidene]-N'-cyano-2-ethoxypyridine-3-carboximidamide;

N-[(2Z)-5-tert-butyl-3-(3-methylbut-2-enyl)-1,3-thiazol-2(3H)-ylidene]-5-chloro-N'-cyano-2-methoxybenzenecarboximidamide;

N-[(2Z)-5-tert-butyl-3-(3,3,3-trifluoropropyl)-1,3-thiazol-2(3H)-ylidene]-5-chloro-N'-cyano-2-methoxybenzenecarboximidamide;

N-[(2Z)-5-tert-butyl-3-(3,3,3-trifluoropropyl)-1,3-thiazol-2(3H)-ylidene]-N',5-dicyano-2-(2-methoxyethoxy)benzenecarboximidamide;

N-[(2Z)-5-tert-butyl-3-isobutyl-1,3-thiazol-2(3H)-ylidene]-N',5-dicyano-2-(2-methoxyethoxy)benzenecarboximidamide;

N-[(2Z)-5-tert-butyl-3-isobutyl-1,3-thiazol-2(3H)-ylidene]-5-chloro-N'-cyano-2-ethoxybenzenecarboximidamide;

N-[(2Z)-5-tert-butyl-3-isobutyl-1,3-thiazol-2(3H)-ylidene]-5-chloro-N'-cyano-2-(cyclopropyloxy)benzenecarboximidamide;

N-[(2Z)-5-tert-butyl-3-isobutyl-1,3-thiazol-2(3H)-ylidene]-N',5-dicyano-2-ethoxybenzenecarboximidamide;

N-[(2Z)-5-tert-butyl-3-{[1-(methylsulfonyl)azetidin-3-yl]methyl}-1,3-thiazol-2(3H)-ylidene]-5-chloro-N'-cyano-2-methoxybenzenecarboximidamide;

N-[(2Z)-5-tert-butyl-3-isobutyl-1,3-thiazol-2(3H)-ylidene]-N',5-dicyano-2-(cyclobutyloxy)benzenecarboximidamide;

N-[(2Z)-5-tert-butyl-3-(3,3,3-trifluoropropyl)-1,3-thiazol-2(3H)-ylidene]-N',5-dicyano-2-(cyclobutyloxy)benzenecarboximidamide;

N-[(2Z)-5-tert-butyl-3-isobutyl-1,3-thiazol-2(3H)-ylidene]-N'-cyano-2-fluoro-3-(trifluoromethyl)benzenecarboximidamide;

N-[(2Z)-5-tert-butyl-3-isobutyl-1,3-thiazol-2(3H)-ylidene]-N',5-dicyano-2-(2,2,2-trifluoroethoxy)benzenecarboximidamide;

N-[(2Z)-5-tert-butyl-3-(3,3,3-trifluoropropyl)-1,3-thiazol-2(3H)-ylidene]-N',5-dicyano-2-(2,2,2-trifluoroethoxy)benzenecarboximidamide;

N-[(2Z)-5-tert-butyl-3-isobutyl-1,3-thiazol-2(3H)-ylidene]-N'-cyano-2-fluoro-5-(trifluoromethyl)benzenecarboximidamide;

N-[(2Z)-5-tert-butyl-3-{2-[methyl(methylsulfonyl)amino]ethyl}-1,3-thiazol-2(3H)-ylidene]-5-chloro-N'-cyano-2-methoxybenzenecarboximidamide;

N-[(2Z)-5-tert-butyl-3-isobutyl-1,3-thiazol-2(3H)-ylidene]-N'-cyano-2-ethoxy-5-(trifluoromethyl)benzenecarboximidamide;

N-[(2Z)-5-tert-butyl-3-isobutyl-1,3-thiazol-2(3H)-ylidene]-N'-cyano-2-(2,2,2-trifluoroethoxy)-5-(trifluoromethyl)benzenecarboximidamide;

N-[(2Z)-5-tert-butyl-3-(tetrahydro-2H-pyran-4-ylmethyl)-1,3-thiazol-2(3H)-ylidene]-5-chloro-N'-cyano-2-methoxybenzenecarboximidamide;

N-[(2Z)-3-butyl-5-tert-butyl-1,3-thiazol-2(3H)-ylidene]-5-chloro-N'-cyano-2-(2,2,2-trifluoroethoxy)benzenecarboximidamide;

N-[(2Z)-5-tert-butyl-3-(cyclobutylmethyl)-1,3-thiazol-2(3H)-ylidene]-5-chloro-N'-cyano-2-methoxybenzenecarboximidamide;

N-[(2Z)-5-tert-butyl-3-(4,4,4-trifluorobutyl)-1,3-thiazol-2(3H)-ylidene]-5-chloro-N'-cyano-2-methoxybenzenecarboximidamide;

N-[(2Z)-5-tert-butyl-3-but-3-ynyl-1,3-thiazol-2(3H)-ylidene]-5-chloro-N'-cyano-2-methoxybenzenecarboximidamide;

5-chloro-N'-cyano-2-methoxy-N-[(2Z)-5-methyl-3-(1,3-thiazol-4-ylmethyl)-1,3-thiazol-2(3H)-ylidene]benzenecarboximidamide;

5-chloro-N'-cyano-2-methoxy-N-[(2Z)-5-methyl-3-[(2R)-tetrahydrofuran-2-ylmethyl]-1,3-thiazol-2(3H)-ylidene]benzenecarboximidamide;

N'-cyano-N-[(2Z)-5-methyl-3-[(2R)-tetrahydrofuran-2-ylmethyl]-1,3-thiazol-2(3H)-ylidene]-2-oxatricyclo[3.3.1.1$^{3,7}$]decane-1-carboximidamide;

N'-cyano-N-[(2Z)-3-(2-methoxyethyl)-4,5-dimethyl-1,3-thiazol-2(3H)-ylidene]-2,2,3,3-tetramethylcyclopropanecarboximidamide;

5-chloro-N-[(2Z)-5-chloro-3-(1,3-thiazol-4-ylmethyl)-1,3-thiazol-2(3H)-ylidene]-N'-cyano-2-methoxybenzenecarboximidamide;

N-[(2Z)-5-bromo-3-(1,3-thiazol-4-ylmethyl)-1,3-thiazol-2(3H)-ylidene]-5-chloro-N'-cyano-2-methoxybenzenecarboximidamide;

N-[(2Z)-5-tert-butyl-3-(1,3-thiazol-4-ylmethyl)-1,3-thiazol-2(3H)-ylidene]-5-chloro-N'-cyano-2-methoxybenzenecarboximidamide;

N-[(2Z)-5-tert-butyl-3-[(2R)-tetrahydrofuran-2-ylmethyl]-1,3-thiazol-2(3H)-ylidene]-5-chloro-N'-cyano-2-[(Z)-(methoxyimino)methyl]benzenecarboximidamide;

5-chloro-N'-cyano-N-[(2Z)-3-(cyclobutylmethyl)-1,3-thiazol-2(3H)-ylidene]-2-methoxybenzenecarboximidamide;

N-[(2Z)-5-tert-butyl-3-[(2-methyl-1,3-thiazol-4-yl)methyl]-1,3-thiazol-2(3H)-ylidene]-5-chloro-N'-cyano-2-methoxybenzenecarboximidamide;

5-chloro-N'-cyano-N-[(2Z)-1-isobutyl-4,4-dimethyl-1,4,6,7-tetrahydro-2H-pyrano[4,3-d][1,3]thiazol-2-ylidene]-2-methoxybenzenecarboximidamide;

N-[(2Z)-3-butyl-7,7-dimethyl-6,7-dihydro-4H-pyrano[3,4-d][1,3]thiazol-2(3H)-ylidene]-5-chloro-N'-cyano-2-methoxybenzenecarboximidamide;

5-chloro-N'-cyano-N-[(2Z)-3-isobutyl-4,4,6,6-tetramethyl-4,6-dihydrofuro[3,4-d][1,3]thiazol-2(3H)-ylidene]-2-methoxybenzenecarboximidamide;

5-chloro-N'-cyano-N-[(2Z)-3-(cyclobutylmethyl)-4,4,6,6-tetramethyl-4,6-dihydrofuro[3,4-d][1,3]thiazol-2(3H)-ylidene]-2-methoxybenzenecarboximidamide;

5-chloro-N'-cyano-N-[(2Z)-5-cyclohexyl-3-(2-methoxyethyl)-1,3-thiazol-2(3H)-ylidene]-2-methoxybenzenecarboximidamide;

5-chloro-N'-cyano-N-[(2Z)-1-isobutyl-1,4,6,7-tetrahydro-2H-pyrano[4,3-d][1,3]thiazol-2-ylidene]-2-methoxybenzenecarboximidamide;

N-[(2Z)-3-butyl-4-tert-butyl-1,3-thiazol-2(3H)-ylidene]-5-chloro-N'-cyano-2-methoxybenzenecarboximidamide;

N-[(2Z)-3-butyl-6,7-dihydro-4H-pyrano[3,4-d][1,3]thiazol-2(3H)-ylidene]-5-chloro-N'-cyano-2-methoxybenzenecarboximidamide;

N-[(2Z)-5-tert-butyl-3-(2-morpholin-4-ylethyl)-1,3-thiazol-2(3H)-ylidene]-5-chloro-N'-cyano-2-methoxybenzenecarboximidamide;

N-[(2Z)-5-tert-butyl-3-neopentyl-1,3-thiazol-2(3H)-ylidene]-N'-(5-chloro-2-methoxyphenyl)-N''-cyanoguanidine;

N-[(2Z)-5-tert-butyl-3-[(2R)-tetrahydrofuran-2-ylmethyl]-1,3-thiazol-2(3H)-ylidene]-N''-cyano-N'-(1,2-dimethylpropyl)guanidine;

N-[(2Z)-5-tert-butyl-3-neopentyl-1,3-thiazol-2(3H)-ylidene]-5-chloro-N'-cyano-2-methoxybenzenecarboximidamide;

N-2-adamantyl-N'-[(2Z)-5-tert-butyl-3-[(2R)-tetrahydrofuran-2-ylmethyl]-1,3-thiazol-2(3H)-ylidene]-N''-cyanoguanidine;

N-1-adamantyl-N'-[(2Z)-5-tert-butyl-3-[(2R)-tetrahydrofuran-2-ylmethyl]-1,3-thiazol-2(3H)-ylidene]-N''-cyanoguanidine;

N-[(1S,2S,4R)-bicyclo[2.2.1]hept-2-yl]-N'-[(2Z)-5-tert-butyl-3-[(2R)-tetrahydrofuran-2-ylmethyl]-1,3-thiazol-2(3H)-ylidene]-N''-cyanoguanidine;

N-[(2Z)-5-tert-butyl-3-[(2R)-tetrahydrofuran-2-ylmethyl]-1,3-thiazol-2(3H)-ylidene]-N''-cyano-N'-[(1R)-1,2-dimethylpropyl]guanidine;

N-[(2Z)-5-tert-butyl-3-[(2R)-tetrahydrofuran-2-ylmethyl]-1,3-thiazol-2(3H)-ylidene]-N''-cyano-N'-[(1S)-1,2-dimethylpropyl]guanidine;

N-[(2Z)-5-bromo-3-(cyclobutylmethyl)-1,3-thiazol-2(3H)-ylidene]-5-chloro-N'-cyano-2-methoxybenzenecarboximidamide;

5-chloro-N-[(2Z)-5-chloro-3-(cyclobutylmethyl)-1,3-thiazol-2(3H)-ylidene]-N'-cyano-2-methoxybenzenecarboximidamide;

N-[(2Z)-5-bromo-3-isobutyl-1,3-thiazol-2(3H)-ylidene]-5-chloro-N'-cyano-2-methoxybenzenecarboximidamide;

N-[(2Z)-5-tert-butyl-3-(2-cyanoethyl)-1,3-thiazol-2(3H)-ylidene]-5-chloro-N'-cyano-2-methoxybenzenecarboximidamide;

5-chloro-N'-cyano-N-[(2Z)-3-(cyclobutylmethyl)-4-methyl-1,3-thiazol-2(3H)-ylidene]-2-methoxybenzenecarboximidamide;

5-chloro-N'-cyano-N-[(2Z)-3-(cyclobutylmethyl)-5-(1-hydroxy-1-methylethyl)-4-methyl-1,3-thiazol-2(3H)-ylidene]-2-methoxybenzenecarboximidamide; and N-[(2Z)-5-tert-butyl-3-[(2R)-piperidin-2-ylmethyl]-1,3-thiazol-2(3H)-ylidene]-5-chloro-N'-cyano-2-methoxybenzenecarboximidamide;

or a pharmaceutically acceptable salt thereof.

28. A pharmaceutical composition comprising a therapeutically effective amount of a compound of formula (I) according to claim 1, or a pharmaceutically acceptable salt thereof, in combination with a pharmaceutically acceptable carrier.

* * * * *

UNITED STATES PATENT AND TRADEMARK OFFICE
CERTIFICATE OF CORRECTION

PATENT NO.        : 7,875,640 B2  
APPLICATION NO.   : 12/051538  
DATED             : January 25, 2011  
INVENTOR(S)       : Kolasa et al.

Page 1 of 1

It is certified that error appears in the above-identified patent and that said Letters Patent is hereby corrected as shown below:

Claims:

Column 150 Line 36 Delete "C(O)OR$_1$" Insert -- C(O)OR$_{W1}$ --

Signed and Sealed this  
Twenty-fifth Day of December, 2012

David J. Kappos  
*Director of the United States Patent and Trademark Office*